(12) United States Patent
Tartaglia et al.

(10) Patent No.: US 6,977,240 B1
(45) Date of Patent: Dec. 20, 2005

(54) METHODS OF USING THE OB RECEPTOR ANTIBODIES TO TREAT BODYWEIGHT DISORDERS

(75) Inventors: Louis A. Tartaglia, Watertown, MA (US); Robert I. Tepper, Weston, MA (US); Janice A. Culpepper, Brookline, MA (US); David W. White, Holbrook, MA (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 584 days.

(21) Appl. No.: 09/950,149

(22) Filed: Sep. 10, 2001

Related U.S. Application Data

(63) Continuation of application No. 09/069,781, filed on Apr. 29, 1998, now Pat. No. 6,287,782, which is a continuation-in-part of application No. 08/864,564, filed on May 28, 1997, now Pat. No. 6,395,498, which is a continuation-in-part of application No. 08/708,123, filed on Sep. 3, 1996, now Pat. No. 6,482,927, which is a continuation-in-part of application No. 08/638,524, filed on Apr. 26, 1996, now Pat. No. 6,548,269, which is a continuation-in-part of application No. 08/599,455, filed on Jan. 22, 1996, now Pat. No. 5,972,621, which is a continuation-in-part of application No. 08/583,153, filed on Dec. 28, 1995, now Pat. No. 6,506,877, which is a continuation-in-part of application No. 08/570,142, filed on Dec. 11, 1995, now Pat. No. 6,509,189, which is a continuation-in-part of application No. 08/569,485, filed on Dec. 8, 1995, now abandoned, which is a continuation-in-part of application No. 08/566,622, filed on Dec. 4, 1995, now abandoned, which is a continuation-in-part of application No. 08/562,663, filed on Nov. 27, 1995, now abandoned.

(51) Int. Cl.[7] .................................. A61K 39/395
(52) U.S. Cl. .................. 514/2; 530/388.22; 530/350; 530/389.1; 530/387.1; 530/387.3
(58) Field of Search ................ 514/2; 530/388.22, 530/350

(56) References Cited

U.S. PATENT DOCUMENTS

| | | | |
|---|---|---|---|
| 5,643,748 A | | 7/1997 | Snodgrass et al. |
| 5,935,810 A | * | 8/1999 | Friedman et al. ........... 435/69.1 |
| 5,965,521 A | * | 10/1999 | Stephens et al. ............... 514/2 |

FOREIGN PATENT DOCUMENTS

| | | |
|---|---|---|
| WO | WO 93/07294 | 4/1993 |
| WO | WO 96/08510 | 3/1996 |
| WO | WO 97/12037 A | 4/1997 |
| WO | WO 97/25424 A | 7/1997 |
| WO | WO 97/25425 A | 7/1997 |
| WO | WO 97/25425 * | 7/1997 |

OTHER PUBLICATIONS

Kovacina et al., "Characterization of the Endogenous Insulin Receptor-related Receptor in Neuroblastomas", The Journal of Biological Chemistry, Vo. 270, No. 4, pp. 1881–1887, 1995.*

Fernandez–Pol, "Epidermal Growth Factor Receptor of A431 Cells". The Journal of Biological Chemistry, Vo. 260, No. 8, pp. 5003–5011, 1985.*

Tepper et al., "Role for ceramide as an endogenous mediator of Fas–induced cytotoxicity", Proc. Natl. Acad. Sce. USA, vol. 92, pp. 8443–8447, Aug. 1995.*

Zeigler et al., "Cellular and Molecular Characterization of the Role of the FLK–2/FLT–3 Receptor Tyrosine Kinase in Hematopoietic Stem Cells", Blood, Vo. 84, No. 8, pp. 2422–2430, Oct. 15, 1994.*

Pelleymounter et al., Science, 269:540–543, 1995.*

Halaas et al., Science, 269:543–546, 1995.*

Campfield et al., Science, 269:546–549, 1995.*

Friedman et al., Cell, 69:217–220, 1992.*

Tartaglia et al., Cell, 83:1263–1271, Dec. 29, 1995.*

Kovacina et al., "Characterization of the Endogenous Insulin Receptor-related Receptor in Neuroblastomas", The Journal of Biological Chemistry, Vo. 270, No. 4, pp. 1881–1887, 1995.*

Fernandez–Pol, "Epidermal Growth Factor Receptor of A431 Cells". The Journal of Biological Chemistry, Vo. 260, No. 8, pp. 5003–5011, 1985.*

Tepper et al., "Role for ceramide as an endogenous mediator of Fas–induced cytotoxicity". Proc. Natl. Acad. Sce. USA, vol. 92, pp. 8443–8447, Aug. 1995.*

Annotation for T73849 from Washington Merck EST Project, Mar. 2, 1995.

Annotation for T74249 from Washington Merck EST Project, Mar. 2, 1995.

Bray, G. A., "1989 McCollum Award Lecture. Genetic and hypothalamic mechanisms for obesity—finding the needle in the haystack", Am. J. Clin. Nutr., 50:891–902, 1989.

Bray et al., "Hypothalamic and Genetic Obesity in Experimental animals: an Autonomic and Endocrine Hypothesis", Physiological Reviews, 59:719–809, 1979.

(Continued)

Primary Examiner—Lorraine Spector
Assistant Examiner—Elieen B. O'Hara
(74) Attorney, Agent, or Firm—Millennium Pharmaceuticals, Inc.

(57) ABSTRACT

The present invention relates to the discovery, identification and characterization of nucleotides that encode Ob receptor (ObR), a receptor protein that participates in mammalian body weight regulation. The invention encompasses obR nucleotides, host cell expression systems, ObR proteins, fusion proteins, polypeptides and peptides, antibodies to the receptor, transgenic animals that express an obR transgene, or recombinant knock-out animals that do not express the ObR, antagonists and agonists of the receptor, and other compounds that modulate obR gene expression or ObR activity that can be used for diagnosis, drug screening, clinical trial monitoring, and/or the treatment of body weight disorders, including but not limited to obesity, cachexia and anorexia.

6 Claims, 34 Drawing Sheets

OTHER PUBLICATIONS

Figure 2A:
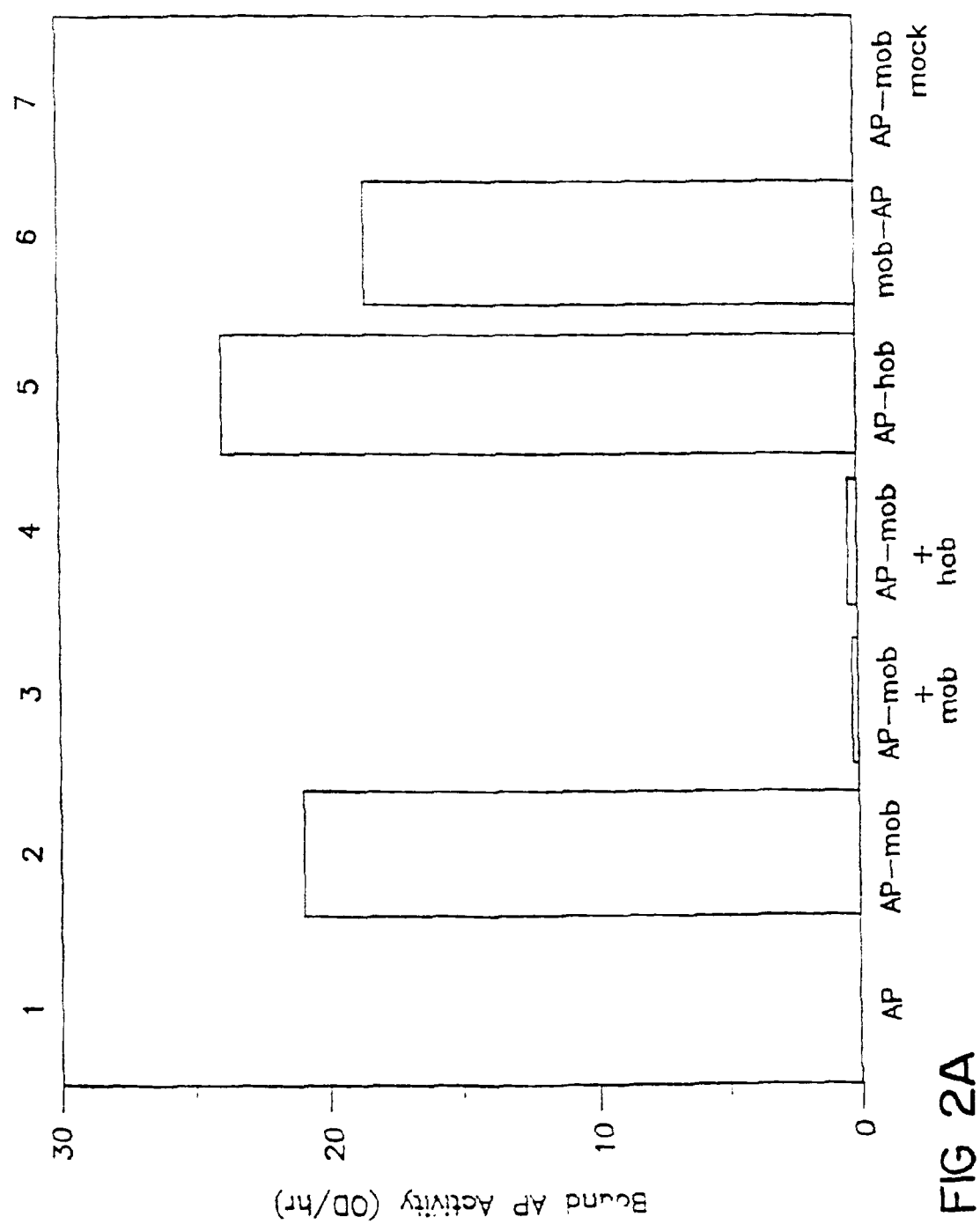

Campfield et al., "Recombinant Mouse OB Protein: Evidence for a Peripheral Signal Linking Adiposity and Central Neural Networks", Science, 269:546–549, 1995.

Chen et al., "Evidence that the Diabetes Gene Encodes the Leptin Receptor: Identification of a Mutation in the Leptin Receptor Gene in db/db Mice", Cell, 84:491–495, 1996.

Chua et al., "Phenotypes of Mouse diabetes and Rat fatty due to Mutations in the OB (Leptin) Receptor", Science, 271:877–1024, 1996.

Coiffi et al., "Novel B219/OB Receptor Isoforms: Possible role of Leptin in Hematopoiesis and Reproduction", Nature Medicine, 2(5):585–589, 1996.

Coleman, D. L., "Effects of Parabiosis of Obese with Diabetes and Normal Mice", Diabetologia, 9:294–298, 1973.

Coleman, D. L., "Obese and Diabetes: Two Mutant Genes Causing Diabetes–Obesity Syndrome in Mice", Diabetologia, 14:141–148, 1978.

Considine et al., "Evidence Against Either a Premature Stop Codon or the Absence of Obese Gene mRNA in Human Obesity", J. Clin. Invest., 95:2986–2988, 1995.

Considine et al., "The Hypothalamic Leptin Receptor in Humans: Identification of Incidential Sequence . . . ", Diabetes, 19:992–994, 1996.

Friedman et al., "Tackling a Weighty Problem", Cell, 69:217–220, 1992.

Gura, T., "Antisense Has Growing Pains", Science, 270:575–557, 1995.

Halaas et al., "Weight–Reducing Effects of the Plasma Protein Encoded by the obese Gene", Science, 269:543–546, 1995.

Hamilton et al., "Increased obese mRNA expression in omental fat cells from massively obese humans", Nature Med., 1:(9)953–956, 1995.

Hollenbaugh et al., "Current Protocols in Immunology", New York, pp. 10.19.1–10.19.11, 1992.

Hummel et al., "Diabetes, a New Mutation in the Mouse", Science, 153:1127–1128, 1966.

James, W., "Towards Gene–Inhibition Therapy: A Review of Progress and Prospects in the Field of Antiviral Antisense Nucleic . . . ", Antiviral Chem. & Chemo., 2(4):191–214, 1991.

Ledley, F., "Nonviral Gene Therapy: the Promise of Genes as Pharmaceutical Products", Human Gene Therapy, 6:1120–1144, 1995.

Lee et al., "Abnormal splicing of the Leptin receptor in diabetic mice", Nature, 379:632–635, 1996.

Lonnqvist et al., "Overexpression of the obese (ob) gene in adipose tissue of human obese subjects", Nature Med., 1:950–953, 1995.

Madej et al., "Threading Analysis Suggests that the Obese Gene Product may be a Helical Cytokine", FEBS Letters, 373:13–18, 1995.

Maffei et al., "Leptin levels in human and rodent: Measurements of plasma leptin and ob RNA in obese and weight–reudced subjects", Nature Med., 1:1155–1161, 1995.

Miller et al., "Gene Transfer and Antisense Nucleic Acid Techniques", Parasitology Today, 10(3):92–97, 1994.

Mulligan, R., "The Basic Science of Gene Therapy", Science, 260:926–931, 1993.

Murakami et al., "Cloning of RAT Obese cDNA and its Expression in Obese Rats", Biochem. & Biophys. Res. Com., 209(3):944–952, 1995.

Nishina et al., "Atherosclerosis in Genetically Obese Nice: The Mutants Obese, Diabetes, Fat, Tubby, and Lethal Yellow", Metabolism, 43:(5)554–558, 1994.

Pelleymounter et al., "Effects of the obese Gene Product on Body Weight Regulation in ob/ob Mice", Science, 269:540–543, 1995.

Redemann et al., "Anti–Oncogenic Activity of Signalling–Defective Epidermal Growth Factor Receptor Mutants", Mol. & Cell. Biol., 12(2):491–498, 1992.

Sealfon, S., Receptor Molecular Biology: Methods in Neuroscience, San Diego: Academic Press, 25:278–301 and 470–509, 1995.

Seed et al., "Developments in Expression Cloning", Current Opinion in Biotech., 6:567–573, 1995.

Stein et al., "Antisense Oligonucleotides as Therapeutic Agents—Is the Bullet Really Magic?", Science, 261:1004–1012, 1993.

Stephens et al., "The role of neuropeptide Y in the antiobesity action of the gene product", Nature, 377:530–532, 1995.

Stull et al., "Antigene, Ribozyme and Aptame Nucleic Acid Drugs: Progress and Prospects", Pharm. Res., 12:465–483, 1995.

Tartaglia et al., "Identification and Expression Cloning of a Leptin Receptor, OB–R", Cell, 83:1263–1271, 1995.

Wang et al., "A Novel Leptin Receptor Isoform in Rat", FEBS, 392:87–90, 1996.

Wu–Pong, S., "Oligonucleotides: Opportunities for Drug therapy and Research", Pharm. Tech., pp. 102–114, 1994.

Zhang et al., "Positional cloning of the mouse obese gene and its human homologue", Nature, 372:425–431, 1994.

Maffei, M. et al., Proc. Natl. Acad. Sci USA 92 :6957–6960 (1995).

* cited by examiner

GTCGACCCACGCGTCCGGAGGAATCGTTCTGCAAATCCAGGTGTACACCTCTGAAGAAAG

| M   | M   | C   | Q   | K   | F   | Y   | V   | V   | L   | H   | W   | E   | F   | L   | Y   | V   | I   | A   | 20  |
| ATG | ATG | TGT | CAG | AAA | TTC | TAT | GTG | GTT | TTG | CAC | TGG | GAA | TTT | CTT | TAT | GTG | ATA | GCT | 60  |

| A   | L   | N   | L   | A   | Y   | P   | I   | S   | P   | W   | K   | F   | C   | A   | P   | N   | G   | P   | 40  |
| GCA | CTT | AAC | CTG | GCA | TAT | CCA | ATC | TCT | CCC | TGG | AAA | TTT | TGT | GCC | CCA | AAC | GGA | CCG | 120 |

| N   | I   | T   | D   | S   | F   | L   | S   | A   | K   | G   | A   | P   | N   | A   | S   | Y   | V   | L   | 60  |
| AAC | ACA | ACC | GAT | TCC | TTT | CTC | TCA | GCT | AAA | GGA | GCT | CCA | AAT | GCC | TCG | TAC | GTT | TTG | 180 |

| K   | G   | A   | S   | E   | A   | I   | V   | F   | G   | F   | G   | N   | S   | G   | E   | Q   | N   | V   | P   | 80  |
| AAG | GGG | GCT | TCT | GAA | GCA | ATT | GTC | TTT | GGG | TTT | GGG | AAT | TCA | AGT | GAG | CAA | AAC | GTC | CCT | 240 |

| E   | L   | S   | K   | T   | N   | T   | E   | G   | K   | V   | K   | A   | S   | V   | F   | 100 |
| GAG | TTA | TCC | AAA | ACA | AAC | ACT | GAA | GGG | AAG | GTG | AAG | GCT | TCA | GTT | TTT | 300 |

| A   | L   | I   | D   | N   | W   | D   | I   | A   | K   | M   | G   | L   | V   | F   | 120 |
| GCA | CTC | ACA | GAC | AAC | TGG | GAC | ATA | GCT | AAA | ATG | GGG | CTT | ACA | TTC | 360 |

| R   | Q   | G   | V   | N   | P   | E   | K   | N   | P   | F   | K   | G   | D   | D   | P   | 140 |
| CGC | CAG | GGT | GTA | AAC | CCA | GAG | AAG | AAC | CCC | TTC | AAG | GGG | GAC | GAC | CCA | 420 |

| I   | Y   | H   | M   | D   | L   | P   | L   | V   | D   | D   | S   | R   | G   | N   | Y   | P   | V   | H   | 160 |
| ATC | TAT | CAT | ATG | GAT | CTA | CCT | CTG | GTT | GAT | GAT | TCG | CGG | GGA | AAT | TAT | CCA | GTG | CAT | 480 |

| L   | Q   | T   | V   | Q   | N   | L   | P   | E   | V   | L   | P   | E   | C   | K   | D   | S   | 180 |
| TTA | CAG | ACT | GTC | CAA | AAC | CTG | CCT | GAA | GTC | CTT | CCA | GAA | TGT | AAG | GAC | AGC | 540 |

| F   | Q   | N   | C   | N   | Q   | L   | P   | V   | H   | C   | E   | I   | L   | V   | P   | 200 |
| TTT | CAG | GTC | AAC | CAA | CTG | CCT | GTA | CAT | TGT | GAA | ATC | TTG | GTC | CCG | 600 |

| R   | A   | K   | L   | N   | Y   | A   | L   | M   | Y   | L   | E   | I   | T   | S   | V   | S   | 220 |
| AGA | GCC | AAA | CTC | AAC | TAC | GCT | CTT | ATG | TAT | TTG | GAA | ATC | ACA | TCT | GTG | AGT | 660 |

FIG. 1A

| | | | | | | | | | | | |
|---|---|---|---|---|---|---|---|---|---|---|---|
| F TTT | Q CAG | S TCA | P CCT | L CTG | M ATG | S TCA | L CTG | Q CAG | P CCC | M ATG | L CTT | V GTT | V GTG | K AAA | P CCC | D GAT | P CCA | P CCC | L TTA | 240 720 |
| G GGT | L TTG | H CAT | M ATG | E GAA | V GTC | T ACA | D GAT | D GAT | G GGT | N AAT | L TTA | K AAG | I ATT | S TCT | W TGG | D GAC | S AGC | Q CAA | T ACA | 260 780 |
| M ATG | A GCA | P CCA | F TTT | E GAA | L CTT | Q CAA | L CTT | Y TAT | Q CAG | K AAA | L TTA | E GAG | N AAT | S TCT | I ACA | I ATT | V GTA | R AGA | 280 840 |
| E GAG | A GCT | A GCT | E GAA | I ATT | V GTC | S TCA | V GTC | T ACA | L CTT | V GTA | D GAC | G GGT | L CTG | P CCT | G GGA | S TCT | 300 900 |
| S TCA | Y TAT | Q CAG | V GTC | Q CAG | R AGG | S AGC | K AAG | Q CAA | V GTT | Y TAT | W TGG | S AGT | D GAC | W TGG | 320 960 |
| S AGT | S TCA | P CCT | G GGA | S TCG | I ATA | V GTT | F TTT | T ACC | Y TAT | P CCA | K AAA | I ATA | L CTG | T ACT | 340 1020 |
| S AGT | V GTT | G GGA | Q CAG | S TCG | N AAT | A GCT | H CAT | F TTT | R AGG | Y TAC | K AAA | N AAC | E GAA | Q CAG | I ATA | I ATT | S TCC | 360 1080 |
| S TCA | K AAA | Q CAG | I ATA | V GTT | W TGG | V GTT | Y TAC | A GCG | D GAT | K AAA | E GAG | K AAA | L CTG | P CCT | A GCC | R AGA | P CCT | S AGC | 380 1140 |
| I ATT | V GTG | S AGT | D GAC | T ACC | Y TAT | D GAC | A GCA | Y TAT | V GTG | I ATC | A

| AA | Codon |   | AA | Codon |   | AA | Codon |   | AA | Codon |   | AA | Codon | Position |
|---|---|---|---|---|---|---|---|---|---|---|---|---|---|---|

Q L Y H R S L Y C P D S P S I H P T
CAG CTG TAT CAC AGG AGC CTG TAT TGT CCT GAT AGT CCA TCT ATT CAT CCT ACG    480 / 1440

S E P K V L Q R D F Y * F Q P
TCT GAG CCC AAA GTC TTA CAG AGA GAC TTT TAT *   TTC CAG CCA              500 / 1500

I F L L T M T L V I N G L    500 / 1500
ATC TTT CTA TCT GGC TAT ACA ATG TGG ATC AAC AGG TTA GGT TCA              520 / 1560

D S P P T C V L P D S K P P    
GAC TCG CCA CCA ACG TGT GTC CTT CCT GAT AGT AAA CCT CCA                  540 / 1620

V K A E I T V N T G L K E K    
GTA AAA GCA GAG ATT ACT GTA AAC ACT GGA TTA AAA GAA AAG                  560 / 1680

F P E N N L Q F Q I R Y G L T W S G L K    
TTT CCG GAG AAT AAC CTT CAA TTC CAG ATT CGA TAT GGC TTA TTG AGT TGG TCT  580 / 1740

W K T H E V F D A K S R R Y S    
TGG AAG ACA CAT GAG GTA TTC GAT GCA AAG TCA CGG AGG TAT AGT AGC          600 / 1800

L C A V Y Q V T L V M D V K    
CTC TGT GCA GTC TAT CAG GTC ACG CTG GTT ATG GAT GTA AAA                  620 / 1860

S P S Y T D G K T K E R    
AGT CCA AGC TAT ACG GAT GGG ACT AAA AAG GAG AGA                          640 / 1920

F W R K M D K S C S V R Y    
TTT TGG AGA AAA ATG GAT AAA TCA TGT AGT GTG AGG TAC                      660 / 1980

L K P L T * N K R * N T K    
CTT AAG CCC CTG ACG *   AAT AAA AGG *   AAT ACC                          680 / 2040

H R T A H N G T W S E D V G    
CAT CGT ACT GCC CAC AAT GGG ACG TGG TCA GAA GAT GTG GGA                  700 / 2100

```
E   K   *N  V   T   L   L   W   K   P   L   M   K   *N  D   S   C   S   V               676
GAG AAA AAT GTC ACT TTA CTT TGG AAG CCC CTG ATG AAA AAT GAC TCA TGC AGT GTT             2028

Q   R   Y   V   I   H   N   H   K   T   S   *N  W   T   E   D   V   G               696
CAG AGA TAT GTG ATA CAT AAC CAT ACT TCC TGC AAT TGG ACA GAA GAT GTG GGA             2088

*N  H   T   K   F   F   T   W   A   Q   *N  H   T   V   T   A   716
AAT CAC ACG AAA TTC TTC ACT TGG GCA CAA AAT CAT ACA GTT ACG GCC             2148

I   S   T   I   G   V   A   S   V   *N  A   L   T   S   V   L   A   736
ATC TCA ACG ATT GGT GTT GCA TCT GTT AAC GCA CTT TTA ACC TCA GTT CTG GCC             2208

K   V   N   I   S   Q   L   A   S   L   Y   *N  S   I   M   Y   756
AAA GTA AAT ATC TCA CAG CTC GCT AGT CTC TAT AAC AGC ATT ATG TAT             2268

S   W   I   S   P   G   D   K   Y   L   R   Y   F   I   E   W   K   776
TCC TGG ATA TCA CCC GGT GAT AAA TAC CTA AGA TAC TTT ATT GAG TGG AAG             2328

L   *N  I   E   G   F   K   W   E   K   *N   V   K   796
CTT AAT ATA GAA GGT TTT AAA TGG GAG AAG AAT GTT AAG             2388

P   D   H   I   P   K   Y   V   L   K   W   T   S   Q   D   Y   P   I               816
CCC GAT CAT ATC CCC AAG TAT GTA CTA AAA TGG ACT TCT CAA GAT TAC CCA ATA             2448

E   G   V   A   P   L   Y   L   *N  S   I   V   P   I   S   D   S   836
GAA GGT GTG GCA CCA TTA TAT TTA AAT AGT ATT GTA CCA ATT TCC TCT GAT TCC             2508

Q   S   A   G   K   Y   L   I   L   Q   R   M   K   K   I   856
CAG AGT GCA GGA AAA TAT CTA ATA TTA CAA AGA ATG AAA AAG ATT             2568

L   G   T   L   L   I   I   S   H   Q   W   E   F   D   V   P   876
CTT GGA ACA TTA TTA ATA TCA CAC CAA TGG GAA TTT GAT GTT CCG             2628
```

Q   D   S   C   S   H   F   V   E   N   N   I   N   L   G   T   S   S   K   K
CAG GAC AGT TGC TCA CAC TTT GTA GAA AAT AAT ATC AAC TTA GGA ACT TCT AGT AAG AAG

T   F   A   S   Y   M   P   Q   F   Q   T   C   S   T   Q   T   H   K   I   M
ACT TTT GCA TCT TAC ATG CCT CAA TTC CAA ACT TGT TCT ACT CAG ACT CAT AAG ATC ATG

E   N   K   M   C   D   L   T   V   *
GAA AAC AAG ATG TGT GAC CTA ACT GTG TAA TTTCACTGAAGAAACCTTCAGATTTGTGTTATAATGGGT

AATATAAAGTGTAATAGATTATAGTTGTGGGTGGGAGAGAGAAAAGAAACCAGAGTCCAAATTTGAAAATAATTGTTCC

CAACTGAAAAAAAAAAAAAAAAAAAAAAAAAAAAAAAAAAAAAAAAAAA
```

FIG. 3F

| | | |
|---|---|---|
| obr | YFPPKI-LTSYGSNASFHCIYKNE---NQIISSKQIVWWRNLAEKIPEIQ | 378 |
| gp130 | YISPESPVVQLHSNFIAVCVLKEKCMDYFHVNANYIVW-KTNHFTIPKEQ | 78 |
| obr | YSIVSDRVSKVTFSN---LKATRPRGKFTYDAVYCCNEQACHHRYAELYVI | 426 |
| gp130 | YTIINRTASSVTFTDIASLNIQLTCNILTFGQL---EQNVYGITIISGLPP | 126 |
| obr | DVNINISCETDGYLTKMTCRWSPSTIQSLVGSTVQIRYHRRSLYCPDSPS | 476 |
| gp130 | EKPKNLSCIVNE-GKKMRCEWD-GGRETHLETNFTLKSEWATHKFAD--- | 171 |
| obr | IHPTSEPKNCVLQRDGFYEC--VFQPIFLLSGYTMWIRINIISIGSLDSPP | 524 |
| gp130 | -----CKAKRDTPISCTVDYSTVYFVN-IEVWVEAENALGKVISDH | 211 |
| obr | TCVLPDSVVKPLPPSNVKAEIIVN-TGLLKVSWEKPVF-PENNLQFQIRY | 572 |
| gp130 | INFDPVYKVKPNPPHNLSVINSEELSSILKLTWTNPSIKSVIILKYNIQY | 261 |
| obr | GLSGKEIQWKTHEVFDAKSKSASLLVSDL--CAVYVVQVRCRRLDGLGYW | 620 |
| gp130 | RTKDAST-WSQIPPEDTASTRSSFTVQDLKPFIEYVFRIRCMKEDGKGYW | 310 |
| obr | SNWSSPAYTLVMDVKVPMRGPEFWRKMDGDVTKKERNVTLLWKPLTKNDS | 670 |
| gp130 | SDWSEEASGITYEDR-PSKAPSFWYKIDPSHTQGYRTVQLVWKTLPPFEA | 359 |
| obr | LCSYRRYVVKIHRTAHNGTWSEDVGNRTNLTFLWTEPAHTVTVLAVNSLGA | 720 |
| gp130 | NGKILDYEVTL-TRWKSIHLQNYTVNATKLTVNLTN-DRYLATLTVRNI VG | 407 |
| obr | SLVNFNLTFSW-PMSKVSAVESISAYPLSSSCVILSWTISPDDYSILYIV | 769 |
| gp130 | KSDAAVLTIPACDFQATHPVMDIKAFP-KDNMLWVEWT-TPRESVKKY-T | 454 |
| obr | IEWKILNEDDG--MKWLRIPSNVKKFYIHDNFIPIEKYQFSLYPVFMEGV | 817 |
| gp130 | LEWCVLSDKAPCITDWQQEDGTVHRTYLRGNLAESKCYLITVTPVYADGP | 504 |
| obr | GKPKIINGETKDA | 830 |
| gp130 | GSPESIKAYLKQA | 517 |

FIG. 4

```
hobr  MICQKFCVVLLHWEFIYVITAFNLSYPITPWRFKLSCMPP      40
mobr  MMCQKFYVVLLHWEFLYVIAALNLAYPISPWKFKLFCGPP
      * ** **** * *  *  * * hobr  NSTYDYFLLPAGLSKNTSNSNGHYETAVEPKFNSSGTHFS      80
mobr  NTTDDSFLSPAGAPNNASALKGASEAIVEAKFNSSGIYVP
      *  * ** * ***  *  *  *  *   **** * hobr  NLSKTTFHCCFRSEGDRNCSLCADNIEGKTFVSTVNSLVF     120
mobr  ELSKTVFHCCFGNEGGQNCSALTDNTEGKTLASVVKASVF
       ** *** *   *** * * ** * *   ** hobr  QQIDANWNIQCWLKGDLKLFICYVESLFKNLFRNYNYKVH     160
mobr  RQLGVNWDIECWMKGDLTLFICHMEPLPKNPFKNYDSKVH
       *  *** *   **  *   *  *** hobr  LLYVLPEVLEDSPLVPQKGSFQMVHCNCSVHECCECLVPV     200
mobr  LLYDLPEVIDDSPLPPLKDSFQTVQCNCSLRG-CECHVPV
      *  ***  * **  *      ** hobr  PTAKLNDTLLMCLKITSGGVIFQSPLMSVQPINMVKPDPP     240
mobr  PRAKLNYALLMYLEITSAGVSFQSPLMSLQPMLVVKPDPP
      * ** ** * ***  *  *****   ****** hobr  LGLHMEITDDGNLKISWSSPPLVPFPLQYQVKYSENSTTV     280
mobr  LGLHMEVTDDGNLKISWDSQTMAPFPLQYQVKYLENS-TI
      **** ******* *   * ******** hobr  IREADKIVSATSLLVDSILPGSSYEVQVRGKRLDGPGIWS     320
mobr  VREAAEIVSATSLLVDSVLPGSSYEVQVRSKRLDGSGVWS
       *  ******* ******* *** * ** hobr  DWSTPRVFTTQDVIYFPPKILTSVGSNVSFHCIYKKENKI     360
mobr  DWSSPQVFTTQDVVYFPPKILTSVGSNASFHCIYKNENQI
      *** * ***** ********* ***  * hobr  VPSKEIVWWMNLAEKIPQSQYDVVSDHVSKVTFFNLNETK     400
mobr  ISSKQIVWWRNLAEKIPEIQYSIVSDRVSKVTFSNLKATR
       * *  ** **   **  *  * hobr  PRGKFTYDAVYCCNEHECHHRYAELYVIDVNINISCETDG     440
mobr  PRGKFTYDAVYCCNEQACHHRYAELYVIDVNINISCETDG
      *************  ********************* hobr  YLTKMTCRWSTSTIQSLAESTLQLRYHRSSLYCSDIPSIH     480
mobr  YLTKMTCRWSPSTIQSLVGSTVQLRYHRRSLYCPDSPSIH
      ********  *   **** ** *  *** hobr  PISEPKDCYLQSDGFYECIFQPIFLLSGYTMWIRINHSLG     520
mobr  PTSEPKNCVLQRDGFYECVFQPIFLLSGYTMWIRINHSLG
      * ****  *  * ******************* hobr  SLDSPPTCVLPDSVVKPLPPSSVKAEITINIGLLKISWEK     560
mobr  SLDSPPTCVLPDSVVKPLPPSNVKAEITVNTGLLKVSWEK
      ********************* ******* * **** ***
```

FIG. 5A

| | | |
|---|---|---|
| hobr<br>mobr | PVFPENNLGFQIRYGLSGKEVGWKMYEVYDAKSKSVSLPV<br>PVFPENNLGFQIRYGLSGKEIGWKTHEVFDAKSKSASLLV | 600 |
| hobr<br>mobr | PDLCAVYAVQVRCKRLDGLGYWSNWSNPAYTVVMDIKVPM<br>SDLCAVYVVQVRCRRLDGLGYWSNWSSPAYTLVMDVKVPM | 640 |
| hobr<br>mobr | RGPEFWRIINGDTMKKEKNVTLLWKPLMKNDSLCSVQRYV<br>RGPEFWRKMDGDVTKKERNVTLLWKPLTKNDSLCSVRRYV | 680 |
| hobr<br>mobr | INHHTSCNGTWSEDVGNHTKFTFLWTEGAHTVTVLAINSI<br>VKHRTAHNGTWSEDVGNRTNLTFLWTEPAHTVTVLAVNSL | 720 |
| hobr<br>mobr | GASVANFNLTFSWPMSKVNIVQSLSAYPLNSSCVIVSWIL<br>GASLVNFNLTFSWPMSKVSAVESLSAYPLSSSCVILSWTL | 760 |
| hobr<br>mobr | SPSDYKLMYFIIEWKNLNEDGEIKWLRISSSVKKYYIHDH<br>SPDDYSLLYLVIEWKILNEDDGMKWLRIPSNVKKFYIHDN | 800 |
| hobr<br>mobr | FIPIEKYQFSLYPIFMEGVGKPKIINSFTQDDIEKHQSDA<br>FIPIEKYQFSLYPVFMEGVGKPKIINGFTKDAIDKQQNDA | 840 |
| hobr<br>mobr | GLYVIVPVIISSSILLLGTLLISHQRMKKLFWEDVPNPKN<br>GLYVIVPIIISSCVLLLGTLLISHQRMKKLFWDDVPNPKN | 880 |
| hobr<br>mobr | CSWAQGLNFQKPETFEHLFIKHTASVTCGPLLLEPETISE<br>CSWAQGLNFQKRTDTL | 920 |
| hobr | DISVDTSWKNKDEMMPTTVVSLLSTTDLEKGSVCISDQFN | 960 |
| hobr | SVNFSEAEGTEVTYEDESQRQPFVKYATLISNSKPSETGE | 1000 |
| hobr | EQGLINSSVTKCFSSKNSPLKDSFSNSSWEIEAQAFFILS | 1040 |
| hobr | DQHPNIISPHLTFSEGLDELLKLEGNFPEENNDKKSIYYL | 1080 |
| hobr | GVTSIKKRESGVLLTDKSRVSCPFPAPCLFTDIRVLQDSC | 1120 |
| hobr | SHFVENNINLGTSSKKTFASYMPQFQTCSTQTHKIMGNKM | 1160 |
| hobr | CDLTV | 1165 |

FIG. 5B

```
GTCGACCCACGCGTCCGGAGGAATCGTTCTGCAAATCCAGGTGTACACCTCTGAAGAAAG
 M   M   C   Q   K   F   Y   V   L   L   H   W   E   F   L   Y   V   I   A       20
ATG ATG TGT CAG AAA TTC TAT GTG GTT TTG TTA CAC TGG GAA TTT CTT TAT GTG ATA GCT   60
 A   L   N   L   A   Y   P   S   V   L   P   W   K   F   K   L   G   P   P       40
GCA CTT AAC CTG GCA TAT CCA ATC TCT CTT CCC TGG AAA TTT AAG TTG GGA CCA CCG      120
 N   T   T   D   D   S   F   L   A   I   V   E   A   K   F   N   A   S   L       60
AAC ACA ACC GAT GAT TCC TTT CTC TCA GCA ATT GTT GAA GCT AAA TTT AAT GCC TCG GCT TTG  180
 K   G   A   S   E   K   T   H   V   F   G   Q   N   Y   V   P       80
AAG GGG GCT TCT GAA AAA ACA GTC CAC GTG TTT GGG AAT GAG CAA TAC GTT CCT        240
 E   L   S   K   T   N   I   H   G   K   V   V   K   G   D   L       100
GAG TTA TCC AAA ACA AAC ATT ACT GAA GGG AAG GTA GTG AAA GGG GAC TTG          300
 A   L   T   D   N   W   B   P   K   M   K   N   Y   P   L       120
GCA CTC ACA GAC AAC TGG ATA CCT AAG ATG TGG AAA AAT TAT CCC CTG             360
 R   Q   L   G   V   E   L   C   W   N   D   S   K   D       140
CGC CAG CTA GGT GTA GAG TGC TGG AAC GAC TCT AAG GTC            420
 I   C   H   M   P   K   Y   R   G   E   C   K   P       160
ATC TGT CAT ATG CCA AAG TAT CGG GGA GAG TGT CAT CCC            480
 L   Y   D   L   P   E   V   I   D   L   P   V   Y   200
CTT TAT GAT CTG CCT GAA GTC ATA GAT CTG CCC GTA          540
 F   Q   N   S   Q   L   L   C   S   E   C   V       220
TTT CAG AAC TAC CAA CTC AGT GAA TGT GTG AGT          600
 R   A   K   N   Y   A   L   M   Y   L   E   I   S       220
AGA GCC AAA AAC TAC GCT CTT ATG TAT TTG GAA ATC ACA GCC GGG GTG AGT       660
```

FIG. 6A

| | | | | | | | | | | |
|---|---|---|---|---|---|---|---|---|---|---|
| F<br>TTT | Q<br>CAG | S<br>TCA | P<br>CCT | L<br>CTG | M<br>ATG | S<br>TCA | L<br>CTG | Q<br>CAG | P<br>CCC | M<br>ATG | L<br>CTT | V<br>GTT | V<br>GTG | K<br>AAA | P<br>CCC | D<br>GAT | P<br>CCA | P<br>CCC | L<br>TTA | 240<br>720 |
| G<br>GGT | L<br>TTG | H<br>CAT | M<br>ATG | E<br>GAA | V<br>GTC | T<br>ACA | D<br>GAT | G<br>GGT | N<br>AAT | L<br>TTA | K<br>AAG | L<br>TTA | I<br>ATT | S<br>TCT | W<br>TGG | D<br>GAC | S<br>AGC | Q<br>CAA | T<br>ACA | 260<br>780 |
| M<br>ATG | A<br>GCA | P<br>CCA | F<br>TTT | P<br>CCG | L<br>CTT | Q<br>CAA | Y<br>TAT | Q<br>CAG | V<br>GTG | K<br>AAA | Y<br>TAT | L<br>TTA | E<br>GAG | N<br>AAT | S<br>TCT | D<br>GAC | I<br>ATT | V<br>GTA | R<br>AGA | 280<br>840 |
| E<br>GAG | A<br>GCT | A<br>GCA | E<br>GAA | I<br>ATT | V<br>GTC | S<br>TCA | A<br>GCT | T<br>ACA | Y<br>TAT | L<br>CTG | L<br>CTG | V<br>GTA | D<br>GAT | L<br>CTT | S<br>TCT | P<br>CCT | G<br>GGA | S<br>TCT | W<br>TGG | 300<br>900 |
| S<br>TCA | Y<br>TAT | E<br>GAG | V<br>GTC | Q<br>CAG | V<br>GTG | R<br>AGG | S<br>AGC | R<br>AGA | L<br>CTG | D<br>GAT | V<br>GTG | G<br>GGT | Y<br>TAT | S<br>AGT | W<br>TGG | K<br>AAG | W<br>TGG | W<br>AGT | I<br>ATC | 320<br>960 |
| S<br>AGT | S<br>TCA | Q<br>CAG | V<br>GTC | F<br>TTT | T<br>ACC | K<br>AAG | Q<br>CAA | D<br>GAT | V<br>GTT | Y<br>TAT | G<br>GGT | S<br>TCA | F<br>TTT | P<br>CCA | K<br>AAA | I<br>AAA | L<br>CTG | T<br>ACT | 340<br>1020 |
| S<br>TCA | G<br>GGA | S<br>TCG | N<br>AAT | A<br>GCT | S<br>TCT | F<br>TTT | H<br>CAT | C<br>TGC | A<br>ATC | N<br>AAT | L<br>CTA | A<br>GCT | E<br>GAG | S<br>TCC | N<br>AAC | E<br>GAA | P<br>CCT | N<br>AAC | I<br>ATC | S<br>TCC | 360<br>1080 |
| S<br>TCA | D<br>GAC | V<br>GTC | R<br>CGA | Y<br>TAT | D<br>GAC | V<br>GTG | W<br>TGG | R<br>AGG | V<br>AAT | Y<br>TAC | T<br>ACC | F<br>TTC | V<br>GTT | T<br>ACC | Y<br>TAC | C<br>TGC | N<br>AAT | E<br>GAG | Q<br>CAG | S<br>AGC | 380<br>1140 |
| I<br>ATT | V<br>GTG | S<br>AGT | D<br>GAC | R<br>CGA | V<br>GTT | A<br>GCA | V<br>GTG | Y<br>TAC | K<br>AAA | E<br>GAG | K<br>AAA | I<br>ATC | P<br>CCT | K<br>AAA | A<br>GCG | A<br>GCC | H<br>CAT | R<br>AGA | P<br>CCT | R<br>CGA | 400<br>1200 |
| G<br>GGG | K<br>AAG | Q<br>CAG | V<br>GTC | V<br>GTT | D<br>GAC | T<br>ACC | Y<br>TAT | V<br>GTG | K<br>AAA | Y<br>TAC | K<br>AAA | N<br>AAT | F<br>TTC | S<br>TCC | N<br>AAC | L<br>CTG | Q<br>CAG | E<br>GAG | R<br>AGA | H<br>CAC | H<br>CAC | R<br>CGC | Y<br>TAT | 420<br>1260 |
| A<br>GCT | E<br>GAA | L<br>TTA | Y<br>TAC | V<br>GTG | I<br>ATC | D<br>GAT | V<br>GTC | N<br>AAT | I<br>ATC | N<br>AAT | I<br>ATA | S<br>TCA | C<br>TGT | E<br>GAA | T<br>ACT | D<br>GAC | G<br>GGG | Y<br>TAT | L<br>TTA | 440<br>1320 |

FIG. 6B

| T ACT | K AAA | M ATG | T ACT | C TGC | R AGA | W TGG | S TCA | P CCC | S AGC | T ACA | I ATC | Q CAA | S TCA | L CTA | V GTG | G GGA | S AGC | T ACT | V GTG | 460 1380 |
| Q CAG | L CTG | R AGG | Y TAT | H CAC | R AGG | S AGC | S AGC | L CTG | S AGC | Y TAT | C TGT | P CCT | S AGT | P CCA | I ATT | H CAT | P CCT | I ATA | ACG |  480 1440 |
| S TCT | E GAG | P CCC | K AAA | N AAC | C TGC | V GTC | Y TAT | L TTA | Q CAG | Y TAT | C TGT | D GAT | Y TAT | E GAA | V GTT | F TTC | Q CAG | P CCA | CCA |  500 1500 |
| I ATC | F TTT | L CTA | P CCA | P CCA | T ACG | I ATT | G GGC | T ACA | M ATG | R AGG | I ATC | N AAC | H CAT | L TTA | V GTT | G GGT | L TTC | — CTT |  520 1560 |
| D GAC | S TCG | P CCA | C CGA | P CCA | T ACG | V GTC | L TTA | E GAG | V GTA | S TCC | V GTA | K AAA | P CCA | G GGT | K AAG | S TCA | N AAC |  540 1620 |
| V GTA | K AAA | A GCA | E GAG | N AAT | L CTT | I ATT | T ACT | V GTA | N AAC | L CTT | Q CAA | K AAA | V GTA | G GTA | L CTA | E GAA | K CAA |  560 1680

| | | | | | | | | | | |
|---|---|---|---|---|---|---|---|---|---|---|
| H CAT | R CGT | T ACT | A GCC | H CAC | N AAT | G GGG | T ACG | W TGG | S TCA | E GAA | D GAT | V GTG | G GGA | N AAT | R CGG | T ACC | N AAT | L CTC | T ACT | 700 2100 |
| F TTC | L CTG | T TGG | V GTG | T ACA | E GAA | P CCA | A GCG | H CAC | T ACT | V GTT | T ACA | V GTT | L CTG | A GCT | V GTC | N AAT | S TCC | G GGC | A GCT | 720 2160 |
| S TCC | L CTT | V GTG | N AAT | F TTT | A GCT | P CCA | N AAC | L CTT | T ACC | S TCA | W TGG | P CCC | M ATG | S AGT | K AAA | V GTC | A GCT | V GTG | E GAG | 740 2220 |
| S TCA | L CTC | S AGT | A GCT | Y TAT | S AGC | P CCC | L CTG | L CTG | Y TAT | S AGC | S AGC | V GTT | C TGT | K AAA | S AGT | W TGG | T ACA | L CTG | S ICA | P CCT | 760 2280 |
| D GAT | D GAT | Y TAT | S AGT | L CTG | L TTA | R AGA | Y TAT | L CTG | V GTT | I ATT | E GAA | W TGG | K AAG | I ATC | L CTT | N AAT | E GAA | D GAT | G GGA | 780 2340 |
| M ATG | K AAG | W TGG | L CTT | R AGA | I ATT | P CCC | K AAA | F TTT | F TTT | Y TAT | K AAA | K AAG | F TTT | Y TAT | M ATG | Q CAG | H CAC | D GAT | N AAT | F TTT | AT! | 800 2400 |
| P CCC | I ATC | E GAG | K AAA | Y TAT | T TAT | A GCT | Q CAG | F TTT | T ACC | I ATA | L CTT | A GCT | S TCT | A GCT | P CCA | V GTA | K AAG | M ATG | E GAA | Q CAG | G GGA | K AAA | 820 2460 |
| K AAG | I ATA | I ATT | N AAT | G GGT | V GTA | P CCC | I ATA | S AGT | I ATT | I ATT | K AAA | D GAC | A GCT | S TCC | I ATC | C TGT | L CTG | Q CAG | L CTC | G GGA | A GCA | L CTG | 840 2520 |
| Y TAT | V GTC | I ATT | G GGA | R AGA | M

FIG. 6E

```
        Q   F   Q   I   C   S   T   H   S   H   K   I   M   E   N   K   M   C   D   L           1160
        CAA TTT CAA ACC TGT TCC ACG CAC AGT CAC AAG ATA ATG GAG AAT AAG ATG TGT GAC TTA          3480

T   V   *                                                                               1162
        ACT GTG TAA                                                                             3489

TCTCATTCCAAGAAGCCTCAAGGTTCCATTCCAGTAGAGCCTGTCATGTATAATGTGTTCTTTATTGTTGTGGATGTGG
        GAGACAAGTGTCAGAATCTAGTGTGAAAATGATTGTTCCAAACTAAGTGTGTCTATTTTCTCTCAGTAATACANATGA
        AACATATGAGGAAGCCCTCATTAATCTAGTAATGTAGATGGACTCTTACTGAATATATTCCAAGATACTTGGGAAGT
        CTCCCTAATTCTAGCTAAAAATAAACCCAGGAANTAGAACTACTAAACACTGAATCTGGAAAAAAAAAAAAAAAAAAG
```

FIG. 6F

```
mobr  MMCQKFYVVLLHWEFLYVIAALNLAYPISPWKFKLFCGPPNTTDDSFLSPAGAPNNASAL
hobr  MICQKFCVVLLHWEFIYVITAFNLSYPITPWRFKLSCMPPNSTYDYFLLPAGLSKNTSNS mobr  KGASEAIVEAKFNSSGIYVPELSKTVFHCCFSNEQGGNCSALTDNTEGKTLASVVKASVF
hobr  NGHYETAVEPKFNSSGTHFSNLSKTTFHCCFRSEGDRNCSLCADNIEGKTFVSTVNSLVF mobr  ROLGVNWDIECWMKGDLTLFICHMEPLPKNPFKNYDSKVHLLYDLPEVIDDSPLPPLKDS
hobr  QQIDANWNIQCWLKGDLKLFICYVESLFKNLFRNYNYKVHLLYVLPEVLEDSPLVPQKGS mobr  FQTVGCNCSLRG-CECHVPVPRAKLNYALLMYLEITSAGVSFQSPLMSLQPMLVVKPDPP
hobr  FQMVHCNCSVHECCECLVPVPTAKLNDTLLMCLKITSGGVIFQSPLMSVQPINMVKPDPP mobr  LGLHMEVTDDGNLKISWDSGTMAPFPLQYGVKYLENS-TIVREAAEIVSATSLLVDSVLP
                                         X
hobr  LGLHMEITDDGNLKISWSSPPLVPFPLQYGVKYSENSTTVIREADKIVSATSLLVDSILP mobr  GSSYEVQVRSKRLDGSGVWSDWSSPQVFTTQDVVYFPPKILTSVGSNASFHCIYKNENQI
hobr  GSSYEVQVRGKRLDGPGIWSDWSTPRVFTTQDVIYFPPKILTSVGSNVSFHCIYKKENKI mobr  ISSKQIVWWRNLAEKIPEIQYSIVSDRVSKVTFSNLKATRPRGKFTYDAVYCCNEQACHH
hobr  VPSKEIVWWMNLAEKIPQSQYDVVSDHVSKVTFFNLNETKPRGKFTYDAVYCCNEHECHH mobr  RYAELYVIDVNINISCETDGYLTKMTCRWSPSTIQSLVGSTVQLRYHRRSLYCPDSPSIH
hobr  RYAELYVIDVNINISCETDGYLTKMTCRWSTSTIQSLAESTLQLRYHRSSLYCSDIPSIH mobr  PTSEPKNCVLQRDGFYECVFQPIFLLSGYTMWIRINHSLGSLDSPPTCVLPDSVVKPLPP
hobr  PISEPKDCYLQSDGFYECIFQPIFLLSGYTMWIRINHSLGSLDSPPTCVLPDSVVKPLPP mobr  SNVKAEITVNTGLLKVSWEKPVFPENNLQFQIRYGLSGKEIQWKTHEVFDAKSKSASLLV
hobr  SSVKAEITINIGLLKISWEKPVFPENNLQFQIRYGLSGKEVQWKMYEVYDAKSKSVSLPV mobr  SDLCAVYVVQVRCRRLDGLGYWSNWSSPAYTLVMDVKVPMRGPEFWRKMDGDVTKKERNV
hobr  PDLCAVYAVQVRCKRLDGLGYWSNWSNPAYTVVMDIKVPMRGPEFWRIINGDTMKKEKNV mobr  TLLWKPLTKNDSLCSVRRYVVKHRTAHNGTWSEDVGNRTNLTFLWTEPAHTVTVLAVNSL
hobr  TLLWKPLMKNDSLCSVQRYVINHHTSCNGTWSEDVGNHTKFTFLWTEQAHTVTVLAINSI mobr  GASLVNFNLTFSWPMSKVSAVESLSAYPLSSSCVILSWTLSPDDYSLLYLVIEWKILNED
hobr  GASVANFNLTFSWPMSKVNIVQSLSAYPLNSSCVIVSWILSPSDYKLMYFIIEWKNLNED mobr  DGMKWLRIPSNVKKFYIHDNFIPIEKYQFSLYPVFMEGVGKPKIINGPTKDAIDKQQNDA
hobr  GEIKWLRISSSVKKYYIHDHFIPIEKYQFSLYPIFMEGVGKPKIINSPTQDDIEKHQSDA
```

FIG. 7A

```
mobr  GLYVIVPIISSCVLLLGTLLISHQRMKKLFWDDVPNPKNCSWAQGLNFQKPETFEHLFT
hobr  GLYVIVPVIISSSILLLGTLLISHQRMKKLFWEDVPNPKNCSWAQGLNFQKPETFEHLFI mobr  KHAESVIFGPLLLEPEPISEEISVDTAWKNKDEMVPAAMVSLLLTTPDPESSSICISDQC
hobr  KHTASVTCGPLLLEPETISEDISVDTSWKNKDEMMPTTVVS-LLSTTDLEKGSVCISDQF mobr  NSANFSGSQSTQVTCEDECQRQPSVKYATLVSNDKLVETDEEQGFIHSPVSNCISSNHSP
hobr  NSVNFSEAEGTEVTYEDESQRQPFVKYATLISNSKPSETGEEQGLINSSVTKCFSSKNSP mobr  LRQSFSSSSWETEAQTFFLLSDQQPTMISPQLSFS-GLDELLELEGSFPEENHREKSVCY
hobr  LKDSFSNSSWEIEAQAFFILSDGHPNIISPHLTFSEGLDELLKLEGNFPEENNDKKSIYY mobr  LGVTSVNRRESGVLLTGEAGILCTFPAQCLFSDIRILQERCSHFVENNLSLGTSGEN-FV
hobr  LGVTSIKKRESGVLLTDKSRVSCPFPAPCLFTDIRVLQDSCSHFVENNINLGTSSKKTFA mobr  PYMPQFQTCSTHSHKIMENKMCDLTV
hobr  SYMPQFQTCSTQTHKIMGNKMCDLTV
```

FIG. 7B

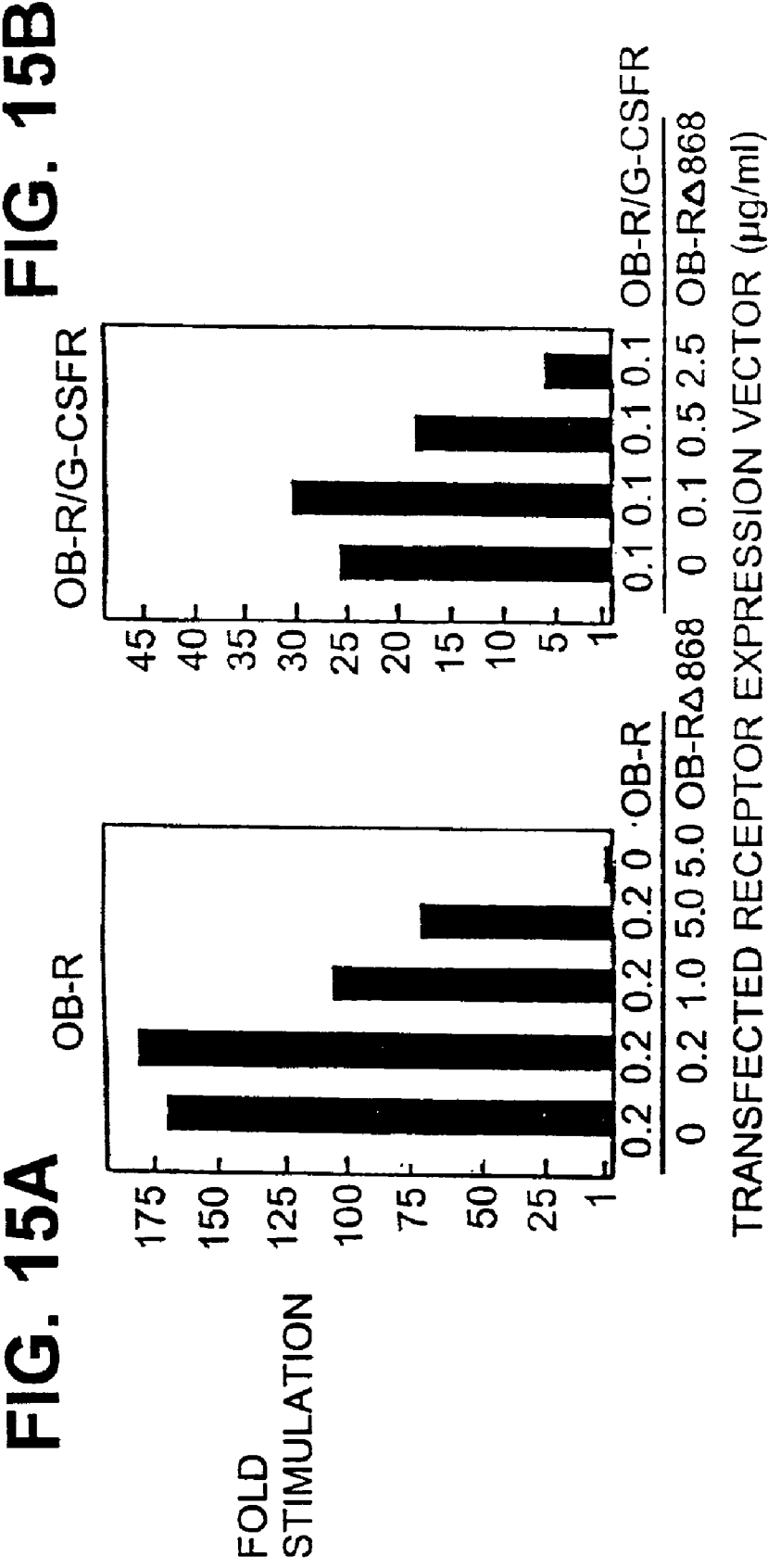

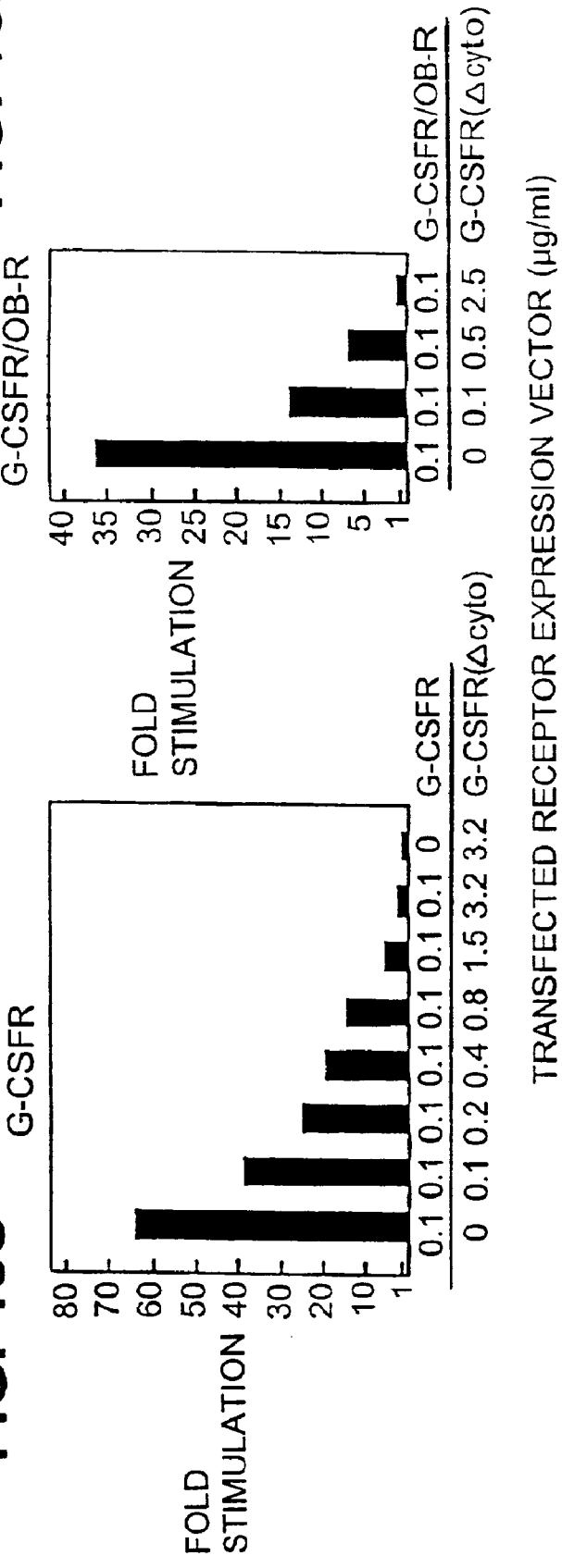

METHODS OF USING THE OB RECEPTOR ANTIBODIES TO TREAT BODYWEIGHT DISORDERS

CROSS REFERENCE TO RELATED APPLICATIONS

This application is a continuation of application Ser. No. 09/069,781, filed Apr. 29, 1998, now U.S. Pat. No. 6,287,782; which is a continuation in part of application Ser. No. 08/864,564, filed May 28, 1997, now U.S. Pat. No. 6,395,498; which is a continuation-in-part of application Ser. No. 08/708,123, filed Sep. 3, 1996, now U.S. Pat. No. 6,482,927; which is a continuation-in-part of application Ser. No. 08/638,524 filed Apr. 26, 1996, now U.S. Pat. No. 6,548,269; which is a continuation-in-part of application Ser. No. 08/599,455, filed Jan. 22, 1996, now U.S. Pat. No. 5,972,621; which is a continuation-in-part of application Ser. No. 08/583,153, filed Dec. 28, 1995, now U.S. Pat. No. 6,506,877; which is a continuation-in-part of application Ser. No. 08/570,142, filed Dec. 11, 1995, now U.S. Pat. No. 6,509,189; which is a continuation-in-part of application Ser. No. 08/569,485, filed Dec. 8, 1995, now abandoned: which is a continuation-in-part of application Ser. No. 08/566,622, filed Dec. 4, 1995, now abandoned; which is a continuation-in-part of application Ser. No. 08/562,663, filed Nov. 27, 1995, now abandoned; all of which are hereby incorporated by reference in their entirety.

1. INTRODUCTION

The present invention relates to the discovery, identification and characterization of nucleotides that encode Ob receptor (ObR), a receptor protein that participates in mammalian body weight regulation. The invention encompasses obR nucleotides, host cell expression systems, ObR proteins, fusion proteins, polypeptides and peptides, antibodies to the receptor, transgenic animals that express an obR transgene, or recombinant knock-out animals that do not express the ObR, antagonists and agonists of the receptor, and other compounds that modulate obR gene expression or ObR activity that can be used for diagnosis, drug screening, clinical trial monitoring, and/or the treatment of body weight disorders, including but not limited to obesity, cachexia and anorexia.

2. BACKGROUND OF THE INVENTION

Obesity represents the most prevalent of body weight disorders, and it is the most important nutritional disorder in the western world, with estimates of its prevalence ranging from 30% to 50% within the middle-aged population. Other body weight disorders, such as anorexia nervosa and bulimia nervosa which together affect approximately 0.2% of the female population of the western world, also pose serious health threats. Further, such disorders as anorexia and cachexia (wasting) are also prominent features of other diseases such as cancer, cystic fibrosis, and AIDS.

Obesity, defined as an excess of body fat relative to lean body mass, also contributes to other diseases. For example, this disorder is responsible for increased incidences of diseases such as coronary artery disease, stroke, and diabetes. (See, e.g., Nishina, P. M. et al., 1994, *Metab.* 43:554–558.) Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and/or level of gene products or activity (Friedman, J. M. et al., 1991, *Mammalian Gene* 1:130–144).

The epidemiology of obesity strongly shows that the disorder exhibits inherited characteristics (Stunkard, 1990, *N. Eng. J. Med.* 322:1483). Moll et al. have reported that, in many populations, obesity seems to be controlled by a few genetic loci (Moll et al. 1991, *Am. J. Hum. Gen.* 49:1243). In addition, human twin studies strongly suggest a substantial genetic basis in the control of body weight, with estimates of heritability of 80–90% (Simopoulos, A. P. & Childs B., eds., 1989, In Genetic Variation and Nutrition in Obesity, World Review of Nutrition and diabetes 63, S. Karger, Basel, Switzerland; Borjeson, M., 1976, *Acta. Paediatr. Scand.* 65:279–287).

Studies of non-obese persons who deliberately attempted to gain weight by systematically over-eating were found to be more resistant to such weight gain and able to maintain an elevated weight only by very high caloric intake. In contrast, spontaneously obese individuals are able to maintain -heir status with normal or only moderately elevated caloric intake. In addition, it is a commonplace experience in animal husbandry that different strains of swine, cattle, etc., have different predispositions to obesity. Studies of the genetics of human obesity and of models of animal obesity demonstrate that obesity results from complex defective regulation of both food intake, food induced energy expenditure and of the balance between lipid and lean body anabolism.

There are a number of genetic diseases in man and other species which feature obesity among their more prominent symptoms, along with, frequently, dysmorphic features and mental retardation. For example, Prader-Willi syndrome (PWS) affects approximately 1 in 20,000 live births, and involves poor neonatal muscle tone, facial and genital deformities, and generally obesity.

In addition to PWS, many other pleiotropic syndromes which include obesity as a symptom have been characterized. These syndromes are more genetically straightforward, and appear to involve autosomal recessive alleles. The diseases, which include, among others, Ahlstroem, Carpenter, Bardet-Biedl, Cohen, and Morgagni-Stewart-Monel Syndromes.

A number of models exist for the study of obesity (see, e.g., Bray, G. A., 1992, *Prog. Brain Res.* 93:333–341, and Bray, G. A., 1989, *Amer. J. Clin. Nutr.* 5:891–902). For example, animals having mutations which lead to syndromes that include obesity symptoms have been identified, and attempts have been made to utilize such animals as models for the study of obesity. The best studied animal models, to date, for genetic obesity are mice models. For reviews, see for example, Friedman, J. M. et al., 1991, *Mamm. Gen.* 1:130–144; Friedman, J. M. and Liebel, R. L., 1992, *Cell* 69:217–220.

Studies utilizing mice have confirmed that obesity is a very complex trait with a high degree of heritability. Mutations at a number of loci have been identified which lead to obese phenotypes. These include the autosomal recessive mutations obese (ob), diabetes (db), fat (fat) and tubby (tub). In addition, the autosomal dominant mutations Yellow at the acouti locus and Adipose (Ad) have been shown to contribute to an obese phenotype.

The ob and db mutations are on chromosomes 6 and 4, respectively, but lead to a complex, clinically similar phenotype of obesity, evident starting at about one month of age, which includes hyperphagia, severe abnormalities in glucose and insulin metabolism, very poor thermoregulation and non-shivering thermogenesis, and extreme torpor and underdevelopment of the lean body mass. This complex phenotype has made it difficult to identify the primary defect attributable to the mutations (Bray G. A., et al., 1989 *Amer. J. Clin. Nutr.* 5:891–902)

Using molecular and classical genetic markers, the db gene has been mapped to midchromosome 4 (Friedman et al., 1991, *Mamm. Gen.* 1:130–144). The mutation maps to a region of the mouse genome that is syntonic with human, suggesting chat, if there is a human homolog of db, it is likely to map to human chromosome 1 p.

The ob gene and its human homologue have recently been cloned (Zhang, Y. et al., 1994, *Nature* 372:425–432). The gene appears to produce a 4.5 kb adipose tissue messenger RNA which contains a 167 amino acid open reading frame. The predicted amino acid sequence of the ob gene product indicates that it is a secreted protein and may, therefore, play a role as part of a signalling pathway from adipose tissue which may serve to regulate some aspect of body fat deposition. Further, recent studies have shown that recombinant Ob protein, also known as leptin, when exogenously administered, can at least partially correct the obesity-related phenotype exhibited by ob mice (Pelleymounter, M. A. et al., 1995, *Science* 269:540–543; Halalas, J. L. et al., 1995, *Science* 269:543–546; Campfield, L. A. et al., 1995, *Science* 269:546–549). Recent studies have suggested that obese humans and rodents (other than ob/ob mice) are not defective in their ability to produce ob mRNA or protein, and generally produce higher levels than lean individuals (Maffei et al., 1995, *Nature Med.* 1(11):1155–1161; Considine et al., 1995, *J. Clin. Invest.* 95(6):2986–2988; Lohnqvist et al., 1995, *Nature Med.* 1:950–953; Hamilton et al., 1995, *Nature Med.* 1:953–956). These data suggest that resistance to normal or elevated levels of Ob may be more important than inadequate Ob production in human obesity. However, the receptor for the ob gene product, thought to be expressed in the hypothalamus, remains elusive.

Homozygous mutations at either the fat or tub loci cause obesity which develops more slowly than that observed in ob and db mice (Coleman, D. L., and Eicher, E. M., 1990, *J. Heredity* 81:424–427), with tub obesity developing slower than that observed in fat animals. This feature of the tub obese phenotype makes the development of tub obese phenotype closest in resemblance to the manner in which obesity develops in humans. Even so, however, the obese phenotype within such animals can be characterized as massive in that animals eventually attain body weights which are nearly two times the average weight seen in normal mice.

The fat mutation has been mapped to mouse chromosome 8, while the tub mutation has been mapped to mouse chromosome 7. According to Naggert et al., the fat mutation has recently been identified (Naggert, J. K., et al., 1995, *Nature Genetics* 10:135–141). Specifically, the fat mutation appears to be a mutation within the Cpe locus, which encodes the carboxypeptidase (Cpe) E protein. Cpe is an exopeptidase involved in the processing of prohormones, including proinsulin.

The dominant Yellow mutation at the agouti locus, causes a pleiotropic syndrome which causes moderate adult onset obesity, a yellow coat color, and a high incidence of tumor formation (Herberg, L. and Coleman, D. L., 1977, *Metabolism* 26:59), and an abnormal anatomic distribution of body fat (Coleman, D. L., 1978, *Diabetologia* 14:141–148). This mutation may represent the only known example of a pleiotropic mutation that causes an increase, rather than a decrease, in body size. The mutation causes the widespread expression of a protein which is normally seen only in neonatal skin (Michaud, E. J. et al., 1994, *Genes Devel.* 8:1463–1472).

Other animal models include fa/fa (fatty) rats, which bear many similarities to the ob/ob and db/db mice, discussed above. One difference is that, while fa/fa rats are very sensitive to cold, their capacity for non-shivering thermogenesis is normal. Torpor seems to play a larger part in the maintenance of obesity in fa/fa rats than in the mice mutants. In addition, inbred mouse strains such as NZO mice and Japanese KK mice are moderately obese. Certain hybrid mice, such as the Wellesley mouse, become spontaneously fat. Further, several desert rodents, such as the spiny mouse, do not become obese in their natural habitats, but do become so when fed on standard laboratory feed.

Animals which have been used as models for obesity have also been developed via physical or pharmacological methods. For example, bilateral lesions in the ventromedial hypothalamus (VMH) and ventrolateral hypothalamus (VLH) in the rat are associated, respectively, with hyperphagia and gross obesity and with aphagia, cachexia and anorexia. Further, it has been demonstrated that feeding monosodium-glutamate (MSG) or gold thioglucose to newborn mice also results in an obesity syndrome.

Each of the rodent obesity models is accompanied by alterations in carbohydrate metabolism resembling those in Type II diabetes in man. For example, from both ob and db, congenic C57BL/KS mice develop a severe diabetes with ultimate β cell necrosis and islet atrophy, resulting in a relative insulinopenia, while congenic C57BL/6J ob and db mice develop a transient insulin-resistant diabetes that is eventually compensated by β cell hypertrophy resembling human Type II diabetes.

With respect to ob and db mice, the phenotype of these mice resembles human obesity in ways other than the development of diabetes, in that the mutant mice eat more and expend less energy than do lean controls (as do obese humans). This phenotype is also quite similar to that seen in animals with lesions of the ventromedial hypothalamus, which suggests that both mutations may interfere with the ability to properly integrate or respond to nutritional information within the central nervous system. Support for this hypothesis comes from the results of parabiosis experiments (Coleman, D. L. 1973, *Diabetologica* 9:294–298) that suggest ob mice are deficient in a circulating satiety factor and that db mice are resistant to the effects of the ob factor. These experiments have led to the conclusion that obesity in these mutant mice may result from different defects in an afferent loop and/or integrative center of the postulated feedback mechanism that controls body composition.

In summary, therefore, obesity, which poses a major, worldwide health problem, represents a complex, highly heritable trait. Given the severity, prevalence and potential heterogeneity of such disorders, there exists a great need for the identification of those genes and gene products that participate in the control of body weight.

It is an objective of the invention to provide modulators of body weight, to provide methods for diagnosis of body weight disorders, to provide therapy for such disorders, and to provide assay systems for the screening of substances that can be used to control body weight.

3. SUMMARY OF THE INVENTION

The present invention relates to the discovery, identification and characterization of nucleotides that encode Ob receptor (ObR), a novel receptor protein that participates in the control of mammalian body weight. ObR, described for the first time herein, is a transmembrane protein that spans the cellular membrane once and is involved in signal transduction triggered by the binding of its natural ligand, Ob, also known as leptin. ObR has amino acid sequence motifs found in the Class I cytokine receptor family, and is most related to the gp130 signal transducing component of the IL-6 receptor, the G-CSF receptor, and the LIF receptor. The results presented in the working examples herein demonstrate that a long-form ObR (predominantly expressed in the hypothalamus) transduces signal via a STAT mediated pathway typical of IL-6 type cytokine receptors, whereas a major naturally occurring truncated form or a mutant form found in obese db/db mice does not. The long form ObR can mediate activation of STAT proteins and stimulate transcription through IL-6 responsive gene elements. Reconstitution experiments indicate that, although ObR mediates intracellular signals with a specificity similar to IL-6 type cytokine receptors, signaling appears to be independent of the gp130 signal transducing component of the IL-6 type cytokine receptors.

The ObR mRNA transcript, which is about 5 kb long, is expressed in the choroid plexus, the hypothalamus and other tissues, including lung and liver. The murine short forms described herein encode receptor proteins of 894 FIGS. 1A–1D and 893 amino acids; murine long form obR cDNAs and human obR cDNAs, described herein, encode receptor proteins of 1162 amino acids and 1165 amino acids, respectively FIGS. 1A–1D and FIGS. 3A–3F. The ObR has a typical hydrophobic leader sequence (about 22 amino acids long in both forms of murine ObR, and about 20 amino acids long in human ObR); an extracellular domain (about 815 amino acids long in both forms of murine ObR, and about 819 amino acids long in human ObR); a short transmembrane region (about 23 amino acids long in both forms of murine ObR and human ObR); and a cytoplasmic domain. The transcripts encoding the murine ObR short and long form (FIG. 6) are identical until the fifth codon 5' of the stop codon of the short form and then diverge completely, suggestive of alternative splicing. As described herein, the cytoplasmic domain encoded by the 894 amino acid murine short form obR cDNA is 34 amino acids, while that encoded by the murine long form obR cDNA (302 amino acids) is approximately the same length as the cytoplasmic domain encoded by the human obR cDNA (303 amino acids). The deduced amino acid sequences from murine long form ObR and human ObR are homologous throughout the length of the coding region and share 75% identity FIGS. 7A–7B.

The obese phenotype of the db mouse results from a G→T transversion in the obR gene. This transversion creates a splice donor site which in turn leads to aberrant processing of obR long form mRNA in db mutants. In db mutants this aberrant processing generates long form mRNAs which encode a truncated ObR protein that is identical to the 894 amino acid short form ObR. Like the short form ObR, the mutant long form ObR lacks most of the cytoplasmic domain and is incapable of transducing a signal via a STAT mediated pathway. The signalling competant long form ObR, which is absent in the db/db mice, is required for body weight maintenance.

The invention encompasses the following nucleotides, host cells expressing such nucleotides, and the expression products of such nucleotides: (a) nucleotides that encode mammalian ObRs, including the human ObR, and the obR gene product; (b) nucleotides that encode portions of the ObR that correspond to its functional domains, and the polypeptide products specified by such nucleotide sequences, including but not limited to the extracellular domain (ECD), the transmembrane domain (TM), and the cytoplasmic domain (CD); (c) nucleotides that encode mutants of the ObR in which all or a part of one of the domains is deleted or altered, and the polypeptide products specified by such nucleotide sequences, including out not limited to soluble receptors in which all or a portion of the TM is deleted, and nonfunctional receptors in which all or a portion of the CD is deleted; (d) nucleotides chat encode fusion proteins containing the ObR or one of its domains (e.g., the extracellular domain) fused to another polypeptide.

The invention also encompasses agonists and antagonists of ObR, including small molecules, large molecules, mutant ob proteins that compete with native Ob, and antibodies, as well as nucleotide sequences that can be used to inhibit obR gene expression (e.g., antisense and ribozyme molecules, and gene or regulatory sequence replacement constructs) or to enhance obR gene expression (e.g., expression constructs that place the obR gene under the control of a strong promoter system), and transgenic animals that express an obR transgene or "knock-outs" that do not express ObR.

In addition, the present invention encompasses methods and compositions for the diagnostic evaluation, typing and prognosis of body weight disorders, including obesity and cachexia, and for the identification of subjects having a predisposition to such conditions. For example, obR nucleic acid molecules of the invention can be used as diagnostic hybridization probes or as primers for diagnostic PCR analysis for the identification of obR gene mutations, allelic variations and regulatory defects in the obR gene. The present invention further provides for diagnostic kits for the practice of such methods.

Further, the present invention also relates to methods for the use of the obR gene and/or obR gene products for the identification of compounds which modulate, i.e., act as agonists or antagonists, of obR gene expression and or obR gene product activity. Such compounds can be used as agents to control body weight and, in particular, as therapeutic agents for the treatment of body weight and body weight disorders, including obesity, cachexia and anorexia.

Still further, the invention encompasses methods and compositions for the treatment of body weight disorders, including obesity, cachexia, and anorexia. Such methods and compositions are capable of modulating the level of obR gene expression and/or the level of obR gene product activity.

This invention is based, in part, on the surprising discovery, after an extensive survey of numerous cell lines and tissues, of a high affinity receptor for Ob in the choroid plexus of the brain, the identification and cloning of obR cDNA from a library prepared from choroid plexus mRNA, characterization of its novel sequence, mapping the obR gene to the same genetic interval in the mouse genome as the db gene maps, and characterization of the ObR as a transmembrane receptor of the Class I cytokine receptor family. obR mRNA was detected in other tissues, including the hypothalamus.

The full-length ObR, expressed predominantly in the hypothalamus signals transduces through activation of STAT proteins and stimulation of transcription through IL-6 responsive gene elements. The ability of the full-length long form ObR to signal is in contrast to the naturally occurring truncated form or the mutant form found in db/db mice which are unable to mediate signal transduction. The invention also includes forms of ObR lacking one or another of the intracellular domains important for signalling and induction of gene expression.

In another aspect the invention features a method for identifying candidate therapeutic agents for the treatment of a body weight disorder, comprising:

a) providing a cell which expresses a mammalian Ob receptor, the cell harboring a reporter construct, the reporter construct including a sequence encoding a detectable protein (e.g., β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), alkaline phosphatase or xanthine guaninephosphoribosyltransferase (XGPRT)), the sequence encoding the detectable protein being operably linked to a Ob receptor responsive regulatory element (e.g., IL-6 RE or HRRE);

b) contacting the cell with a test compound;

c) measuring the expression of the detectable protein in the presence of the test compound;

d) wherein an increase or a decrease in the expression of the detectable protein in the presence of the test compound compared to the absence of the test compound indicates that the test compound is a candidate therapeutic agent for treatment of a body weight disorder.

The sequence encoding the detectable protein is operably linked to the Ob receptor responsive regulatory element if expression of the protein is altered by activation of the Ob receptor (e.g., activation caused by the binding of leptin to the Ob receptor).

In other embodiments the contacting with the test compound takes place in the presence of an ob receptor agonist or antagonist. The invention also features a compound identified using the method described above.

In another aspect the invention features a method of inducing weight loss in a mammal by administering to the mammal a compound (e.g., a small molecule or an antibody) that activates the ob receptor or the ob receptor signalling pathway.

3.1. Definitions

As used herein, the following terms, whether used in the singular or plural, will have the meanings indicated:

Ob: means the Ob protein described in Zhang, Y. et al., 1994, Nature 372:425–432, which is incorporated herein by reference in its entirety, which is also known as leptin. ob includes molecules that are homologous to Ob or which bind to ObR. Ob fusion proteins having an N-terminal alkaline phosphatase domain are referred to herein as AP-Ob fusion proteins, while ob fusion proteins having a C-terminal alkaline phosphatase domain are referred to herein as Ob-AP fusion proteins.

obR nucleotides or coding sequences: means nucleotide sequences encoding ObR protein, polypeptide or peptide fragments of ObR protein, or ObR fusion proteins. obR nucleotide sequences encompass DNA, including genomic DNA (e.g. the obR gene) or cDNA, or RNA.

ObR: means Ob receptor protein. Polypeptides or peptide fragments of ObR protein are referred to as ObR polypeptides or ObR peptides. Fusions of ObR, or ObR polypeptides or peptide fragments to an unrelated protein are referred to herein as ObR fusion proteins.

A functional ObR refers to a protein which binds ob with high affinity in vivo or in vitro.

| | |
|---|---|
| ECD: | means "extracellular domain". |
| TM: | means "transmembrane domain". |
| CD: | means "cytoplasmic domain". |

4. DESCRIPTION OF THE FIGURES

FIGS. 1A–1D. Nucleotide sequence (SEQ ID NO: 1) and deduced amino acid sequence (SEQ ID NO:2) of murine obR (short form) cDNA encoding murine short form ObR protein (894 amino acids). The domains of short form murine ObR are: signal sequence (amino acid residue 1 to about amino acid residue 22), extracellular domain (from about amino acid residue 23 to about amino acid residue 837), transmembrane domain (from about amino acid residue 838 to about amino acid residue 860), and cytoplasmic domain (from about amino acid residue 861 to about amino acid residue 894). Potential N-linked glycosylation sites in the extracellular domain are indicated by asterisks above the first amino acid of the N-X-S and N-X-T motifs. Underscores indicate motifs conserved in the class I cytokine receptor family.

Figures 2, 2B:
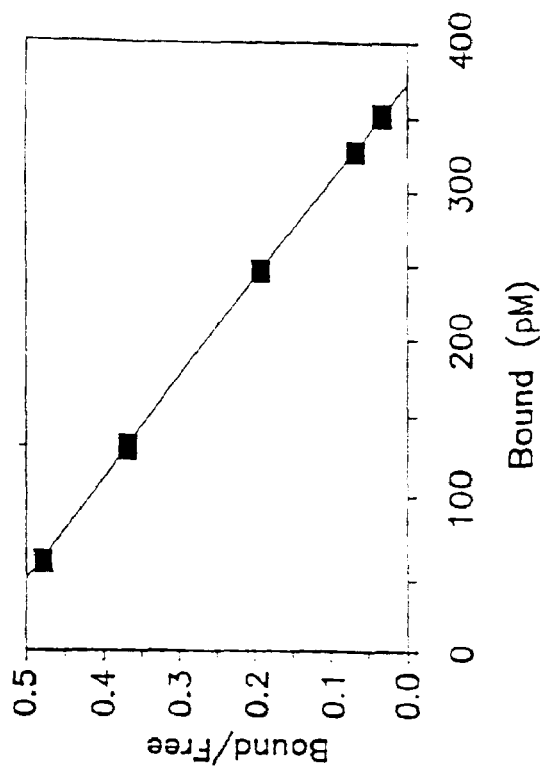
Figures 1, 2B:
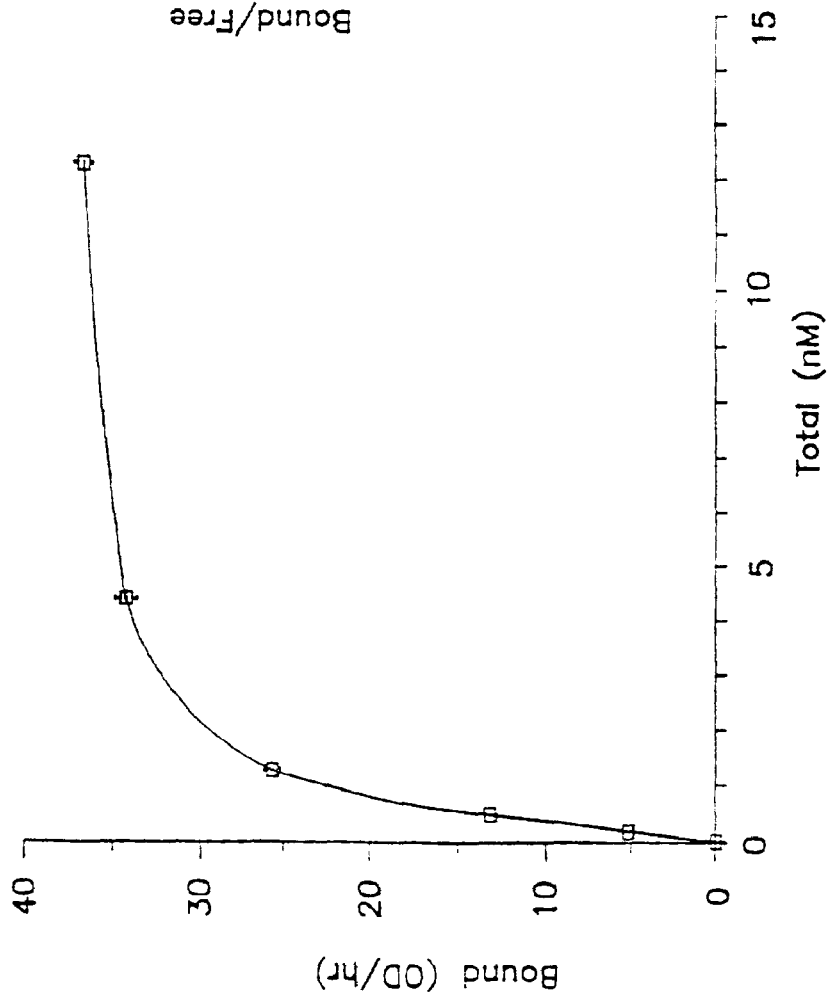

FIG. 2B-1 Binding isotherm and Scatchard analysis of the interaction of AP-Ob and ObR. COS-7 cells transfected with the obR cDNA were incubated with various concentrations of the AP-Ob (mouse) fusion protein FIG. 2B-2. Scatchard transformation is shown as an inset. Paragraph beginning at page 16, line 3, please replace the paragraph with the following text:

FIGS. 3A–3F. Nucleotide sequence (SEQ D NO:3) and deduced amino acid sequence (SEQ ID NO:4) of human obR cDNA encoding human ObR protein. The domains of human ObR are: signal sequence (from amino acid residue 1 to about amino acid residue 20), extracellular domain (from about amino acid residue 21 to about amino acid residue 839), transmembrane domain (from about amino acid residue 840 to about amino acid residue 862), and cytoplasmic domain (from about amino acid residue 863 to about amino acid residue 1165). Also depicted are 5' untranslated nucleotide sequences. Potential N-linked glycosylation sites in the extracellular domain are indicated by asterisks above the first amino acid of the N-X-S and N-X-T motifs. Underscores indicate motifs conserved in the class I cytokine receptor family.

FIG. 4. Alignment of the extracellular domains of the murine ObR (amino acid residues 333–830 of SEQ ID NO:2) and human gp130 (SEQ ID NO:5). Identical residues (black) and conservative changes (gray) are indicated by shading around the corresponding amino acids. Conservative changes (as defined by FASTA) are indicated.

FIGS. 5A–5B. Alignment of mouse ObR (short form shown in FIG. 1 (SEQ ID NO:2)) and human ObR (SEQ ID NO:4). Amino acids that are identical between the two sequences are indicated by a star.

FIGS. 6A–6F. Nucleotide sequence (SEQ ID NO:42) and deduced amino acid sequence (SEQ ID NO:43) of murine long form obR cDNA encoding murine long form ObR protein. The domains of long form murine ObR are: signal sequence (amino acid residue 1 to about amino acid residue 22), extracellular domain (from about amino acid residue 23 to about amino acid residue 837), transmembrane domain (from about amino acid residue 838 to about amino acid residue 860), and cytoplasmic domain (from about amino acid residue 861 to about amino acid residue 1162).

FIGS. 7A–7B. Alignment of the long forms of human (SEQ ID NO:4) and murine (SEQ ID NO:43) ObR. Identical residues and conservative changes are indicated by two asterisks or one asterisk, respectively. Conservative changes indicated are as defined by FASTA. Abbreviations: mobr-1, murine ObR long form; and hobr, human homolog.

Figure 8:
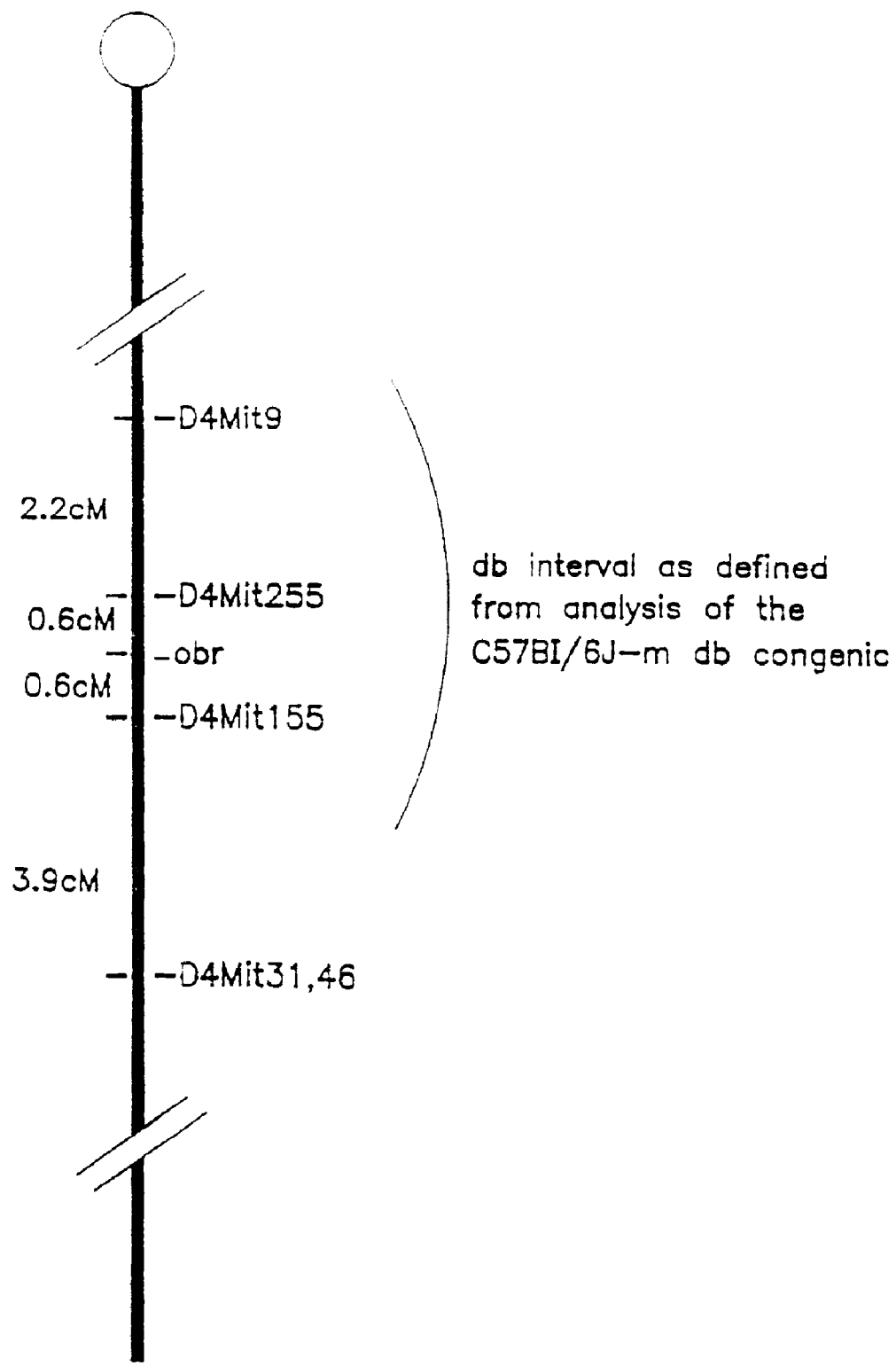

FIG. 8. Location of the gene encoding ObR on mouse chromosome 4.

Figure 9:
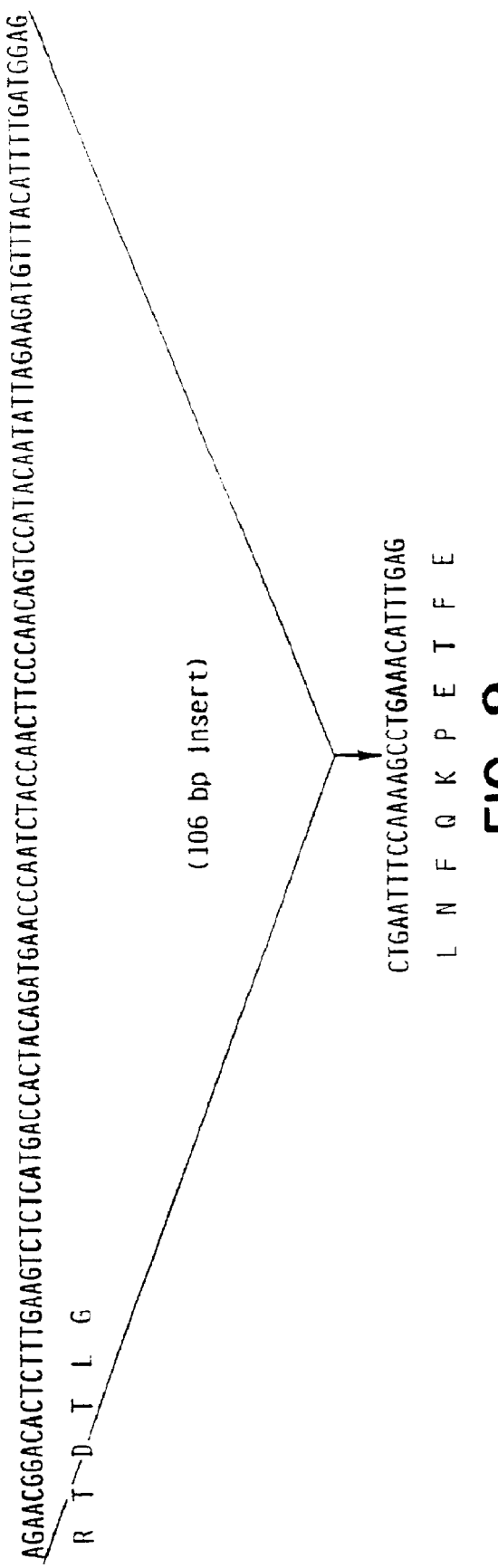

FIG. 9. Nucleotide sequence of the 106 base pair insert (residues 2727–2833 of SEQ ID NO: 1) in the long form transcript of db/db. The precise position of the insertion in the deduced amino acid sequence near the insertion region (residues 2713–2742 of SEQ ID NO:42) are shown.

Figure 10:
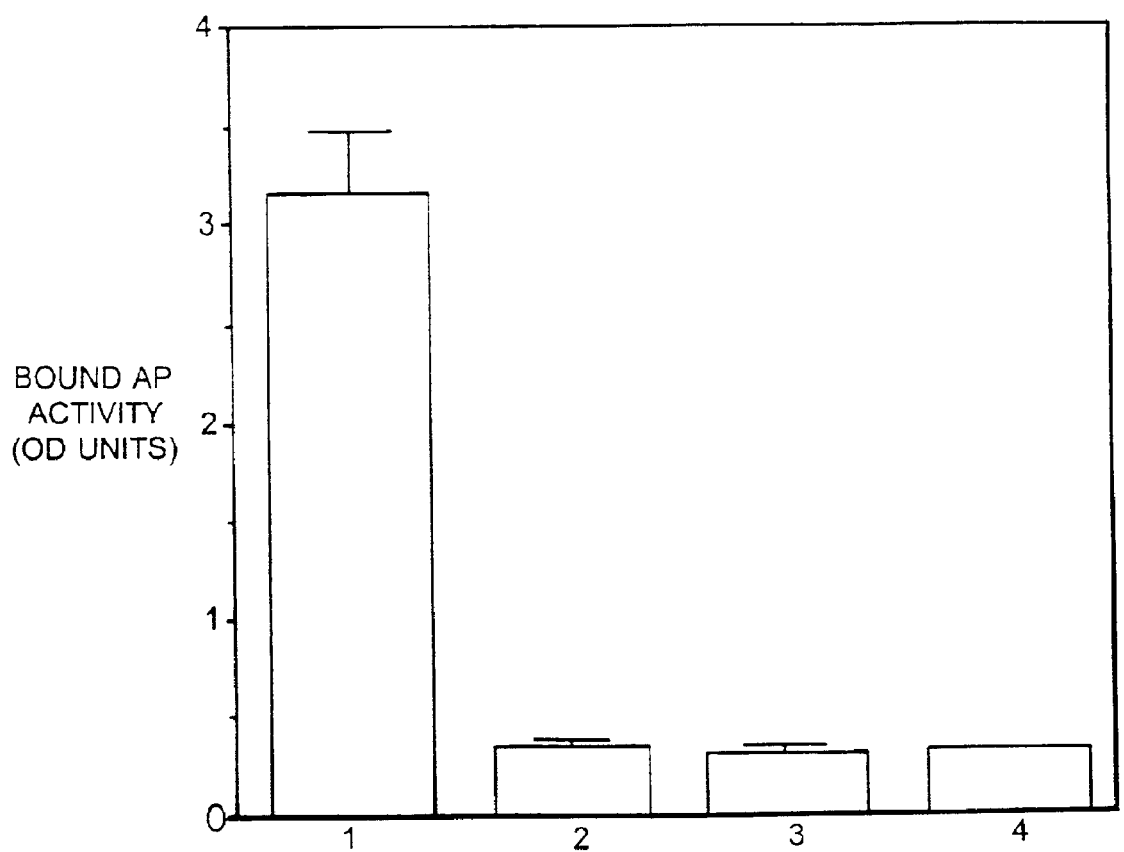

FIG. 10. Bar graph depicting ObR-Ig neutralization of OB protein. COS cell were transiently transfected with the ObR cDNA and tested for their ability to bind 0.5 nM AP-OB. Column 1 shows the high levels of specific binding observed in the absence of ObR-IgG fusion protein. Columns 2, 3, and 4 show the near complete inhibition of binding observed with three different column fractions of purified ObR IgG.

Figure 11A:
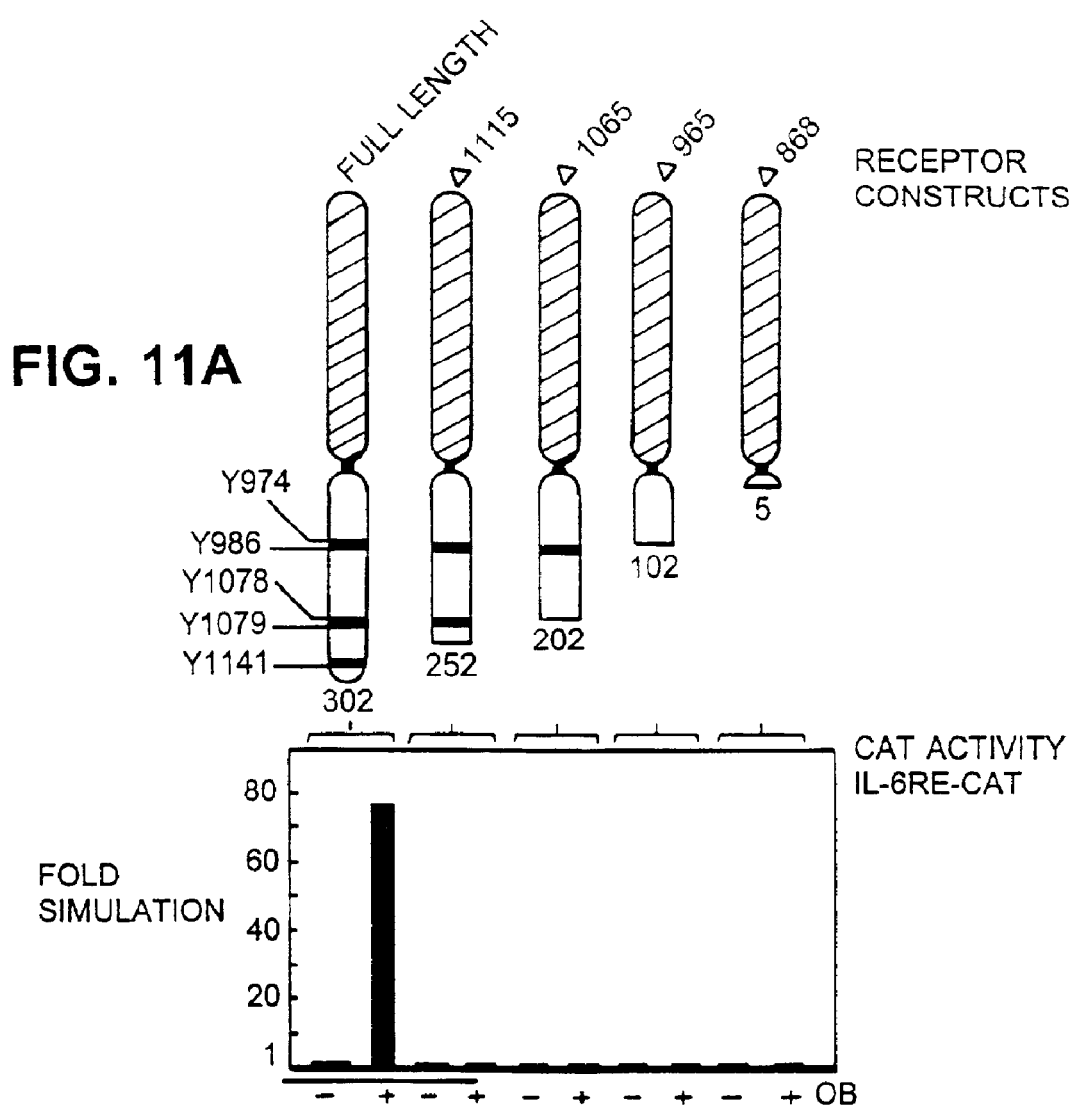

FIG. 11A. Schematic drawings of various C-terminal deletion mutants of ObR protein. The names and predicted length (aa) of the proteins are shown above each protein. The extracellular domains are shown as striped, the transmembrane domains are shown as black, and the cytoplasmic domains are shown as white. The location of tyrosine residues in the cytoplasmic domain are indicated by horizontal bars (Y986, Y1079, and Y1141 are conserved between human and murine ObR). The length of the cytoplasmic domains (aa) are shown below each protein.

Figure 11B:
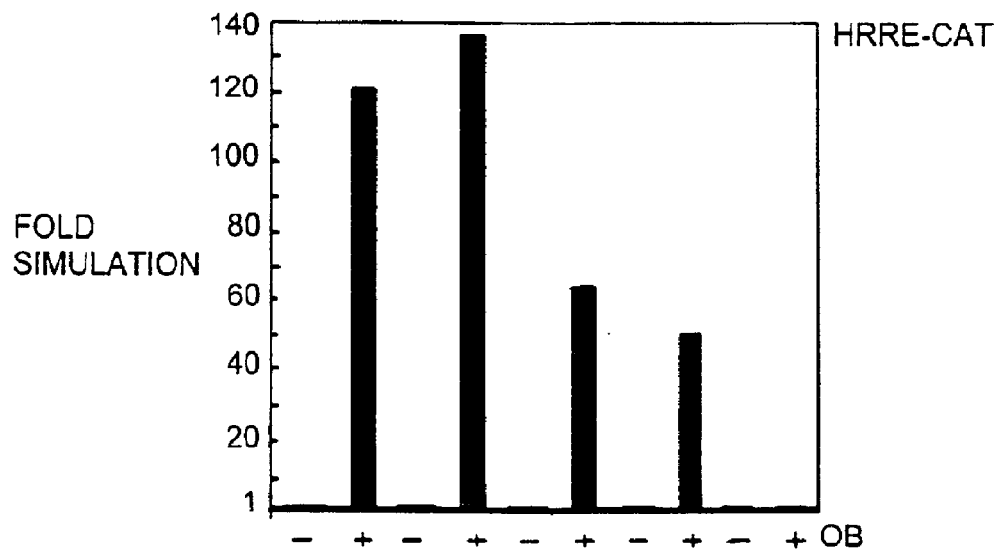

FIG. 11B. A bar graph depicting the results of CAT assays employing an IL-6RE-CAT expression construct upper panel) or a HRRE-CAT expression construct (lower panel) and the ObR deletion mutants of FIG. 11A. H-35 cells were transfected with cDNAs encoding the ObR mutant and either IL-6RE-CAT or HRRE-CAT. Subcultures of cells were treated for 24 hours with serum-free medium alone (−) or serum-free medium containing mouse leptin (+). CAT activity was determined and is expressed relative to values obtained for untreated control cultures.

Figure 12:
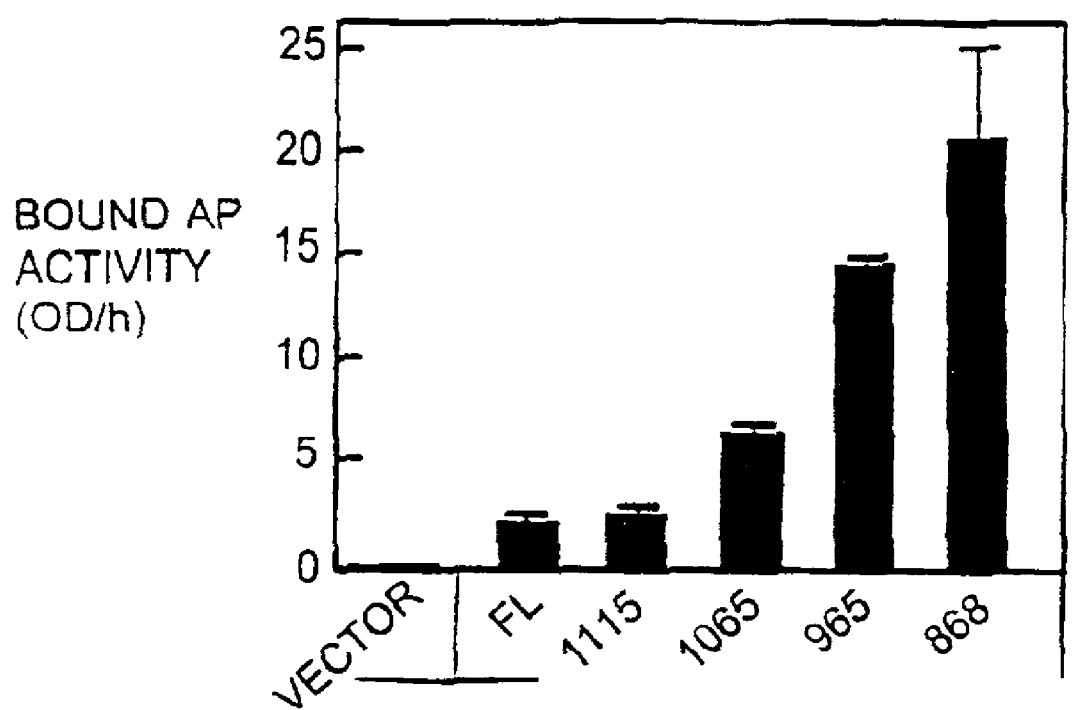

FIG. 12. A bar graph depicting the results of an AP-Ob fusion protein binding assay. COS-7 cells were transfected with a cDNA encoding the indicated ObR protein. Forty-eight hours later, cells were incubated with 1 nM AP-ob fusion protein. Bars show the average of two binding assays. The error bars indicate the difference between the two assays.

Figure 13A:
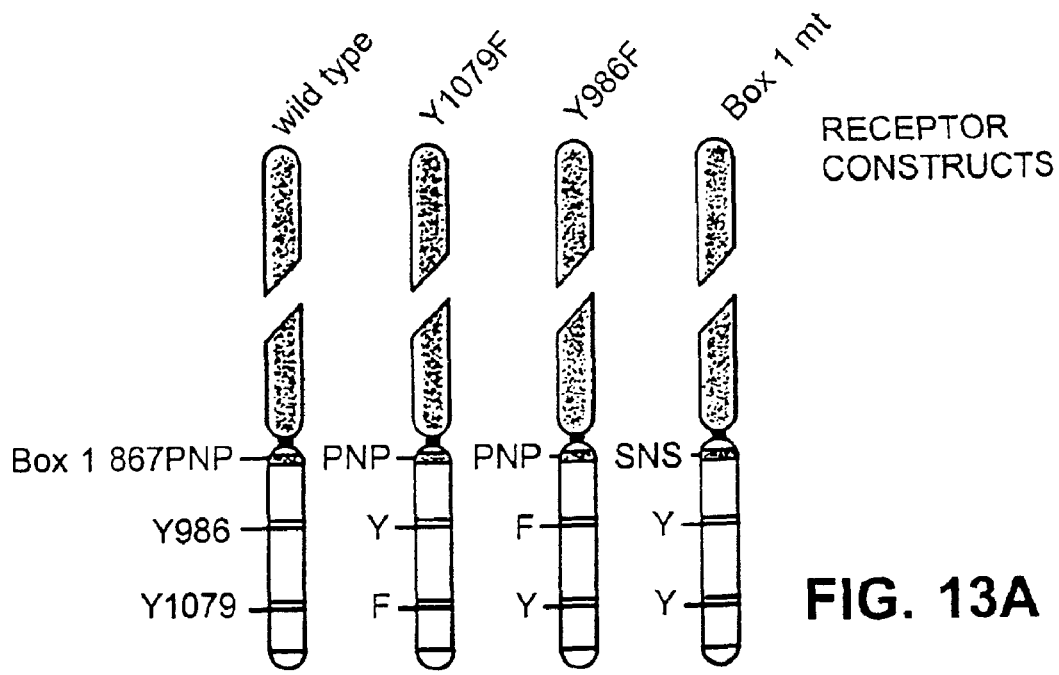

FIG. 13A. Schematic drawings of various mutant ObR proteins. The location of tyrosine residues 986 and 1079 are indicated. The location of the "box 1" sequence is also indicated.

Figure 13B:
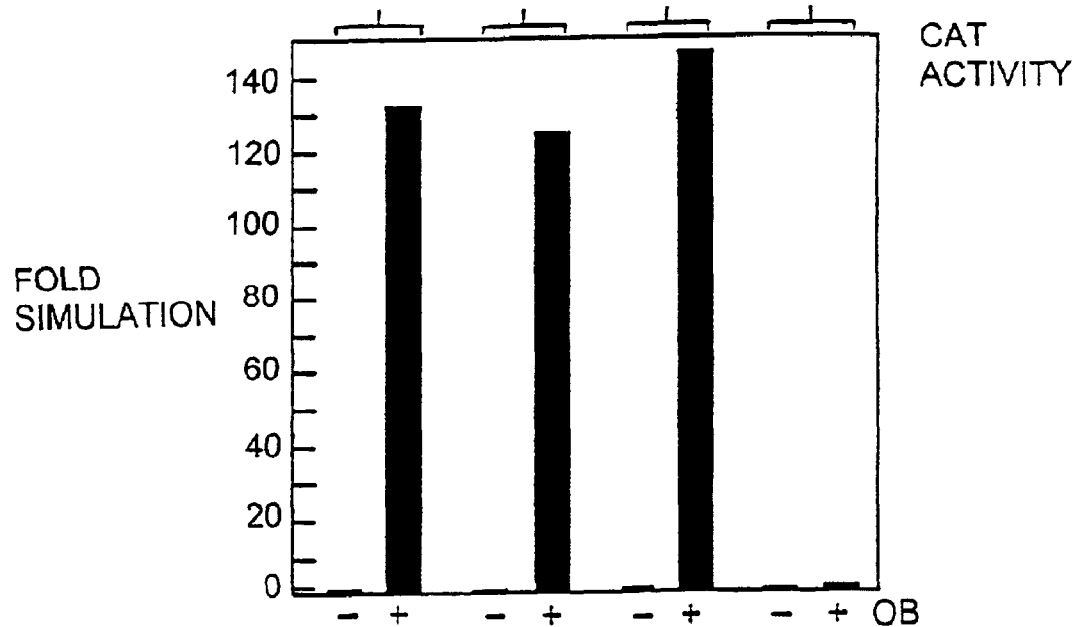

FIG. 13B. Bar graph depicting the results of a HRRE-CAT induction assay. H-35 cells were co-transfected with HRRE-CAT and expression constructs for either OB-RY986F, OB-RY1079F or O-R(box 1 mt). Subcultures of cells were treated for 24 hours with serum-free medium containing human leptin. CAT activity was determined and is expressed relative to values obtained for untreated control cultures.

Figure 14A:
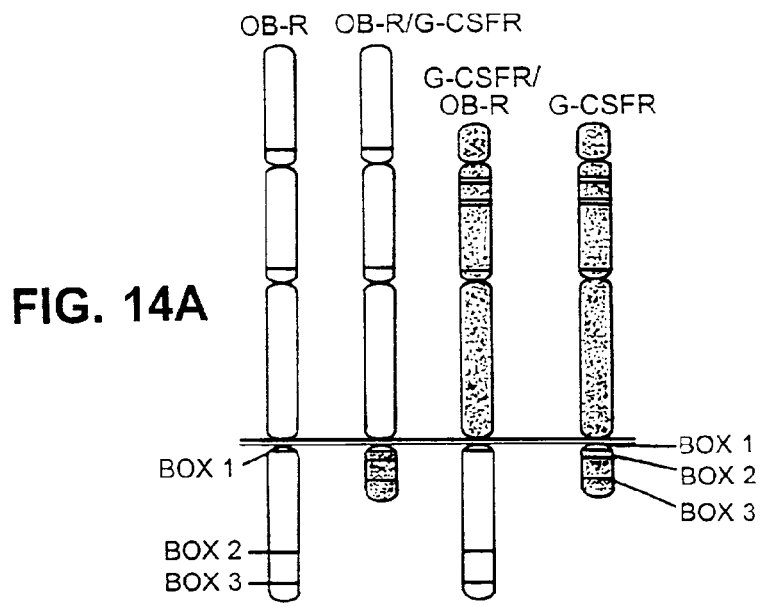

FIG. 14A. Schematic drawings of various receptor chimeras. The portions derived from G-CSFR are shaded; the portions derived from ObR are not. The locations of the predicted Box 1, Box 2, and Box 3 motifs are indicated.

Figure 14B:
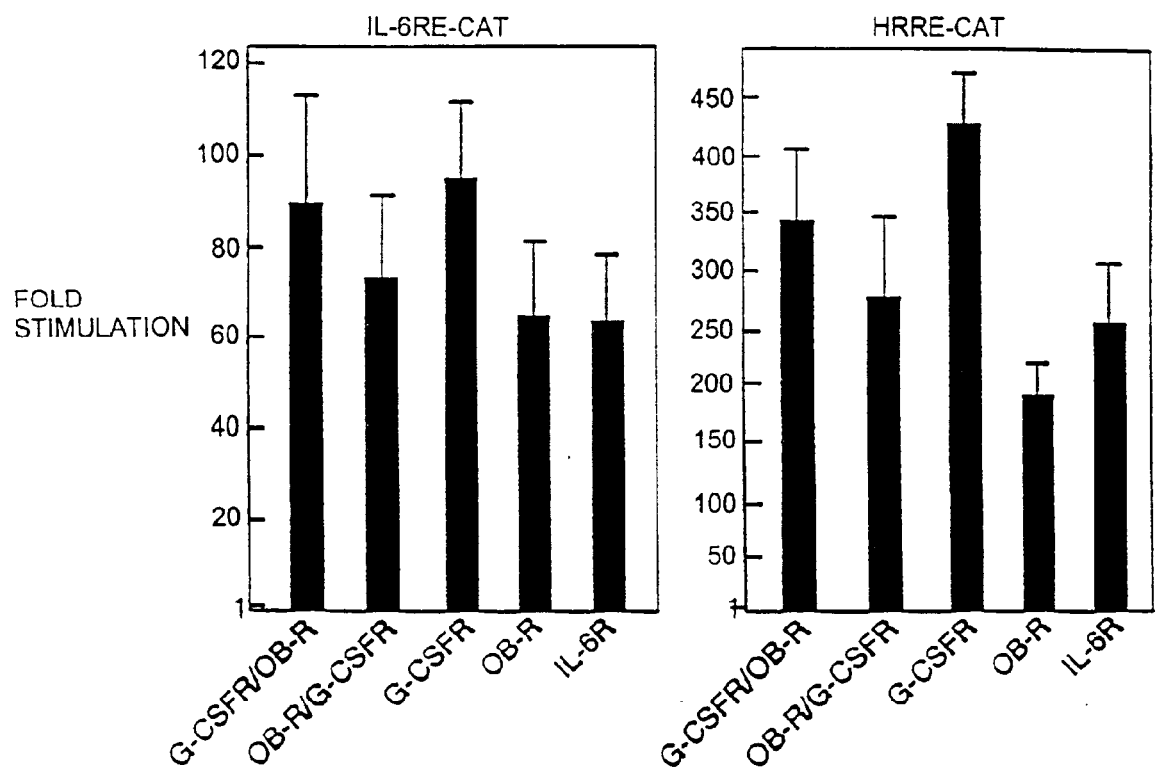

FIG. 14B. Bar graphs depicting the results of IL-6RE-CAT (left panel) and HRRE-CAT induction assays. H-35 cells were co-transfected with expression plasmids for the indicated receptor (ObR, G-CSFR, or chimeric) and IL-6-RE-CAT or HREE-CAT expression construct. Cells were stimulated with the appropriate ligand and CAT activity was determined as in the experiments described in FIG. 11. All values are expressed relative to untreated control cultures (mean±std deviation of 3 to 4 experiments).

FIG. 15A. Bar graph depicting the results of HRRE-CAT induction assays. H-35 cells were co-transfected with HRRE-CAT and the indicated amount of ObR and OB-RΔ868-1165. Cells were stimulated with leptin, and CAT activity was determined as in the experiments described in FIG. 11. All values are expressed relative to the untreated cultures.

FIG. 15B. Bar graph depicting the results of IL-6RE-CAT induction assays. H-35 cells were co-transfected with IL-6RE-CAT and the indicated amount of ObR/G-CSFR and OB-RΔ868-1165. Cells were stimulated with leptin, and CAT activity was determined as in the experiments described in FIG. 11. All values are expressed relative to the untreated cultures.

FIG. 15C. Bar graph depicting the results of IL-6RE-CAT induction assays. H-35 cells were co-transfected with IL-6RE-CAT and the indicated amount of G-CSFR and G-CSFR(Δcyto). Cells were stimulated with G-CSF, and CAT activity was determined as in the experiments described in FIG. 11. All values are expressed relative to the untreated cultures.

FIG. 15D. Bar graph depicting the results of IL-6RE-CAT induction assays. H-35 cells were co-transfected with IL-6RE-CAT and the indicated amount of G-CSFR/ObR and G-CSFR(Δcyto). Cells were stimulated with G-CSF, and CAT activity was determined as in the experiments described in FIG. 11. All values are expressed relative to the untreated cultures.

Figure 15E:
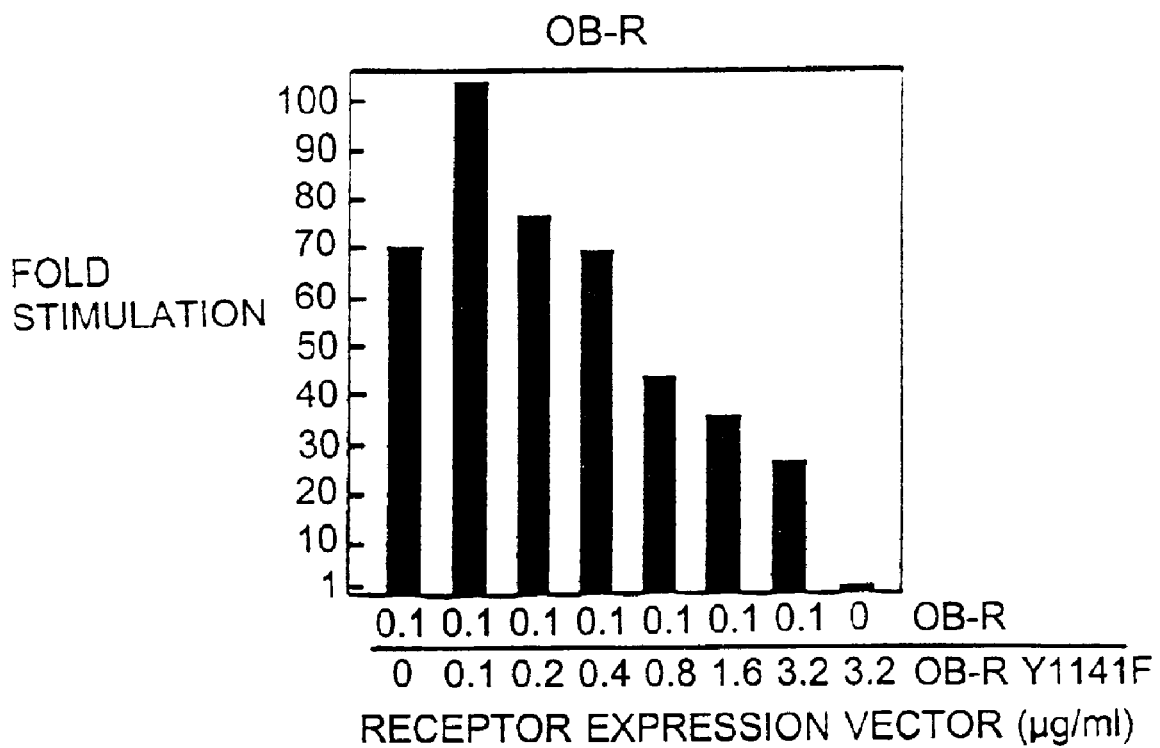

FIG. 15E. Bar graph depicting the results of IL-6RE-CAT induction assays. H-35 cells were co-transfected with IL-6RE-CAT and the indicated amount of ObR and O-RY1141F. Cells were stimulated with leptin, and CAT activity was determined as in the experiments described in FIG. 11. All values are expressed relative to the untreated cultures.

Figure 16:
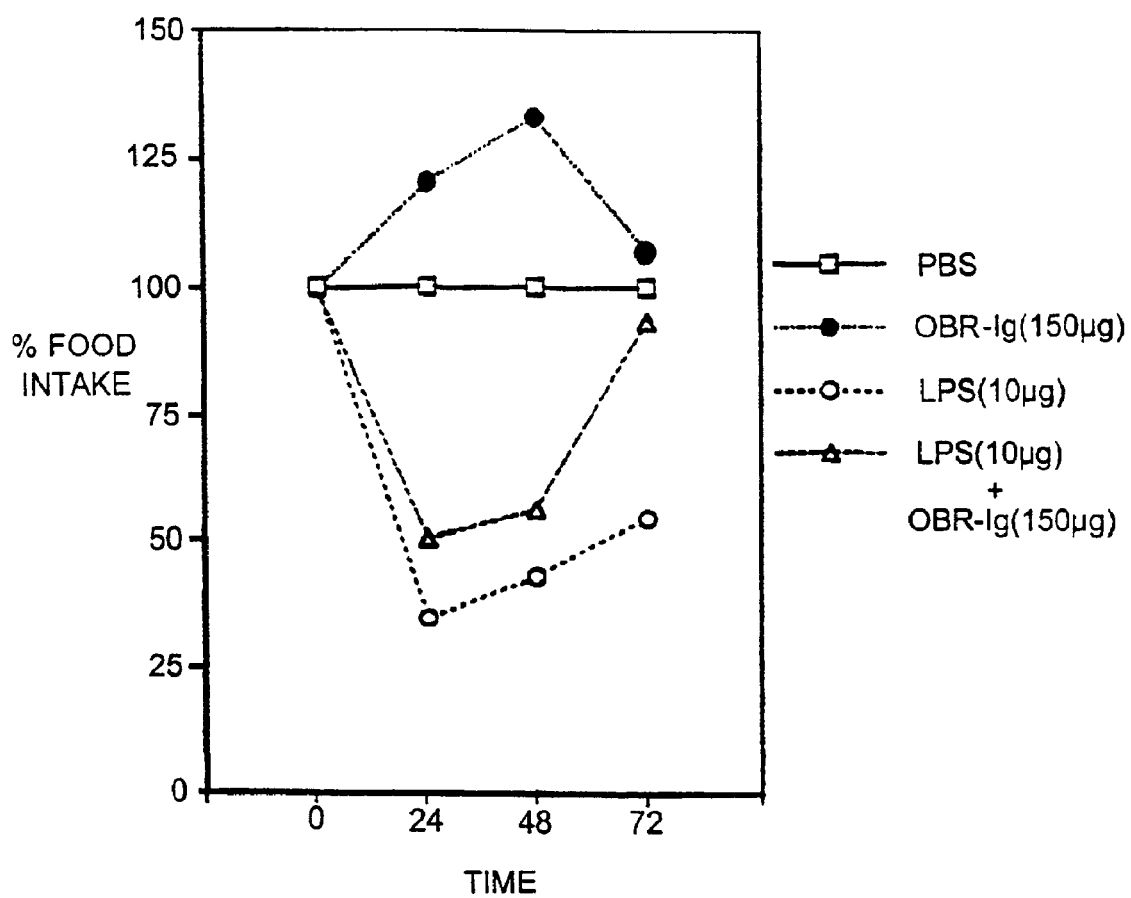

FIG. 16. Line graph depicting % food intake over time in mice treated with PBS (□), an ob receptor-Ig fusion protein (150 μg/mouse; •), LPS (10 μg/mouse; o), and LPS (10 μg/mouse) with the Ob receptor-Ig fusion protein (150 μg/mouse) (Δ)

5. DETAILED DESCRIPTION OF THE INVENTION

ObR, described for the first time herein, is a novel receptor protein that participates in body weight regulation. ObR is a transmembrane protein that spans the membrane once and belongs to the Class I family of cytokine receptors, and is most closely related to the gp130 signal transducing component of the IL-6 receptor, the G-CSF receptor, and the LIF receptor. Signal transduction is triggered by the binding of Ob to the receptor. Neutralization of Ob, removal of Ob, or interference with its binding to ObR results in weight gain. ObR mRNA is detected in the choroid plexus, and other tissues, including the hypothalamus.

The invention encompasses the use of obR nucleotides, ObR proteins and peptides, as well as antibodies to the ObR (which can, for example, act as ObR agonists or antagonists), antagonists that inhibit receptor activity or expression, or agonists that activate receptor activity or increase its expression in the diagnosis and treatment of body weight disorders, including, but not limited to obesity, cachexia and anorexia in animals, including humans. the diagnosis of an ObR abnormality in a patient, or an abnormality in the ObR signal transduction pathway, will assist in devising a proper treatment or therapeutic regimen. In addition, obR nucleotides and ObR proteins are useful for the identification of compounds effective in the treatment of body weight disorders regulated by the ObR.

In particular, the invention described in the subsections below encompasses OR, polypeptides or peptides corresponding to functional domains of the ObR (e.g., ECD, TM or CD), mutated, truncated or deleted ObRs (e.g. an ObR with one or more functional domains or portions thereof deleted, such as ΔTM and/or ΔCD), ObR fusion proteins (e.g. an ObR or a functional domain of ObR, such as the ECD, fused to an unrelated protein or peptide such as an immunoglobulin constant region, i.e., IgFc), nucleotide sequences encoding such products, and host cell expression systems that can produce such ObR products.

The invention also features Ob receptors having an amino acid sequence that is substantially identical to a defined amino acid sequence.

By "substantially identical" is meant a polypeptide or nucleic acid having a sequence that is at least 85%; preferably 90%, and more preferably 95% or more identical to the sequence of the reference amino acid or nucleic acid sequence. For polypeptides, the length of the reference polypeptide sequence will generally be at least 16 amino acids, preferably at least 20 amino acids, more Preferably at least 25 amino acids, and most preferably 35 amino acids. For nucleic acids, the length of the reference nucleic acid sequence will Generally be at least 50 nucleotides, preferably at least 50 nucleotides, more preferably at least 75 nucleotides, and most preferably 110 nucleotides.

Sequence identity can be measured using sequence analysis software (e.g., Sequence Analysis Software Package of the Genetics Computer Group, University of Wisconsin Biotechnology Center, 1710 University Avenue, Madison, Wis. 53705) with the default Parameters specified therein.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical co a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria.

The invention also encompasses antibodies and anti-idiotypic antibodies (including Fab fragments), antagonists and agonists of the ObR, as well as compounds or nucleotide constructs that inhibit expression of the obR gene (transcription factor inhibitors, antisense and ribozyme molecules, or gene or regulatory sequence replacement constructs), or promote expression of ObR (e.g., expression constructs in which obR coding sequences are operatively associated with expression control elements such as promoters, promoter/enhancers. etc.). The invention also relates to host cells and animals genetically engineered to express the human ObR (or mutants thereof) or to inhibit or "knock-out" expression of the animal's endogenous ObR.

The ObR proteins or peptides, ObR fusion proteins, obR nucleotide sequences, antibodies, antagonists and agonists can be useful for the detection of mutant ObRs or inappropriately expressed ObRs for the diagnosis of body weight disorders such as obesity, anorexia or cachexia. The ObR proteins or peptides, ObR fusion proteins, obR nucleotide sequences, host cell expression systems, antibodies, antagonists, agonists and genetically engineered cells and animals can be used for screening for drugs effective in the treatment of such body weight disorders. The use of engineered host cells and/or animals may offer an advantage in that such systems allow not only for the identification of compounds that bind to the ECD of the ObR, but can also identify compounds that affect the signal transduced by the activated ObR.

Finally, the ObR protein products (especially soluble derivatives such as peptides corresponding to the ObR ECD, or truncated polypeptides lacking the TM domain.) and fusion protein products (especially ObR-Ig fusion proteins, i.e., fusions of the ObR or a domain of the ObR, e.g., ECD, ΔTM to an IgFc), antibodies and anti-idiotypic antibodies (including Fab fragments), antagonists or agonists (including compounds that modulate signal transduction which may act on downstream targets in the ObR signal transduction pathway) can be used or therapy of such diseases. For example, the administration of an effective amount of soluble ObR ECD, ΔTM ObR or an ECD-IgFc fusion protein or an anti-idiotypic antibody (or its Fab) that mimics the ObR ECD would "mop up" or "neutralize" endogenous Ob, and prevent or reduce binding and receptor activation, leading to weight gain. Nucleotide constructs encoding such ObR products can be used to genetically engineer host cells to express such ObR products in vivo; these genetically engineered cells function as "bioreactors" in the body delivering a continuous supply of the ObR, ObR peptide, soluble ECD or ΔTM or ObR fusion protein that will "mop up" or neutralize Ob. Nucleotide constructs encoding functional ObRs, mutant ObRs, as well as anti-sense and ribozyme molecules can be used in "gene therapy" approaches for the modulation of ObR expression and/or activity in the treatment of body weight disorders. Thus, the invention also encompasses pharmaceutical formulations and methods for treating body weight disorders.

The invention is based, in part, on the surprising discovery of a high affinity receptor for ob expressed at significant concentration in the choroid plexus. This discovery was made possible by using a novel alkaline phosphatase/Ob (AP-Ob) fusion protein for in situ staining of cells and tissue. Competition studies with unlabeled Ob confirmed that the in situ binding observed was specific for Ob. Murine obR cDNA was identified using AP-Ob fusion protein to screen an expression library of cDNAs synthesized from murine choroid plexus mRNA and transiently transfected into mammalian COS cells. A clone, famj5312, expressing the short form of a high affinity receptor for Ob was identified and sequenced. Sequence analysis revealed that the obR cDNA and predicted amino acid sequence are novel sequences containing amino acid regions indicating that ObR is a member of the Class I family of receptor proteins. Mapping studies described herein demonstrate that the obR gene mass to the db locus. The data presented herein demonstrate further that the db gene is a mutant obR gene, which expresses an aberrantly spliced obR long form message that encodes a protein identical to the short form murine ObR. The famj5312 sequence was utilized to screen a human fetal brain cDNA library, which resulted in the identification of a human obR cDNA clone fahj5312d, described herein. Oligonucleotide primers designed on the basis of the human cDNA sequence were used to clone the human genomic DNA clone, h-obR-p87, also described herein. mRNA encoding the murine long form of ObR was cloned from murine hypothalamus using degenerate primers designed on the human ObR cytoplasmic domain.

Various aspects of the invention are described in greater detail in the subsections below.

5.1. The ObR Gene

The cDNA sequence (SEQ ID NO: 1) and deduced amino acid sequence (SEQ ID NO:2) of murine short form (894 amino acids long) and murine long form ObR are shown in FIGS. 1A–1D and 6A–6F, respectively. The signal sequence of both murine short and long form ObR extends from amino acid residue 1 to about amino acid residue 22 of FIGS. 1A–1D and 6A–6F, respectively; the extracellular domain of both forms of murine ObR extends from about amino acid residue 23 to about amino acid residue 837 of FIGS. 1A–1D and 6A–6F; the transmembrane domain of both forms of murine ObR extends from about amino acid residue 838 to about amino acid residue 860 of FIGS. 1A–1D and 6A–6F; and the cytoplasmic domain of the murine short form ObR extends from about amino acid residue 861 to about amino acid residue 894 of FIGS. 1A–1D, while that of the long form extends from amino acid residue 861 to about amino acid residue 1162 of FIGS. 6A–6F. At least one other short form of murine ObR has been identified, which is one amino acid shorter (i.e., 893 amino acids) than the sequence shown in FIGS. 1A–1D. The sequence at the C-terminus differs from the sequence shown in FIGS. 1A–1D, in that residues 890–894 (RTDTL) are not present; and instead, residues 890–893 of the second short form have the following sequence: IMWI.

The cDNA sequence (SEQ ID NO:3) and deduced amino acid sequence (SEQ ID NO:4) of human ObR are shown in FIGS. 3A–3F. The human ObR signal sequence extends from amino acid residue 1 to about amino acid residue 20 of FIGS. 3A–3F; the extracellular domain of human ObR extends from about amino acid residue 21 to about amino acid residue 839 of FIGS. 3A–3F; the transmembrane domain of human ObR extends from about amino acid residue 840 to about amino acid residue 862 of FIGS. 3A–3F; and the cytoplasmic domain of human ObR extends from about amino acid residue 863 to about amino acid residue 1165 of FIGS. 3A–3F. Sequences derived from the human cDNA clone were used to design primers that were used to clone the human genomic obR, h-obR-p87, as described in the examples, infra.

Data presented in the working examples, infra, demonstrate that the obR gene maps to the db locus, and that the db gene is a mutant obR gene which is expressed in db mice as an aberrantly spliced transcript resulting in an mRNA species containing an insert of approximately 106 nucleotides (nt) in the portion encoding the cytoplasmic domain of ObR. The insert produces a mutation that results in a transcript that encodes a prematurely truncated long form that is identical to murine short form ObR.

The obR nucleotide sequences of the invention include: (a) the DNA sequence shown in FIGS. 1A–1D(SEQ ID NO: 1), 3A–3F(SEQ ID NO:3) or 6A–6F(SEQ ID NO:42) or contained in the cDNA clone famj5312 within *E. coli* strain 5312B4F3 as deposited with the American Type Culture Collection (ATCC), or contained in the cDNA clone fahj5312d within *E. coli* strain h-obRD as deposited with the ATCC, or contained in the human genomic clone, h-obR-p87 as deposited with the ATCC; (b) nucleotide sequence that encodes the amino acid sequence shown in FIGS. 1A–1D(SEQ ID NO:2), 3A–3F(SEQ ID NO:4) or 6A–6F (SEQ ID NO:43), or the ObR amino acid sequence encoded by the cDNA clone famj5312 as deposited with the ATCC, or the cDNA clone fahj5312d as deposited with the ATCC, or contained in the human genomic clone, h-obR-p87 as deposited with the ATCC; (c) any nucleotide sequence that hybridizes to the complement of the DNA sequence shown in FIGS. 1A–1D(SEQ ID NO:1). 3A–3F(SEQ ID NO:3)or 6A–6F(SEQ ID NO:42) or contained in the cDNA clone famj5312 as deposited with the ATCC, or contained in the cDNA clone fahj5312d as deposited with the ATCC, or contained in the human genomic clone, h-obR-p87 as deposited with the ATCC under highly stringent conditions, for example, hybridization to filter-bound DNA in 0.5 M $NaHPO_4$, 7% sodium dodecyl sulfate (SDS), 1 mM EDTA at 65□ C, and washing in 0.1×SSC/0.1% SDS at 68□ C (Ausubel F. M. et al., eds., 1989, *Current Protocols in Molecular Biology*, Vol. I, Green Publishing Associates, Inc., and John Wiley & sons, Inc., New York, at p. 2.10.3) and encodes a functionally equivalent gene product; and (d) any nucleotide sequence that hybridizes to the complement of the DNA sequences that encode the amino acid sequence shown in FIGS. 1A–1D(SEQ ID NO:2), 3A–3F(SEQ ID NO:4) or 6A–6F(SEQ ID NO:43) contained in cDNA clone famj5312 as deposited with the ATCC, or contained in the cDNA clone fahj5312d as deposited with the ATCC, or contained in the human genomic clone, h-obR-p87 as deposited with the ATCC under less stringent conditions, such as moderately stringent conditions, for example, washing in 0.2×SSC/0.1% SDS at 42□ C (Ausubel et al., 1989, supra), yet which still encodes a functionally equivalent obR gene product. Functional equivalents of the ObR include naturally occurring ObR present in other species, and mutant ObRs whether naturally occurring or engineered. The invention also includes degenerate variants of sequences (a) through (d).

The invention also includes nucleic acid molecules, preferably DNA molecules, that hybridize to, and are therefore the complements of, the nucleotide sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, for example, to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as obR antisense molecules, useful, for example, in obR gene regulation (for and/or as antisense primers in amplification reactions of obR gene nucleic acid sequences). With respect to obR gene regulation, such techniques can be used to regulate, for example, cachexia and/or anorexia. Further, such sequences may be used as part of ribozyme and/or triple helix sequences, also useful for obR gene regulation. Still further, such molecules may be used as components of diagnostic methods whereby, for example, the presence of a particular obR allele responsible for causing a weight disorder, such as obesity, may be detected.

In addition to the obR nucleotide sequences described above, full length obR cDNA or gene sequences present in the same species and/or homologs of the obR gene present in other species can be identified and readily isolated, without undue experimentation, by molecular biological techniques well known in the art. The identification of homologs of obR in related species can be useful for developing animal model systems more closely related to humans for purposes of drug discovery. For example, expression libraries of cDNAs synthesized from choroid plexus mRNA derived from the organism of interest can be screened using labeled Ob derived from that species, for example, an AP-Ob fusion protein. Alternatively, such cDNA libraries, or genomic DNA libraries derived from the organism of interest can be screened by hybridization using the nucleotides described herein as hybridization and amplification probes. Furthermore, genes at other genetic loci within the genome that encode proteins which have extensive homology to one or more domains of the obR gene product can also be identified via similar techniques. In the case of cDNA libraries, such screening techniques can identify clones derived from alternatively spliced transcripts in the same or different species.

Screening can be by filter hybridization, using duplicate filters. The labeled probe can contain at least 15–30 base pairs of the obR nucleotide sequence, as shown in FIGS. 1A–1D(SEQ ID NO:1), 3A–3F(SEQ ID NO:3), or 6A–6F (SEQ ID NO:42). The hybridization washing conditions used should be of a lower stringency when the cDNA library is derived from an organism different from the type of organism from which the labeled sequence was derived. With respect to the cloning of a human obR homolog, using murine obR probes, for example, hybridization can, for example, be performed at 65□ C overnight in Church's buffer (7% SDS, 250 mM NaHPO$_4$, 2 μM EDTA, 1% BSA). Washes can be done with 2×SSC, 0.1% SDS at 65□ C. and then at 0.1×SSC, 0.1% SDS at 65□ C.

Low stringency conditions are well known to those of skill in the art, and will vary predictably depending on the specific organisms from which the library and the labeled sequences are derived. For guidance regarding such conditions see, for example, Sambrook et al., 1989, *Molecular Cloning, A Laboratory Manual,* Cold Springs Harbor Press, N.Y.; and Ausubel et al., 1989, *Current Protocols in Molecular Biology,* Green Publishing Associates and Wiley Interscience, N.Y.

Alternatively, the labeled obR nucleotide probe may be used to screen a genomic library derived from the organism of interest, again, using appropriately stringent conditions. The identification and characterization of human genomic clones is helpful for designing diagnostic tests and clinical protocols for treating body weight disorders in human patients. For example, sequences derived from regions adjacent to the intron/exon boundaries of the human gene can be used to design primers for use in amplification assays to detect mutations within the exons, introns, splice sites (e.g. splice acceptor and/or donor sites), etc., that can be used in diagnostics.

Further, an obR gene homolog may be isolated from nucleic acid of the organism of interest by performing PCR using two degenerate oligonucleotide primer pools designed on the basis of amino acid sequences within the obR gene product disclosed herein. The template for the reaction may be cDNA obtained by reverse transcription of mRNA prepared from, for example, human or non-human cell lines or tissue, such as choroid plexus, known or suspected to express an obR gene allele.

The PCR product may be subcloned and sequenced to ensure that the amplified sequences represent the sequences of an obR gene. The PCR fragment may then be used to isolate a full length cDNA clone by a variety of For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the obR gene, such as, for example, choroid plexus or brain tissue). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see for example, Sambrook et al., 1989, supra.

The obR gene sequences may additionally be used to isolate mutant obR gene alleles. Such mutant alleles may be isolated from individuals either known or proposed to have a genotype which contributes to the symptoms of body weight disorders such as obesity, cachexia or anorexia. Mutant alleles and mutant allele products may then be utilized in the therapeutic and diagnostic systems described below. Additionally, such obR gene sequences can be used to detect obR gene regulatory (e.g., promoter or promotor/enhancer) defects which can affect body weight.

A cDNA of a mutant obR gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant obR allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant obR allele to that of the normal obR allele, the mutation(s) responsible for the loss or alteration of function of the mutant obR gene product can be ascertained.

Alternatively, a genomic library can be constructed using DNA obtained from an individual suspected of or known to carry the mutant obR allele, or a cDNA library can be constructed using RNA from a tissue known, or suspected, to express the mutant obR allele. The normal obR gene or any suitable fragment thereof may then be labeled and used as a probe to identify the corresponding mutant obR allele in such libraries. Clones containing the mutant obR gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant obR allele in an individual suspected of or known to carry such a mutant allele. In this manner, gene products made by the putatively mutant tissue may be expressed and screened using standard antibody screening techniques in conjunction with antibodies raised against the normal obR gene product as described, below, in Section 5.3. (For screening techniques, see, or example, Harlow, E. and Lane, eds., 1988, *Antibodies. A Laboratory Manual,* Cold Spring Harbor Press, Cold Spring Harbor.) Additionally, screening can be accomplished by screening with labeled Ob fusion proteins, such as, for example, AP-ob or Ob-AP fusion proteins. In cases where an obR mutation results in an expressed gene product with altered function (e.g., as a result of a missense or a frameshift mutation), a polyclonal set of antibodies to ObR are likely to cross-react with the mutant ObR gene product. Library clones detected via their reaction with such labeled antibodies can be purified and subjected to sequence analysis according to methods well known to chose of skill in the art.

The invention also encompasses nucleotide sequences that encode mutant ObRs, peptide fragments of the ObR, truncated ObRs, and ObR fusion proteins. These include, but are not limited to nucleotide sequences encoding mutant ObRs described in section 5.2 infra; polypeptides or peptides corresponding to the ECD, TM and/or CD domains of the ObR or portions of these domains; truncated ObRs in which one or two of the domains is deleted, e.g., a soluble ObR lacking the TM or both the TM and CD regions, or a truncated, nonfunctional ObR lacking all or a portion of the CD region. Nucleotides encoding fusion proteins may include by are not limited to full length ObR, truncated ObR or peptide fragments of ObR fused to an unrelated protein or peptide, such as for example, a transmembrane sequence, which anchors the ObR ECD to the cell membrane; an Ig Fc domain which Increases the stability and half life of the resulting fusion protein (e.g., ObR-Ig) in the bloodstream; or an enzyme, fluorescent protein, luminescent protein which can be used as a marker.

The invention also encompasses (a) DNA vectors that contain any of the foregoing ObR coding sequences and/or their complements (i.e., antisense); (b) DNA expression vectors that contain any of the foregoing ObR coding sequences operatively associated with a regulatory element that directs the expression of the coding sequences; and (c) genetically engineered host cells that contain any of the foregoing ObR coding sequences operatively associated with a regulatory element that directs the expression of the coding sequences in the host cell. As used herein, regulatory elements include but are not limited to inducible and non-inducible promoters, enhancers, operators and owner elements known to those skilled in the are that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

5.2. ObR Proteins and Polypeptides

ObR protein, polypeptides and peptide fragments, mutated, truncated or deleted forms of the ObR and/or ObR fusion proteins can be prepared for a variety of uses, including but not limited to the generation of antibodies, as reagents in diagnostic assays, the identification of other cellular gene products involved in the regulation of body weight, as reagents in assays for screening for compounds that can be used in the treatment of body weight disorders, and as pharmaceutical reagents useful in the treatment of body weight disorders related to the ObR.

FIGS. 1A–1D and 6A–6F show the amino acid sequence of a murine short form (SEQ ID NO::2) and long form (SEQ ID NO:43) ObR protein, respectively. In both of these forms of ObR, the signal sequence extends from amino acid 1 to about amino acid 22; the ECD extends from about amino acid 23 to about amino acid 837; and the TM extends from about amino acid 838 to about amino acid 860. In the short form of murine ObR, the CD extends from about amino acid 861 to about amino acid 894 (or to 893 in the second short form), while in the long form it extends from about amino acid 861 to about amino acid 1162. FIGS. 3A–3F shows the amino acid sequence of a human ObR (SEQ ID NO:4). The signal sequence extends from amino acid residue 1 to about amino acid residue 20; the ECD extends from about amino acid residue 21 to about amino acid residue 839; the TM extends from about amino acid residue 840 to about amino acid residue 862; and the CD extends from about amino acid residue 863 to about amino acid residue 1165.

The ObR sequence begins with a methionine in a DNA sequence context consistent with a translation initiation site, followed by a typical hydrophobic signal sequence of peptide secretion. The predicted mature extracellular domain for both forms of murine ObR is identical and is 815 amino acids long, whereas the ECD predicted for human ObR is 819 amino acids long. The extracellular domain of ObR shows many features of the class I cytokine receptor family (reviewed in Heldin, 1995, *Cell* 80:213–223), and is most closely related to the gp130 signal transducing component of the IL-6 receptor (Taga et al., 1989, *Cell* 58:573–581), the G-CSF receptor (Fukunaga et al., 1990, *Cell* 61:341–350), and the LIF receptor (Gearing et al., 1991, *Science* 255:1434–1437). in fact, the data presented herein demonstrate that the long form ObR signals through activation of STAT proteins—a hallmark of the signal transduction pathway mediated by the IL-6 type cytokine receptor family.

An alignment between the extracellular domains of the murine ObR and gp130 is shown in FIG. 4. Although the overall amino acid sequence identity between these two molecules is low (24%), the characteristically conserved cysteine residues, the Trp-Ser-X-Trp-Ser motif (SEQ ID NO:6; amino acid residues 317–321 and 620–624 in the murine sequence shown in FIGS. 1A–1D (SEQ ID NO2); amino acid residues 319–323 and 622–626 in the human sequence shown in FIGS. 3A–3F (SEQ ID NO:4), and conservation of other residues within this group of proteins (reviewed in Kishimoto et al., 1994, *Cell* 76:253–262) is clearly evident. The amino acid sequences of murine short form ObR and human ObR are highly homologous throughout the length of murine short form ObR (FIGS. 5A–5B). In fact, the deduced amino acid sequence identity between the murine short form and human clones (78%) is the same or greater than that seen when comparing the murine and human forms of gp130 (Saito et al., 1992, *J. Immunol.* 148:4066–4071), the LIF receptor (Gough et al., 1988, *Proc. Natl. Acad. Sci. USA* 85:2623–2627), and the G-CSF receptor (Fukanaga et al., 1990, *Proc. Natl. Acad. Sci. USA* 87:8702–8706). Similarly, the deduced amino acid sequences from murine and human long forms of ObR are homologous throughout the length of the coding region and share 75% identity (FIGS. 7A–7B).

Potential N-linked glycosylation sites (i.e., amino acid sequence motif N-X-S or N-X-T) are found in the ECD of both murine and human ObR. At least twenty potential N-linked glycosylation sites can be identified in the murine ObR ECD sequence shown in FIGS. 1A–1D (SEQ ID NO:2)

and 6A–6F (SEQ ID NO:43) (see tripeptide motifs starting at amino acid residues 23, 41, 56, 73, 81, 98, 187, 206, 276, 347, 397, 433, 516, 624, 659, 670, 688, 697, 728, and 750); whereas at least sixteen potential N-linked glycosylation sites can be identified in the human ObR ECD sequence shown in FIGS. 3A–3F(SEQ ID NO:4) (see tripeptide motifs starting at amino acid residues 41, 56, 73, 98, 187, 275, 345, 431, 514, 622, 657, 668, 686, 695, 698 and 726). The extracellular domain of both the murine and human ObR is followed by a predicted transmembrane domain of 23 amino acids.

The murine cDNA shown in FIGS. 1A–1D(SEQ ID NO:1) encodes a short cytoplasmic domain (34 amino acids). Amino acids 5–24 of the murine ObR cytoplasmic domain (i.e., amino acid residues 865 to 884 in FIGS. 1A–1D(SEQ ID NO:1) show 47% identity to membrane proximal sequences of the intracellular domain of the LIF receptor, and contain a box1 Jak interaction sequence (Narazaki et al., 1994, Proc. Natl. Acad. Sci. USA 91:2285–2289). Interestingly, the human cDNA encodes a protein with a much longer intracellular domain than murine short form ObR. Although the murine short form and human intracellular domains are highly conserved up to the final five residues of murine short form ObR, the human intracellular domain continues to a length similar to that of gp130. The nucleotide sequences of the murine short form and human clones are also very similar throughout the coding region of murine short form ObR, but then diverge completely near the murine short form ObR stop codon.

The short cytoplasmic domain of the murine short form cDNAs described herein is characteristic of several class I cytokine receptor polypeptides (reviewed in Kishimoto et al., 1994, Cell 76:253–262). However, the results reported herein demonstrate that the short form ObR does not activate signal transduction via the STAT pathway which is mediated by the long form ObR. In fact, the three receptors to which ObR shows the strongest homology all have long cytoplasmic domains important in intracellular signaling. This opened the possibility that the murine short form ObR clone isolated was chimeric or encoded a rare aberrantly spliced form not representing the major form expressed within the choroid plexus. To address this issue, eight murine clones were selected that were independently identified in the library screen, and each was amplified (in subpools of 150 clones each) by PCR with primers made to sequences 3' of the stop codon. Results verified that all eight clones contained these same 3' untranslated sequences. In addition, the C-terminus of five independently isolated clones was sequenced and all shown to have the same stop codon. Finally, reverse transcription PCR with total RNA from choroid plexus isolated from a mouse strain (C57B1/KsJ) different from that which the cDNA library was derived, generated an identical PCR product containing a stop codon in the same location. These data indicated that the isolated murine short form clone is neither chimeric nor a rare aberrant splice event, but rather is likely to be the predominant form of this receptor in the murine choroid plexus. The data presented herein indicate that in some tissues, alternatively spliced forms of mouse ObR exist with longer intracellular domains (the long form); i.e., the wild-type obR gene is expressed in two forms, one mRNA transcript having an insert of about 100 nucleotides encodes ObR having a short cytoplasmic domain, and another mRNA transcript encodes ObR having a long cytoplasmic domain that is homologous to the human CD.

The murine cDNA shown in FIGS. 6A–6F (SEQ ID NO:42) encodes the long form ObR. As described supra, the amino acids encoding the ECD and TM of the murine long form ObR are identical to those for the murine short form. The murine long form cDNA, however, encodes a cytoplasmic domain (302 amino acids) that is approximately the same length as the cytoplasmic domain encoded by the human ObR cDNA. Unlike the ObR short forms, the ObR encoded by the nucleotide sequence of the murine long form continues to be similar to that of the human ObR throughout the cytoplasmic domain.

The data presented herein also indicate that db is a mutant of the long form murine obR gene. The db mutant expresses an aberrantly spliced transcript containing an insert of about 106 nucleotides in the portion of the mRNA encoding the CD. Although the transcript is long, the inserted sequence produces a mutation that results in a transcript that encodes a truncated ObR protein that is identical to the short forms of ObR and therefore, lacks most of the CD. The data shown herein demonstrate that, unlike the long form ObR, the short form ObR, i.e., the form of the receptor associated with the obese phenotype in db/db mice, does not transduce signal mediated by the STAT pathway. Therefore, it appears that the signalling-competant long form ObR is actively involved in body weight regulation and maintenance.

In sum, messenger RNA for several major ObR forms have been identified. The predominant ObR mRNA found in most tissues encodes a transmembrane protein with a short cytoplasmic domain of 34 amino acid residues referred to as the short form. In hypothalamus, an obR mRNA exists which encodes a protein with an identical extracellular domain as the short form, but with a 302 residue-long cytoplasmic domain, referred to as the long form. The db mutation leads to the production of an aberrant splice product of long form transcript, resulting in a protein with truncated cytoplasmic domain. Interestingly, the mRNA for the long form of ObR in the db/db mice encodes a protein with an identical structure to the naturally occurring short form. The loss of this carboxyterminal region is proposed to render the ObR inactive and is predicted to generate the obese phenotype in db/db mice.

Sequence information indicated that ObR might exert a signaling action similar to that of G-CSFR, LIFR, and gp130 (Stahl & Yancopoulos, 1993, Cell 74;587–590; Kishimoto, et al., 1995, Blood 86:1243–1254). Signaling by these receptors entails, among others, the activation of receptor-associated kinases of the Janus kinase family which contribute to the phosphorylation and activation of the DNA binding activity of STAT1, STAT3 and STAT5 (Ihle, 1995, Nature 377:591–594; Kishimoto, et al., 1995, Blood 86:1243–1254). This process, in turn, has been correlated with induced transcription of genes that contain binding sites for the STAT proteins such as the hepatic genes encoding acute phase plasma proteins (Lai et al., 1995, J. Biol. Chem. 270:23254–23257). To address whether the cloned ObR isoforms are indeed signaling receptor molecules, ObR was introduced into established tissue culture cell lines and the cell response to OB treatment was compared with that mediated by the structurally-related IL-6-type cytokine receptors. The results presented in the example infra demonstrate that the long form ObR is a signal-transducing molecule. In particular, the results show that the long form ObR shares functional specificity with IL-6-type cytokine receptors. The results also show that the short form ObR does not signal via the STAT pathway transduced by the ObR long form. Thus, it appears that the long form ObR, but not the short form, is involved in maintenance of body weight.

The ObR amino acid sequences of the invention include the amino acid sequence shown in FIGS. 1A–1D (SEQ ID NO:2), FIGS. 3A–3F (SEQ ID NO:4) or FIGS. 6A–6F (SEQ ID NO:42), or the amino acid sequence encoded by cDNA clone famj5312 as deposited with the ATCC, or encoded by cDNA clone fahj5312d as deposited with the ATCC, or encoded by the human genomic clone h-obR-p87, as deposited with the ATCC. Further, ObRs of other species are encompassed by the invention. In fact, any ObR protein encoded by the obR nucleotide sequences described in Section 5.1, above, are within the scope of the invention.

The invention also encompasses proteins that are functionally equivalent to the ObR encoded by the nucleotide sequences described in Section 5.1, as judged by any of a number of criteria, including but not limited to the ability to bind Ob, the binding affinity for Ob, the resulting biological effect of Ob binding, for example, signal transduction, a change in cellular metabolism (e.g., ion flux, tyrosine phosphorylation) or change in phenotype when the ObR equivalent is present in an appropriate cell type (such as the amelioration, prevention or delay of the obese phenotype, i.e., the db or ob phenotype), or weight loss. Such functionally equivalent ObR proteins include but are not limited co additions or substitutions of amino acid residues within the amino acid sequence encoded by the obR nucleotide sequences described, above, in Section 5.1, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to obR DNA (using random mutagenesis techniques well known co those skilled in the art) and the resulting mutant ObRs tested for activity, site-directed mutations of the obR coding sequence can be engineered (using site-directed mutagenesis techniques well known to those skilled in the art) to generate mutant ObRs with increased function, for example, higher binding affinity for Ob, and/or greater signalling capacity; or decreased function, for example, lower binding affinity for Ob, and/or decreased signal transduction capacity.

For example, the alignment of mouse short form ObR FIGS. 1A–1D (SEQ ID NO:2) and the human ObR homolog FIGS. 3A–3F (SEQ ID NO:4) is shown in FIGS. 5A–5B in which identical amino acid residues are indicated by a star. Mutant ObRs can be engineered so that regions of identity (indicated by stars in FIGS. 5A–5B ) are maintained, whereas the variable residues (unstarred in FIGS. 5A–5B) are altered, for example, by deletion or insertion of an amino acid residue(s) or by substitution of one or more different amino acid residues. Conservative alterations at the variable positions can be engineered in order to produce a mutant ObR that retains function; for example, Ob binding affinity or signal transduction capability or both. Non-conservative changes can be engineered at these variable positions to alter function, for example, Ob binding affinity or signal transduction capability, or both. Alternatively, where alteration of function is desired, deletion or non-conservative alterations of the conserved regions (i.e., identical amino acids indicated by stars in FIGS. 5A–5B) can be engineered. For example, deletion or non-conservative alterations (substitutions or insertions) of the CD, for example, amino acid residues 861–894 (FIGS. 1A–1D (SEQ ID NO:2)) of murine ObR, or amino acid residues 863–1165 (FIGS. 3A–3F (SEQ ID NO:4)) of human ObR, or portions of the CD, for example, amino acid residues 861–884 (FIGS. 1A–1D (SEQ ID NO:2)) of murine ObR, or amino acid residues 863–886 (FIGS. 3A–3F (SEQ ID NO:4) of human ObR (the box 1 Jak interaction domain) can be engineered to produce a mutant ObR that binds Ob but is signalling-incompetent. Non-conservative alterations to the starred residues in the ECD shown in FIGS. 5A–5B can be engineered to produce mutant ObRs with altered binding affinity for Ob. The same mutation strategy can also be used to design mutant ObRs based on the alignment of murine long ObR form and the human ObR homolog shown in FIGS. 7A–7B in which identical amino acid residues are indicated by a double asterisk.

FIG. 4 shows the alignment of the ECD of murine ObR ((amino acid residues 333–830 of SEQ ID NO:2) with human gp130 (SEQ ID NO:5), in which identical residues are indicated in black, and conservative changes are indicated in grey. Presumably, regions of identity and conservation are important for maintaining tertiary structure of the ECD, whereas the variable regions may contribute to specificity of each receptor for its ligand. Therefore, ObR mutants with altered binding affinity for Ob may be engineered by altering the variable regions shown in FIG. 4. Such ObR mutants can be designed so as to preserve the ObR amino acid sequences that are boxed in FIG. 4 (both black and grey boxes) or to contain one or more conservative substitutions derived from the gp130 sequence shown in the grey boxes of FIG. 4.

Other mutations to the obR coding sequence can be made to generate ObRs that are better suited for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur in the ECD (N-X-S or N-X-T), and/or an amino acid deletion at the second position of any one or more such recognition sequences in the ECD will prevent glycosylation of the ObR at the modified tripeptide sequence. (See, e.g., Miyajima et al., 1986, *EMBO J.* 5:1193–1197).

Peptides corresponding to one or more domains of the ObR (e.g., ECD, TM, or CD), truncated or deleted ObRs (e.g., ObR in which the TM and/or CD is deleted) as well as fusion proteins in which the full length ObR, an ObR peptide or truncated ObR is fused to an unrelated protein are also within the scope of the invention and can be designed on the basis of the obR nucleotide and ObR amino acid sequences disclosed in this Section and in Section 5.1, above. Such fusion proteins include but are not limited to IgFc fusions which stabilize the ObR protein or peptide and prolong half-life in vivo; or fusions to any amino acid sequence that allows the fusion protein to be anchored to the cell membrane, allowing the ECD to be exhibited on the cell surface; or fusions to an enzyme, fluorescent protein, or luminescent protein which provide a marker function.

While the ObR polypeptides and peptides can be chemically synthesized (e.g., see Creighton, 1983, *Proteins; Structures and Molecular Principles,* W.H. Freeman & Co., N.Y.), large polypeptides derived from the ObR and the full length ObR itself may advantageously be produced by recombinant DNA technology using techniques well known in the art for expressing nucleic acid containing obR gene sequences and/or coding sequences. Such methods can be used to construct expression vectors containing the obR nucleotide sequences described in Section 5.1 and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding obR nucleotide sequences may be chemically synthesized using, for example, synthesizers. See, for example, the techniques described in *Oligonucleotide Synthesis*, 1984, Gait, M. J. ed., IRL Press, Oxford, which is incorporated by reference herein in its entirety.

A variety of host-expression vector systems may be utilized to express the obR nucleotide sequences of the invention. Where the ObR peptide or polypeptide is a soluble derivative (e.g., ObR peptides corresponding to the ECD; truncated or deleted ObR in which the TM and/or CD are deleted) the peptide or polypeptide can be recovered from the culture, i.e., from the host cell in cases where the ObR peptide or polypeptide is not secreted, and from the culture media in cases where the ObR peptide or polypeptide is secreted by the cells. However, the expression systems also encompass engineered host cells that express the ObR or functional equivalents in situ, i.e., anchored in the cell membrane. Purification or enrichment of the ObR from such expression systems can be accomplished using appropriate detergents and lipid micelles and methods well known to those skilled in the art. However, such engineered host cells themselves may be used in situations where it is important not only to retain the structural and functional characteristics of the ObR, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing obR nucleotide sequences; yeast (e.g., *Saccharomyces, Pichia*) transformed with recombinant yeast expression vectors containing the obR nucleotide sequences; insect cell systems infected with recombinant virus expression vectors (e.g., baculovirus) containing the obR sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing obR nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the obR gene product being expressed. For example, when a large quantity of such a protein is to be produced, for the generation of pharmaceutical compositions of ObR protein or for raising antibodies to the ObR protein, for example, vectors which direct the expression of high levels of fusion protein products that are readily purified may be desirable. Such vectors include, but are not limited to, the *E. coli* expression vector pUR278 (Ruther et al., 1983, *EMBO J*. 2:1791), in which the obR coding sequence may be ligated individually into the vector in frame with the lacZ coding region so that a fusion protein is produced; pIN vectors (Inouye & Inouye, 1985, *Nucleic Acids Res.* 13:3101–3109; Van Heeke & Schuster, 1989, *J. Biol. Chem.* 254:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica,* nuclear polyhidrosis virus (AcNPV) is used as a vector to express foreign genes. The virus grows in *Spodoptera frugiperda* cells. The obR gene coding sequence may be cloned individually into non-essential regions (for example the polyhedrin gene) of the virus and placed under control of an AcNPV promoter (for example the polyhedrin promoter). Successful insertion of obR gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, *J. Virol.* 46:584; Smith, U.S. Pat. No. 4,215,051).

In mammalian host cells, a number of viral-based expression systems may be utilized. In cases where an adenovirus is used as an expression vector, the obR nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the obR gene product in infected hosts. (E.g., See Logan & Shenk, 1984, *Proc. Natl. Acad. Sci. USA* 81:3655–3659). Specific initiation signals may also be required for efficient translation of inserted obR nucleotide sequences. These signals include the ATG initiation codon and adjacent sequences. In cases where an entire obR gene or cDNA, including its own initiation codon and adjacent sequences, is inserted into the appropriate expression vector, no additional translational control signals may be needed. However, in cases where only a portion of the obR coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, *Methods in Enzymol.* 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, and in particular, choroid plexus cell lines.

For long-term, high-yield production of recombinant proteins, stable expression is preferred. For example, cell lines which stably express the obR sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the obR gene product. Such engineered cell lines may be particularly useful in screening and evaluation of compounds that affect the endogenous activity of the obR gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$-nitriloacetic acid-agarose columns and histidine-tagged proteins are selectively eluted with imidazole-containing buffers.

The obR gene products can also be expressed in transgenic animals. Animals of any species, including, but not limited to, mice, rats, rabbits, guinea pigs, pigs, micro-pigs, goats, and non-human primates, for example, baboons, monkeys, and chimpanzees may be used to generate obR transgenic animals.

Any technique known in the art may be used to introduce the obR transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci. USA 82:6148–6152); gene targeting in embryonic stem cells (Thompson et al., 1989, Cell 56:313–321); electroporation of embryos (Lo, 1983, Mol. Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the obR transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89:6232–6236). The regulatory sequences required for such a cell-type specific activation will depend upon the particular cell type of interest, and will be apparent to those of skill in the art. When it is desired that the obR gene transgene be integrated into the chromosomal site of the endogenous obR gene, gene targeting is preferred. Briefly, when such a technique is to be utilized, vectors containing some nucleotide sequences homologous to the endogenous obR gene are designed for the purpose of integrating, via homologous recombination with chromosomal sequences, into and disrupting the function of the nucleotide sequence of the endogenous obR gene. The transgene may also be selectively introduced into a particular cell type, thus inactivating the endogenous obR gene in only that cell type, by following, for example, the teaching of Gu et al. (Gu, et al., 1994, Science 265:103–106). The regulatory sequences required for such a cell-type specific inactivation will depend upon the particular cell type of interest, and will be apparent to those of skill in the art.

Once transgenic animals have been generated, the expression of the recombinant obR gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of obR gene-expressing tissue, may also be evaluated immunocytochemically using antibodies specific for the obR transgene product.

5.3. Antibodies to ObR Proteins

Antibodies that specifically recognize one or more epitopes of ObR, or epitopes of conserved variants of ObR, or peptide fragments of the ObR are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of the ObR in a biological sample and may, therefore, be utilized as part in a diagnostic or prognostic technique whereby patients may be tested for abnormal amounts of ObR. Such antibodies may also be utilized in conjunction with, for example, compound screening schemes, as described, below, in Section 5.5, for the evaluation of the effect of test compounds on expression and/or activity of the obR gene product. Additionally, such antibodies can be used in conjunction with the gene therapy techniques described, below, in Section 5.6, to, for example, evaluate the normal and/or engineered ObR-expressing cells prior co their introduction into the patient. Such antibodies may additionally be used as a method for the inhibition of abnormal ObR activity. Thus, such antibodies may, therefore, be utilized as part of weight disorder treatment methods.

For the production of antibodies, various host animals may be immunized .by injection with the ObR, an ObR peptide (e.g., one corresponding the a functional domain of the receptor, such as ECD, TM or CD), truncated ObR polypeptides (ObR in which one or more domains, e.g., the TM or CD, has been deleted), functional equivalents of the ObR or mutants of the ObR. Such host animals may include but are not limited to rabbits, mice, and rats, to name but a few. Various adjuvants may be used to increase the immunological response, depending on the host species, including but not limited co Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein (1975, *Nature* 256:495–497; and U.S. Pat. No. 4,376,110), the human B-cell hybridoma technique (Kosbor et al., 1983, *Immunology Today* 4:72; Cole et al., 1983, *Proc. Natl. Acad. Sci. USA* 80:2026–2030), and the EBV-hybridoma technique (Cole et al., 1985, *Monoclonal Antibodies And Cancer Therapy,* Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, *Proc. Natl. Acad. Sci. USA* 81:6851–6855; Neuberger et al., 1984, *Nature* 312:604–608; Takeda et al., 1985, *Nature* 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, *Science* 242:423–426; Huston et al., 1988, *Proc. Natl. Acad. Sci. USA* 85:5879–5883; and Ward et al., 1989, *Nature* 334:544–46) can be adapted to produce single chain antibodies against obR gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, *Science* 246:1275–1281) to allow rapid and easy identification of monoclonal Fab fragments with the desired specificity.

Antibodies to the ObR can, in turn, be utilized to generate anti-idiotype antibodies that "mimic" the ObR, using techniques well known to those skilled in the art. (See, e.g., Greenspan & Bona, 1993, *FASEB J.* 7(5):437–444; and Nissinoff, 1991, *J. Immunol.* 147(8):2429–2438). For example, antibodies which bind to the ObR ECD and competitively inhibit the binding of Ob to the ObR can be used to generate anti-idiotypes that "mimic" the ECD and, therefore, bind and neutralize Ob. Such neutralizing anti-idiotypes or Fab fragments of such anti-idiotypes can be used in therapeutic regimens to neutralize Ob and promote weight gain.

5.4. Diagnosis of Body Weight Disorder Abnormalities

A variety of methods can be employed for the diagnostic and prognostic evaluation of body weight disorders, including obesity, cachexia and anorexia, and for the identification of subjects having a predisposition co such disorders.

Such methods may, for example, utilize reagents such as the obR nucleotide sequences described in Section 5.1, and ObR antibodies, as described, in Section 5.3. Specifically, such reagents may be used, for example, for: (1) the detection of the presence of obR gene mutations, or the detection of either over- or under-expression of obR mRNA relative to the non-body weight disorder state; (2) the detection of either an over- or an under-abundance of obR gene product relative to the non-body weight disorder state; and (3) the detection of perturbations or abnormalities in the signal transduction pathway mediated by ObR.

The methods described herein may be performed, for example, by utilizing pre-packaged diagnostic kits comprising at least one specific obR nucleotide sequence or ObR antibody reagent described herein, which may be conveniently used, e.g., in clinical settings, to diagnose patients exhibiting body weight disorder abnormalities.

For the detection of obR mutations, any nucleated cell can be used as a starting source for genomic nucleic acid. For the detection of obR gene expression or obR gene products, any cell type or tissue in which the obR gene is expressed, such as, for example, choroid plexus cells, may be utilized.

Nucleic acid-based detection techniques are described, below, in Section 5.4.1. Peptide detection techniques are described, below, in Section 5.4.2.

5.4.1. Detection of the obR Gene and Transcripts

Mutations within the obR gene can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving obR gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of obR gene-specific mutations can involve for example, contacting and incubating nucleic acids including recombinant DNA molecules, cloned genes or degenerate variants thereof, obtained from a sample, for example, derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within the obR gene. Preferably, the lengths of these nucleic acid reagents are at least 15 to 30 nucleotides. After incubation, all non-annealed nucleic acids are removed from the nucleic acid:obR molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled obR nucleic acid reagents is accomplished using standard techniques well-known to those in the art. The obR gene sequences to which the nucleic acid reagents have annealed can be compared to the annealing pattern expected from a normal obR gene sequence in order to determine whether an obR gene mutation is present.

Alternative diagnostic methods for the detection of obR gene specific nucleic acid molecules, in patient samples or other appropriate cell sources, may involve their amplification, for example, by PCR (the experimental embodiment set forth in Mullis, K. B. 1987, U.S. Pat. No. 4,683,202), followed by the detection of the amplified molecules using techniques well known to those of skill in the art. The resulting amplified sequences can be compared to those which would be expected if the nucleic acid being amplified contained only normal copies of the obR gene in order to determine whether an obR gene mutation exists.

Additionally, well-known genotyping techniques can be performed to identify individuals carrying obR gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms, which can be utilized for the identification of obR gene mutations, have been described. These methods capitalize on the presence of variable numbers of short, tandemly repeated DNA sequences between the restriction enzyme sites. For example, Weber (U.S. Pat. No. 5,075,217, which is incorporated herein by reference in its entirety) describes a DNA marker based on length polymorphisms in blocks of $(dC-dA)_n-(dG-dT)_n$ short tandem repeats. The average separation of $(dC-dA)_n-(dG-dT)_n$ clocks is estimated to be 30,000–60,000 bp. Markers that are so closely spaced exhibit a high frequency co-inheritance, and are extremely useful in the identification of genetic mutations, such as, for example, mutations within the obR gene, and the diagnosis of diseases and disorders related to obR mutations.

Also, Caskey et al. (U.S. Pat. No. 5,364,759, which is incorporated herein by reference in its entirety) describe a DNA profiling assay for detecting short tri- and tetra-nucleotide repeat sequences. The process includes extracting the DNA of interest, such as the obR gene, amplifying the extracted DNA, and labelling the repeat sequences to form a genotypic map of the individuals DNA.

The level of obR gene expression can also be assayed by detecting and measuring obR transcription. For example, RNA from a cell type or tissue known, or suspected, to express the obR gene, such as brain, especially choroid plexus cells, can be isolated and tested utilizing hybridization or PCR techniques such as those described above. The isolated cells can be obtained from cell culture or from a patient. The analysis of cells taken from culture may be a necessary step in the assessment of cells to be used as part of a cell-based gene therapy technique or, alternatively, to test the effect of compounds on the expression of the obR gene. Such analyses can reveal both quantitative and qualitative aspects of the expression pattern of the obR gene, including activation or inactivation of obR gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the obR nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product can be made such that the product can be visualized by standard ethidium bromide staining or by utilizing any other suitable nucleic acid staining method.

Additionally, it is possible to perform such obR gene expression assays in situ, i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (See, e.g., Nuovo, G. J., 1992, *PCR In Situ Hybridization: Protocols And Applications*, Raven Press, NY)

Alternatively, if a sufficient quantity of the appropriate cells can be obtained, standard Northern analysis can be performed to determine the level of mRNA expression of the obR gene.

5.4.2. Detection of the obR Gene Products

Antibodies directed against wild type or mutant obR gene products or conserved variants or peptide fragments thereof, which are discussed, above, in Section 5.3, can also be used as body weight disorder diagnostics and prognostics, as described herein. Such diagnostic methods, can be used to detect abnormalities in the level of obR gene expression, or abnormalities in the structure and/or temporal, tissue, cellular, or subcellular location of the ObR, and may be performed in vivo or in vitro, such as, for example, on biopsy tissue.

For example, antibodies directed to epitopes of the ObR ECD can be used in vivo to detect the pattern and level of expression of the ObR in the body. Such antibodies can be labeled, for example, with a radio-opaque or other appropriate compound and injected into a subject in order co visualize binding to the ObR expressed in the body using methods such as X-rays, CAT-scans, or MRI. Labeled antibody fragments, for example, the Fab or single chain antibody comprising the smallest portion of the antigen binding region, are preferred for this purpose to promote crossing the blood-brain barrier and permit labeling ObRs expressed in the choroid plexus.

Additionally, any ObR fusion protein or ObR conjugated protein whose presence can be detected, can be administered. For example, ObR fusion or conjugated proteins labeled with a radio-opaque or other appropriate compound can be administered and visualized in vivo, as discussed, above for labeled antibodies. Further such Ob fusion proteins as AP-Ob on Ob-Ap fusion proteins can be utilized For in vitro diagnostic procedures.

Alternatively, immunoassays or fusion protein detection assays, as described above, can be utilized on biopsy and autopsy samples in vitro to permit assessment of the expression pattern of the ObR. Such assays are not confined co the use of antibodies that define the ObR ECD, but can include the use of antibodies directed to epitopes of any of the domains of the ObR, for example, the ECD, the TM and/or CD. The use of each or all of these labeled antibodies will yield useful information regarding translation and intracellular transport of the ObR to the cell surface, and can identify defects in processing.

The tissue or cell type to be analyzed will generally include those which are known, or suspected, to express the obR gene, such as, for example, choroid plexus cells. The protein isolation methods employed herein can, for example, be such as those described in Harlow and Lane (Harlow, E. and Lane, D., 1988, *Antibodies: A Laboratory Manual,* Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the obR gene.

For example, antibodies, or fragments of antibodies, such as those described, above, in Section 5.3, useful in the present invention may be used to quantitatively or qualitatively detect the presence of obR gene products or conserved variants or peptide fragments thereof. This can be accomplished, for example, by immunofluorescence techniques employing a fluorescently labeled antibody .see below, this Section) coupled with light microscopic, flow cytometric, or fluorimetric detection. Such techniques are especially preferred if such obR gene products are expressed on the cell surface.

The antibodies (or fragments thereof) or Ob fusion or conjugated proteins useful in the present invention can, additionally, be employed histologically, as in immunofluorescence, immunoelectron microscopy or non-immuno assays, for in situ detection of obR gene products or conserved variants or peptide fragments thereof, or for Ob binding (in the case of labeled Ob fusion protein).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of the obR gene product, or conserved variants or peptide fragments, or ob binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for obR gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying obR gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles, or soluble proteins. The support may then be washed with suitable buffers followed by treatment with the detectably labeled ObR antibody or Ob fusion protein. The solid phase support may then be washed with the buffer a second time to remove unbound antibody or fusion protein. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of ObR antibody or ob fusion protein may be determined according to well known methods. Those skilled in the art will be able to determine operative and optimal assay conditions for each determination by employing routine experimentation.

With respect to antibodies, one of the ways in which the ObR antibody can be detectably labeled is by linking the same to an enzyme and use in an enzyme immunoassay (EIA) (Voller, A., *The Enzyme Linked Immunosorbent Assay* (ELISA), 1978, *Diagnostic Horizons* 2:1–7, Microbiological Associates Quarterly Publication, Walkersville, Md.); Voller, A. et al., 1978, *J. Clin. Pathol.* 31:507–520; Butler, J. E., 1981, *Meth. Enzymol.* 73:482–523; Maggio, E. (ed.), 1980, *Enzyme Immunoassay,* CRC Press, Boca Raton, Fla.; Ishikawa, E. et al., (eds.), 1981, *Enzyme Immunoassay,* Kgaku Shoin, Tokyo). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling she antibodies or antibody fragments, it is possible co detect ObR through the use of a radioimmunoassay (RIA) (see, for example, Weintraub, B., *Principles of Radioimmunoassays, Seventh Training Course on Radioligand Assay Techniques,* The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type or chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase, and aequorin.

5.5. Screening Assays for Compounds that Modulate ObR Expression or Activity The following assays are designed to identify compounds that interact with (e.g., bind to) ObR (including, but not limited to the ECD or CD of ObR), compounds that interact with (e.g., bind to) intracellular proteins that interact with ObR (including, but not limited to, the TM and CD of ObR), compounds that interfere with the interaction of ObR with transmembrane or intracellular proteins involved in ObR-mediated signal transduction, and to compounds that modulate the activity of an obR gene (i.e., modulate the level of obR gene expression) or modulate the level of ObR. Assays can additionally be utilized which identify compounds that bind to obR gene regulatory sequences (e.g., promoter sequences) and which may modulate obR gene expression. See e.g., Platt, *J. Biol. Chem.* 269:28558–28562, 1994, which is incorporated herein by reference in its entirety.

Compounds that can be screened in accordance with the invention include, but are not limited to peptides, antibodies and fragments thereof, and ocher organic compounds (e.g., peptidomimetics) that bind to the ECD of the ObR and either mimic the activity triggered by the natural ligand (i.e., agonists) or inhibit the activity triggered by the natural ligand (i.e., antagonists); as well as peptides, antibodies or fragments thereof, and other organic compounds that mimic the ECD of the ObR (or a portion thereof) and bind to and "neutralize" natural ligand.

Such compounds can include, but are not limited to, peptides such as, for example, soluble peptides, including but not limited to members of random peptide libraries; (see, e.g., Lam, et al., *Nature* 354:82–84, 1991; Houghten, et al., *Nature* 354:84–86, 1991), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, *Cell* 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Other compounds that can be screened in accordance with the invention include but are not limited to small organic molecules that are able to cross the blood-brain barrier, gain entry into an appropriate cell (e.g., a cell in the choroid plexus or in the hypothalamus) and affect the expression of the obR gene or some other gene involved in the ObR signal transduction pathway (e.g., by interacting with the regulatory region or transcription factors involved in gene expression); or such compounds that affect the activity of the ObR (e.g., by inhibiting or enhancing the enzymatic activity of the CD) or the activity of some other intracellular factor involved in the ObR signal transduction pathway, such as, for example, gp130.

Computer modelling and searching technologies permit identification of compounds, or the improvement of already identified compounds, that can modulate ObR expression or activity. Having identified such a compound or composition, the active sites or regions are identified. Such active sites might typically be ligand binding sites, such as the interaction domains of Ob with ObR itself. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures can be measured with a complexed ligand, natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. Compounds found from this search are potential ObR modulating compounds.

Alternatively, these methods can be used to identify improved modulating compounds from an already known modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner, systematic variations in composition, such as by varying side groups, can be quickly evaluated to obtain modified modulating compounds or ligands of improved specificity or activity.

Further experimental and computer modeling methods useful to identify modulating compounds based upon identification of the active sites of Ob, ObR, and related transduction and transcription factors will be apparent to those of skill in the art.

Examples of molecular modelling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen, et al., 1988, Acta *Pharmaceutical Fennica* 97:159–166; Ripka, *New Scientist* 54–57 (Jun. 16, 1988); McKinaly and Rossmann, 1989, *Annu. Rev. Pharmacol. Toxiciol.* 29:111–122; Perry and Davies, *OSAR: Quantitative Structure-Activity Relationships in Drug Design* pp. 189–193 (Alan R. Liss, Inc. 1989); Lewis and Dean, 1989, *Proc. R. Soc. Lond.* 236:125–140 and 141–162; and, with respect to a model receptor for nucleic acid components, Askew et al., 1989, *J. Am. Chem. Soc.* 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in elaborating the biological function of the obR gene product, and for ameliorating body weight disorders. Assays for testing the effectiveness of compounds, identified by, for example, techniques such as those described in Section 5.5.1 through 5.5.3, are discussed, below, in Section 5.5.4.

5.5.1. In Vitro Screening Assays for Compounds that Bind to ObR

In vitro systems may be designed to identify compounds capable of interacting with (e.g., binding to) ObR (including, but not limited to, the ECD or CD of ObR). Compounds identified can be used, for example, in modulating the activity of wild type and/or mutant obR gene products; in elaborating the biological function of the ObR; in screens for identifying compounds that disrupt normal ObR interactions; or can in themselves disrupt such interactions.

The principle of the assays used to identify compounds that bind to the ObR involves preparing a reaction mixture of the ObR and the test compound under conditions and for a time sufficient to allow the two components to interact and bind, thus forming a complex which can be removed and/or detected in the reaction mixture. The ObR species used can vary depending upon the goal of the screening assay. For example, where agonists of the natural ligand are sought, the full length ObR, or a soluble truncated ObR, for example, in which the TM and/or CD is deleted from the molecule, a peptide corresponding to the ECD or a fusion protein containing the ObR ECD fused to a protein or polypeptide that affords advantages in the assay system (e.g., labeling, isolation of the resulting complex, etc.) can be utilized. where compounds that interact with the cytoplasmic domain are sought to be identified, peptides corresponding to the ObR CD and fusion proteins containing the ObR CD can be used.

The screening assays can be conducted in a variety of ways. For example, one method to conduct such an assay would involve anchoring the ObR protein, polypeptide, peptide or fusion protein or the test substance onto a solid phase and detecting ObR/test compound complexes anchored on the solid phase at the end of the reaction. In one embodiment of such a method, the ObR reactant may be anchored onto a solid surface, and the test compound, which is not anchored, may be labeled, either directly or indirectly.

In practice, microtiter plates may conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; for example, using a labeled antibody specific for the previously nonimmobilized component (the antibody, in turn, can be directly labeled or indirectly labeled with a labeled anti-Ig antibody)

Alternatively, a reaction can be conducted in a liquid phase, the reaction products separated from unreacted components, and complexes detected; for example, using an immobilized antibody specific for ObR protein, polypeptide, peptide or fusion protein or the test compound to anchor any complexes formed in solution, and a labeled antibody specific for the other component of the possible complex to detect anchored complexes.

Alternatively, cell-based assays can be used to identify compounds that interact with ObR. To this end, cell lines that express ObR, or cell lines (e.g., COS cells, CHO cells, fibroblasts, etc.) that have been genetically engineered to express ObR (e.g., by transfection or transduction of ObR DNA) can be used. Interaction of the test compound with, for example, the ECD of obR expressed by the host cell can be determined by comparison or competition with native Ob.

5.5.2. Assays for Intracellular Proteins that Interact with the ObR

Any method suitable for detecting protein-protein interactions may be employed for identifying transmembrane proteins or intracellular proteins that interact with ObR. Among the traditional methods which may be employed are co-immunoprecipitation, crosslinking and co-purification through gradients or chromatographic columns of cell lysates or proteins obtained from cell lysates and the ObR co identify proteins in the lysate that interact with the ObR. For these assays, the ObR component used can be a full length ObR, a soluble derivative lacking the membrane-anchoring region (e.g., a truncated ObR in which the TM is deleted resulting in a truncated molecule containing the ECD fused to the CD), a peptide corresponding to the CD or a fusion protein containing the CD of ObR. Once isolated, such an intracellular protein can be identified and can, in turn, be used, in conjunction with standard techniques, to identify proteins with which it interacts. For example, at least a portion of the amino acid sequence of an intracellular protein which interacts with the ObR can be ascertained using techniques well known to those of skill in the art, such as via the Edman degradation technique. (See, e.g., Creighton, 1983, *Proteins: Structures and Molecular Principles*, W.H. freeman & Co., N.Y., pp. 34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel, supra, and *PCR Protocols: A Guide to Methods and Applications*, 1990, Innis, M. et al., eds. Academic Press, Inc., New York).

Additionally, methods may be employed that result in the simultaneous identification of genes which encode the transmembrane or intracellular proteins interacting with ObR. These methods include, for example, probing expression libraries, in a manner similar to the well known technique of antibody probing of λgt11 libraries, using labeled ObR protein, or an ObR polypeptide, peptide, or fusion protein, e.g., an ObR polypeptide or ObR domain fused to a marker (e.g., an enzyme, fluorophore, luminescent protein, or dye), or an Ig-Fc -domain.

One method chat detects protein interactions in vivo, the two-hybrid system, is described in detail For illustration only and not by way of limitation. One version of this system has been described (Chien et al., 1991, *Proc. Natl. Acad. Sci. USA*, 88:9578–9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to an obR nucleotide sequence encoding ObR, an ObR polypeptide, peptide, or fusion protein, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, ObR may be used as the bail gene product. Total genomic or cDNA sequences are fused to the DNA encoding an activation domain. This library and a plasmid encoding a hybrid of a bait obR gene product fused to the DNA-binding domain are cotransformed into a yeast reporter strain, and the resulting transformants are screened for those that express the reporter gene. For example, and not by way of limitation, a bait obR gene sequence, such as the open reading frame of obR (or a domain of obR), as depicted in FIGS. 1A–1D (SEQ ID NO: 1), FIGS. 3A–3F (SEQ ID NO:3), or FIGS. 6A–6F (SEQ ID NO:42) can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait obR gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait obR gene-GAL4 fusion plasmid into a yeast strain which contains a lacZ gene driven by a promoter which contains GAL4 activation sequence. A cDNA encoded protein, fused to GAL4 transcriptional activation domain, that interacts with bait obR gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait obR gene-interacting protein using techniques routinely practiced in the art.

5.5.3. Assays for Compounds that Interfere with ObR/intracellular of ObR/Transmembrane Macromolecule Interaction The macromolecules that interact with the ObR are referred to, for purposes of this discussion, as "binding partners." These binding partners are likely to be involved in the ObR signal transduction pathway, and therefore, in the role of ObR in body weight regulation. Therefore, it is desirable to identify compounds that interfere with or disrupt the interaction of such binding partners with ob. These compounds can be used, for example, to regulate the activity of the ObR, and thereby control body weight disorders associated with ObR activity.

The basic principle of the assay systems used to identify compounds that interfere with the interaction between the ObR and its binding partner or partners involves preparing a reaction mixture containing ObR protein, polypeptide, peptide, or fusion protein as described in Sections 5.5.1 and 5.5.2 above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the ObR moiety and its binding partner. Control reaction mixtures are incubated without the test compound or with a placebo. The formation of any complexes between the ObR moiety and the binding partner is then detected. The formation of a complex in the control reaction, but not in the reaction mixture containing the test compound, indicates that the compound interferes with the interaction of the ObR and the interactive binding partner. Additionally, complex formation within reaction mixtures containing the test compound and normal ObR protein may also be compared to complex formation within reaction mixtures containing the test compound and a mutant ObR. This comparison may be important in those cases wherein it is desirable to identify compounds that disrupt interactions of mutant but not normal ObRs.

The assay for compounds that interfere with the interaction of the ObR and binding partners can be conducted in a heterogeneous or homogeneous format. Heterogeneous assays involve anchoring either the ObR moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the ObR moiety and interactive binding partner. Alternatively, test compounds that disrupt preformed complexes, for example, compounds with higher binding constants that displace one of the components from the complex, can be tested by adding the test compound to the reaction mixture after complexes have been formed. The various formats are described briefly below.

In a heterogeneous assay system, either the ObR moiety or the interactive binding partner, is anchored onto a solid surface, while the non-anchored species is labeled, either directly or indirectly. In practice microtiter plates are conveniently utilized. The anchored species can be immobilized by non-covalent or covalent attachments. Non-covalent attachment can be accomplished simply by coating the solid surface with a solution of the obR gene product or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; for example, using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; for example, using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or which disrupt preformed complexes can be identified.

In an alternate embodiment of the invention, a homogeneous assay can be used. In this approach, a preformed complex of the ObR moiety and the interactive binding partner is prepared in which either the ObR or its binding partner is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt ObR/intracellular binding partner interaction can be identified.

In a particular embodiment, an ObR fusion can be prepared for immobilization. For example, the ObR or a peptide fragment, for example, corresponding to the CD, can be fused to a glutathione-S-transferase (GST) gene using a fusion vector, such as pGEX-5X-1, in such a manner that its binding activity is maintained in the resulting fusion protein.

The interactive binding partner can be purified and used to raise a monoclonal antibody, using methods routinely practiced in the art and described above, in Section 5.3. This antibody can be labeled with the radioactive isotope $^{125}$I, for example, by methods routinely practiced in the art. In a heterogeneous assay, for example, the GST-ObR fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the obR gene product and the interactive binding partner can be detected by measuring the amount of radioactivity that remains associated with the glutathione-agarose beads. A successful inhibition of the interaction by the test compound will result in a decrease in measured radioactivity.

Alternatively, the GST-ObR fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the ObR/binding partner interaction can be detected by adding the labeled antibody and measuring the radioactivity associated with the beads.

In another embodiment of the invention, these same techniques can be employed using peptide fragments that correspond to the binding domains of the ObR and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, an obR gene product can be anchored to a solid material, as described above, by making a GST-ObR fusion protein and allowing it to bind to glutathione agarose beads. The interactive binding partner can be labeled with a radioactive isotope, such as $^{35}$S, and cleaved with a proteolytic enzyme such as trypsin. Cleavage products can then be added to the anchored GST-obR fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

5.5.4. Assays for Identification of Compounds that Ameliorate Body Weight Disorders Compounds, including but not limited to binding compounds identified via assay techniques such as those described above, in Sections 5.5.1 through 5.5.3, can be tested for the ability to ameliorate body weight disorder symptoms, including obesity. The assays described above can identify compounds that affect ObR activity (e.g., compounds that bind to the ObR, inhibit binding of the natural ligand, and either activate signal transduction (agonists) or block activation (antagonists), and compounds that bind to the natural ligand of the ObR and neutralize ligand activity); or compounds that affect obR gene activity (by affecting obR gene expression, including molecules, e.g., proteins or small organic molecules, that affect or interfere with splicing events so that expression of the full length or the truncated form of the ObR can be modulated). However, it should be noted that the assays described can also identify compounds that modulate ObR signal transduction (e.g., compounds which affect downstream signalling events, such as inhibitors or enhancers of tyrosine kinase or phosphatase activities which participate in transducing the signal activated by ob binding to the ObR). The identification and use of such compounds which affect another step in the ObR signal transduction pathway in which the obR gene and/or obR gene product is involved and, by affecting this same pathway can modulate the effect of ObR on the development of body weight disorders are within the scope of the invention. Such compounds can be used as part of a therapeutic method for the treatment of body weight disorders.

The invention encompasses cell-based and animal model-based assays for the identification of compounds exhibiting such an ability to ameliorate body weight disorder symptoms. Such cell-based assay systems can also be used as the "gold standard" to assay for purity and potency of the natural ligand, Ob, including recombinantly or synthetically produced Ob and Ob mutants.

Cell-based systems can be used to identify compounds that can act to ameliorate body weight disorder symptoms. Such cell systems can include, for example, recombinant or non-recombinant cells, such as cell lines, which express the obR gene. For example choroid plexus cells, hypothalamus cells, or cell lines derived from choroid plexus or hypothalamus can be used. In addition, expression host cells (e.g., COS cells, CHO cells, fibroblasts) genetically engineered to express a functional ObR and to respond to activation by the natural Ob ligand, e.g., as measured by a chemical or phenotypic change, induction of another host cell gene, change in ion flux (e.g., $Ca^{++}$), tyrosine phosphorylation of host cell proteins, etc., can be used as an end point in the assay.

In utilizing such cell systems, cells may be exposed to a compound suspected of exhibiting an ability to ameliorate body weight disorder symptoms, at a sufficient concentration and for a time sufficient to elicit such an amelioration of body weight disorder symptoms in the exposed cells. After exposure, the cells can be assayed to measure alterations in the expression of the obR gene, for example, by assaying cell lysates for obR mRNA transcripts (e.g., by Northern analysis) or for obR protein expressed in the cell; compounds that regulate or modulate expression of the obR gene are good candidates as therapeutics. Alternatively, the cells are examined to determine whether one or more body weight disorder-like cellular phenotypes has been altered to resemble a more normal or more wild type, non-body weight disorder phenotype, or a phenotype more likely to produce a lower incidence or severity of disorder symptoms. Still further, the expression and/or activity of components of the signal transduction pathway of which ObR is a part, or the activity of the ObR signal transduction pathway itself can be assayed.

For example, after exposure, the cell lysates can be assayed for the presence of tyrosine phosphorylation of host cell proteins, as compared to lysates derived from unexposed control cells. The ability of a test compound to inhibit tyrosine phosphorylation of host cell proteins in these assay systems indicates that the test compound inhibits signal transduction initiated by ObR activation. The cell lysates can be readily assayed using a Western blot format; i.e., the host cell proteins are resolved by gel electrophoresis, transferred to a support, and probed using a anti-phosphotyrosine detection antibody (e.g., an anti-phosphotyrosine antibody labeled with a signal generating compound, such as radiolabel, fluorophore, enzyme, etc.) (See, e.g., Glenney et al., 1988, *J. Immunol. Methods* 109:277–285; Frackelton et al., 1983, *Mol. Cell. Biol.* 3:1343–1352). Alternatively, an ELISA format could be used in which a particular host cell protein involved in the ObR signal transduction pathway is immobilized using an anchoring antibody specific for the target host cell protein, and the presence or absence of phosphotyrosine on the immobilized host cell protein is detected using a labeled anti-phosphotyrosine antibody. (See, King et al., 1993, *Life Sciences* 53:1465–1472). In yet another approach, ion flux, such as calcium ion flux, can be measured as an end point for ObR stimulated signal transduction.

Alternatively, activation of STAT proteins, and stimulation of transcription mediated through IL-6 responsive gene elements can be measured to test the ability of a compound to regulate ObR mediated signal transduction. For example, a recombinant expression vector can be engineered to contain the IL-6 responsive element sequences cloned adjacent to a reporter gene and regulation of ObR activity may be measured by assaying for reporter gene activity. Reporter genes that may be used include, but are not limited to those encoding chloramphenicol acetyl transferase (CAT), firefly luciferase, or human growth hormone.

In addition, animal-based body weight disorder systems, which may include, for example, ob, db and ob/db mice, can be used to identify compounds capable of ameliorating body weight disorder-like symptoms. Such animal models may be used as test substrates for the identification of drugs, pharmaceuticals, therapies and interventions which can be effective in treating such disorders. For example, animal models can be exposed to a compound, suspected of exhibiting an ability to ameliorate body weight disorder symptoms, at a sufficient concentration and for a time sufficient to elicit such an amelioration of body weight disorder symptoms in the exposed animals. The response of the animals to the exposure may be monitored by assessing the reversal of disorders associated with body weight disorders such as obesity. With regard to intervention, any treatments which reverse any aspect of body weight disorder-like symptoms would be considered as candidates for human body weight disorder therapeutic intervention. Dosages of test agents may be determined by deriving dose-response curves, as discussed in Section 5.7.1, below.

5.6. The Treatment of Body Weight, Including Body Weight Disorders

The invention encompasses methods and compositions for modifying body weight and treating body weight disorders, including but not limited to obesity, cachexia and anorexia. Because a loss of normal obR gene product function results in the development of an obese phenotype, an increase in obR gene product activity, or activation of the ObR pathway (e.g., downstream activation) would facilitate progress towards a normal body weight state in obese individuals exhibiting a deficient level of obR gene expression and/or obR activity.

Alternatively, symptoms of certain body weight disorders such as, for example, cachexia, which involve a lower than normal body weight phenotype, may be ameliorated by decreasing the level of obR gene expression, and/or obR gene activity, and/or downregulating activity of the ObR pathway (e.g., by targeting downstream signalling events). Different approaches are discussed below.

5.6.1. Inhibition of ObR Expression or ObR Activity to Promote Weight Gain

Any method that neutralizes ob or inhibits expression of the obR gene (either transcription or translation) can be used to effectuate weight gain. Such approaches can be used to treat body weight disorders such as anorexia or cachexia. Such methods can also be useful for agricultural applications; i.e., to increase the weight of livestock animals.

For example, the administration of soluble peptides proteins, fusion proteins, or antibodies (including anti-idiotypic antibodies) that bind to and "neutralize" circulating Ob, the natural ligand for the ObR, can be used to effectuate weight gain. To this end, peptides corresponding to the ECD of ObR, soluble deletion mutants of ObR (e.g., ΔTMObR mutants), or either of these ObR domains or mutants fused to another polypeptide (e.g., an IgFc polypeptide) can be utilized. Alternatively, anti-idiotypic antibodies or Fab fragments of antiidiotypic antibodies that mimic the ObR ECD and neutralize ob can be used (see Section 5.3, supra). Such ObR peptides, proteins, fusion proteins, anti-idiotypic antibodies or Fabs are administered to a subject in amounts sufficient to neutralize Ob and to effectuate weight gain.

ObR peptides corresponding to the ECD having the amino acid sequence shown in FIGS. 1A–1D (SEQ ID NO:2) or 6A–6F(SEQ ID NO:43), from about amino acid residue 23 to about amino acid residue 837, or having the amino acid sequence shown in FIGS. 3A–3F (SEQ ID NO:4), from about amino acid residue 21 to about amino acid residue 839, can be used. ObR ? TM mutants in which all or part of the 23 amino acid hydrophobic anchor sequence (e.g., about amino acid residue 838 to amino acid residue 860 in FIGS. 1A–1D (SEQ ID NO:2) or 6A–6F (SEQ ID NO: 43), or about amino acid residue 840 to about amino acid residue 862 in FIGS. 3A–3F (SEQ ID NO: 4)) could also be used. Fusion of the ObR, the ObR ECD or the ? TMObR to an IgFc polypeptide should not only increase the stability of the preparation, but will increase the half-life and activity of the ObR-Ig fusion protein in vivo. The Fc region of the Ig portion of the fusion protein can be further modified to reduce immunoglobulin effector function. See Section 10, infra.

In a specific embodiment described herein, the extracellular domains of the mouse or human ObR were fused to the IgG constant region. As indicated in FIG. 10, purified ObR-IgG was able to potently inhibit, or neutralize, the binding of the AP-OB fusion protein to cell surface ObR (See Section 10.4).

In an alternative embodiment for neutralizing circulating Ob, cells that are genetically engineered to express such soluble or secreted forms of ObR can be administered to a patient, whereupon they will serve as "bioreactors" in vivo to provide a continuous supply of the Ob neutralizing protein. Such cells may be obtained from the patient or an MHC compatible donor and can include, but are not limited to fibroblasts, blood cells (e.g., lymphocytes), adipocytes, muscle cells, endothelial cells, etc. The cells are genetically engineered in vitro using recombinant DNA techniques to introduce the coding sequence for the ObR ECD, ΔTMObR, or for ObR-Ig fusion protein (e.g., ObR-, ECD- or ΔTMObR-IgFc fusion proteins) into the cells, for example, by transduction (using viral vectors, and preferably vectors that, integrate the transgene into the cell genome) or transfection procedures, including but not limited to the use of plasmids, cosmids, YACs, electroporation, liposomes, etc. The obR coding sequence can be placed under the control of a strong constitutive or inducible promoter or promoter/enhancer to achieve expression and secretion of the ObR peptide or fusion protein. The engineered cells that express and secrete the desired ObR product can be introduced into the patient systemically, for example, in the circulation, intraperitoneally, at the choroid plexus, or hypothalamus. Alternatively, the cells can be incorporated into a matrix and implanted in the body. For example, genetically engineered fibroblasts can be implanted as part of a skin graft; genetically engineered endothelial cells can be implanted as part of a vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous cells, they can be administered using well known techniques that prevent the development of a host immune response against the introduced cells. For example, the cells can be introduced in an encapsulated form which, while allowing for an exchange of components with the immediate extracellular environment, does not allow the introduced cells to be recognized by the host immune system.

In an alternate embodiment, weight gain therapy can be designed to reduce the level of endogenous obR gene expression, for example, using antisense or ribozyme approaches to inhibit or prevent translation of obR mRNA transcripts; triple helix approaches to inhibit transcription of the obR gene; or targeted homologous recombination to inactivate or "knock out" the obR gene or its endogenous promoter. Because the obR gene is expressed in the brain, including the choroid plexus and hypothalamus, delivery techniques should be preferably designed to cross the blood-brain barrier (see PCT WO89/10134, which is incorporated by reference herein in its entirety). Alternatively, the antisense, ribozyme or DNA constructs described herein could be administered directly to the site containing the target cells; for example, the choroid plexus and/or hypothalamus.

Antisense approaches involve the design of oligonucleotides (either DNA or RNA) that are complementary to ObR mRNA. The antisense oligonucleotides will bind to the complementary obR mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, for example, the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'-non-translated, non-coding regions of the obR shown in FIGS. 1A–1D (SEQ ID NO:1) (murine short form), FIGS. 6A–6F(SEQ ID NO:42) (murine long form) or FIGS. 3A–3F (SEQ ID NO:3) (human long form) could be used in an antisense approach to inhibit translation of endogenous obR mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of ObR mRNA, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, or at least 50 nucleotides in length.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide can include other appended groups such as peptides (e.g., for targeting host cell receptors in vivo), or agents facilitating transport across the cell membrane (see, e.g., Letsinger et al., 1989, Proc. Natl. Acad. Sci. USA 86:6553–6556; Lemaitre et al., 1987, Proc. Natl. Acad. Sci. USA 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide can be conjugated to another molecule, for example, a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, *Nucl. Acids Res.* 15:6625–6641). The oligonucleotide is a 2'-O-methylribonucleotide (Inoue et al., 1987, *Nucl. Acids Res.* 15:6131–6148), or a chimeric RNA-DNA analogue (Inoue et al., 1987, *FEBS Lett.* 215:327–330).

Oligonucleotides of the invention can be synthesized by standard methods known in the art, for example, by use of an automated DNA synthesizer (such as are commercially available from Biosearch, Applied Biosystems, etc.). As examples, phosphorothioate oligonucleotides can be synthesized by the method of Stein et al. (1988, *Nucl. Acids Res.* 16:3209), methylphosphonate oligonucleotides can be prepared by use of controlled pore glass polymer supports (Sarin et al., 1988, *Proc. Natl. Acad. Sci. USA* 85:7448–7451), etc.

While antisense nucleotides complementary to the obR coding region sequence could be used, those complementary to the transcribed untranslated region are most preferred. For example, antisense oligonucleotides having the following sequences can be utilized in accordance with the invention:
a) 5'-CATCTTACTTCAGAGAA-3' (SEQ ID NO:7), which is complementary to nucleotides −14 to +3 in FIGS. 3A–3F (SEQ ID NO:3);
b) 5'-CATCTTACTTCAGAGAAGTACAC-3' (SEQ ID NO:8), which is complementary to nucleotides −20 to +3 in FIGS. 3A–3F(SEQ ID NO:3);
c) 5'-CATCTTACTTCAGAGAAGTACACCCATAA-3' (SEQ D NO:9), which is complementary to nucleotides −26 to +3 in FIGS. 3A–3F(SEQ ID NO:3);
d) 5'-CATCTTACTTCAGAGAAGTACACCCATAATCCTCT-3' (SEQ ID NO:10), which is complementary to nucleotides −32 to +3 in FIGS. 3A–3F(SEQ ID NO:3);
e) 5'-AATCATCTTACTTCAGAGAAGTACACCCATAATCC-3' (SEQ ID NO:11), which is complementary to nucleotides −29 to +6 in FIGS. 3A–3F(SEQ ID NO:3);
f) 5'-CTTACTTCAGAGAAGTACACCCATAATCC-3' (SEQ ID NO:12), which is complementary to nucleotides −29 to −1 in FIGS. 3A–3F(SEQ ID NO:3);
g) 5'-TCAGAGAAGTACACCCATAATCC-3' (SEQ ID NO:13), which is complementary to nucleotides −29 to −7 in FIGS. 3A–3F(SEQ ID NO:3);
h) 5'-AAGTACACCCATAATCC-3' (SEQ ID NO:14), which is complementary to nucleotides −29 to −13 in FIGS. 3A–3F(SEQ ID NO:3).

The antisense molecules should be delivered to cells which express the ObR in vivo, e.g., the choroid plexus and/or hypothalamus. A number of methods have been developed for delivering antisense DNA or RNA to cells; for example, antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore, a preferred approach utilizes a recombinant DNA construct in which the antisense oligonucleotide is placed under the control of a strong pol III or pol II promoter. The use of such a construct to transfect target cells in the patient will result in the transcription of sufficient amounts or single stranded RNAs that will form complementary base pairs with the endogenous obR transcripts and thereby prevent translation of the obR mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid vectors, viral vectors, or other vectors known in the art co be useful For replication and expression of nucleic acids in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304–310), the promoter contained in the 3' long terminal repeat of Rous sarcoma virus (Yamamoto et al., 1980, *Cell* 22:787–797), the herpes thymidine kinase promoter (Wagner et al., 1981, *Proc. Natl. Acad. Sci. USA* 78:1441–1445), the regulatory sequences of the metallothionein gene (Brinster et al., 1982, *Nature* 296:39–42), etc. Any type of plasmid, cosmid, YAC, or viral vector can be used to prepare the recombinant DNA construct which can be introduced directly into the tissue site; for example, the choroid plexus or hypothalamus. Alternatively, viral vectors can be used which selectively infect the desired tissue; (e.g., for brain, herpesvirus vectors may be used), in which case administration may be accomplished by another route (e.g., systemically).

Ribozyme molecules designed to catalytically cleave obR mRNA transcripts can also be used to prevent translation of obR mRNA and expression of ObR. (See, e.g., PCT International Publication WO90/11364, published Oct. 4, 1990; Sarver et al., 1990, *Science* 247:1222–1225). While ribozymes that cleave mRNA at site specific recognition sequences can be used to destroy obR mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, *Nature* 334:585–591. There are hundreds of potential hammerhead ribozyme cleavage sites within the nucleotide sequence of human obR cDNA (FIG. 3). Preferably the ribozyme is engineered so that the cleavage recognition site is located near the 5' end of the obR mRNA; i.e., to increase efficiency and minimize the intracellular accumulation of non-functional mRNA transcripts.

For example, hammerhead ribozymes having the following sequences can be utilized in accordance with the invention:

a) 5'-ACAGAAUUUUGACAAAUCAAAGCAGANNN NUCUGAGNAGUCCUUACUUCAGAGAA-3' (SEQ ID NO:15), which will cleave human obR mRNA between nucleotides −1 and 1 in FIGS. 3A–3F(SEQ ID NO:3);

b) 5'-GGCCCGGGCAGCCUGCCCAAAGCCG-GNNNNCCGGAGNAGUCGCCAGACCGGC UCGUG-3' (SEQ ID NO:16), which will cleave between nucleotides −175 and −176 in FIGS. 3A–3F(SEQ ID NO:3);

c) 5'-UGGCAUGCAAGACAAAGCAGGNNNNCCUGA GNAGUCCUUAAAUCUCCAAGGAGUAA-3' (SEQ ID NO:17), which will cleave between nucleotides 102 and 103 in FIGS. 3A–3F(SEQ ID NO:3);

d) 5'-UAUAUGACAAAGCUGUNNNNACAGAGNAGU CCUUGUGUGGUAAAGACACG-3' (SEQ ID NO:18), which will cleave between nucleotides 994 and 995 in FIGS. 3A–3F(SEQ ID NO:3);

e) 5'-AGCACCAAUUGAAUUGAUGGC-CAAAGCGGGNNNNCCCGAGNAGUCAAC-CGUAACAGU AUGU-3' (SEQ ID NO:19), which will cleave between nucleotides 2142 and 2143 in FIGS. 3A–3F(SEQ ID NO:3);

f) 5'-UGAAAUUGUUUCAGGCUCCAAAGCCG-GNNNNCCGGAGNAGUCAAGAAGAGGACCACA UGUCACUGAUGC-3' (SEQ ID NO:20), which will cleave between nucleotides 2736 and 2737 in FIGS. 3A–3F(SEQ ID NO:3);

g) 5'-GUUUCUUCAGUGAAAUUACACAAAG-CAGCNNNNGCUGAGNAGUCAGUUAGGUCACA CAUC-3' (SEQ ID NO:21), which will cleave between nucleotides 3492 and 3493 in FIGS. 3A–3F(SEQ ID NO:3);

h) 5'-ACCCAUUAUAACACAAAGCUGANNNNUCAG AGNAGUCAUCUGAAGGUUUCUUC-3' (SEQ ID NO:22), which will cleave between nucleotides 3521 and 3522 in FIGS. 3A–3F(SEQ ID NO:3).

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, *Science* 224:574–578; Zaug and Cech, 1986, *Science* 231:470–475; Zaug, et al., 1986, *Nature* 324:429–433; published International patent application No. WO 88/04300 by University Patents Inc.; Been and Cech, 1986, *Cell* 47:207–216). The Cech-type ribozymes have an eight basepair active site that hybridizes to a target RNA sequence, whereafter cleavage of the target RNA takes place. The invention encompasses those Cech-type ribozymes that target eight basepair active site sequences that are present in obR.

As in the antisense approach, the ribozymes can be composed of modified oligonucleotides (e.g. for improved stability, targeting, etc.) and should be delivered to cells which express the ObR in vivo, for example, hypothalamus and/or the choroid plexus. A preferred method of delivery involves using a DNA construct "encoding" the ribozyme under the control of a strong constitutive pol III or pol II promoter, so that transfected cells will produce sufficient quantities of the ribozyme to destroy endogenous obR messages and inhibit translation. Because ribozymes, unlike antisense molecules, are catalytic, a lower intracellular concentration is required for efficiency.

Endogenous obR gene expression can also be reduced by inactivating or "knocking out" the obR gene or its promoter using targeted homologous recombination. (E.g., see Smithies et al., 1985, *Nature* 317:230–234; Thomas & Capecchi, 1987, *Cell* 51:503–512; Thompson et al., 1989, *Cell* 5:313–321; each of which is incorporated by reference herein in its entirety). For example, a mutant, non-functional ObR (or a completely unrelated DNA sequence) flanked by DNA homologous to the endogenous obR gene (either the coding regions or regulatory regions of the obR gene) can be used, with or without a selectable marker and/or a negative selectable marker, to transfect cells that express ObR in vivo. Insertion of the DNA construct, via targeted homologous recombination, results in inactivation of the obR gene. Such approaches are particularly suited in the agricultural field where modifications to ES (embryonic stem) cells can be used to generate animal offspring with an inactive ObR (e.g., see Thomas & Capecchi, 1987, supra and Thompson et al., 1989, supra). However, this approach can be adapted for use in humans provided the recombinant DNA constructs are directly administered or targeted to the required site in vivo using appropriate viral vectors, for example, herpes virus vectors for delivery to brain tissue; for example, the hypothalamus and/or choroid plexus.

Alternatively, endogenous obR gene expression can be reduced by targeting deoxyribonucleotide sequences complementary to the regulatory region of the obR gene (i.e., the obR promoter and/or enhancers) to form triple helical structures that prevent transcription of the obR gene in target cells in the body. (See generally, Helene, C. 1991, *Anticancer Drug Des.* 6(6):569–84; Helene, C. et al., 1992, *Ann. N.Y. Acad. Sci.* 660:27–36; and Maher, L. J., 1992, *Bioassays* 14(12):807–15).

In yet another embodiment of the invention, the activity of ObR can be reduced using a "dominant negative" approach to effectuate weight gain. To this end, constructs that encode defective ObRs can be used in gene therapy approaches to diminish the activity of the ObR in appropriate target cells. For example, nucleotide sequences that direct host cell expression of ObRs in which the CD (e.g., FIGS. 1A–1D(SEQ ID NO:2), amino acid residues 861–894; FIGS. 6A–6F(SEQ ID NO:43), amino acid residues 861–1162; or FIGS. 3A–3F(SEQ ID NO:4), amino acid residues 863–1165), or a portion of the CD (e.g., the box 1 Jak interaction sequence; FIGS. 1A–1D (SEQ ID NO:2) and 6A–6F(SEQ ID NO:43), amino acid residues 861–884; or FIGS. 3A–3F(SEQ ID NO:4), amino acid residues 863–886) is deleted or mutated can be introduced into cells in the choroid plexus or hypothalamus (either by in vivo or ex vivo gene therapy methods described above). Alternatively, targeted homologous recombination can be utilized to introduce such deletions or mutations into the subject's endogenous obR gene in the hypothalamus or choroid plexus. The engineered cells will express non-functional receptors (i.e., an anchored receptor that is capable of binding its natural ligand, but incapable of signal transduction). Such engineered cells present in the choroid plexus or hypothalamus should demonstrate a diminished response to the endogenous Ob ligand, resulting in weight gain.

5.6.2. Restoration or Increase in ObR Expression or Activity to Promote Weight Loss With respect to an increase in the level of normal obR gene expression and/or ObR gene product activity, obR nucleic acid sequences can be utilized for the treatment of body weight disorders, including obesity. Where the cause of obesity is a defective ObR, treatment can be administered, for example, in the form of gene replacement therapy. Specifically, one or more copies of a normal obR gene or a portion of the obR gene that directs the production of an obR gene product exhibiting normal function, can be inserted into the appropriate cells within a patient or animal subject, using vectors which include, but are not limited to, adenovirus, adeno-associated virus, retrovirus, and herpes virus vectors, in addition to other particles that introduce DNA into cells, such as liposomes.

Because the obR gene is expressed in the brain, including the choroid plexus and hypothalamus, such gene replacement therapy techniques should be capable of delivering obR gene sequences to these cell types within patients. Thus, the techniques for delivery of the obR gene sequences should be designed to readily cross the blood-brain barrier. These techniques are well known to those of skill in the art (see, e.g., PCT application, publication No. WO89/10134, which is incorporated herein by reference in its entirety), or, alternatively, should involve direct administration of such obR gene sequences to the site of the cells in which the obR gene sequences are to be expressed. Alternatively, targeted homologous recombination can be utilized to correct the defective endogenous obR gene in the appropriate tissue; e.g., choroid plexus and/or hypothalamus. In animals, targeted homologous recombination can be used to correct the defect in ES cells in order to generate offspring with a corrected trait.

Additional methods that can be utilized to increase the overall level of obR gene expression and/or ObR activity include the introduction of appropriate ObR-expressing cells, preferably autologous cells, into a patient at positions and in numbers which are sufficient to ameliorate the symptoms of body weight disorders, including obesity. Such cells can be either recombinant or non-recombinant. Among the cells that can be administered to increase the overall level of obR gene expression in a patient are normal cells, preferably choroid plexus cells, or hypothalamic cells, which express the obR gene. The cells can be administered at the anatomical site in the brain, or as part of a tissue graft located at a different site in the body. Such cell-based gene therapy techniques are well known to those skilled in the art, see, for example, Anderson, et al., U.S. Pat. No. 5,399,349; Mulligan & Wilson, U.S. Pat. No. 5,460,959.

Finally, compounds, identified in the assays described above, that stimulate or enhance the signal transduced by activated ObR, for example, by activating downstream signalling proteins in the ObR cascade, and thereby by-passing the defective ObR, can be used to achieve weight loss. The formulation and mode of administration will depend upon the physico-chemical properties of the compound. The administration should include known techniques that allow for a crossing of the blood-brain barrier.

5.7. Pharmaceutical Preparations and Methods of Administration

The compounds that are determined to affect obR gene expression or ObR activity can be administered to a patient at therapeutically effective doses to treat or ameliorate weight disorders, including obesity, cachexia, and anorexia. A therapeutically effective dose refers to chat amount of the compound sufficient to result in amelioration of symptoms of body weight disorders.

5.7.1. Effective Dose

Toxicity and therapeutic efficacy of such compounds can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography (HPLC).

10 5.7.2. Formulations and Use

Pharmaceutical compositions for use in accordance with the present invention can be formulated in a conventional manner using one or more physiologically acceptable carriers or excipients.

Thus, the compounds and their physiologically acceptable salts and solvates can be formulated for administration by inhalation or insufflation (either through the mouth or the nose) or oral, buccal, parenteral, or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Capsules and cartridges of, for example, gelatin for use in an inhaler or insufflator can be formulated containing a powder mix of the compound and a suitable powder base such as lactose or starch.

The compounds can be formulated for parenteral administration by injection, for example, by bolus injection or continuous infusion. Formulations for injection can be presented in unit dosage form, for example, in ampoules or in multi-dose-containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, for example, sterile pyrogen-free water, before use.

The compounds can also be formulated in rectal compositions such as suppositories or retention enemas, for example, containing conventional suppository bases such as cocoa butter or other glycerides.

In addition to the formulations described previously, the compounds can also be formulated as a depot preparation. Such long acting formulations may be administered by implantation (e.g., subcutaneously or intramuscularly), or by intramuscular injection. Thus, for example, the compounds can be formulated with suitable polymeric or hydrophobic materials (e.g., as an emulsion in an acceptable oil), or ion exchange resins, or as sparingly soluble derivatives, for example, as a sparingly soluble salt.

The compositions can, if desired, be presented in a pack or dispenser device which can contain one or more unit dosage forms containing the active ingredient. The pack can, for example, comprise metal or plastic foil, such as a blister pack. The pack or dispenser device can be accompanied by instructions for administration.

6. EXAMPLE

In Situ Localization of ObR

In the Example Presented herein, it is demonstrated via binding studies with Ob (leptin)-alkaline phosphatase (AP) fusion proteins that high affinity Ob receptor is present in mammalian choroid plexus tissue. It is further demonstrated that the fusion protein binding observed was Ob-specific, and not due to a non-specific alkaline phosphatase-based artifact.

6.1. Materials and Methods

Construction and Expression of Ob-Alkaline Phosphatase (AP) Fusion Proteins. Two types of fusion protein were generated. Specifically, Ob-AP fusion proteins were generated in which the AP portion was at the carboxyl terminus of the fusion protein, and AP-Ob fusion proteins were generated in which the AP portion was at the amino terminus of the fusion protein.

To produce mouse and human Ob-AP and AP-Ob fusion constructs, cDNA sequences were amplified by standard polymerase chain reaction (PCR) procedures. For mouse and human Ob-AP fusions, nucleotide sequences encoding the entire open reading frames of mouse and human Ob, respectively were amplified from the corresponding cDNAs. Restriction sites at the end of the amplification primers were cut with HindIII and BamHI (mouse) and inserted into the HindIII-BglII polylinker site of APtag-2, or BamHI and BglII (human) and inserted into the BglII site of APtag-2. For mouse and human AP-Ob fusion constructs, a new AP fusion vector expressing an AP molecule with its own signal peptide was first generated (APtag-3) by replacing sequences between the HindIII and XhoI sites of APtag-2 with PCR amplified sequences of secreted placental alkaline phosphatase (including signal sequence). A BglII site was placed so that fusions introduced into this site would be in-frame with the AP protein. The sequences of the predicted mature forms of mouse and human Ob were then PCR amplified from the corresponding cDNAs. Restriction sites at the end of the amplification primers were cut with BamHI and BglII and inserted into the BglII site of APtag-3.

Each plasmid was transiently transfected into COS-7 cells (11.25 $\mu$g/150 mm plate). Cells were grown to confluence and then media-conditioned for 3 days. Cells were then centrifuged, 0.45 $\mu$m filtered, and stored at 4° C. with 20 mM Hepes (pH 7.0) and 0.05% sodium azide. Conditioned media were tested and quantitated for AP activity in a 96-well plate reader as described by Flanagan and Leder (Flanagan, J. G. and Leder, P., 1990, *Cell* 63:185–194), except that homoarginine was omitted from all assays.

In Situ Fusion Protein Binding. Quartered mouse brains, isolated choroid plexus, cells, and cell lines were rinsed once with HBHA (Hank's balanced salt solution with 0.5 mg/ml BSA, 0.1% NaN$_3$, 20 mM HEPES [pH 7.0]) in 12-well plates. Tissue was then incubated with tissue culture supernatants containing AP-Ob fusion, Ob-AP fusion, or control supernatants (i.e., supernatants containing unfused AP only, containing AP-OB or OB-AP fusion proteins plus 80-fold molar excess of *E. coli*-derived recombinant OB, or supernatants from mock-transfected COS cells), for 75 minutes with gentle rotation, at room temperature. Samples were then treated as described previously (Cheng, H. J. and Flanagan, J. G., 1994, *Cell* 79:157–168).

6.2. Results

To search for the ob receptor, Ob-alkaline phosphatase fusion proteins were constructed which would allow colorimetric detection of Ob binding. Specifically, cDNA molecules encoding the mouse and human Ob proteins were inserted into the expression vectors APtag-2 and APtag-3, as described, above, in Section 6.1. Insertion into the expression vector APtag-2 resulted in a fusion. protein with Ob at the N-terminus of the fusion protein and placental alkaline phosphatase (AP) at the C-terminus. The resulting fusion protein is referred to as Ob-AP. Insertion into the vector APtag-3 resulted in fusion proteins with AP at the N-terminus fused to the predicted mature form of the ob protein at the C-terminus. The resulting fusion protein is referred to as AP-Ob. Both forms of murine fusion proteins were secreted and both were produced at the predicted molecular weight of approximately 81 kDa.

Several strategies were employed in an effort to identify cells or tissues expressing the Ob receptor. Each of the cells, cell lines, and tissues tested as described herein were at least potentially involved in body weight regulation. The first strategy employed was to attempt direct binding assays with the Ob-AP and AP-Ob fusion proteins. Cell lines examined by this strategy included the placental cell lines Be Wo (ATCC No. CCL98) and JAR (ATCC No. HTB144); the muscle cell lines L6 (ATCC No. CRL1458) and BC3H (ATCC No. CRL1443); the neural cell lines PC12 (ATCC No. CRL1721) and NB41A3 (ATCC No. CCL147); the preadipose cell line 3T3-L1 (ATCC No. CRL173); and the liver cell line Hepa1-6 (ATCC No. CRL1830). Also tested by this method were primary cultures from hypothalamus and primary cultures from cerebellum. None of these studies yielded positive binding results.

Second, attempts were made to identify cell lines expressing Ob receptor by examining changes in gene expression in response to the presence of recombinant Ob protein. The rationale being that changes in gene expression, whether obR gene expression or the expression of genes further downstream in the Ob/ObR-related signal transduction pathway, would identify cells in which ObR was present.

This analysis was done by standard differential display analysis (see Pardee et al., U.S. Pat. No. 5,262,311) of RNA derived from Ob-treated or untreated cells. Briefly, RNA was isolated from cells which either had or had not been exposed to Ob, and was amplified via RT-PCR in a manner which allowed a direct quantitative comparison of the levels of individual transcripts present in the RNA derived from the Ob-treated cell lines relative to the Ob-untreated cell lines. Ob Cell lines tested by this approach were INS-1, 3T3-L1, Hepa1-6, L6, PC12, NB41A3 and BC3H. In addition, primary hypothalamic cultures were also tested. None of the cells tested exhibited a detectable quantitative difference in expression pattern based on whether the cells had or had not been treated with Ob.

Third, attempts to identify cells expressing Ob receptor were made by treating cells with recombinant Ob protein and assaying for signs of signal transduction pathway activation. Specifically, cAMP changes were monitored via $^3$H uptake, and tyrosine phosphorylation changes were assayed via Western blots treated with anti-phosphotyrosine antibodies. Over twenty cell lines were examined in this manner. Specifically, these cell lines included the mouse cell lines Y1 (adrenal cortex; ATCC No. CCL79), BC3H (smooth muscle-brain tumor; ATCC No. CRL1443), P19 (embryonal carcinoma; ATCC No. CRL1825), 3T3L1 (preadipocyte; ATCC No. CRL173), Hepa1-6 (hepatoma; ATCC No. CRL1830), C2C12 (myoblast; ATCC No. CRL1772), NMUMG (mammary gland, normal epithelial; ATCC No. CRL1636), MM5MT (mammary gland; ATCC No. CRL1637), NB41A3 (neuroblastoma; ATCC No. CCL147), AtT20 (pituitary; ATCC No. CCL89), N MU LI (liver; ATCC No. CRL1638), BNL CL2 (liver; ATCC No. TIB73), and NCTC-1469 (liver; ATCC No. CCL91); rat cell lines, including L6 (myoblast; ATCC No. CRL1458), PC12 (adrenal chromaffin; ATCC No. CRL1721), and H-4-II1-E (hepatoma; ATCC No. CRL1548); and human cell lines, including SW872 (liposarcoma; ATCC No. HTB92), Hepa G2 (liver; ATCC No. HB8065), and neuroblastoma cell lines, including SK-N-SH (ATCC No. HTB11). Again, no Ob-dependent differences were observed in any of the cells tested.

After an extensive search of mammalian cell lines and tissues, adult mouse brains were quartered, treated with AP-Ob fusion protein, washed, and tested for bound AP activity of the fusion protein using histological techniques, as described, above, in Section 6.1. Reproducible binding of the AP-Ob fusion protein was observed in the rodent brain choroid plexus (within the lateral and third brain ventricals). No AP-Ob staining was observed, however, in the brain tissues surrounding the choroid plexus. The choroid plexus is a tissue largely responsible for the generation of the cerebral spinal fluid. Further, choroid plexus tissue is considered to be one of the "guardians" of the blood-brain barrier.

Control AP staining was performed on tissues treated with unfused AP and on tissues that had been treated with AP-Ob in the presence of an excess of unfused Ob added to compete for the binding of the fusion protein. Staining similar to that observed for the Ab-Ob fusion protein was not observed in either of these controls, demonstrating that the AP-Ob binding observed was Ob-specific, and not due to an AP-based artifact.

In summary, therefore, only after employing several strategies, was a cell surface molecule which binds Ob located; and this cell surface molecule was found within a specific region of the brain, the choroid plexus.

7. EXAMPLE

Cloning of the Murine ObR Gene

Described, below, in Section 7.2.1, is the successful cloning of a short form ob receptor cDNA, famj5312, from expression libraries constructed using murine choroid plexus RNA. The expression libraries were screened using AP-Ob fusion protein binding, as described, above, in the Example presented in Section 6. Section 7.2.2, below, describes the nucleotide sequence of the short form Ob receptor coding region and, further, describes the amino acid sequence of the Ob short form receptor protein. Section 7.2.3, below, describes competitive binding studies demonstrating that the protein encoded by the isolated cDNA encodes a receptor exhibiting high affinity binding for both mouse and human Ob protein. Section 7.2.4 describes studies that verify the authenticity of the isolated obR cDNA clone.

The high affinity Ob binding exhibited by the ObR, coupled with its homology to the Class I family of cytokine receptors, as described, below, indicates that the ObR is involved in the control of mammalian body weight, via signal transduction triggered by its binding to ob ligand.

7.1. Materials and Methods

Choroid Plexus mRNA Isolation. Total RNA was isolated from 300 mouse choroid plexuses in batches of 100, using the guanidinium isothiocyanate/CsCl method of Chirgwin et al. (1979, *Biochemistry* 18:5294) as described by R. Selden In Current Protocols for Molecular Biology (4.2.3 Supplement 14). After quantitation, the RNA was diluted to 1 mg/ml in distilled, deionized water and incubated for 30 minutes at 37° C. with an equal volume of DNase solution (20 mM $MgCl_2$; 2 mM DTT, 0.1 units DNase, 0.6 units RNase inhibitor in TE) to remove contaminating DNA. The RNA was extracted with phenol/chloroform/isoamyl alcohol, and ethanol precipitated. After quantitation at 260 nm, an aliquot was electrophoresed to check the integrity of the RNA. A total of 320 µg of total RNA was purified.

Poly $A^+$ RNA was isolated using an Oligotex-dT kit (catalog # 70042) from Qiagen (Chatsworth, Calif.) as described by the manufacturer. After quantitation, the mRNA was ethanol precipitated and resuspended at 1 mg/ml in distilled, deionized, DEPC-treated water. A total of 11 µg of poly $A^+$ RNA was purified.

Library Construction. cDNA was synthesized according to the method of Gubler and Hoffman (*Gene* 25:263, 1983) using a Superscript Plasmid cDNA synthesis kit (Catalog # Series 8248) purchased from Life Technologies (Gaithersburg, Md.). The cDNA obtained was ligated into the NotI/SalI sites of the mammalian expression vector pMET7, a modified version of pME18S, which utilizes the SRα promoter as described previously (Takebe, Y. et al., 1988, *Mol. Cel. Biol.* 8:466). This vector was chosen because it contains a strong eukaryotic promoter, is expressed in COS7 cells, contains the ampicillin resistance gene, and is only 3.0 kb in length. The small size of the vector is important because it increases the probability of cloning large cDNAs. Other comparable vectors are 4.8 kb and larger, thereby increasing the chances of imperfect replication, and reducing the probability of cloning large cDNAs. Ligated cDNA was ethanol precipitated and resuspended in distilled, deionized, DEPC-treated water at 25 ng/ml. One µl of the DNA was transformed by electroporation per 40 µl of electrocompetent DH10B *E. coli* in a 0.1 cm cuvette.

cDNA was synthesized twice and used to construct two independent mouse choroid plexus libraries: mCP (mouse choroid plexus) A and mCP D.

DNA Preparation. Based on titers of the cDNA transformations, 96-deepwell plates were inoculated with 150 cfu/well of primary transformants in 1 ml of Luria broth containing ampicillin (LB-amp). Primary transformants that were grown only 1 hour at 37° C. prior to aliquoting were used to avoid the overgrowth of smaller insert clones and thus underrepresentation of larger clones in the 150 cfu pools. Cultures were grown 15–16 hours at 37° C. with aeration. Prior to prepping, 100 µl of cell suspension was removed and added to 100 µl of 50% glycerol, mixed, and stored at −80° C. (glycerol freeze plate).

DNA was prepared using the Wizard™ Minipreps DNA Purification Systems (Promega, Madison, Wis.; Catalog No. A7100) employing modifications for a 96-well format.

The protocol was as follows:

1) Cultures were centrifuged in 96-deepwell plates at 3200 rpm, for 10 minutes, at 4° C., and the supernatants were removed.
2) 140 µl each of cell resuspension solution (50 mM Tris-HCl (pH 7.5), 10 mM EDTA, 100 µg/ml RNase A), cell lysis solution (0.2 M NaOH; 1.0% SDS) and neutralization solution (1.32 M Potassium acetate, pH 4.8) were added, in order, with vortexing 14 seconds after addition of each reagent, to ensure good mixing.
3) Plates were placed in ice water for 15 minutes.
4) Samples were centrifuged at 3200 rpm, for 10 minutes, at 4° C.
5) Supernatants were transferred to 96-well Polyfiltronics polypropylene filterplate (10 micron, 0.8 ml).
6) 500 µl WP resin were added and incubated 3–5 minutes at room temperature; suction was applied to the plate.
7) Samples were washed three times with 640 µl of the resuspension solution.
8) Samples were centrifuged at 3200 rpm, for 5 minutes, at room temperature, to remove residual buffer.
9) Samples were eluted 2–5 minutes with 40 µl room temperature water.
10) Eluted DNA was centrifuged through to microwell plates at 3200 rpm, for 5 minutes, at room temperature.
11) DNA was quantitated.

Pooling Strategy. The pooling strategy was devised to provide optimal sized pools, 1200 cfu, for transfection and detection, and quick breakdown to the smaller pools of 150. Once a positive pool of 150 was identified, between 400 to 800 individual clones were needed to provide representation of the pool. Using a single pool of 1200 cfu initially would have meant fewer DNA probes but would have required the use of more individual clones (3200–6400) in the final identification step, thereby requiring significantly more time to identify a positive clone.

DNAs totalling 5 µg were pooled equally from eight wells, one column, to give a total of 1200 cfu. Thus, each 96-well plate gave rise to 12 pooled DNAs for transfection into COS-7 cells.

When a positive pool was identified, DNA was prepared from each of the eight wells constituting the pool and retransfected into COS-7 cells. When a positive well was identified, the well was broken down by plating out an aliquot of the glycerol freeze of that well such that several thousand individual colonies were obtained. For each positive well, between 400 and 800 colonies were picked and arrayed in a 96-well format, DNA was obtained, as described above, and the DNA from 24 wells was pooled for transfection. DNA representing each individual clone from a positive row was isolated and transfected for final identification.

Quantitative Ob cell surface binding analysis. Quantitative cell surface binding assays with AP-Ob fusion proteins were performed essentially as described previously for Kit-AP (Flanagan, J. G. and Leder, P., 1990, *Cell* 63:185–194).

Ob Protein. The recombinant murine Ob protein used herein has been described previously (campfield et al., 1995, *Science* 269:546–549). The recombinant human Ob protein used herein was purified from Baculovirus supernatants with a monoclonal antibody column containing monoclonal antibody directed against human ob. The purified recombinant human Ob protein was judged by standard Coomasie blue staining to be greater than 95% pure.

DNA Sequencing. Sequencing and sequence assembly were performed as described previously (International Polycystic Kidney Consortium, 1995, *Cell* 81:289–298).

Northern Analysis. Northern blot analysis of poly $A^-$ mRNA from various tissues (Clontech) was probed, using standard techniques (Chirgwin, J. M. et al. 1979, *Biochemistry* 18:5294–5299), with labeled DNA amplified from sequences encoding the murine ObR extracellular domain.

RT-PCR. Reverse transcription PCR (RT-PCR) reactions were performed on 1 µg total RNA utilizing standard techniques (Zhang, Y. et al., 1994, *Nature* 372:425–432). Specifically, first strand cDNA was prepared using random hexamers. The first strand cDNA was then PCR amplified using primers derived from sequences encoding the ObR extracellular domain or G3PDH control primers.

7.2. Results

7.2.1. Cloning of the OB Receptor From Mouse Choroid Plexus

The strong, Ob-specific binding of the AP-Ob fusion protein to the murine choroid plexus described above, in the Example presented in Section 6, suggested that an ob receptor could be expressed at high levels within this tissue. In order to attempt to clone a cDNA encoding the Ob receptor, therefore, the choroid plexuses from 300 mice were dissected, and a total of 11 µg poly A⁺ RNA was isolated from the tissue to be used to construct cDNA libraries as described above, in Section 7.1.

Initially, 3 µg poly A⁺ were used to generate cDNA, to be used in constructing mouse choroid plexus cDNA library A (mCPA). All of the cDNAs generated that were greater than 500 bp in size (261 ng) were pooled and 90 ng were ligated to pMET7. Transformation of this ligated cDNA into electrocompetent DH10B *E. coli* resulted in a library of approximately $7.2 \times 10^5$ cfu, with an average size of 1 kb.

Recognizing that cDNA library A did not contain a sufficient number of clones containing inserts large enough to encode a receptor at a statistically reasonable frequency, a second 3 µg of poly A⁺ RNA was used to generate 758 ng of cDNA. 32 ng of cDNA representing the largest two fractions of cDNA were pooled and ligated into pMET7. Transformation of these ligated cDNA molecules resulted in mouse choroid plexus library D (mCP D), with $2.4 \times 10^5$ cfu and an average insert size of 2 kb. Using only the largest two fractions of cDNA ensured that the library would be biased towards large cDNAs. This was confirmed by characterizing the insert sizes of ten clones; seven clones had inserts greater than 2 kb in length and no clones were seen with inserts smaller than 1 kb. This was in contrast to the library A where 16 out of 20 clones were smaller than 1 kb.

DNA representing $6 \times 10^5$ cfu (40 plates) was prepared and pooled from the mouse choroid plexus library A. DNA representing $2.4 \times 10^5$ cfu (16 plates) was prepared from mouse choroid plexus library D.

For screening purposes, the libraries were produced as pools of 150 clones, with a mixture of 8 pools being used in each transfection (i.e., 1200 clones/transfection). Pooled DNA was transiently transfected into COS-7 cells, and the cells were screened by incubation with supernatants containing the murine AP-Ob fusion protein, washed, and stained for AP activity in situ, all as described, above, in Sections 6.1 and 6.2. Once a positive pool was identified, the 8 individual subpools were each tested separately, and the resulting positive subpool was further subdivided until a single positive clone was identified.

A total of 632 DNA pools were derived from libraries A and D, with a total of 10 independent positive pools being identified. All of these positive pools were successfully broken down into subpools of 150 clones each, and one positive subpool was further subdivided until a single positive clone was identified. The clone, which contained a 5.1 kB cDNA insert, was designated famj5312.

7.2.2. The Ob Receptor (ObR) and ObR Gene

The famj5312 murine obR cDNA clone isolated, as described above, in Section 7.2.1, contained an insert of approximately 5.1 kb. The nucleotide sequence obtained from this clone is depicted in FIGS. 1A–1D(SEQ ID NO:1). The nucleotide sequence of the clone revealed a single open reading frame, the ObR derived amino acid sequence of which is also depicted in FIGS. 1A–1D (SEQ ID NO:2).

The deduced 894 amino acid sequence of the murine ObR protein begins with a methionine whose codon is within a DNA sequence that is consistent with a translation initiation size. The ObR amino acid sequence begins with a hydrophobic signal sequence from amino acid residues 1–23, which is typical of proteins that are to be either membrane-associated or secreted.

The murine Ob receptor protein contains a single hydrophobic transmembrane domain from amino acid residues 838–860, indicating that the ob receptor spans the cell membrane once.

The position of the transmembrane domain indicates that the extracellular portion of the mature murine ObR protein spans from amino acid residue 24 to amino acid residue 837. A database search reveals that the extracellular domain of ObR contains regions of homology which place ObR into the Class I family of cytokine receptors (for reviews, see, e.g., Heldin, C.-H., 1995, *Cell* 80:213–223; and Kishimoto, T. and Tetsuya, T., 1994, *Cell* 76:253–252). ObR appears to be most closely related to the gp130 signal transducing component of the IL-6 receptor, the GSF receptor and the LIF receptor. Alignment studies of ObR and gp130 amino acid sequences revealed that, although the overall sequence identity between the two proteins is low, the characteristic conserved cysteine residues, the Trp-Ser-X-Trp-Ser motif, and other amino acid residues conserved within the class I family of proteins are clearly evident.

Following the single transmembrane domain, the murine Obr protein contains a short cytoplasmic domain of 34 amino acids (i.e., amino acid residues 861–894). Homology comparisons also reveal that the first twenty three amino acids of the ObR cytoplasmic domain show a 30% identity to membrane proximal sequences of the LIF receptor.

Reverse transcription PCR amplification of obR mRNA from total RNA confirmed the presence of obR transcript (a single band of about 5 kb) in choroid plexus, and also demonstrated its presence in hypothalamus. Further, Northern blot analysis of poly A⁺ RNA derived from several mouse tissues revealed that obR mRNA is present in additional tissues, such as lung and kidney.

7.2.3. The OB Receptor Strongly Binds OB Protein

An analysis of the binding of AP-Ob to the ObR encoded by the obR cDNA described above, in Section 7.2.2, was conducted. The results of this analysis, depicted in FIG. 2, demonstrate that the ObR exhibits strong, Ob-specific binding to both mouse and human Ob protein.

A quantitative analysis of the binding of the AP fusion proteins is shown in FIGS. 2A–2B-1 and 2B-2. After transient transfection of the ObR clone into COS cells, strong binding of 1 nM murine AP-Ob is detected (relative to mock transfected COS cells or ObR transfected COS cells incubated with unfused AP) (FIG. 2A). This binding is nearly completely inhibited by 100 nM untagged recombinant mouse or human leptin protein, demonstrating that this receptor can bind native Ob. A fusion between AP and human Ob also binds mouse ObR with high affinity, as does a fusion protein with mouse leptin at the N-terminus and AP at the C-terminus (Ob-AP). Scatchard analysis of the binding of mouse AP-Ob FIGS. 2B-1 and 2B-2 produced a value for the dissociation constant ($K_D$) of $0.7 \times 10^{-9}$ M.

7.2.4. Authenticity of the famj5312 Clone

The authenticity of the isolated obR famj5312 clone was tested in several ways. First, 8 independently isolated clones (in subpools of 150 clones each) were PCR amplified with primers made to obR sequences 3' of the stop codon. Sequencing verified that all 8 clones contained the same 3' untranslated sequences. In addition, the regions of 5 independently isolated clones encoding the ObR C-terminus were sequenced and each was shown to utilize the same stop codon. Finally, reverse transcription PCR (rt-PCR) of choroid plexus total RNA isolated from a different mouse strain (C57/BLKsJ) than that from which the cDNA libraries were derived generated an identical PCR product containing a stop codon in the same location. These data indicated that the isolated famj5312 cDNA clone was neither a chimeric clone nor was it the result of a rare aberrant splicing event, but, rather, represents a clone which encodes the predominant form of the ObR receptor in the choroid plexus.

7.2.5. Cloning Mouse Long Form ObR Encoding Nucleic Acids

As described herein, we have cloned the murine ObR long form. In order to find the mouse homolog of the human long form of the obR gene FIGS. 3A–3F(SEQ ID NO:3), semi-nested PCR was performed on first strand cDNA isolated from mouse hypothalamus, Ks, and choroid plexus, db and Ks, with 5' primers from the region just before mouse short form starts to diverge from the human long form, and 3' degenerate primers designed from the human ObR homolog intracellular region. The complete transcript was further characterized by 3' RACE.

Total. mRNA was prepared from C57B1/KS (KS) and C57B1/KS-db (db) choroid plexus and hypothalamus. cDNA was reverse-transcribed from 1 $\mu$g of cDNA of mRNA using random hexamer or oligo dT as primer with Superscript Reverse Transcriptase from GIBCO-BRL. A total 24 $\mu$g of cDNA was made. For PCR, cDNA was diluted 1:200 and 3 $\mu$g of the diluted cDNA was used in a 25 $\mu$l reaction.

The first round of PCR reactions used a 5' primer encoding the mouse ObR protein sequence PNPKNCSW (SEQ ID NO:29), and consisting of nucleotides 5'-CCAAACCCCAAGAATTGTTCCTGG-3' (SEQ ID NO:30), and a reverse degenerate primer complementary to the nucleotide sequence encoding KIMENKMCD (SEQ ID NO:31), adjacent to the carboxy terminus of the human long form and consisting of nucleotides 5'-TC(GA)CACAT(CT)TT(GA)TT(GATC)CCCATTATCTT-3' (SEQ ID NO:32).

For the second round of PCR reactions, the 3' primer was the same, and the 5' primer, which was internal to the previous 5' primer, encoded the mouse ObR protein sequence AQGLNFQK (SEQ ID NO:33), and consisted of nucleotides 5-GCACAAGGACTGAATTTCCAAAAG-3' (SEQ ID NO:34).

PCR reactions were carried out as described above, except the nested PCR profile was 94° C. for 3 minutes; 94° C. for 30 seconds, 57° for 30 seconds, 72° C. for 40 seconds for 30 cycles; 72° C. for 5 minutes for one cycle.

DNA sequencing was performed on the automatic ABI 373A and 377 DNA sequencer by using the Taq cycle™ sequencing kit (Applied Biosystems, Foster City, Calif.). Sequence analysis was performed using Sequencher.

Semi-nested PCR of the nucleic acids encoding the intracellular domain of murine long form ObR was also performed on mRNA isolated from hypothalamus in order to obtain sufficient quantities of a specific PCR product encoding the mouse long form of obR gene. Sequencing of the PCR product FIGS. 6A–6F(SEQ ID NO:42) confirmed that this DNA encodes the mouse homolog of the long form of ObR. The transcripts of the short and long forms are identical until the fifth codon 5' of the stop codon of the short form and then diverge completely, suggestive of alternative splicing. The deduced amino acid sequences from mouse long form and the human ObR are homologous throughout the length of the coding region and share 75% identity FIGS. 7A–7B.

7.2.6. Expression Profile or ObR mRNA

As a first step in understanding the tissue distribution of ObR, the expression of its mRNA was examined in various murine tissues. To this end, Northern blot analysis of poly A$^+$ mRNA (2 $\mu$g/lane) obtained from various mouse tissues (heart, brain, spleen, lung, liver, skeletal muscle, kidney, and testes; Clontech, Palo Alto, Calif.) was probed with labelled DNA amplified from sequences encoding the ObR extracellular domain. Hybridizations were done in Rapid-hyb™ buffer (Amersham) at 65° C. following the manufacturer's instructions.

In most tissues, the obR mRNA appears as a single band, slightly larger than 5 kb, indicating that the 5.1 kb cDNA clones described herein are full-length. Of the tissues assayed, expression was seen in lung, kidney, and total brain. No expression was detected in testes.

RT-PCR amplification of the obR mRNA from total RNA confirmed the presence of this transcript in choroid plexus and also demonstrated its presence in hypothalamus. The RT-PCR reactions were performed on 1 $\mu$g total RNA isolated from mouse choroid plexus or hypothalamus. Tissues were isolated from db/db mice (C57B1/BLKsJ background) or +/+ littermate controls. First strand cDNA, prepared using random hexamers, was PCR amplified using primers derived from sequences encoding the ObR extracellular domain or G3PDH control primers. No bands were detected from the amplification of mock reverse-transcribed total RNA controls run in parallel.

8. EXAMPLE

The obR Gene is the db Gene

The experiments and studies described below demonstrate that the obR gene maps to the db locus, and that the obR gene in db mice is a mutant form of obR that results in transcription of an aberrantly spliced mRNA having a 106 nucleotide insert resulting in a truncated long form murine ObR protein that is identical to murine short form ObR.

8.1. The obR Gene Maps Within the db Genetic Interval

In the Example presented herein, studies are described which indicate that the obR gene maps to a 4 to 5 cM region on mouse chromosome 4 which represents the same region to which the db locus maps.

8.1.1. Materials and Methods

PCR Amplification. The following famj5312-derived primers were used for amplification of mouse genomic DNA: forward primer, 5'-GCTGCACTTAACCTGGC-3' (SEQ ID NO:23);reverse primer, 5'-GGATAACTCAGGAACG-3' (SEQ ID NO:24).

The PCR reaction mixture contained 6 $\mu$l of template DNA (10 ng/$\mu$l), 1.4 $\mu$l 10× Perkin Elmer (Norwalk, Conn.) PCR buffer, 1.12 $\mu$l dNTPs (2.5 mM), 1.05 $\mu$l Forward primer (6.6 $\mu$M), 1.05 $\mu$l Reverse primer (6.6 $\mu$M), 0.38 $\mu$l H$_2$O and 3 $\mu$l AmpliTaq Hotstart™ polymerase (Perkin Elmer; 0.5 U/$\mu$l).

The amplification profile was as follows: 94° C., 2 minutes, at which point the ampliTaq was added, then 30 cycles of 94° C. for 40 seconds, 55° C. for 50 seconds, and 72° C. for 30 seconds.

A second set of primers were utilized under the same conditions except that the 55° C. cycle was conducted at 52° C.: forward primer, 5'-CACTATTTGCCCTTCAG-3' (SEQ ID NO:25); reverse primer, 5'-GCCTGAGATAGGGGTGC-3' (SEQ ID NO:26).

Electrophoresis. Samples were run on both nondenaturing 8% acrylamide gels run at 45 W, room temperature, for 3 hours and nondenaturing 10% acrylamide SSCP (single stranded conformational polymorphism) gels run at 20 W, 4° C., for 2.5 hours.

Both types of gels were stained with SYBR Green I and scanned on an MD Fluorimager™. Both types of gels gave interpretable results.

8.1.2. Mapping of the famj5312 obR cDNA Clone

PCR primers were designed from the coding sequence of famj5312 cDNA, as described in Section 8.1. These primers amplified a 192 bp fragment from C57B1/6J genomic DNA, consistent with the base pair length between the two primers in the obR cDNA, and a 195 bp fragment from the wild-type derived *Mus spretus* strain SPRET/Ei. The 3 bp insertion in the *Mus spretus* allele codes for an additional Asn between amino acid residues 45 and 46. The genetic segregation of the *Mus spretus* 195pb allele of ObR was followed in 182 backcross progeny of the cross (C57B1/6J×*Mus spretus*) $F_1$ females×C57B1/6J males by both Single Stranded Conformational Polymorphism (SSCP) gel electrophesis and non-denaturing gel electrophoresis for size determination. The segregation pattern of the *Mus spretus* allele was compared to the segregation pattern of 226 other genetic loci that have been mapped in this backcross panel. By minimizing the number of multiple crossovers between obR and other markers, it was determined that obR maps to murine chromosome 4, approximately 2.2±1.6 cM distal to the marker D4Mit9 and 4.6±1.6 cM proximal of the marker D4Mit46. The genetic map position of obR was further refined by mapping additional genetic markers. The obR gene maps 0.6±0.6 cM distal from D4Mit255 and 0.6±0.6 cM proximal of D4Mit155; see FIG. 8.

Additional primer pairs were designed (forward=5'-CACTATTTGCCCTTCAG-3' (SEQ ID NO:27); reverse 5'-GCCTGAGATAGGGGTGC-3' (SEQ ID NO:28)) from the 3' sequence of famj5312 cDNA, which also revealed a polymorphism on SSCP gels between C57B1/6J genomic DNA and that of the wild derived *Mus spretus* strain SPRET/Ei. Again this permitted the genetic mapping of famj5312 cDNA, now using a different fragment of the clone. The mapping of this polymorphism was 100% concordant with the mapping of famj5312 reported above, both confirming the mapping of obR and indicating that the famj5312 cDNA clone was not chimeric.

8.1.3. Definition of the Murine db Genetic Region

The mouse db gene was originally mapped to mouse chromosome 4 (Hummel, K.-P. et al., 1966, *Science* 153:1127–1128). This genetic localization has been refined (Bahary et al., 1990, *Proc. Natl. Acad. Sci. USA* 87:8642–8646; Bahary et al., 1993, *Genomics* 16:113–122) to place db within a genetic interval of 1.5 cM between the proximal Ornithine decarboxylase 4 (Odc4) locus and the anonymous distal markers D4Rck22 and D4Rck69. Bahary et al. 1993, supra, also report D4Mit205 as being 1.1 cM proximal to Odc4. Hence, relative to D4Mit205, the db gene was mapped approximately 2.2 cM distal.

The db allele originally arose on the C57B1/BLKsJ inbred strain. The db mutation has subsequently been transferred to other genetic backgrounds to form congenic strains. By typing animals of the congenic strain C57B1/6J-m db, it was possible to define the genetic interval within which the db gene had to reside on mouse chromosome 4. By this analysis, the interval that must contain the db gene was defined as the approximate 4 cM between the proximal anonymous DNA marker D4Mit255 and the distal markers D4Mit331 and D4Mit31. (Genetic distance as defined on the Mit map; Dieteich et al., 1994, *Nature Genetics* 7:220–245; Copeland et al., 1993, *Science* 262:67;

Whitehead Institute/MIT Center for Genome Research, Genetic Map of the Mouse, Database Release 10, Apr. 28, 1995). It should be noted that the interval defined by Bahary et al. 1993, supra, appears to be a few centimorgans proximal of the region as defined herein. See FIG. 8, in which the distance between D4Mit255 and D4Mit31 is about 5.1 cm.

By comparing the mapping data for famj5312 with the db mapping data described above, the map position of famj5312, 0.6±0.6 cM distal from D4Mit255 and 0.6±0.6 cM proximal of D4Mit155, is in complete accordance with obR being the db gene.

8.2. The obR Mutation in db Mice Results in a Truncated Long Form Receptor

8.2.1. Materials and Methods

Total mRNA was prepared from C57B1/KS (KS) and C57B1/KS-db (db) choroid plexus and hypothalamus. cDNA was reverse-transcribed from 1 μg of cDNA of mRNA using random hexamer or oligo-dT as primers with Superscript™ Reverse Transcriptase from GIBCO-BRL. A total 24 μg of cDNA was made. For PCR, cDNA was diluted 1:200 and 3 μg of the diluted cDNA was used in a 25 μl reaction.

From the mouse short form cDNA clone, famj53 12, and the long form cDNA clone FIGS. 6A–6F, primers were designed covering the entire coding region of both the short and long forms of obR cDNA. Overlapping PCR fragments with an average size of 600 bp were generated from each sample. PCR products were electrophoresed on an 0.8% low melting agarose gel. DNA was isolated from the gel and agarased. Agarased DNA fragments were sequenced with both end primers as well as internal primers.

PCR Conditions. The 25 μl PCR reaction contained 2 mM MgCl$_2$, 0.5 mM of each primer, 200 mM each of dATP, dTTP, dCTP and dGTP, and 0.5 units of Taq polymerase in 1× Taq polymerase buffer (Perkin-Elmer). All PCR reactions were performed in the GeneAmp™ PCR System 9600 (Perkin-Elmer). Unless otherwise described, the general PCR profile was 94° C. for 3 minutes; 94° C. for 10 seconds, 57° C. for 10 seconds, 72° C. for 40 seconds for 35 cycles; and 72° C. for 5 minutes, for one cycle.

DNA sequencing and Sequence Analysis. DNA sequencing was performed on the automatic ABI 373A and 377 DNA sequencer by using the Taq cycle sequencing kit (Applied Biosystems, Foster City, Calif.). Sequence analysis was performed using Sequencher.

8.2.2. Results

Semi-nested PCR was performed on mRNA isolated from choroid plexuses of KS and db mice. The PCR product generated using the db cDNA as template was approximately 100 bp longer than that using Ks DNA as template. The PCR products from both were directly sequenced. No sequence difference was detected within the coding sequence of the short form of the mRNA species expressed in the choroid plexus of these mice. However, upon the sequencing of the PCR product that was generated starting from the transmembrane domain shared by the two forms and ending in the intracellular domain specific for the long form, a difference became apparent between db/db and control in several tissues. The sequencing data showed that the putative db long form of obR has an additional 106 bp insertion in the normal long form transcript (FIG. 9). This 106 bp includes sequence encoding the last five amino acids, stop codon as well as 88 bp 3' UTR region of the short form. The db long form produces a truncated ObR protein identical to the short form which lacks the intracellular domain. The normal long form was not detected in any db tissues, nor was the db long form detected in control tissues.

To understand the mechanism of this apparent splicing error, the obR genomic sequences of the db/db and control mice were compared. A single nucleotide change of G→T was discovered 2 bp immediately after the 106 bp insertion site in db/db mice. This change creates a splice donor which converts the 106 bp fragment to an exon inserted in the db long form. Because of this insertion, the db long form produces only a truncated protein, which does not have the intracellular signal domain. Since the class I cytokine receptors to which ObR is most closely related all have a long intracellular domain, the long intracellular domain of the long form is crucial for initiating intracellular signal transduction. These data support the role of this receptor in weight modulation, and the failure to produce ObR long form as the cause of the severe obese phenotype in db/db mice.

9. EXAMPLE

Cloning ObR Encoding Nucleic Acids

Described herein is the cloning and identification of cDNA and gemonic DNA which encode human obR.

9.1. Cloning the Human Obr cDNA

The famj5312 cDNA insert was used to probe a human fetal brain cDNA library in the Uni-Zap XR™ vector obtained from Sratagene (La Jolla, Calif.). A cDNA library generated from a human fetal brain was chosen because of the likelihood that this library would contain cDNAs present in the entire brain, including the choroid plexus, the tissue source of the mouse obR cDNA, as well as cDNAs present in the hypothalamus.

The cDNA library was plated on 20 plates with approximately 50,000 pfu/plate. Duplicated filter lifts were done on each plate with Amersham Hybond-N™ nylon membrane filters. The filters were denatured, neutralized, and cross-linked according to standard procedures. The probe was radioactively labelled by random priming in the presence of $^{32}P$ labelled nucleotide. The filters were hybridized with probe overnight at 65° C. in Church's buffer (7% SDS, 250 mM NaHPO$_4$, 2 µM EDTA, 1% BSA). The next day, filters were washed in 2×SSC/0.1% SDS for 20 minutes at 65° C., then in 0.1×SSC/0.1% SDS for 10 minutes. They were then exposed to Kodak film at −80° C. for 5 hours.

After matching duplicated filters, 13 duplicated signals were observed. Secondary plating was followed by plating out 10 µl of 1:1000 dilution of each primary plug. The same probe, hybridization and wash conditions were used as above. Film was exposed at 80° C. for 2 hours. Only 1 of the 13 original positives produced a duplicate signal on the film.

Four independent plaques from the positive plate were processed and excised with ExAssist™ helper phage, XL1-Blue cells and SOLR cells, as described by Stratagene. Excision products were then plated out on LB/Amp plates and incubated at 37° C. overnight. One white colony was picked up from each plate and grown in liquid LB/Amp at 37° C. overnight. The next day, mini-preps were done with the Promega Wizard™ Mini-prep kit. The sizes of the inserts were determined by digesting the mini-prep products with EcoRI and XhoI. One of the four clones (d) had an insert of approximately 6 kb.

DNA for sequencing was prepared using a Qiagen Plasmid Maxi kit.

FIGS. 3A–3F depicts the nucleotide sequence (SEQ ID NO:3) of human obR cDNA encoding the signal sequence (amino acid residue 1 to about amino acid residue 20), extracellular domain (from about amino acid residue 21 to about amino acid residue 839), transmembrane domain (from about amino acid residue 840 to about amino acid residue 862), and cytoplasmic domain (from about amino acid residue 863 to about amino acid residue 1165).

9.2. Cloning Human obR Genomic DNA

As described herein, human obR genomic DNA has been cloned.

The famj5312 cDNA insert was used to probe human high density PAC filters purchased from Genome Systems Inc. (Catalog No. FPAC-3386). The probe was random prime labelled using the Prime-It™ kit (Stratagene; Catalog No. 300392). The hybridization was carried out in Amersham Rapid-hyb™ buffer according co the manufacturer's recommendations. The filters were then washed in 2×SSC/1% SDS at 65° C. and exposed to Kodak film at −80° C.

Eleven putative positive PAC clones were identified. Their grid position was determined, and the clones were purchased from Genome Systems, Inc.

The clone at grid position P298-K6, which we have designated hobr-p87, was further validated as containing the entire ObR coding region by PCR testing with primer pairs from the 5' (obRF4 and obRR4) and 3' (obRS and obRO) ends of the obR open reading frame. The primers used in this validation were as follows:

obRF4:  5'-CTGCCTGAAGTGTTAGAAGA-3';  (SEQ ID NO:35)

obRR4:  5'-GCTGAACTGACATTAGAGGTG-3';  (SEQ ID NO:36)

obRS:  5'-ACCTATGAGGACGAAAGCCAGAGAC-3';  (SEQ ID NO:37)

obRO:  5'-TGTGAGCAACTGTCCTCGAGAACT-3'.  (SEQ ID NO:38)

The hobr-p87 clone was deposited with the ATCC on Dec. 28, 1995.

10. EXAMPLE

Construction of ObR Immunoglobulin Fusion Proteins

10.1 Preparation of OBR-IG Fusion Proteins

The extracellular portion of human ObR is prepared as a fusion protein coupled to an immunoglobulin constant region. The immunoglobulin constant region may contain genetic modifications including chose which reduce or eliminate effector activity inherent in the immunoglobulin structure. (See, e.g., PCT Publication No. WO88/07089, published Sep. 22, 1988). Briefly, PCR overlap extension is applied to join DNA encoding the extracellular portion of human ObR to DNA encoding the hinge, CH2 and CH3 regions of human IgG1. This is accomplished as described in the following subsections.

10.2. Preparation of Gene Fusions

PCR reactions are prepared in 100 µl final volume composed of Pfu polymerase and buffer (Stratagene) containing primers (1 µM each), dNTPs (200 µM each), and 1 ng of template DNA.

DNA fragments corresponding to the DNA sequences encoding the ObR ECD, or a portion thereof that binds Ob, are prepared by polymerase chain reaction (PCR) using primer pairs designed so as to amplify sequences encoding the entire human ObR ECD as well as a small amount of 5' noncoding sequence. For example, the forward primer: 5'-GTCACGATGTCGACGTGTACTTCTCTGAAGT AAGATGATTTG-3' (SEQ ID NO:39) corresponds to nucleotides –20 to +8 in FIGS. 3A–3F(SEQ ID NO:3) with an additional 14 nucleotides (containing a SalI site) at the 5' terminus. The reverse primer: 5'-GTCAGGTCAGAAAAGCTTATCACTCTGTGTTT TTCAATATCATCTTGAGTGAA-3' (SEQ ID NO:40) corresponds to the complement of nucleotides +2482 to +2517 in FIGS. 3A–3F(SEQ ID NO:3), with an additional 18 nucleotides (containing a HindIII site) at the 5' terminus. A cDNA encoding human ObR serves as the template for amplifying the extracellular domain. PCR amplification with these primers generates a DNA fragment that encodes ObR extracellular domain.

In a second PCR reaction, a second set of primers are designed to amplify the IgG constant region (i.e., the hinge, CH2, and CH3, domains) such that the reverse primer has an unique restriction site and the sequence of the forward primer has a 5' terminus that is complementary to the 5' terminal region of the reverse primer used in the ObR ECD amplification, supra (i.e., 5'-AAGCTTTTCTGACCTGACNNN-3' (SEQ ID NO:41)) and that will enable the open reading frame in the ObR encoding nucleotide sequence to continue throughout the length of the IgG nucleotide sequence to be amplified. The template DNA in this reaction is the 2000 nucleotide segment of human IgG heavy chain genomic DNA (Ellison et al., 1982, *Nuc. Acids. Res.* 10:4071–4079).

The complete human obR-IgG fusion segment is prepared by an additional PCR reaction. The purified products of the two PCR reactions above are mixed, denatured (95° C., 1 minute) and then renatured (54° C., 30 seconds) to allow complementary ends of the two fragments to anneal. The strands are filled in using dNTPs and Taq polymerase and the entire fragment amplified using forward PCR primer of the first PCR reaction and the reverse PCR primer of the second PCR reaction. For convenience of cloning into the expression vector, the resulting fragment is then cleaved with restriction enzymes which recognize unique designed sites in the forward PCR primer of the first PCR reaction and the reverse PCR primer of the second PCR reaction. This digested fragment is then cloned into an expression vector that has also been treated with these restriction enzymes.

Sequence analysis is used to confirm structure, and the construct is used to transfect COS cells co test transient expression.

Those skilled in the art are aware of various considerations which influence the choice of expression vector into which the obR-IgG fusion segment is to be cloned, such as the identity of the host organism and the presence of elements necessary for achieving desired transcriptional and translational control. For example, if transient expression is desired, the obR-IgG fusion segment generated supra can be cloned into the expression vector pcDNA-1 (Invitrogen). Alternatively, stable expression of the fusion protein can be achieved by cloning the obR-IgG fusion segment into the expression vector pcDNA-3 (InVitrogen).

Alternatively, mouse and/or human obR-IgG fusion proteins can be generated using an expression vector such as the CD5-IgG1 vector (described by Aruffo et al., 1990, *Cell* 61:1303–1313), which already contains the IgG constant region. According to this method, the DNA fragment encoding the ObR extracellular domain is generated in a PCR reaction so that the open reading frame encoding the ObR extracellular domain is continuous and in frame with that encoding the IgG constant region.

For example, the extracellular domains (including signal peptides) of mouse and human ObR were PCR amplified with Extaq (PanVera Corp.). The following primers were used for amplification of mouse and human ObR in first generation expression constructs. Mouse: Forward primer, 5'-CCCAATGTCGACATGATGTGTCAGAAATTCTAT-3' (SEQ ID NO:45), Reverse primer, 5'-AAAAAGGATCCGGTCATTCTGCTGCTTGTCGAT-3' (SEQ ID NO:46). Human: Forward primer, 5'-CCCAATGTCGACATGGTGTACTTCTCTGAAGTA-3, (SEQ ID NO:47), Reverse primer, 5'-TTTTTGGATCCCACCTGCATCACTCTGGTG-3' (SEQ ID NO:48).

Each forward primer above contains a SalI restriction site and each reverse primer above contains a BamHI restriction site. After amplification using the mouse and human obR cDNAs as templates, the resulting PCR fragments were cloned into the XhoI/BamHI sites of the CD5-IgG vector (Aruffo et al., 1990, *Cell*). The resulting vectors were transiently transfected into COS cells and conditioned media was generated. Immunoprecipitation (IP) of the conditioned media with protein A and analysis by SDS PAGE revealed that the mouse obR IgG fusion was expressed at greater levels than human ObR-IgG. To improve expression of the human ObR-IgG fusion, primers were designed which amplified the extracellular domain of human ObR (without the signal peptide), and this fragment was coligated with sequences encoding the signal-peptide of mouse ObR into the CD5-IgG vector. The following primers used for amplification of the human ObR ECD fragment that was fused with mouse ObR signal peptide. Forward primer, 5'-TTTAACTTGTCATATCCAATTACTCCTTGGAG ATTAAGTTGTCTTGC-3' (SEQ ID NO:49); reverse primer, 5'-TTTTTGGATCCCACCTGCATCACTCTGGTG-3' (SEQ ID NO:50).

After amplification, restriction enzyme digestion, and subcloning, the resulting construct was transiently expressed in COS cells. IP and SDS-PAGE analysis of the resulting conditioned media showed successful expression of the 170 kDa human ObR IgG fusion. An alternative method for enhancing the expression of immunoglobulin fusion proteins, involves insertion of the ObR extracellular domain (not including the signal peptide) into the CD5-IgG1 vector in such a manner that the CD5 signal peptide is fused to the mature ObR extracellular domain. Such a signal peptide fusion has been shown to improve expression of immunoglobulin fusion proteins.

10.3. Preparation of Modified CH2 Domains

The nucleotide sequence of the obR-IgG gene fusion generated supra, can be modified to replace cysteine residues in the hinge region with serine residues and/or amino acids within the CH2 domain which are believed to be required for IgG binding to Fc receptors and complement activation.

Modification of the CH2 domain to replace amino acids thought to be involved in binding to Fc receptor is accomplished as follows. The plasmid construct generated supra, provides the template for modifications of the ObR-IgCγ1 CH2 domain. This template is PCR amplified using the forward PCR primer described in the first PCR reaction supra and a reverse primer designed such that it is homologous to the 5' terminal portion of the CH2 domain of IgG1 except for five nucleotide substitutions designed to change amino acids 234, 235, and 237 (Canfield, S. M. and Morrison, S. L., 1991, *J. Exp. Med.* 173:1483–1491) from Leu to Ala, Leu to Glu, and Gly to Ala, respectively. Amplification with these PCR primers yields a DNA fragment consisting of a modified portion of the CH2 domain. In a second PCR reaction, the template is PCR amplified with the reverse primer used in the second PCR reaction supra, and a forward primer which is designed such that it is complementary to the Ig portion of the molecule and contains the five complementary nucleotide changes necessary for the CH2 amino acid replacements. PCR amplification with these primers yields a fragment consisting of the modified portion of the CH2 domain, an intron, the CH3 domain, and 3' additional sequences. the complete obR-IgCγ1 segment consisting of a modified CH2 domain is prepared by an additional PCR reaction. The purified products of the two PCR reactions above are mixed, denatured (95° C., 1 minute) and then renatured (54° C., 30 seconds) to allow complementary ends of the two fragments to anneal. The strands are filled in using dNTP and Taq polymerase and the entire fragment is amplified using the forward PCR primer of the first PCR reaction and the reverse PCR primer of the second PCR reaction. For convenience of cloning into the expression vector, the resulting fragment is then cleaved with restriction enzymes recognizing sites specific to the forward PCR primer of the first PCR reaction and the reverse PCR primer of the second PCR reaction. This digested fragment is then cloned into an expression vector that has also been treated with these restriction enzymes.

Sequence analysis is used to confirm structure, and the construct is used to transfect COS cells to test transient expression. hIgG ELISA is used to measure/confirm transient expression levels approximately equal to 100 ng protein/ml cell supernatant for the construct. CHO cell lines are transfected for permanent expression of the fusion proteins.

10.4. OBR-Ig Neutralizes Ob Protein

To establish whether the ObR-IgG fusion proteins were capable of binding and neutralizing OB protein (leptin) in vitro and in mice, large scale transient transfections were performed in 293 cells using the mouse ObR-IgG fusion protein. The ObR-IgG protein was purified to near homogeneity on a protein A column and analyzed for its ability to inhibit the binding of an alkaline phosphatase-OB fusion protein (AP-OB) to cell surface ObR.

COS cells were transiently transfected with mouse obR cDNA and tested for their ability to bind 0.5 nM AP-OB. As demonstrated in FIG. 10, purified ObR-IgG was able to potently inhibit, or neutralize, the binding of AP-OB fusion protein to cell surface ObR.

FIG. 10, column 1, shows the high levels of specific binding observed in the absence of ObR-IgG fusion protein. Columns 2, 3, and 4 show the near complete inhibition of binding observed with three different column fractions of purified ObR-IgG.

11. The OBR Long-Form has Signalling Capabilities of IL-6 Type Cytokine Receptors To address whether the cloned ObR isoforms are signaling competent, the ObR gene was introduced into established tissue culture cell lines, and the cell response to OB treatment was compared with that mediated by the structurally-related IL-6 type cytokine receptors. The results presented in this example provide evidence that the ObR long form is a signal-transducing molecule and shares functional specificity with IL-6-type cytokine receptors.

11.1. Materials and Methods

11.1.1 Cells

COS-1, COS-7, H-35 (Baumann et al., 1989, *Ann. N.Y. Acad. Sci.* 557:280–297), HepG2, and Hep3B (Lai et al., 1995, *J. Biol. Chem.* 270:23254–23257) cells were cultured as described. The cells were treated in medium containing 0.5% fetal calf serum alone or supplemented with 1 $\mu$M dexamethasone, 0.1–1000 ng/ml human OB, 1000 ng/ml mouse OB, IL-6 (Genetics Institute) or G-CSF (Immunex Corp.). To inhibit signaling by gp130, the cells were treated wit. the combination of two pan-blocking monoclonal antibodies against human gp130, B-R3 (Chevalier et al., 1995, *N.Y. Acad. Sci.* 762:482–484) and 144 (20 $\mu$g/ml).

11.1.2. Expression Vectors and CAT Reporter Gene Constructs

Expression vectors for the long form of human ObR and the short form of mouse ObR are described above (Sections 7–9). The truncated human G-CSFR(27) (Ziegler et al., 1993, *Mol. Cell. Biol.* 13:2384–2390) and rat STAT1, STAT3 and STAT5B (Lai et al., 1995, *J. Biol. Chem.* 270:23254–23257; Ripperger et al., 1995, *J. Biol. Chem.*, 270:29998–30006) have been described. ObR with a mutated box 3 sequence (Y1141F) was generated by overlap extension PCR using synthetic oligonucleotides encoding the specified amino acid substitution (Higuchi et al., 1988, *Nucleic Acids Res.* 12:5707–5717). The y1141F contains a replacement of the tyrosine at position 1141 with phenyalanine. Plasmid SV-SPORT1 (Life Technologies, Inc.) containing rat STAT3 truncated by 55 carboxy-terminal residues has been generated by converting codons 716 and 717 into two stop codons. The CAT reporter gene constructs, pHRRE-CAT and pIL-6RE-CAT, have been described previously (Lia et al., 1995, *J. Biol. Chem.* 270:23254–23257; Morella et al., 1995, *J. Biol. Chem.* 270:8298–8310)

11.1.3. Cell Transfection and Analysis

COS-1, H-35 and Hep3B cells were transfected with plasmid DNA by the DEAE-dextran method (Lopata et al., 1989, *Nucleic Acids Res.* 12:5707–5717); HepG2 cells by the calcium phosphate method (Graham et al., 1973, *Virology* 52:456–461); and COS-7 cells by the lipofectamine method. Subcultures of COS cells were maintained for 16 hours in serum-free medium prior to the activation of STAT proteins by treatment with cytokines for 15 minutes. DNA binding by STAT proteins was determined by EMSA on whole cell extracts as described in Sadowski et al. (1993, *Science* 26:1739–1744). Double stranded oligonucleotides for the high affinity SIEm67 (Sadowski et al., 1993, *Science* 25:1739–1744) and TB-2 (Ripperger et al., 1995, *J. Biol. Chem.* 270:29998–30005) served as EMSA substrates. CAT gene-transfected cell cultures were treated for 24 hours with cytokines or OB. CAT activities were quantitated by testing serial dilutions of cell extracts, normalized to the expression of the cotransfected marker plasmid pIE-MUP (Morella et al., 1995, *J. Biol. Chem.* 270:3298–8310), and are expressed relative the value of the untreated control cultures in each experimental series (defined as =1.0). Quantitative cell surface binding of the AP-OB fusion protein (Section 6) was done essentially as outlined by Cheng and Flanagan (1994, Cell 79:157–168).

11.2. Results and Discussion

11.2.1. OBR Activates STAT Proteins

To determine whether ObR has the ability to recruit the cellular signaling machinery, COS cells were transiently transfected with expression vectors for the two representative forms of ObR, mouse short form (also corresponding to a mutated form detected in db/db mice) and human long form. Two days after transfection, cells were incubated in 1 nM human or mouse alkaline phosphatase-OB, and cell surface expression of ObR was detected as indicated by specific binding of the alkaline phosphatase-OB (AP-OB) fusion protein. Transfection of the short form ObR resulted in approximately 10-fold higher binding than the long form. Scatchard transformation of binding data performed at multiple AP-OB concentrations indicated that the lower binding observed For the long form was mainly a result of reduced cell surface expression. The mouse short form bound both the murine and human ligands with an affinity of 0.7 nM, and the human long form bound both the murine and human ligands with an affinity of 1.0 nM.

COS-1 cells were co-transfected with expression vectors for human or mouse ObR (2 μg/ml) and the various STAT proteins (3 μg/ml). Co-transfection of the expression vectors for ObR and various STAT isoforms allowed analysis of the ligand-induced activation of specific STAT proteins. The transfected cells were treated for 15 minutes without or with murine OB (100 ng/ml) and activation of DNA binding of the STAT proteins was identified by EMSA using the diagnostic oligonucleotide substrates STE or TB-2. In these experiments, only the long form of ObR activated either endogenous COS STAT proteins, or the co-expressed STAT1, STAT3, or STAT5B. Activation of all STAT isoforms by ObR was ligand dependent. In contrast, the short form of ObR was unable to activate any endogenous or co-transfected STAT proteins despite its high surface expression. Since the long form of ObR activated all the STAT proteins that are also activated by G-CSFR, LIFR, and gp130 (Kishimoto et al., 1995, Blood 86:1243–1254; Lia et al., 1995, J. Biol. Chem. 270:23254–23257), the long form ObR was predicted to stimulate transcription with a specificity of the IL-6-type cytokine receptors.

11.2.2. OBR Signals Induce Gene Expression

Rodent and human hepatoma cell lines have previously been utilized to define the gene-inducing action of ectopically-expressed hematopoietin receptors (Baumann et al., Mol. Cell. Biol. 14:138–146). Consequently, three complementary hepatoma cell lines were applied to characterize ObR signaling. The long or short forms of ObR or human G-CSFR, were introduced into rat H-35 cells, together with the HRRE-CAT reporter gene construct, the expression of which is increased in these cells by signals of many hematopoietin receptors (Morella et al., 1995, J. Biol. Chem. 270:8298–8310). Subcultures were treated for 24 hours with serum-free medium alone or containing cytokines (mOB, LIF, or IL-6) with or without dexamethasone. The long form of ObR mediated ligand-dependent induction of CAT gene expression. The stimulatory action was synergistically enhanced by dexamethasone. The cell response mediated by ObR was highly similar to that of the endogenous IL-6R but characteristically different from the endogenous LIFR. In contrast, the short form of ObR failed to induce gene expression, indicating that the 34 residue cytoplasmic domain, despite the presence of a box 1-related motif, was ineffective in recruitment of the cellular signaling components. The fact that the G-CSFR with a cytoplasmic domain truncated to 27 residues still induced gene transcription in the presence of ligand illustrated that the cells were able to respond to the signal derived from a short, box-1-containing cytoplasmic domain of a hematopoietin receptor. The lack of induction of CAT gene expression in G-CSFR-transfected control cells demonstrates chat H-35 cells do not respond to OB in the absence of transfected ObR.

11.2.3. OBR Functions Independently of gp130

The results described above support the model that the long form of ObR reconstitutes a signaling pathway similar to that of IL-6R. Next, to determine whether gp130 is part of the functional ObR, the long form of ObR was introduced together with HRRE-CAT or IL-6RE-CAT into HepG2 cells and the inhibitory effects of anti gp130 antibodies was assessed.

Treatment of the transfected HepG2 cells with either mouse or human OB produced a similarly strong induction which was in the range of that produced by IL-6 (30–40 fold stimulation). A dose response analysis indicated that maximal regulation was achieved with 100 ng/ml OB. In four independent experiments, it was established that 1–5 ng/ml produced a half-maximal stimulation, and that 1000 ng/ml yielded a stimulation that was consistently below maximum. In the presence of monoclonal antibodies against human gp130, which are known to prevent signaling by all IL-6 type cytokine receptors (Chevalier et al., 1995, N.Y. Acad. Sci. 762:482–484), the stimulation of gene expression by IL-6 was abolished as expected, whereas the regulation by OB was unaffected. These results indicate that ObR functions Independently of gp130 (insensitive to anti-gp130) and that signal initiation may be triggered by receptor homo-oligomerization.

11.2.4. Box 3 Sequence of OBR and STAT3 are Involved in Signaling

Induction of transcription via IL-6 RE is characteristic of the hematopoietin receptors of IL-10R which contain at least one copy of the box 3 motif (YXXQ) in their cytoplasmic domains (Lai et al., 1995, J. Biol. Chem. 270:23254–23257). This box 3 sequence has been implicated in recruiting STAT3 to the receptor as part of its activation by receptor-associated kinases (Lia et al., 1995, J. Biol. Chem. 270:23254–23257); Stahl et al., 1995, Science 267:1349–1353). The long form of ObR FIGS. 3A–3F(SEQ ID NO:3) contains at amino acid position 1141 to 1144 one copy of the box 3 motif that could account for the activation of STAT3 and transcriptional stimulation of IL-6RE-CAT. To assess whether the box 3 motif of ObR and STAT3 were involved in the gene inducing effect of ObR, two complementary reagents were applied: a box 3-mutant ObR and a dominant negative STAT3. The role of box 3-sequence in the long form of ObR was determined by mutating tyrosine at amino acid position 1141 to phenylalanine (Y1141F). Hep G2 and H-35 cells were transfected with an expression vector for wild-type ObR or ObRY1141F (2 μg/ml) together with either pHRRE-CAT or pIL-6RE-CAT. Cells were treated with human OB (100 ng/ml), and the relative change in CAT activity was determined. The mutant ObR transfected into HepG2 cells yielded a lower stimulation of both the HRRE-and IL-6RE-CAT reporter gene constructs than the wild-type ObR. For example, stimulation of HRRE-CAT expression was reduced 40 fold in HepG2 cells and H-35 cells. Stimulation of IL-6RE-CAT was reduced 20-fold in HepG2 cells and 100-fold in H-35 cells. Control experiments indicated that reduced signaling activity of the mutant ObR was not due to compromised surface expression as shown by AP-OB binding. The relative effect of the mutation was more prominent on IL-6RE than on HRRE. A similar experiment carried out in H-35 cells showed that box 3 mutation was correlated with a loss of IL-6RE regulation, whereas HRRE regulation was minimally affected. The results are consistent with previous observations that, in some cell lines, the recruitment of STAT3 was more important in gene induction through IL-6RE then through HRRE (Lai et al., 1995, *J. Biol. Chem.* 270:23254–23257; Morella et al., 1995, *J. Biol. Chem.* 270:8298–8310; Wang et al., 1995, *Blood* 86:1671–1679).

The reduced gene-regulatory effect of the Y1141F ObR mutant was also correlated with a lower activation of STAT proteins. When the mutant ObR was transfected into COS-1 cells, as done for the wild-type ObR, activation of the endogenous COS STAT proteins was not detected. Also, ObR Y1141F was approximately 10 times less effective in Activating overexpressed STAT1 and STAT3 than wild type ObR. Activation of STAT53 was, however, unaffected by the mutation. This profile of STAT activation by ObR Y1141F was in agreement with that observed for box 3-deficient gp130 (Lai et al. , 1995, *J. Biol. Chem.* 270:23254–23257) and G-CSFR (Morella et al., 1995, *J. Biol. Chem.* 270:8298–8310) and would explain the specific changes in the regulation of the reporter gene constructs.

The signal transducing role of STAT3 was determined by using over-expression of STAT3-55C, a mutant STAT3 with a 55 residue carboxy terminal truncation that acts as dominant negative inhibitor of STAT3 action on gene transcription. DNA binding assays such as those described in Section 11.2.1., supra, verified that the long form of ObR efficiently activated DNA binding activity of STAT3-55C. STAT3-55C essentially abolished the ObR mediated induction of IL-6RE and reduced that of HRRE by 50%. These data indicate that in the hepatic cells, ObR engages signal transduction pathways that are also utilized by the IL-6-type cytokine receptors and are sensitive to STAT3-55C.

11.2.5. OBR can Utilize Both STAT3 and STAT5B Gene Induction

Induction of the selected reporter gene constructs in HepG2 or H-35 cells is maximal and not significantly enhanced by over-expressed wild-type STAT proteins. To assess whether the STAT proteins activated by ObR play a positive mediator role, human Hep3B cells were transfected with human ObR together with either pIL-6RE-CAT or pHRRE-CAT, and the expression vector for the STAT proteins. Stimulation of CAT activity by human OB (100 ng/ml) relative to untreated control was determined (mean±S.D.; N=3 to 4). Those hepatoma cells have retained expression of functional IL-6R, but lack the receptors to other IL-6-type cytokines (Baumann et al., 1994, *Mol. Cell. Biol.* 14:138–146). Moreover, these cells have a relatively low level of STAT3 and STAT5, thus permitting testing of the signaling of ObR by gain of function through over-expression of STAT proteins. The results from these experiments indicate that overexpressed STAT3 mediated induction of IL-6RE 15-fold. Overexpressed STAT31 and STAT5B enhanced ObR mediated induction of HRRE-CAT 5-fold and 30-fold, respectively.

11.3. Conclusion

The results presented above document that full length ObR is a signal transducing receptor with a mode of action related to the IL-6-type cytokine receptors. The data also support the hypothesis that the truncated ObR variants, such as the short form expressed in many tissues or encoded by the db mutant transcript, are either signaling-incompetent or exert a reduced signaling repertoire that is not detectable by the tools applied here. The fact that reconstitution of an OB response is achieved at the level of gene expression in hepatic cells strongly suggests that an equivalent process may occur in hypothalamic cells or other cell types that normally express the full-length ObR. The link of ObR to specific signaling pathways utilizing STAT proteins and the knowledge of the specificity of these proteins to control genes through identifiable DNA binding elements may assist in identifying the immediate ObR effects that are relevant to understanding OB action in vivo. The experimental system presented above can also be used to address questions about the functional role, if any, of the naturally occurring short forms of ObR in functional regulation of the long form.

12. Mutational Analysis of OBR

In order to identify regions of the ObR cytoplasmic region important For activation of genes, a number of ObR mutants were created and analyzed. These studies, described below, identified two distinct regions of the ObR cytoplasmic domain important for induction of gene expression.

12.1 Materials and Methods

12.1.1 Cells

COS-1, COS-7, and H-35 cells were cultured as described by Baumann et al., 1989, *Ann. N.Y. Acad. Sci.* 557:280–297. Cells were mock stimulated in medium containing 0.5% fetal calf serum and 1 $\mu$M dexamethasone or treated in the same medium supplemented with 100 ng/ml human leptin (Roche), IL-6 (Genetics Institute), or G-CSF (Immunex Corp.).

12.1.2 Expression Vectors and CAT Reporter Gene Constructs

The expression vectors for the long form of human ObR are described above (Section 9) and rat STAT1, STAT3 and STAT5B have been described previously (Lai et al., 1995, *J. Biol. Chem.* 270:23254–23257; Ripperger et al., 1995, *J. Biol. Chem.* 270:29998–30006). pOB-RΔ1115-1165, pOB-RΔ1065-1165 and pOB-RΔ965-1165, all encoding carboxy-terminal truncated human ObRs, were generated by PCR. Briefly, oligonucleotides spanning the intracellular domain of human ObR were used to generate in-frame stop codons 3' to the specified amino acids. The PCR fragments were digested with EcoRV and XbaI and subcloned into human ObR that had beer digested with EcoRV and XbaI. A similar strategy was used to generate pOB-RΔ868 but with primers generating an MscI-XbaI fragment that replaced endogenous human ObR sequences. pOB-RY1141F, encoding human ObR with a mutated box 3 sequence was prepared as described in Section 11.1.2. ObR mutants pOB-R(box 1 mt), containing PNP to SNS changes in the ObR box 1 motif (aa 876 and 878), and mutants pOB-RY986F and pOB-RY1079F, were generated by overlap extension PCR using synthetic oligonucleotides encoding the specified Tyr to Phe amino acid substitutions (Higuchi et al., 1988, *Nucleic Acids Res.* 16:7351–7367). The CAT reporter gene constructs, pHRRE-CAT and pIL-6-CAT have been described previously (Lai et al., 1995, *J. Biol. Chem.* 270:23254–23257; Morella et al., 1995, *J. Biol. Chem.* 270:8298–8310).

12.1.3 Cell Transfection and Analysis

COS-1 and H-35 cells were transfected by the DEAE-dextran method (Lopata et al., 1984, *Nucleic Acids Res.*

12:5707–5717), and COS-7 cells by the lipofectamine method (Tartaglia et al., 1995, *Cell* 83:1263–1271). For analysis of STAT protein activation, COS cells were maintained for 16 hours in serum-free medium, followed by treatment of cells with 100 ng/ml leptin or G-CSF for 15 minutes.

For CAT assays, transfected cell cultures were subdivided and treated with ligands for 24 hours. CAT reporter activities were determined and are expressed relative to values obtained for untreated control cultures for each experimental series. DNA binding by STAT proteins was analyzed by electromobility shift assay (EMSA) using whole cell extracts as described by Sadowski et al. (1993, *Science* 26:1739–1744). Radiolabeled double stranded oligonucleotides SIEm67 (for STAT1 and STAT3) and TB-2 (for STAT5B) served as binding substrates in the EMSA. Receptor expression in COS cells was analyzed by quantitative cell surface binding of AP-OB fusion protein as described by Cheng and Flanagan (1994, *Cell* 79:157–168).

12.1.4 Immunoblotting

All immunoblotting was performed as described by Baumann et al. (1996, *Proc. Natl. Acad. Sci. U.S.A.* 93:xxx-xxx) and immunoreactive proteins were visualized by enhanced chemiluminescence detection as described by the manufacturer (Amersham). Rabbit polyclonal antiserum specific for STAT5B was obtained from Santa Cruz Biotechnology.

12.2 Results and Discussion

As discussed above, ObR is a member of the class I cytokine receptor superfamily. Receptors of this class lack intrinsic tyrosine kinase activity and are activated by ligand-induced receptor homo-dimerization or hetero-dimerization. In many cases, activation requires activation of receptor-associated kinases of the Janus family (JAKs) (Ihle et al., 1994, *Trends. Biol. Sci.* 19:222–227). JAKs associate with the membrane-proximal domain of the intracellular part of the cytokine receptors, and serve to initiate signal transduction pathways following ligand induced receptor activation. Included among the downstream targets of the JAK proteins are members of the STAT (Signal Transducers and Activators of Transcription) family of transcription factors (Ihle et al., 1994, *Trends. Biol. Sci.* 19:222–227). The STATs are DNA binding transcription factors that contain Src-homology (SH2) domains chat interact with receptor molecules through phosphorylated tyrosine residues. STAT proteins are activated by tyrosine phosphorylation, form heterodimers or homodimers, translocate to the nucleus, and modulate transcription of target genes.

12.2.1 The OBR Intracellular Domain Includes at Least Two Regions Important for Signalling To define regions of the ObR cytoplasmic domain required for signaling, a series of C-terminal deletion mutants were constructed (FIG. 11A). cDNAs encoding these mutants were transiently co-transfected into H-35 cells with either IL-6RE-CAT or HRRE-CAT reporter constructs and assayed for their ability co stimulate transcription (FIG. 11B). C-terminal truncations that remove box 3 sequences (aa 1141–1144) of ObR abolish transcriptional activation via IL-6-RE (FIG. 11B; upper panel). This result is consistent with the fact that a Y to F mutation in the single box 3 motif or ObR completely disrupts signaling in H-35 cells via IL-6RE (Section 11.2.4). In contrast, ObR signaling through HRRE was minimally reduced by removal of extreme C-terminal sequences and was not completely disrupted until removal of the approximately 97 amino acids between 868 and 965 (FIG. 11B).

To ensure that the expression vectors for the various ObR mutants directed the synthesis of surface localized receptor proteins, COS cells transfected with each construct were assayed for receptor expression by AP-OB binding studies. C-terminal truncations of ObR generate proteins that are expressed at the surface and bind ligand (FIG. 12). Moreover, the expression level of ObR increased with progressive truncation of the intracellular domain.

As discussed above, ObR gene induction via IL-6RE correlates with activation of STAT1 and STAT3 whereas ObR gene induction via HRRE was found to correlate with activation of STAT5B. To further evaluate the correlation between HRRE stimulation and STAT5B activation, COS cells were co-transfected with expression plasmids for STAT53 and the ObR deletion mutants. Immunoblotting performed on extracts prepared from these cells revealed that STAT5B was expressed at relatively equal amounts in each of the transfected cultures. Cells were treated with leptin. EMSA analysis was performed, and STAT protein levels were quantitated by Western blotting. Progressive C-terminal truncations of ObR result in a reduced ability to activate STAT5B and detectable STAT5B activation was lost only with removal of the membrane proximal ObR segment (construe: pOBRΔ868-1165). Thus, there appears to be a correlation between loss of ObR STAT5B activation and gene induction via HRRE.

To define the relative contribution of the conserved intracellular domain tyrosine residues and of the membrane proximal box 1 motif to signaling by ObR via HRRE, mutants OB-RY1141F, OB-RY986F, OB-RY1079F and OB-R(box 1 mt) were generated (FIG. 13A). When analyzed in COS cells, AP-OB binding studies demonstrate that these mutants are expressed at the cell surface approximately as well as wild-type ObR. When transfected into H-35 cells, OB-RY986F and OB-RY1079F were unchanged in their ability to regulate HRRE (FIG. 13B). In contrast, mutation of the ObR box 1 motif results in a complete loss of regulation of gene induction through this element. Thus, the box 1 motif of ObR appears to be an important determining factor for the ability of ObR to activate pathways that can modulate gene induction via HRRE.

Gene induction by ObR through IL-6RE requires sequences near the extreme C-terminus of ObR (FIG. 11B). In contrast, ObR gene induction through HRRE does not appear to require these C-terminal sequences. Moreover, gene induction via this element is only minimally affected by removal of ObR intracellular domain sequences of approximately 200 amino acids between amino acids 965–1165 but is dependent upon membrane proximal sequences of the approximately 17 amino acids between amino acids 868 and 965. Consequently, the proposed box 2 motif of ObR (Lee et al., 1996, *Nature* 379:632–635) (human ObR aa 1066–1075) does not appear to contribute to gene induction through HRRE. EMSA analysis suggests gene induction of HRRE correlates with the ability of ObR to activate STAT5B. Interestingly, OB-RΔ965-165, which has been deleted of all intracellular domain tyrosine residues and therefore all potential SH2 docking sites, is still capable of low-level STAT5B activation and transcriptional stimulation through HRRE. Only when membrane proximal sequences of ObR are removed (OB-RΔ868-1165), are both HRRE gene induction and STAT5B activation completely abolished. Consistent with this, OB-R (box-1 mt), containing a mutated box 1 motif, is similarly unable to induce gene induction through HRRE and would be predicted to be unable to activate STAT5B.

13. Multimerization of OBR

The primary structure of ObR suggests that it is closely related to the signaling subunits of the IL-6-type cytokine receptors. Members of this group can be activated by either heterodimerization or homodimerization (Kishimoto et al., 1994, *Cell* 76:253–262; Heldin et al., 1995, *Cell* 80:213–223). Included among the former are the receptors for IL-6, leukemia inhibitory factor (LIF), oncostatin M, IL-11, and ciliary neurotrophic factor (CNTF), all of which share the common signal transducer, gp130 (Kishimoto et al., 1994, *Cell* 76:253–262; Taga et al., 1989, *Cell* 58:573–581). However, ObR appears to signal independently of gp130 (Baumann et al., 1996, *Proc. Natl. Acad. Sci. USA* 93:xxx-xxx. Therefore, ObR may function in the presence of another accessory chain such as the common signaling subunit utilized by receptors for either IL-3, granulocyte macrophage-colony stimulating factor (GM-CSF) and IL5 (IL-3Rβ), or IL-2, IL-4, IL-7 and IL-9 (IL-2Rγ). However, ObR signals in hepatoma cells, which do not express either IL-3Rβ or IL-Rγ (Wang et al., 1995, *Blood* 86:1671–1679; Morella et al., 1995, *J. Biol. Chem.* 270:8298–8310). Alternatively, ObR may be activated by homodimerization as is found for the granulocyte-colony stimulating factor receptor (G-CSFR) (Fukanaga et al., 1991, *EMBO J.* 10:2855–2865; Ishezaka-Ikeda et al., 1993, *Proc. Natl. Acad. Sci. USA* 90:123–127). Therefore, to determine whether ObR has the ability to dimerize and signal as a homodimer, chimeric receptors encoding the extracellular domain of G-CSFR joined to the intracellular domain of ObR or the reciprocal receptor having the extracellular domain of ObR joined to the intracellular domain of G-CSFR were constructed and analyzed (FIG. 14A).

13.1 Materials and Methods

13.1.1 Cells

COS-1, COS-7, and H-35 cells were cultured as described by Baumann et al., 1989, *Ann. N.Y. Acad. Sci.* 557:280–297. Cells were mock stimulated in medium containing 0.5% fetal calf serum and 1 µM dexamethasone or treated in the same medium supplemented with 100 ng/ml human leptin (Roche), IL-6 (Genetics Institute), or G-CSF (Immunex Corp.).

13.1.2 Expression Vectors and CAT Reporter Gene Constructs

The expression vectors for the long form of human ObR are described above (Section 9), full-length G-CSFR or truncated G-CSFR(Δcyto) (Ziegler et al., 1993, *Mol. Cell. Biol.* 13:2384–2390), and rat STAT1, STAT3 and STAT5B have been described previously (Lai et al., 1995, *J. Biol. Chem.* 270:23254–23257; Ripperger et al., 1995, *J. Biol. Chem.* 270:29998–30006). As used herein the term "Δcyto" means deletion of the cytoplasmic domain. The G-CSFR/ObR chimeric receptor was generated by PCR and encodes the extracellular domain of human G-CSFR (aa 1–598) joined near the transmembrane and intracellular domain of human ObR (aa 829–1165). The ObR/G-CSFR chimeric receptor was generated by PCR and encodes the mouse ObR extracellular domain and transmembrane sequences (aa 1–860) joined to the intracellular domain of the human G-CSFR (aa 631–813). The CAT reporter gene constructs, pHRRE-CAT and pIL-6-CAT have been described previously (Lai et al., 1995, *J. Biol. Chem.* 270:23254–23257; Morella et al., 1995, *J. Biol. Chem.* 270:8298–8310).

13.1.3 Cell Transfection and Analysis

COS-1 and H-35 cells were transfected by the DEAE-dextran method (Lopata et al., 1984, *Nucleic Acids Res.* 12:5707–5717), and COS-7 cells were transfected by the lipofectamine method (Tartaglia et al., 1984, *Cell* 83:1263–1271). For analysis of STAT protein activation, COS cells were maintained for 16 hours in serum-free medium, followed by treatment of cells with 100 ng/ml leptin or G-CSF for 15 minutes.

For CAT assays, transfected cell cultures were subdivided and treated with ligands for 24 hours. CAT reporter activities were determined and are expressed relative to values obtained for untreated control cultures for each experimental series. DNA binding by STAT proteins was analyzed by electromobility shift assay (EMSA) using whole cell extracts as described by Sadowski et al. (1993, *Science* 26:1739–1744). Radiolabeled double stranded oligonucleotides SIEm67 (for STAT1 and STAT3) and TB-2 (for STAT5B) served as binding substrates in the EMSA. Receptor expression in COS cells was analyzed by quantitative cell surface binding of AP-OB fusion protein as described by Cheng and Flanagan (1994, *Cell* 79:157–168).

13.1.4 Immunoblotting

All immunoblotting was performed as described by Baumann et al. (1996, *Proc. Natl. Acad. Sci. USA* 93:xxx-xxx) and immunoreactive proteins were visualized by enhanced chemiluminescence detection as described by the manufacturer (Amersham). Rabbit polyclonal antiserum specific for STAT5B was obtained from Santa Cruz Biotechnology. Goat polyclonal antiserum against bacterially expressed extracellular domain of G-CSFR was prepared at Roswell Park Cancer Institute Springville Laboratories.

13.2 Results and Discussion

The experiments described below suggest that, while dimerization of the ObR cytoplasmic domain may be sufficient for signal transduction, higher order homo-oligomers can be formed in response to ligand binding.

13.2.1 Homodimerization OBR Intracellular Domains may be Sufficient for Signal Transduction Since chimeric receptor complexes have proven quite productive for the analysis of the mechanism of cytokine receptor activation (Morella et al., 1995, J. Biol. Chem. 270:8298–8310; Vigon et al., 1993, *Oncogene* 8:2607–2615; Baumann et al., 1994, *Mol. Cell. Biol.* 14:138–146), ObR/G-CSFR and G-CSFR/ObR chimeras were produced and studied as a means to analyze the mechanism of ObR signaling (FIG. 14A). To analyze whether the G-CSFR/ObR chimeric receptor could propagate a ligand induced signal comparable to that for wild-type ObR, the chimera was tested for STAT activation and for transcriptional stimulation. Co-transfection of G-CSFR/ObR with STAT proteins yielded a G-CSF-induced activation of STAT1, STAT3, and STAT5B. This result is similar to the STAT protein activation induced by OB in ObR transfected cells (Section 12). Expression of the chimeric receptor was confirmed by immunoblot analysis of cultures transfected with G-CSFR/ObR. These results suggest that G-CSF mediated dimerization of ObR cytoplasmic domains can generate an ObR-type activation of STAT proteins. In addition, it was found that the G-CSFR/ObR chimera could stimulate transcription as detected by measurement of gene induction in H-35 cells following receptor co-transfection with the IL-6RE and HRRE reporter constructs (FIG. 14B). The response elicited was found to be similar to an induction of the reporter gene constructs by either ObR or endogenous IL-6R.

These results indicate that homodimerization of two ObR cytoplasmic domains can initiate signaling by ObR, similar to the mechanism mediating signaling by wild-type G-CSFR. However, the G-CSFR/ObR chimera could not definitively prove that OB ligand has the capability to dimerize ObR extracellular domains. Consequently, signaling activity by the reciprocal chimera, containing the ObR extracellular domain joined to the G-CSFR intracellular domain, was analyzed (FIG. 14A). Indeed, the ObR/G-CSFR chimera could mediate gene induction comparable to that by wild-type ObR, G-CSFR/ObR, and wild-type G-CSFR (FIG. 14B). Thus, taken together, these results suggest that ObR does not require an accessory chain for signaling, and that aggregation of two ObR intracellular domains appears sufficient for receptor activation.

The fact that aggregation of two ObR intracellular domains is sufficient to generate a signal following ligand-induced activation suggests that ObR may function by receptor homodimerization. If so, signaling by ObR might be "poisoned" by overexpression of a homodimerizing partner that is signaling deficient, similar to what has been shown for members of the receptor tyrosine kinase family (Paulson et al., 1989, J. Biol. Chem. 264:17615–17618; Svensson et al., 1990, J. Biol. Chem. 265:20863–20868; Wen et al., 1992, J. Biol. Chem. 267:2512–2518; Fantl et al., 1993, Annu. Rev. Biochem. 62:453–481). As discussed above (Section 12), ObR containing only the membrane proximal 6 amino acids of the cytoplasmic domain is signaling defective (FIG. 11B). Consequently, experiments were performed to determine whether expression of a truncated, signaling deficient ObR could disrupt signaling by full-length ObR. Cells were co-transfected with increasing amounts of truncated receptor OB-RΔ868-1165 relative to full-length ObR and the ability of these complexes to stimulate expression of a reporter gene construct was assayed. Co-transfection of increasing amounts of truncated ObR does result in decreased signaling by wild-type receptor (FIG. 15A). However, even when there was a large excess of truncated receptor, relative to full-length receptor, the signaling repression observed did not approach the degree of reduction observed for repression of G-CSFR signaling by overexpressed and signaling-deficient truncated G-CSFR(Δcyto) (FIG. 15A and FIG. 15C). The differing sensitivity co dominant negative repression observed for ObR and G-CSFR was a property of their extracellular domains as shown by dominant negative studies with the receptor chimeras (FIG. 15B and FIG. 15C).

A potential explanation for this weak dominant negative repression of ObR is that interaction of two ObR molecules may require functional domains residing in the intracellular region of the receptor. To address this possibility, the dominant negative repression of ObR by a mutant receptor rendered signaling defective by a single amino acid substitution (Y1141F) in the ObR box 3 motif was examined. As described above, this mutation completely abolished the ability of ObR to modulate gene induction via IL-6RE in H-35 cells (Section 12). Consequently, the ability of OB-R (Y1141F) to inhibit wild-type ObR signaling via this enhancer element was investigated. These studies revealed that increasing the ratio of transfected mutant OB-RY1141F to wild-type receptor did not strongly repress signaling (FIG. 15E). Thus, the ObR box 3 mutant and OB-RΔ868-1165 behave similarly in their ability to trans-repress signaling by wild-type ObR. Interestingly, low level expression of either truncated or box 3 mutant ObR receptor generates a slight enhancement of signaling by wild-type ObR. Moreover, a similar pattern was also observed for ObR/G-CSFR signaling in the presence of increasing amounts of truncated OB-RΔ868-1165 (FIGS. 15A, 15B, and 15C).

As discussed above (Section 11), ObR can signal in hepatoma cells in the presence of neutralizing antibodies to the gp130 signal transducing component of the IL-6-type cytokine receptors. Moreover, these hepatoma cells do not express the other characterized cytokine receptor accessory chains IL-2Rγ or IL-3Rβ (Wang et al., 1995, Blood 86:1671–1679; Morella et al., 1995, J. Biol. Chem. 270:8298–8310). Consequently, it is possible that ObR may function by a mechanism involving receptor homodimerization. Among members of the class I cytokine receptor family, signaling by the G-CSFR is predicted to be initiated by ligand-induced receptor homodimerization (Fukanaga et al., 1991, EMBO J. 10:2855–2865; Ishezaka-Ikeda et al., 1993, Proc. Natl. Acad. Sci. USA 90:123–127). As stated above, chimeric receptor complexes have proven quite productive for the analysis of the mechanism of cytokine receptor activation (Morella et al., 1995, supra; Vigon et al., 1993, supra; Baumann et al., 1994, supra), ObR/G-CSFR and G-CSFR/ObR chimeras were produced and studied as a means to analyze the mechanism of ObR signaling. These studies revealed that the G-CSFR/ObR chimera can strongly activate transcription of both the IL-6RE-CAT and HRRE-CAT reporter constructs (FIG. 14B). Since G-CSFR is thought to form a homodimer when G-CSF is bound, this implies that the aggregation of two intracellular ObR domains is sufficient to initiate receptor signaling. In a similar manner, the ObR/G-CSFR chimera also mediates transcriptional activation through IL-6RE and HRRE (FIG. 14B). These results show that leptin binding can dimerize two ObR extracellular chains thus inducing the association of at least two intracellular G-CSFR domains and activation of the receptor complex. Moreover, these results suggest that it may be possible to generate small molecules, peptides, or antibodies that act as ObR agonists through simple crosslinking of two ObR chains.

As would be predicted for receptors that are activated by simple homodimerization, signaling by full length G-CSFR and the G-CSFR/ObR chimera can be greatly diminished by co-expression of a signaling deficient homodimerizing partner. However, OB-RΔ868-1165 was unable to as efficiently repress signaling by full-length ObR or the ObR/G-CSFR chimera. It is therefore possible that leptin binding to cell surface receptors can result in higher-order oligomerization (receptor number>2/complex) as has been shown for IL-10 receptor complexes (Tan et al., 1995, J. Biol. Chem. 21:12906–12911) and for members of the Activin/TGF-βR family (Brand et al., 1993, J. Biol. Chem. 268:11500–11503; Weiser et al., 1993, Mol. Cell. Bol. 13:7239–7247; Wrana et al., 1994, Cell 71:1003–1014; Moustakas et al., 1993, J. Biol. Chem. 268:22215–22218; Henis et al., 1994, J. Cell Biol. 126:139–154). According to this model, ligand binding by full-length ObR or ObR/G-CSFR chimera can lead to aggregation of more than two receptor chains, yet juxtaposition of only two intracellular domains is sufficient for signal generation. Such complexes would be predicted to be highly resistant to dominant negative repression. The strong repression of signaling by G-CSFR(Δcyto) in complexes containing the G-CSFR/ObR chimera demonstrates that ObR intracellular domain can be efficiently repressed when placed in the context of a simple homodimer structure. Although it is possible that OB-RΔ868-1165 localizes to a different region of the membrane than wild-type ObR, it is not likely that mutation of a single tyrosine residue of the ObR intracellular domain (Y1114F) would result in altered receptor membrane localization. Thus, the observation of similar repression effects mediated by either OB-RΔ868-1165 or OB-RY1141F suggests the results described herein are not due to altered membrane 30 localization. Low expression levels of either OB-RΔ868-1165 and OB-RY1141F generate a small enhancement of signaling for full length ObR and the ObR/G-CSFR chimera. This effect could be attributable to either ligand presentation (Andres et al., 1989, *J. Cell Biol.* 109:3137–3145; Massaugue et al., 1992, *Cell* 69:1067–1070; Lin et al., 1993, *Trends. Cell Biol.* 3:14–19), or ligand passing as has previously been observed for. the TNF receptor (Tartaglia et al., 1993, *J. Biol. Chem.* 268:18542–18548).

As noted above, it is possible that the short forms of ObR serve a transport or clearance function in the body (Tartaglia et al., 1995, *Cell* 83:1263–1271). However, the possiblity that the long and short forms of ObR can functionally interact suggests that the short form of ObR could regulate activities of the long form. This is supported by the fact that the major naturally occurring non-signalling short form of ObR in the mouse (containing a 34 amino acid intracellular domain), which also corresponds to the mutant ObR found in the db/db mouse, can repress long form receptor signaling.

14. A Cell Based Assay fpr Identification of Agonists and Antagonists of the OB Receptor Signalling Pathway The following example describes methods for identifying compounds that can be used to treat a body weight disorder. This assay works by identifying compounds (e.g., small molecules, peptides, or antibodies) that function as either agonists or antagonists of the Ob receptor or of any other component of the pathway (e.g., a component of the Ob receptor signalling pathway described above) that is influenced by receptor binding. Compounds that are discovered by performing the assay described herein (or a variation thereof) are considered within the scope of the invention.

In this assay, cells that express the long form of the human or murine Ob receptor (or any other long form, i.e., signalling competent, mammalian Ob receptor and harbor a reporter construct that is responsive to activation of the Ob receptor by leptin are exposed to one or more test compounds in the presence of leptin. Compounds that act as antagonists of the Ob receptor activity will decrease expression of the reporter construct while compounds that act as agonists of the Ob receptor will increase expression of the reporter gene. In many instances, it is desirable to pool test compounds. Thus, 1,000 test compounds can be divided into 100 pools of 10 compounds. Each pool applied to cells which expressed ob receptor and harbor an Ob receptor responsive reporter gene. The level of reporter gene expression is measured and compared to the expression level of otherwise identical cells which are not exposed to the pool of test compounds. The compounds in pools that alter reporter expression can then be tested individually.

Cell Culture and Transfection

Immortalized hypothalamic GnRH neurons (for a description of the production of the cell line, see Mellon et al., 1990, *Neuron* 5:1–10) are one type of cell which can be used in this assay. In one example of the screening assay, these cells are plated on 96-well plates, cultured until they were approximately 70% confluent, and transfected with a cDNA encoding the long form of the murine or the human Ob receptor (Tartaglia, *J. Biol. Chem.* 272:6093–6096, 1997; the long form of the murine Ob receptor is shown in FIGS. 6(SEQ ID NO:43) and the long form of the human Ob receptor, including the signal sequence, is shown in FIGS. 3A–3F (SEQ ID NO:4)) and a cDNA reporter construct. The reporter construct contains a sequence encoding a secreted form of alkaline phosphatase (SEAP; Clontech), which is placed under the control of the Ob Receptor responsive promoter element, IL-6 RE (described above). The constructs are transfected into the cells using Lipofectamine☐ (Life Technologies, Gaithersburg, Md.), according to the manufacturer's instructions.

Contacting Cells with Leptin or Potential Agonists or Potential Antagonists of Ob Receptor Activity Forty-eight hours after transfection, the cultured cells are washed twice with serum-free medium, and contacted with either: (1) leptin alone, at a concentration that does not produce maximal stimulation of the receptor (as a control), or (2) leptin, at the same concentration as applied to the control cells, and one or more test compounds, e.g., a small molecule library (as the experimental group). In both instances, leptin and the compounds are applied to the cells in non-supplemented culture medium. Twenty-four hours later, 100 μl of culture medium are removed, and SEAP activity is assessed by measuring chemiluminescence with the Great Escape™ alkaline phosphatase detection kit. The kit is manufactured by Clontech (Palo Alto, Calif.), and is used according to their directions. Luminescence values are measured using a Microbeta plus™ liquid scintillation counter (Wallac), and can be expressed as arbitrary units of luminescence activity.

An increase in the activity of the reporter in the presence of a test compound, compared with activity in the absence of a test compound, indicates the presence of an agonist of Ob receptor activity. Conversely, a decrease in the activity of the reporter in the presence of a test compound (compared with activity in the absence of a test compound), indicates the presence of an antagonist of Ob receptor activity.

The agonist or antagonist may act at any point in the signalling pathway between binding of leptin to Ob receptor and expression of the reporter gene. Thus, the screening method is broadly useful for identifying compounds that alter signalling components of the Ob receptor pathway.

Modifications of the assay described above will be apparent to those of skill in the art. For example, it will be apparent that any molecule that activates the Ob receptor or the Ob receptor pathway can be used in the assay described above in the place of leptin; for example, one could use a fragment of the leptin molecule that retains the ability to bind to and activate the ob receptor. Alternatively, antibodies may be used to activate the receptor. Similarly, when screening compounds for their ability to activate the Ob receptor (i.e., when searching for receptor agonists), the assay can be carried out in the absence of leptin. In this case, the expression of the reporter construct can simply be compared in cells that are exposed to a putative agonist (i.e., cells that are "treated") and cells that are not (i.e., cells that are "untreated"). In addition, the cell can be a cell that naturally expresses an Ob receptor or that is stably transfected with an Ob receptor-encoding sequence. In events such as these, the assay can be performed by introducing only a reporter construct into the cell.

In addition to the IL-6 RE, the assay can be conducted using a reporter gene that is driven by HRRE (an HRRE-CAT reporter construct is described above). Furthermore, the reporter gene itself can vary; reporter genes commonly used by those of skill in the art include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guaninephosphoribosyltransferase (XGPRT).

To determine whether the agonist or antagonist is specific for the receptor itself, a population of cells can be co-transfected as described above, except with a reporter construct and a construct that encodes a receptor that is related to the Ob receptor by sequence homology, such as a human G-CSF receptor. As discussed above, the Ob receptor of the invention has amino acid sequence motifs found in the Class I cytokine receptor family, and is most related to the gp130 signal transducing component of the IL-6 receptor, the G-CSF receptor, and the LIF receptor. If the activity remains essentially the same as that observed following co-transfection with the reporter construct and a construct encoding an Ob receptor, the agonist or antagonist is exerting a non-specific effect (i.e., the compound is not specific to only the Ob receptor).

Similarly, one can determine whether the agonist or antagonist is interacting with a component of the signalling pathway downstream from the Ob receptor (rather than interacting with the receptor itself) by co-transfecting cells with the reporter construct and a construct that encodes a chimeric polypeptide consisting of the extracellular domain of the Ob receptor and an intracellular domain of G-CSF. If the activity of the reporter is decreased or increased in cells transfected with the chimera, the respective agonist or antagonist is not specific for the ob receptor pathway.

Accordingly, the invention features methods for identifying a compound useful for the treatment of a body weight disorder. One method is performed by contacting a compound with a cell that contains a reporter gene whose expressing is altered as a consequence of activation of the Ob receptor. An increase or decrease in expression of the reporter gene indicates the presence of a compound that alters activity of the Ob receptor signalling pathway, and which is therefore a candidate therapeutic agent for treatment of a body weight disorder. A second method can be performed by contacting a cell comprising a reporter gene that is expressed following activation of the Ob receptor with (a) the compound, and (b) an agonist of the ob receptor. In this case, a decrease in expression of the reporter gene, relative to the level of expression when only the agonist is applied, indicates the presence of a compound that antagonizes the Ob receptor, and which is therefore a candidate therapeutic agent for treatment of a body weight disorder. Alternatively, the effect of the compound on reporter gene expression in the presence of an agnoist of the Ob receptor (e.g., leptin) can be measured).

15. Administration of an OBR-Ig Fusion Protein Increases Food Intake

To determine whether an ObR-Ig fusion protein is active when administered to animals (i.e., whether it can alter food intake), a chimeric protein containing the murine Ob receptor and an immunoglobulin protein was injected into normal mice and mice that developed anorexia following treatment with endotoxin. This model is described in Grunfeld et al., 1997, *J. Clin Invest.* 97:2152–2157. For guidance in the construction of ObR-immunoglobulin fusion proteins, see Example 10, supra.

Male C57BL/6J mice (14–16 weeks of age) were housed in metabolic cages (2 mice/cage) and provided with standard laboratory rodent chow. The animals were allowed to adapt to their environment for several days before beginning the experiment. Lipopolysaccharide (LPS) (*E. coli* 05:B5) was freshly prepared in phosphate buffered saline (PBS) and injected intraperitoneally (i.p.) at a dose of 10 μg/mouse. The Ob receptor-IgG fusion protein was also prepared in PBS and injected intravenously at a dose of 150 μg/mouse. In one group of animals, both LPS and the Ob receptor-IgG fusion protein were administered. In this group, the fusion protein was administered twice; at the same time the LPS was administered, and 24 hours later. Food intake was monitored every 24 hours for 4 days by weighing the amount of food remaining in the cage. The results are shown in FIG. 16, where each data point represents the average food intake of animals in each group. Food intake by mice that received the Ob receptor-Ig fusion protein was greater than the food intake by mice that received PBS. In addition, LPS treated mice that also received the Ob receptor-Ig fusion protein had a greater food intake than mice that received LPS alone: 72 hours after LPS administration, the mice that also received the Ob receptor-Ig fusion protein were eating nearly as well as the control (PBS treated) mice, whereas animals that received LPS without the Ob receptor-Ig fusion protein still exhibited a 50% reduction in food intake. Therefore, administration of an ObR-Ig fusion protein has been demonstrated to modulate food intake in vivo in both normal and anorexic mammals.

16. SOCS-1 Interacts with JAK-2 and Inhibits ObR Signaling

A yeast two hybrid screen was used to identify proteins that interact with the JH1 domain of JAK2, a protein which interacts with ObR. The identification of proteins which interact with JAK2 is important because such proteins are likely to play a role in signal transduction initiated by the binding of leptin to ObR. The JH1 domain of JAK2 is of particular interest because it is the most C-terminal domain of JAK2 that possesses kinase activity. The results presented in these examples demonstrate that: 1) that two forms of SOCS-1 interact with JAK2; and 2) the expression of SOCS-1 in cells expressing ObR can inhibit ObR mediated signaling.

16.1 Materials and Methods 16.1.1 Cells

Yeast strain HF7c (MATa, ura3-52, his3-200, lys2-801, ade2-101, trp1-901, leu2-3,112, gal4-542, gal80-538, LYS2::GAL1$_{UAS}$-GAL1$_{TATA}$-HIS3, URA3::GAL4$_{17mers(x3)}$-CyC1$_{TATA}$-lacZ; Feilotter et al., 1994, *Nucl. Acids Res.* 22:1502–1503) was used in the yeast two hybrid screen. Standard yeast media including synthetic complete medium lacking L-leucine, L-tryptophan, and L-histidine were prepared and yeast genetic manipulations were performed as described by Sherman (1991, *Meth. Enzymol.* 194:3–21). Yeast transformations were performed using standard protocols (Gietz et al., 1992, *Nucleic Acids Res.* 20:1425; Ito et al., 1983, *J. Bacteriol.* 153:163–168). Plasmid DNAs were isolated from yeast strains using standard techniques (Hoffman and Winston, 1987, *Gene,* 57:267–272).

16.1.2 Plasmids

Plasmid pGBT9, a TRP1 amp$^r$ vector encoding the DNA binding domain of GAL4 (amino acids 1–147; Bartel et al., 1993, *Cellular Interactions in Development* _153–159.), was used to create a plasmid, pRG54, which encodes a GAL4 DNA binding domain-JAK2 JH1 domain hybrid protein. To create pRG54, DNA encoding amino acids 839–1129 of murine JAK2 (Silvennoinen et al., 1993, *Proc.*

*Nat. Acad. Sci. USA,* 90:8429–8433) was amplified by PCR and cloned in frame to the portion of pGBT9 encoding the DNA binding domain of AL4. Plasmid pRG54 was transformed into two-hybrid screening strain HF7c for screening. Plasmid pACTII, which encodes the activation domain of GAL4 (amino acids 768–881), was used co generate the library used in the two hybrid screen.

Plasmid pMET7, a mammalian expression vector which utilizes the SRα promoter (Tartaglia et al., 1995, Cell 83:1263–1271), was used to create plasmid pMET7-SOCS1, a plasmid used to express a portion of murine SOCS-1b, described in greater detail below.

Plasmid pMET7-H60, which encodes the long form of human ObR (Tartaglia et al. (1995) Cell 83:1263–1271), and the STAT-responsive reporter gene construct pIL6RE-SEAP (White et al., 1997, *J. Biol. Chem.* 272:4065–4071) have been described previously.

16.1.3 Two-Hybrid Screening

Two-hybrid screening was carried out essentially as described by Bartel et al. (1993, *Cellular Interactions in Development.* _.153–159.). Briefly, by inserting murine hypothalmic cDNA adjacent to the DNA sequence within pACTII that encodes the GAL4 activation domain, library of hybrid proteins was created. Approximately $10^7$ clones from this library were screened by first selecting for clones which are able to grow on synthetic complete medium lacking L-leucine, L-tryptophan, and L-histidine and then using a filter disk beta-galactosidase (beta-gal) assay (Brill et al., 1994, *Mol. Biol. Cell,* 5:297–312) to identify clones which encoded potential interacting proteins. Colonies to be tested were grown as patches of cells on appropriate medium at 30° C. overnight and then replica plated onto Whatman #50 paper (Schleicher & Schuell, #576) that had been placed on the test medium in petri dishes. After growth overnight at 30° C., the paper disks were removed from the plates and the cells on them were permeabilized by immediately immersing the paper disks in liquid nitrogen for 30 seconds. The disks were then thawed at room temperature for 20 seconds and placed in petri dishes that contained a disk of Whatman #3 paper (Schleicher & Schuell, #593) saturated with 2.5 ml of Z buffer containing 37 μl of 2% weight per volume of the chromogenic beta-gal substrate X-gal. The disks were incubated at 30° C. and inspected periodically for the development of the blue color diagnostic of beta-gal activity in this assay. The assay was stopped by removing the paper disk containing the patches of cells and air drying it.

16.1.4 ObR Signaling Assay

The 293 cells were used in the ObR signaling assay. These cells were grown in DMEM supplemented with 10% fetal bovine serum. Transfections were carried out using lipofectamine (Gibco/BRL; Gaithersburg, Md.). For the activity assays, cells were transfected with 1 μg of the pIL6RE-SEAP reporter plasmid, 3 μg of pMET7-H60 encoding ObR receptor, and 3 μg of pMET7-SOCS1 encoding SOCS-1, as indicated. Forty eight hours after transfection the cells were washed twice with serum-free medium and then treated with leptin for 24h in non-supplemented cell culture medium. SEAP reporter activity was measured as previously described (White et al., 1997, *Proc. Nat. Acad. Sci. USA,* 94:10657–10662).

16.2 Results and Discussion

16.2.1 Two Forms of SOCS-1 Interacts with the JH1 Domain of JAK2

To identify proteins which are part of the ObR signaling pathway, a yeast two hybrid system was used to identify proteins that interact with the JH1 domain of JAK2.

DNA encoding the JH1 domain of murine JAK2 (amino acids 839–1129) was cloned into pGBT9 to create a plasmid, pRG54, encoding a GAL4 DNA-binding domain-JAK2 fusion gene. Yeast HF7c cells transformed with this construct grew on synthetic complete medium lacking L-tryptophan, but did not grow on synthetic complete medium lacking L-tryptophan and L-histidine. This demonstrates that the GAL4 DNA-binding domain-JAK2 fusion does not have intrinsic transcriptional activation activity.

HF7c cells harboring pRG54 and a beta-galactosidase reporter under the control of GAL4 DNA-binding recognition elements were transformed with a library of clones composed of mouse hypothalamic cDNA fused to DNA encoding the activation domain of GAL4. Ten million transformants were obtained. In this screen, clones which contain a mouse cDNA encoding a polypeptide that interacts with the JH1 domain of JAK2 will both grow on synthetic complete medium lacking L-leucine, L-tryptophan, and L-histidine and express the beta-galactosidase reporter gene. Seventy nine such clones were identified, and 39 of these colones were characterized further.

The 5' end of the cDNA insert of each of the 39 clones encoding potential JAK2 interacting proteins was sequenced. This sequencing revealed that the cDNA inserts of eight of the 39 clones (clones 11, 12, 18, 32, 50, 77, 102, and 115) encoded a portion of murine SOCS-1. The genomic sequence of murine SOCS-1 has been published (Schluter et al., 1996, *Mol. Reprod. Dev.* 43:1–6; Genbank Accession No. Z47352). The sequence of the 5' end of the inserts of clones 11, 12, 18, 32, 50, 77, 102, and 115 are included in Table 1. The nucleotide numbers in Table 1 refer to the genomic SOCS-1 sequence (Genbank Accession No. Z47352).

TABLE 1

SOCS-1 clones

| Clone Form | 5' Fusion junction | SOCS-1 Splice |
|---|---|---|
| 11 | 12319–12679 | SOCS-1b |
| 12 | 12319–12739 | SOCS-1b |
| 18 | 11873–11957/12467–12827 | SOCS-1a |
| 32 | 11873–11957/12467–12857 | SOCS-1a |
| 50 | 11873–11957/12467–12847 | SOCS-1a |
| 77 | 11873–11957/12467–12827 | SOCS-1a |
| 102 | 12478–12838 | — |
| 115 | 11877–11957/12467/12847 | SOCS-1a |

Analysis of the fusion junctions and the clones revealed that the various clones represented two apparent splice variants of murine SOCS-1 (SOCS-1a and SOCS-1b).

SOCS-1a clones contain nucleotides 11873–11957 of the previously identified SOCS-1 genomic clone followed by sequences starting at nucleotide 12467 of the genomic SOCS-1 clone. SOCS-1a is most likely a product of splicing an intron between nucleotide 11957 and 12467 of the SOCS-1 genomic clone. Consensus splice donor and acceptor sites are present at nucleotides 1158/9 and 12465–7. The SOCS-1b clones begin at nucleotide 12419 of the published genomic sequence, a region that falls within the SOCS-1a intron. Neither the SOCS-1a nor the SOCS-1b clones contain an stop codon upstream of the published SOCS-1 open reading frame, allowing a read-through from the GAL4 activation domain encoding sequences into the SOCS-1 open reading frame. Various SOCS-1 clones have been previously identified (Naka et al. (1997) Nature 387:924–929; Starr et al. (1997) Nature 387:917–921; and Endo et al. (1997) Nature 387:921–924) but the existence of alternate splice forms does not appear to have been recognized. Co-transformation of clone 11 (which includes has sequences present in SOCS-1b) or clone 102 (which includes sequences present in both SOCS-1a and SOCS-1b) both of which encode a fusion protein comprising a portion of SOCS-1a into yeast HF7c cells along with pGBT9, which encodes the GAL4 DNA-binding domain alone, or pRG54, which encodes the GAL4 DNA binding domain fused to the JAK2 JH1 domain, revealed that both clone 11 and clone 102 encode polypeptides which interact with the JH1 domain of JAK2, but not the unrelated GAL4 DNA binding domain.

16.2.4 Tissue Distribution of SOCS-1

To determine the relative abundance and tissue distribution of SOCS-1a and SOCS-1b, a poly $A^+$ mRNA Northern blot was analyzed with two different probes. The first probe, which corresponds to nucleotides 12146–12464 of murine genomic SOCS-1, was designed to recognize SOCS-1b, but not SOCS-1a (the "SOCS-1b probe"). The second probe, which corresponds to nucleotides 13228–13504 of murine genomic SOCS-1, recognizes a 3' untranslated region common to both SOCS-1a and SOCS-1b (the "SOCS-1a/SOCS-1b probe").

Both the SOCS-1b probe and the SOCS-1a/SOCS-1b probe hybridized to a 1.8 kb transcript that was most abundant in spleen and lung. The 1.8 kb transcript was also observed in all other tissues examined (heart, brain, liver, muscle, kidney and testis). The SOCS-1a/SOCS-1b probe, but not the SOCS-1b probe, hybridized to a 1.4 kb transcript that was most abundant in spleen and lung. The 1.4 kb transcript was present at lower levels in all other tissues examined (heart, brain, liver, muscle, kidney and testis). In blots probed with the SOCS-1a/SOCS-1b probe, the 1.4 kb transcript was much more abundant than the 1.8 kb transcript in all tissues examined. These results suggest that the sizes of the SOCS-1a and SOCS-1b transcripts are 1.4 kb and 1.8 kb respectively, and that there are no apparent differences between tissues with respect to the relative amounts of the two transcripts.

16.2.5 SOCS-1 Inhibits ObR-Mediated Signaling

To determine whether SOCS-1 can inhibit ObR-mediated signaling by leptin, 293 cells were cotransfected with a reporter plasmid that is responsive to STAT activation (pIL6-RE-SEAP) and either: 1) a plasmid which expresses the long form of human ObR; or 2) a plasmid which expresses the long form of human ObR and a plasmid which expresses a portion of SOCS-1b (nucleotides 12506–13411 of the murine SOCS-1 genomic clone; corresponds to the SOCS-1b portion of clone 11 in Table 1) The transfected cells were stimulated with 100 ng/ml leptin for 24 hours. After leptin stimulation, the activity of the pIL-6RE-SEAP reporter was determined by measuring the amount of alkaline phosphatase secreted into the medium.

Measurement of reporter activity demonstrated that, in the presence of leptin, expression of the STAT responsive reporter was increased eight-fold when ObR was also expressed by the cells. However, no activation of the STAT responsive reporter was observed occurred when the cells expressed both ObR and SOCS-1.

Because SOCS-1 inhibits ObR signalling, it may be possible to modulate ObR activity by modulating the expression or activity of SOCS-1 or by modulating the binding of SOCS-1 to JAK2. In addition, one can use SOCS-1 to identify candidate therapeutic compounds which alter the expression or activity of SOCS-1.

One can identify candidate therapeutic compounds for the treatment of a body weight disorder by providing a cell which expresses a mammalian Ob receptor protein, a mammalian JAK2 protein, and a mammalian SOCS-1 protein, and which contains a reporter construct which includes a sequence encoding a detectable protein operably linked to an Ob receptor responsive regulatory element; contacting the cell with a test compound; measuring the expression of the detectable protein in the presence of the test compound; and identifying those agents which cause an increase or a decrease in the expression of the detectable protein. One can also identify candidate therapeutic compounds for the treatment of a body weight disorder by: contacting a protein comprising an Ob receptor protein cytoplasmic domain with a polypeptide which includes the JH1 domain of a mammalian JAK2 protein, a mammalian SOCS-1 protein, and a test compound; measuring the binding of the JH1 domain polypeptide to the SOCS-1 protein in the presence of the test compound; and identifying agents which increase or a decrease in the binding of the JH1 domain polypeptide to SOCS-1.

17. Deposit of Microorganisms

The following microorganisms were deposited with the American Type Culture Collection (ATCC), Rockville, Md., on the dates indicated and were assigned the indicated accession number:

| Microorganism | Clone | ATCC Access. No. | Date of Deposit |
| --- | --- | --- | --- |
| E. coli strain 5312B4F3 | famj5312 | 69952 | Nov. 22, 1995 |
| E. coli h-ObRD | fahj5312d | 69963 | Dec. 5, 1995 |
| E. coli h-ObR-p87 | h-ObR-p87 | 69972 | Dec. 28, 1995 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

SEQUENCE LISTING (1) GENERAL INFORMATION:

(iii) NUMBER OF SEQUENCES: 50

(2) INFORMATION FOR SEQ ID NO: 1:

(i) SEQUENCE CHARACTERISTICS:
      (A) LENGTH: 3097 base pairs
      (B) TYPE: nucleic acid
      (C) STRANDEDNESS: double
      (D) TOPOLOGY: unknown (ii) MOLECULE TYPE: cDNA (ix) FEATURE:
      (A) NAME/KEY: Coding Sequence
      (B) LOCATION: 61...2742

(xi) SEQUENCE DESCRIPTION: SEQ ID NO: 1:

```
GTCGACCCAC GCGTCCGGAG GAATCGTTCT GCAAATCCAG GTGTACACCT CTGAAGAAAG          60

ATG ATG TGT CAG AAA TTC TAT GTG GTT TTG TTA CAC TGG GAA TTT CTT          108
Met Met Cys Gln Lys Phe Tyr Val Val Leu Leu His Trp Glu Phe Leu
 1               5                  10                  15

TAT GTG ATA GCT GCA CTT AAC CTG GCA TAT CCA ATC TCT CCC TGG AAA          156
Tyr Val Ile Ala Ala Leu Asn Leu Ala Tyr Pro Ile Ser Pro Trp Lys
             20                  25                  30

TTT AAG TTG TTT TGT GGA CCA CCG AAC ACA ACC GAT GAC TCC TTT CTC          204
Phe Lys Leu Phe Cys Gly Pro Pro Asn Thr Thr Asp Asp Ser Phe Leu
         35                  40                  45

TCA CCT GCT GGA GCC CCA AAC AAT GCC TCG GCT TTG AAG GGG GCT TCT          252
Ser Pro Ala Gly Ala Pro Asn Asn Ala Ser Ala Leu Lys Gly Ala Ser
 50                  55                  60

GAA GCA ATT GTT GAA GCT AAA TTT AAT TCA AGT GGT ATC TAC GTT CCT          300
Glu Ala Ile Val Glu Ala Lys Phe Asn Ser Ser Gly Ile Tyr Val Pro
 65                  70                  75                  80

GAG TTA TCC AAA ACA GTC TTC CAC TGT TGC TTT GGG AAT GAG CAA GGT          348
Glu Leu Ser Lys Thr Val Phe His Cys Cys Phe Gly Asn Glu Gln Gly
                 85                  90                  95

CAA AAC TGC TCT GCA CTC ACA GAC AAC ACT GAA GGG AAG ACA CTG GCT          396
Gln Asn Cys Ser Ala Leu Thr Asp Asn Thr Glu Gly Lys Thr Leu Ala
             100                 105                 110

TCA GTA GTG AAG GCT TCA GTT TTT CGC CAG CTA GGT GTA AAC TGG GAC          444
Ser Val Val Lys Ala Ser Val Phe Arg Gln Leu Gly Val Asn Trp Asp
         115                 120                 125

ATA GAG TGC TGG ATG AAA GGG GAC TTG ACA TTA TTC ATC TGT CAT ATG          492
Ile Glu Cys Trp Met Lys Gly Asp Leu Thr Leu Phe Ile Cys His Met
 130                 135                 140

GAG CCA TTA CCT AAG AAC CCC TTC AAG AAT TAT GAC TCT AAG GTC CAT          540
Glu Pro Leu Pro Lys Asn Pro Phe Lys Asn Tyr Asp Ser Lys Val His
145                 150                 155                 160

CTT TTA TAT GAT CTG CCT GAA GTC ATA GAT GAT TCG CCT CTG CCC CCA          588
Leu Leu Tyr Asp Leu Pro Glu Val Ile Asp Asp Ser Pro Leu Pro Pro
                 165                 170                 175

CTG AAA GAC AGC TTT CAG ACT GTC CAA TGC AAC TGC AGT CTT CGG GGA          636
Leu Lys Asp Ser Phe Gln Thr Val Gln Cys Asn Cys Ser Leu Arg Gly
             180                 185                 190

TGT GAA TGT CAT GTG CCG GTA CCC AGA GCC AAA CTC AAC TAC GCT CTT          684
Cys Glu Cys His Val Pro Val Pro Arg Ala Lys Leu Asn Tyr Ala Leu
         195                 200                 205

CTG ATG TAT TTG GAA ATC ACA TCT GCC GGT GTG AGT TTT CAG TCA CCT          732
```

```
                                                     -continued

Leu Met Tyr Leu Glu Ile Thr Ser Ala Gly Val Ser Phe Gln Ser Pro
    210                 215                 220

CTG ATG TCA CTG CAG CCC ATG CTT GTT GTG AAA CCC GAT CCA CCC TTA        780
Leu Met Ser Leu Gln Pro Met Leu Val Val Lys Pro Asp Pro Pro Leu
225                 230                 235                 240

GGT TTG CAT ATG GAA GTC ACA GAT GAT GGT AAT TTA AAG ATT TCT TGG        828
Gly Leu His Met Glu Val Thr Asp Asp Gly Asn Leu Lys Ile Ser Trp
                245                 250                 255

GAC AGC CAA ACA ATG GCA CCA TTT CCG CTT CAA TAT CAG GTG AAA TAT        876
Asp Ser Gln Thr Met Ala Pro Phe Pro Leu Gln Tyr Gln Val Lys Tyr
                260                 265                 270

TTA GAG AAT TCT ACA ATT GTA AGA GAG GCT GCT GAA ATT GTC TCA GCT        924
Leu Glu Asn Ser Thr Ile Val Arg Glu Ala Ala Glu Ile Val Ser Ala
                275                 280                 285

ACA TCT CTG CTG GTA GAC AGT GTG CTT CCT GGA TCT TCA TAT GAG GTC        972
Thr Ser Leu Leu Val Asp Ser Val Leu Pro Gly Ser Ser Tyr Glu Val
        290                 295                 300

CAG GTG AGG AGC AAG AGA CTG GAT GGT TCA GGA GTC TGG AGT GAC TGG       1020
Gln Val Arg Ser Lys Arg Leu Asp Gly Ser Gly Val Trp Ser Asp Trp
305                 310                 315                 320

AGT TCA CCT CAA GTC TTT ACC ACA CAA GAT GTT GTG TAT TTT CCA CCC       1068
Ser Ser Pro Gln Val Phe Thr Thr Gln Asp Val Val Tyr Phe Pro Pro
                325                 330                 335

AAA ATT CTG ACT AGT GTT GGA TCG AAT GCT TCT TTT CAT TGC ATC TAC       1116
Lys Ile Leu Thr Ser Val Gly Ser Asn Ala Ser Phe His Cys Ile Tyr
                340                 345                 350

AAA AAC GAA AAC CAG ATT ATC TCC TCA AAA CAG ATA GTT TGG TGG AGG       1164
Lys Asn Glu Asn Gln Ile Ile Ser Ser Lys Gln Ile Val Trp Trp Arg
        355                 360                 365

AAT CTA GCT GAG AAA ATC CCT GAG ATA CAG TAC AGC ATT GTG AGT GAC       1212
Asn Leu Ala Glu Lys Ile Pro Glu Ile Gln Tyr Ser Ile Val Ser Asp
370                 375                 380

CGA GTT AGC AAA GTT ACC TTC TCC AAC CTG AAA GCC ACC AGA CCT CGA       1260
Arg Val Ser Lys Val Thr Phe Ser Asn Leu Lys Ala Thr Arg Pro Arg
385                 390                 395                 400

GGG AAG TTT ACC TAT GAC GCA GTG TAC TGC TGC AAT GAG CAG GCG TGC       1308
Gly Lys Phe Thr Tyr Asp Ala Val Tyr Cys Cys Asn Glu Gln Ala Cys
                405                 410                 415

CAT CAC CGC TAT GCT GAA TTA TAC GTG ATC GAT GTC AAT ATC AAT ATA       1356
His His Arg Tyr Ala Glu Leu Tyr Val Ile Asp Val Asn Ile Asn Ile
                420                 425                 430

TCA TGT GAA ACT GAC GGG TAC TTA ACT AAA ATG ACT TGC AGA TGG TCA       1404
Ser Cys Glu Thr Asp Gly Tyr Leu Thr Lys Met Thr Cys Arg Trp Ser
                435                 440                 445

CCC AGC ACA ATC CAA TCA CTA GTG GGA AGC ACT GTG CAG CTG AGG TAT       1452
Pro Ser Thr Ile Gln Ser Leu Val Gly Ser Thr Val Gln Leu Arg Tyr
        450                 455                 460

CAC AGG CGC AGC CTG TAT TGT CCT GAT AGT CCA TCT ATT CAT CCT ACG       1500
His Arg Arg Ser Leu Tyr Cys Pro Asp Ser Pro Ser Ile His Pro Thr
465                 470                 475                 480

TCT GAG CCC AAA AAC TGC GTC TTA CAG AGA GAC GGC TTT TAT GAA TGT       1548
Ser Glu Pro Lys Asn Cys Val Leu Gln Arg Asp Gly Phe Tyr Glu Cys
                485                 490                 495

GTT TTC CAG CCA ATC TTT CTA TTA TCT GGC TAT ACA ATG TGG ATC AGG       1596
Val Phe Gln Pro Ile Phe Leu Leu Ser Gly Tyr Thr Met Trp Ile Arg
                500                 505                 510

ATC AAC CAT TCT TTA GGT TCA CTT GAC TCG CCA CCA ACG TGT GTC CTT       1644
Ile Asn His Ser Leu Gly Ser Leu Asp Ser Pro Pro Thr Cys Val Leu
        515                 520                 525
```

-continued

| | | |
|---|---|---|
| CCT GAC TCC GTA GTA AAA CCA CTA CCT CCA TCT AAC GTA AAA GCA GAG<br>Pro Asp Ser Val Val Lys Pro Leu Pro Pro Ser Asn Val Lys Ala Glu<br>530                        535                   540 | 1692 |
| ATT ACT GTA AAC ACT GGA TTA TTG AAA GTA TCT TGG GAA AAG CCA GTC<br>Ile Thr Val Asn Thr Gly Leu Leu Lys Val Ser Trp Glu Lys Pro Val<br>545                   550                 555               560 | 1740 |
| TTT CCG GAG AAT AAC CTT CAA TTC CAG ATT CGA TAT GGC TTA AGT GGA<br>Phe Pro Glu Asn Asn Leu Gln Phe Gln Ile Arg Tyr Gly Leu Ser Gly<br>                 565                  570                575 | 1788 |
| AAA GAA ATA CAA TGG AAG ACA CAT GAG GTA TTC GAT GCA AAG TCA AAG<br>Lys Glu Ile Gln Trp Lys Thr His Glu Val Phe Asp Ala Lys Ser Lys<br>            580                  585               590 | 1836 |
| TCT GCC AGC CTG CTG GTG TCA GAC CTC TGT GCA GTC TAT GTG GTC CAG<br>Ser Ala Ser Leu Leu Val Ser Asp Leu Cys Ala Val Tyr Val Val Gln<br>            595                 600               605 | 1884 |
| GTT CGC TGC CGG CGG TTG GAT GGA CTA GGA TAT TGG AGT AAT TGG AGC<br>Val Arg Cys Arg Arg Leu Asp Gly Leu Gly Tyr Trp Ser Asn Trp Ser<br>610                        615                  620 | 1932 |
| AGT CCA GCC TAT ACG CTT GTC ATG GAT GTA AAA GTT CCT ATG AGA GGG<br>Ser Pro Ala Tyr Thr Leu Val Met Asp Val Lys Val Pro Met Arg Gly<br>625                        630                 635               640 | 1980 |
| CCT GAA TTT TGG AGA AAA ATG GAT GGG GAC GTT ACT AAA AAG GAG AGA<br>Pro Glu Phe Trp Arg Lys Met Asp Gly Asp Val Thr Lys Lys Glu Arg<br>                 645                  650               655 | 2028 |
| AAT GTC ACC TTG CTT TGG AAG CCC CTG ACG AAA AAT GAC TCA CTG TGT<br>Asn Val Thr Leu Leu Trp Lys Pro Leu Thr Lys Asn Asp Ser Leu Cys<br>            660                  665               670 | 2076 |
| AGT GTG AGG AGG TAC GTT GTG AAG CAT CGT ACT GCC CAC AAT GGG ACG<br>Ser Val Arg Arg Tyr Val Val Lys His Arg Thr Ala His Asn Gly Thr<br>               675                  680               685 | 2124 |
| TGG TCA GAA GAT GTG GGA AAT CGG ACC AAT CTC ACT TTC CTG TGG ACA<br>Trp Ser Glu Asp Val Gly Asn Arg Thr Asn Leu Thr Phe Leu Trp Thr<br>690                        695                 700 | 2172 |
| GAA CCA GCG CAC ACT GTT ACA GTT CTG GCT GTC AAT TCC CTC GGC GCT<br>Glu Pro Ala His Thr Val Thr Val Leu Ala Val Asn Ser Leu Gly Ala<br>705                        710                 715               720 | 2220 |
| TCC CTT GTG AAT TTT AAC CTT ACC TTC TCA TGG CCC ATG AGT AAA GTG<br>Ser Leu Val Asn Phe Asn Leu Thr Phe Ser Trp Pro Met Ser Lys Val<br>               725                  730               735 | 2268 |
| AGT GCT GTG GAG TCA CTC AGT GCT TAT CCC CTG AGC AGC AGC TGT GTC<br>Ser Ala Val Glu Ser Leu Ser Ala Tyr Pro Leu Ser Ser Ser Cys Val<br>            740                  745               750 | 2316 |
| ATC CTT TCC TGG ACA CTG TCA CCT GAT GAT TAT AGT CTG TTA TAT CTG<br>Ile Leu Ser Trp Thr Leu Ser Pro Asp Asp Tyr Ser Leu Leu Tyr Leu<br>            755                 760               765 | 2364 |
| GTT ATT GAA TGG AAG ATC CTT AAT GAA GAT GAT GGA ATG AAG TGG CTT<br>Val Ile Glu Trp Lys Ile Leu Asn Glu Asp Asp Gly Met Lys Trp Leu<br>770                        775                 780 | 2412 |
| AGA ATT CCC TCG AAT GTT AAA AAG TTT TAT ATC CAC GAT AAT TTT ATT<br>Arg Ile Pro Ser Asn Val Lys Lys Phe Tyr Ile His Asp Asn Phe Ile<br>785                        790                 795               800 | 2460 |
| CCC ATC GAG AAA TAT CAG TTT AGT CTT TAC CCA GTA TTT ATG GAA GGA<br>Pro Ile Glu Lys Tyr Gln Phe Ser Leu Tyr Pro Val Phe Met Glu Gly<br>                 805                  810               815 | 2508 |
| GTT GGA AAA CCA AAG ATA ATT AAT GGT TTC ACC AAA GAT GCT ATC GAC<br>Val Gly Lys Pro Lys Ile Ile Asn Gly Phe Thr Lys Asp Ala Ile Asp<br>            820                  825               830 | 2556 |
| AAG CAG CAG AAT GAC GCA GGG CTG TAT GTC ATT GTA CCC ATA ATT ATT<br>Lys Gln Gln Asn Asp Ala Gly Leu Tyr Val Ile Val Pro Ile Ile Ile<br>               835                  840               845 | 2604 |

```
TCC TCT TGT GTC CTA CTG CTC GGA ACA CTG TTA ATT TCA CAC CAG AGA      2652
Ser Ser Cys Val Leu Leu Leu Gly Thr Leu Leu Ile Ser His Gln Arg
    850                 855                 860

ATG AAA AAG TTG TTT TGG GAC GAT GTT CCA AAC CCC AAG AAT TGT TCC      2700
Met Lys Lys Leu Phe Trp Asp Asp Val Pro Asn Pro Lys Asn Cys Ser
865                 870                 875                 880

TGG GCA CAA GGA CTG AAT TTC CAA AAG AGA ACG GAC ACT CTT              2742
Trp Ala Gln Gly Leu Asn Phe Gln Lys Arg Thr Asp Thr Leu
                885                 890

TGAAGTCTCT CATGACCACT ACAGATGAAC CCAATCTACC AACTTCCCAA CAGTCCATAC    2802

AATATTAGAA GATGTTTACA TTTTGATGGA GGGAAACAAA CCTAAACTAT GGTTTGAATG    2862

ACTAAGAAAT AACATTTGAT GAGCTTATTA GAGAAGTGTA TATTTTGTGG CCACAATGTA    2922

GGTTTGATGT AGTTCAGTTT GGGACATATG CTTGATTTTC AGGGCATCAA AAATTTAAAG    2982

TTGATATTCA TGGACTCTGC ATTTTATTTC TTAAGTCATA AAATGATAAT GGTGTGACGG    3042

TTGGTGTCAG AACCTATTTG GGTACAGATC ACCAAAATAT GGTAGGTAAT GCCTT         3097
```

(2) INFORMATION FOR SEQ ID NO: 2:

(i) SEQUENCE CHARACTERISTICS:
        (A) LENGTH: 894 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO: 2:

```
Met Met Cys Gln Lys Phe Tyr Val Val Leu Leu His Trp Glu Phe Leu
 1               5                  10                  15

Tyr Val Ile Ala Ala Leu Asn Leu Ala Tyr Pro Ile Ser Pro Trp Lys
                20                  25                  30

Phe Lys Leu Phe Cys Gly Pro Pro Asn Thr Thr Asp Asp Ser Phe Leu
            35                  40                  45

Ser Pro Ala Gly Ala Pro Asn Asn Ala Ser Ala Leu Lys Gly Ala Ser
 50                  55                  60

Glu Ala Ile Val Glu Ala Lys Phe Asn Ser Ser Gly Ile Tyr Val Pro
 65                  70                  75                  80

Glu Leu Ser Lys Thr Val Phe His Cys Cys Phe Gly Asn Glu Gln Gly
                85                  90                  95

Gln Asn Cys Ser Ala Leu Thr Asp Asn Thr Glu Gly Lys Thr Leu Ala
                100                 105                 110

Ser Val Val Lys Ala Ser Val Phe Arg Gln Leu Gly Val Asn Trp Asp
            115                 120                 125

Ile Glu Cys Trp Met Lys Gly Asp Leu Thr Leu Phe Ile Cys His Met
130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Asp Ser Pro Leu Pro Pro
                165                 170                 175

Leu Lys Asp Ser Phe Gln Thr Val Gln Cys Asn Cys Ser Leu Arg Gly
            180                 185                 190

Cys Glu Cys His Val Pro Val Pro Arg Ala Lys Leu Asn Tyr Ala Leu
        195                 200                 205

Leu Met Tyr Leu Glu Ile Thr Ser Ala Gly Val Ser Phe Gln Ser Pro
```

```
            210                 215                 220
Leu Met Ser Leu Gln Pro Met Leu Val Val Lys Pro Asp Pro Leu
225                 230                 235                 240

Gly Leu His Met Glu Val Thr Asp Asp Gly Asn Leu Lys Ile Ser Trp
                245                 250                 255

Asp Ser Gln Thr Met Ala Pro Phe Pro Leu Gln Tyr Gln Val Lys Tyr
                260                 265                 270

Leu Glu Asn Ser Thr Ile Val Arg Glu Ala Ala Glu Ile Val Ser Ala
                275                 280                 285

Thr Ser Leu Leu Val Asp Ser Val Leu Pro Gly Ser Ser Tyr Glu Val
                290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro
                325                 330                 335

Lys Ile Leu Thr Ser Val Gly Ser Asn Ala Ser Phe His Cys Ile Tyr
                340                 345                 350

Lys Asn Glu Asn Gln Ile Ile Ser Ser Lys Gln Ile Val Trp Trp Arg
                355                 360                 365

Asn Leu Ala Glu Lys Ile Pro Glu Ile Gln Tyr Ser Ile Val Ser Asp
370                 375                 380

Arg Val Ser Lys Val Thr Phe Ser Asn Leu Lys Ala Thr Arg Pro Arg
385                 390                 395                 400

Gly Lys Phe Thr Tyr Asp Ala Val Tyr Cys Cys Asn Glu Gln Ala Cys
                405                 410                 415

His His Arg Tyr Ala Glu Leu Tyr Val Ile Asp Val Asn Ile Asn Ile
                420                 425                 430

Ser Cys Glu Thr Asp Gly Tyr Leu Thr Lys Met Thr Cys Arg Trp Ser
                435                 440                 445

Pro Ser Thr Ile Gln Ser Leu Val Gly Ser Thr Val Gln Leu Arg Tyr
                450                 455                 460

His Arg Arg Ser Leu Tyr Cys Pro Asp Ser Pro Ser Ile His Pro Thr
465                 470                 475                 480

Ser Glu Pro Lys Asn Cys Val Leu Gln Arg Asp Gly Phe Tyr Glu Cys
                485                 490                 495

Val Phe Gln Pro Ile Phe Leu Leu Ser Gly Tyr Thr Met Trp Ile Arg
                500                 505                 510

Ile Asn His Ser Leu Gly Ser Leu Asp Ser Pro Thr Cys Val Leu
                515                 520                 525

Pro Asp Ser Val Val Lys Pro Leu Pro Pro Ser Asn Val Lys Ala Glu
530                 535                 540

Ile Thr Val Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Ser Gly
                565                 570                 575

Lys Glu Ile Gln Trp Lys Thr His Glu Val Phe Asp Ala Lys Ser Lys
                580                 585                 590

Ser Ala Ser Leu Leu Val Ser Asp Leu Cys Ala Val Tyr Val Val Gln
                595                 600                 605

Val Arg Cys Arg Arg Leu Asp Gly Leu Gly Tyr Trp Ser Asn Trp Ser
610                 615                 620

Ser Pro Ala Tyr Thr Leu Val Met Asp Val Lys Val Pro Met Arg Gly
625                 630                 635                 640
```

```
Pro Glu Phe Trp Arg Lys Met Asp Gly Asp Val Thr Lys Lys Glu Arg
            645                 650                 655

Asn Val Thr Leu Leu Trp Lys Pro Leu Thr Lys Asn Asp Ser Leu Cys
            660                 665                 670

Ser Val Arg Arg Tyr Val Val Lys His Arg Thr Ala His Asn Gly Thr
            675                 680                 685

Trp Ser Glu Asp Val Gly Asn Arg Thr Asn Leu Thr Phe Leu Trp Thr
            690                 695                 700

Glu Pro Ala His Thr Val Thr Val Leu Ala Val Asn Ser Leu Gly Ala
705                 710                 715                 720

Ser Leu Val Asn Phe Asn Leu Thr Phe Ser Trp Pro Met Ser Lys Val
            725                 730                 735

Ser Ala Val Glu Ser Leu Ser Ala Tyr Pro Leu Ser Ser Ser Cys Val
            740                 745                 750

Ile Leu Ser Trp Thr Leu Ser Pro Asp Asp Tyr Ser Leu Leu Tyr Leu
            755                 760                 765

Val Ile Glu Trp Lys Ile Leu Asn Glu Asp Asp Gly Met Lys Trp Leu
770                 775                 780

Arg Ile Pro Ser Asn Val Lys Lys Phe Tyr Ile His Asp Asn Phe Ile
785                 790                 795                 800

Pro Ile Glu Lys Tyr Gln Phe Ser Leu Tyr Pro Val Phe Met Glu Gly
            805                 810                 815

Val Gly Lys Pro Lys Ile Ile Asn Gly Phe Thr Lys Asp Ala Ile Asp
            820                 825                 830

Lys Gln Gln Asn Asp Ala Gly Leu Tyr Val Ile Val Pro Ile Ile Ile
            835                 840                 845

Ser Ser Cys Val Leu Leu Leu Gly Thr Leu Leu Ile Ser His Gln Arg
            850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Arg Thr Asp Thr Leu
            885                 890

(2) INFORMATION FOR SEQ ID NO: 3:

(i) SEQUENCE CHARACTERISTICS:
        (A) LENGTH: 3871 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: Coding Sequence
        (B) LOCATION: 194...3688

(xi) SEQUENCE DESCRIPTION: SEQ ID NO: 3:

GGCACGAGCC GGTCTGGCTT GGGCAGGCTG CCCGGGCCGT GGCAGGAAGC CGGAAGCAGC      60

CGCGGCCCCA GTTCGGGAGA CATGGCGGGC GTTAAAGCTC TCGTGGCATT ATCCTTCAGT     120

GGGGCTATTG GACTGACTTT TCTTATGCTG GGATGTGCCT TAGAGGATTA TGGGTGTACT     180

TCTCTGAAGT AAG ATG ATT TGT CAA AAA TTC TGT GTG GTT TTG TTA CAT        229
            Met Ile Cys Gln Lys Phe Cys Val Val Leu Leu His
              1               5                  10

TGG GAA TTT ATT TAT GTG ATA ACT GCG TTT AAC TTG TCA TAT CCA ATT       277
Trp Glu Phe Ile Tyr Val Ile Thr Ala Phe Asn Leu Ser Tyr Pro Ile
         15                  20                  25
```

-continued

| | |
|---|---|
| ACT CCT TGG AGA TTT AAG TTG TCT TGC ATG CCA CCA AAT TCA ACC TAT<br>Thr Pro Trp Arg Phe Lys Leu Ser Cys Met Pro Pro Asn Ser Thr Tyr<br>  30                  35                  40 | 325 |
| GAC TAC TTC CTT TTG CCT GCT GGA CTC TCA AAG AAT ACT TCA AAT TCG<br>Asp Tyr Phe Leu Leu Pro Ala Gly Leu Ser Lys Asn Thr Ser Asn Ser<br> 45                  50                  55                  60 | 373 |
| AAT GGA CAT TAT GAG ACA GCT GTT GAA CCT AAG TTT AAT TCA AGT GGT<br>Asn Gly His Tyr Glu Thr Ala Val Glu Pro Lys Phe Asn Ser Ser Gly<br>                    65                  70                  75 | 421 |
| ACT CAC TTT TCT AAC TTA TCC AAA ACA ACT TTC CAC TGT TGC TTT CGG<br>Thr His Phe Ser Asn Leu Ser Lys Thr Thr Phe His Cys Cys Phe Arg<br>                80                  85                  90 | 469 |
| AGT GAG CAA GAT AGA AAC TGC TCC TTA TGT GCA GAC AAC ATT GAA GGA<br>Ser Glu Gln Asp Arg Asn Cys Ser Leu Cys Ala Asp Asn Ile Glu Gly<br>             95                 100                 105 | 517 |
| AAG ACA TTT GTT TCA ACA GTA AAT TCT TTA GTT TTT CAA CAA ATA GAT<br>Lys Thr Phe Val Ser Thr Val Asn Ser Leu Val Phe Gln Gln Ile Asp<br>        110                 115                 120 | 565 |
| GCA AAC TGG AAC ATA CAG TGC TGG CTA AAA GGA GAC TTA AAA TTA TTC<br>Ala Asn Trp Asn Ile Gln Cys Trp Leu Lys Gly Asp Leu Lys Leu Phe<br>125                 130                 135                 140 | 613 |
| ATC TGT TAT GTG GAG TCA TTA TTT AAG AAT CTA TTC AGG AAT TAT AAC<br>Ile Cys Tyr Val Glu Ser Leu Phe Lys Asn Leu Phe Arg Asn Tyr Asn<br>                145                 150                 155 | 661 |
| TAT AAG GTC CAT CTT TTA TAT GTT CTG CCT GAA GTG TTA GAA GAT TCA<br>Tyr Lys Val His Leu Leu Tyr Val Leu Pro Glu Val Leu Glu Asp Ser<br>            160                 165                 170 | 709 |
| CCT CTG GTT CCC CAA AAA GGC AGT TTT CAG ATG GTT CAC TGC AAT TGC<br>Pro Leu Val Pro Gln Lys Gly Ser Phe Gln Met Val His Cys Asn Cys<br>        175                 180                 185 | 757 |
| AGT GTT CAT GAA TGT TGT GAA TGT CTT GTG CCT GTG CCA ACA GCC AAA<br>Ser Val His Glu Cys Cys Glu Cys Leu Val Pro Val Pro Thr Ala Lys<br>190                 195                 200 | 805 |
| CTC AAC GAC ACT CTC CTT ATG TGT TTG AAA ATC ACA TCT GGT GGA GTA<br>Leu Asn Asp Thr Leu Leu Met Cys Leu Lys Ile Thr Ser Gly Gly Val<br>205                 210                 215                 220 | 853 |
| ATT TTC CAG TCA CCT CTA ATG TCA GTT CAG CCC ATA AAT ATG GTG AAG<br>Ile Phe Gln Ser Pro Leu Met Ser Val Gln Pro Ile Asn Met Val Lys<br>                225                 230                 235 | 901 |
| CCT GAT CCA CCA TTA GGT TTG CAT ATG GAA ATC ACA GAT GAT GGT AAT<br>Pro Asp Pro Pro Leu Gly Leu His Met Glu Ile Thr Asp Asp Gly Asn<br>            240                 245                 250 | 949 |
| TTA AAG ATT TCT TGG TCC AGC CCA CCA TTG GTA CCA TTT CCA CTT CAA<br>Leu Lys Ile Ser Trp Ser Ser Pro Pro Leu Val Pro Phe Pro Leu Gln<br>        255                 260                 265 | 997 |
| TAT CAA GTG AAA TAT TCA GAG AAT TCT ACA ACA GTT ATC AGA GAA GCT<br>Tyr Gln Val Lys Tyr Ser Glu Asn Ser Thr Thr Val Ile Arg Glu Ala<br>    270                 275                 280 | 1045 |
| GAC AAG ATT GTC TCA GCT ACA TCC CTG CTA GTA GAC AGT ATA CTT CCT<br>Asp Lys Ile Val Ser Ala Thr Ser Leu Leu Val Asp Ser Ile Leu Pro<br>285                 290                 295                 300 | 1093 |
| GGG TCT TCG TAT GAG GTT CAG GTG AGG GGC AAG AGA CTG GAT GGC CCA<br>Gly Ser Ser Tyr Glu Val Gln Val Arg Gly Lys Arg Leu Asp Gly Pro<br>                305                 310                 315 | 1141 |
| GGA ATC TGG AGT GAC TGG AGT ACT CCT CGT GTC TTT ACC ACA CAA GAT<br>Gly Ile Trp Ser Asp Trp Ser Thr Pro Arg Val Phe Thr Thr Gln Asp<br>            320                 325                 330 | 1189 |
| GTC ATA TAC TTT CCA CCT AAA ATT CTG ACA AGT GTT GGG TCT AAT GTT<br>Val Ile Tyr Phe Pro Pro Lys Ile Leu Thr Ser Val Gly Ser Asn Val | 1237 |

-continued

```
                335                 340                 345
TCT TTT CAC TGC ATC TAT AAG AAG GAA AAC AAG ATT GTT CCC TCA AAA      1285
Ser Phe His Cys Ile Tyr Lys Lys Glu Asn Lys Ile Val Pro Ser Lys
    350                 355                 360

GAG ATT GTT TGG TGG ATG AAT TTA GCT GAG AAA ATT CCT CAA AGC CAG      1333
Glu Ile Val Trp Trp Met Asn Leu Ala Glu Lys Ile Pro Gln Ser Gln
365                 370                 375                 380

TAT GAT GTT GTG AGT GAT CAT GTT AGC AAA GTT ACT TTT TTC AAT CTG      1381
Tyr Asp Val Val Ser Asp His Val Ser Lys Val Thr Phe Phe Asn Leu
                385                 390                 395

AAT GAA ACC AAA CCT CGA GGA AAG TTT ACC TAT GAT GCA GTG TAC TGC      1429
Asn Glu Thr Lys Pro Arg Gly Lys Phe Thr Tyr Asp Ala Val Tyr Cys
        400                 405                 410

TGC AAT GAA CAT GAA TGC CAT CAT CGC TAT GCT GAA TTA TAT GTG ATT      1477
Cys Asn Glu His Glu Cys His His Arg Tyr Ala Glu Leu Tyr Val Ile
            415                 420                 425

GAT GTC AAT ATC AAT ATC TCA TGT GAA ACT GAT GGG TAC TTA ACT AAA      1525
Asp Val Asn Ile Asn Ile Ser Cys Glu Thr Asp Gly Tyr Leu Thr Lys
430                 435                 440

ATG ACT TGC AGA TGG TCA ACC AGT ACA ATC CAG TCA CTT GCG GAA AGC      1573
Met Thr Cys Arg Trp Ser Thr Ser Thr Ile Gln Ser Leu Ala Glu Ser
445                 450                 455                 460

ACT TTG CAA TTG AGG TAT CAT AGG AGC AGC CTT TAC TGT TCT GAT ATT      1621
Thr Leu Gln Leu Arg Tyr His Arg Ser Ser Leu Tyr Cys Ser Asp Ile
                465                 470                 475

CCA TCT ATT CAT CCC ATA TCT GAG CCC AAA GAT TGC TAT TTG CAG AGT      1669
Pro Ser Ile His Pro Ile Ser Glu Pro Lys Asp Cys Tyr Leu Gln Ser
        480                 485                 490

GAT GGT TTT TAT GAA TGC ATT TTC CAG CCA ATC TTC CTA TTA TCT GGC      1717
Asp Gly Phe Tyr Glu Cys Ile Phe Gln Pro Ile Phe Leu Leu Ser Gly
            495                 500                 505

TAC ACA ATG TGG ATT AGG ATC AAT CAC TCT CTA GGT TCA CTT GAC TCC      1765
Tyr Thr Met Trp Ile Arg Ile Asn His Ser Leu Gly Ser Leu Asp Ser
510                 515                 520

CCA CCA ACA TGT GTC CTT CCT GAT TCT GTG GTG AAG CCA CTG CCT CCA      1813
Pro Pro Thr Cys Val Leu Pro Asp Ser Val Val Lys Pro Leu Pro Pro
525                 530                 535                 540

TCC AGT GTG AAA GCA GAA ATT ACT ATA AAC ATT GGA TTA TTG AAA ATA      1861
Ser Ser Val Lys Ala Glu Ile Thr Ile Asn Ile Gly Leu Leu Lys Ile
                545                 550                 555

TCT TGG GAA AAG CCA GTC TTT CCA GAG AAT AAC CTT CAA TTC CAG ATT      1909
Ser Trp Glu Lys Pro Val Phe Pro Glu Asn Asn Leu Gln Phe Gln Ile
        560                 565                 570

CGC TAT GGT TTA AGT GGA AAA GAA GTA CAA TGG AAG ATG TAT GAG GTT      1957
Arg Tyr Gly Leu Ser Gly Lys Glu Val Gln Trp Lys Met Tyr Glu Val
            575                 580                 585

TAT GAT GCA AAA TCA AAA TCT GTC AGT CTC CCA GTT CCA GAC TTG TGT      2005
Tyr Asp Ala Lys Ser Lys Ser Val Ser Leu Pro Val Pro Asp Leu Cys
590                 595                 600

GCA GTC TAT GCT GTT CAG GTG CGC TGT AAG AGG CTA GAT GGA CTG GGA      2053
Ala Val Tyr Ala Val Gln Val Arg Cys Lys Arg Leu Asp Gly Leu Gly
605                 610                 615                 620

TAT TGG AGT AAT TGG AGC AAT CCA GCC TAC ACA GTT GTC ATG GAT ATA      2101
Tyr Trp Ser Asn Trp Ser Asn Pro Ala Tyr Thr Val Val Met Asp Ile
                625                 630                 635

AAA GTT CCT ATG AGA GGA CCT GAA TTT TGG AGA ATA ATT AAT GGA GAT      2149
Lys Val Pro Met Arg Gly Pro Glu Phe Trp Arg Ile Ile Asn Gly Asp
        640                 645                 650

ACT ATG AAA AAG GAG AAA AAT GTC ACT TTA CTT TGG AAG CCC CTG ATG      2197
```

```
                Thr Met Lys Lys Glu Lys Asn Val Thr Leu Leu Trp Lys Pro Leu Met
                            655                 660                 665

AAA AAT GAC TCA TTG TGC AGT GTT CAG AGA TAT GTG ATA AAC CAT CAT        2245
Lys Asn Asp Ser Leu Cys Ser Val Gln Arg Tyr Val Ile Asn His His
            670                 675                 680

ACT TCC TGC AAT GGA ACA TGG TCA GAA GAT GTG GGA AAT CAC ACG AAA        2293
Thr Ser Cys Asn Gly Thr Trp Ser Glu Asp Val Gly Asn His Thr Lys
685                 690                 695                 700

TTC ACT TTC CTG TGG ACA GAG CAA GCA CAT ACT GTT ACG GTT CTG GCC        2341
Phe Thr Phe Leu Trp Thr Glu Gln Ala His Thr Val Thr Val Leu Ala
                705                 710                 715

ATC AAT TCA ATT GGT GCT TCT GTT GCA AAT TTT AAT TTA ACC TTT TCA        2389
Ile Asn Ser Ile Gly Ala Ser Val Ala Asn Phe Asn Leu Thr Phe Ser
            720                 725                 730

TGG CCT ATG AGC AAA GTA AAT ATC GTG CAG TCA CTC AGT GCT TAT CCT        2437
Trp Pro Met Ser Lys Val Asn Ile Val Gln Ser Leu Ser Ala Tyr Pro
            735                 740                 745

TTA AAC AGC AGT TGT GTG ATT GTT TCC TGG ATA CTA TCA CCC AGT GAT        2485
Leu Asn Ser Ser Cys Val Ile Val Ser Trp Ile Leu Ser Pro Ser Asp
            750                 755                 760

TAC AAG CTA ATG TAT TTT ATT ATT GAG TGG AAA AAT CTT AAT GAA GAT        2533
Tyr Lys Leu Met Tyr Phe Ile Ile Glu Trp Lys Asn Leu Asn Glu Asp
765                 770                 775                 780

GGT GAA ATA AAA TGG CTT AGA ATC TCT TCA TCT GTT AAG AAG TAT TAT        2581
Gly Glu Ile Lys Trp Leu Arg Ile Ser Ser Ser Val Lys Lys Tyr Tyr
                785                 790                 795

ATC CAT GAT CAT TTT ATC CCC ATT GAG AAG TAC CAG TTC AGT CTT TAC        2629
Ile His Asp His Phe Ile Pro Ile Glu Lys Tyr Gln Phe Ser Leu Tyr
            800                 805                 810

CCA ATA TTT ATG GAA GGA GTG GGA AAA CCA AAG ATA ATT AAT AGT TTC        2677
Pro Ile Phe Met Glu Gly Val Gly Lys Pro Lys Ile Ile Asn Ser Phe
            815                 820                 825

ACT CAA GAT GAT ATT GAA AAA CAC CAG AGT GAT GCA GGT TTA TAT GTA        2725
Thr Gln Asp Asp Ile Glu Lys His Gln Ser Asp Ala Gly Leu Tyr Val
            830                 835                 840

ATT GTG CCA GTA ATT ATT TCC TCT TCC ATC TTA TTG CTT GGA ACA TTA        2773
Ile Val Pro Val Ile Ile Ser Ser Ser Ile Leu Leu Leu Gly Thr Leu
845                 850                 855                 860

TTA ATA TCA CAC CAA AGA ATG AAA AAG CTA TTT TGG GAA GAT GTT CCG        2821
Leu Ile Ser His Gln Arg Met Lys Lys Leu Phe Trp Glu Asp Val Pro
                865                 870                 875

AAC CCC AAG AAT TGT TCC TGG GCA CAA GGA CTT AAT TTT CAG AAG CCA        2869
Asn Pro Lys Asn Cys Ser Trp Ala Gln Gly Leu Asn Phe Gln Lys Pro
            880                 885                 890

GAA ACG TTT GAG CAT CTT TTT ATC AAG CAT ACA GCA TCA GTG ACA TGT        2917
Glu Thr Phe Glu His Leu Phe Ile Lys His Thr Ala Ser Val Thr Cys
            895                 900                 905

GGT CCT CTT CTT TTG GAG CCT GAA ACA ATT TCA GAA GAT ATC AGT GTT        2965
Gly Pro Leu Leu Leu Glu Pro Glu Thr Ile Ser Glu Asp Ile Ser Val
            910                 915                 920

GAT ACA TCA TGG AAA AAT AAA GAT GAG ATG ATG CCA ACA ACT GTG GTC        3013
Asp Thr Ser Trp Lys Asn Lys Asp Glu Met Met Pro Thr Thr Val Val
925                 930                 935                 940

TCT CTA CTT TCA ACA ACA GAT CTT GAA AAG GGT TCT GTT TGT ATT AGT        3061
Ser Leu Leu Ser Thr Thr Asp Leu Glu Lys Gly Ser Val Cys Ile Ser
                945                 950                 955

GAC CAG TTC AAC AGT GTT AAC TTC TCT GAG GCT GAG GGT ACT GAG GTA        3109
Asp Gln Phe Asn Ser Val Asn Phe Ser Glu Ala Glu Gly Thr Glu Val
            960                 965                 970
```

-continued

| | |
|---|---|
| ACC TAT GAG GAC GAA AGC CAG AGA CAA CCC TTT GTT AAA TAC GCC ACG<br>Thr Tyr Glu Asp Glu Ser Gln Arg Gln Pro Phe Val Lys Tyr Ala Thr<br>               975                    980                 985 | 3157 |
| CTG ATC AGC AAC TCT AAA CCA AGT GAA ACT GGT GAA GAA CAA GGG CTT<br>Leu Ile Ser Asn Ser Lys Pro Ser Glu Thr Gly Glu Glu Gln Gly Leu<br>               990                    995               1000 | 3205 |
| ATA AAT AGT TCA GTC ACC AAG TGC TTC TCT AGC AAA AAT TCT CCG TTG<br>Ile Asn Ser Ser Val Thr Lys Cys Phe Ser Ser Lys Asn Ser Pro Leu<br>005                  1010               1015               1020 | 3253 |
| AAG GAT TCT TTC TCT AAT AGC TCA TGG GAG ATA GAG GCC CAG GCA TTT<br>Lys Asp Ser Phe Ser Asn Ser Ser Trp Glu Ile Glu Ala Gln Ala Phe<br>             1025               1030               1035 | 3301 |
| TTT ATA TTA TCA GAT CAG CAT CCC AAC ATA ATT TCA CCA CAC CTC ACA<br>Phe Ile Leu Ser Asp Gln His Pro Asn Ile Ile Ser Pro His Leu Thr<br>             1040               1045               1050 | 3349 |
| TTC TCA GAA GGA TTG GAT GAA CTT TTG AAA TTG GAG GGA AAT TTC CCT<br>Phe Ser Glu Gly Leu Asp Glu Leu Leu Lys Leu Glu Gly Asn Phe Pro<br>             1055               1060               1065 | 3397 |
| GAA GAA AAT AAT GAT AAA AAG TCT ATC TAT TAT TTA GGG GTC ACC TCA<br>Glu Glu Asn Asn Asp Lys Lys Ser Ile Tyr Tyr Leu Gly Val Thr Ser<br>      1070               1075               1080 | 3445 |
| ATC AAA AAG AGA GAG AGT GGT GTG CTT TTG ACT GAC AAG TCA AGG GTA<br>Ile Lys Lys Arg Glu Ser Gly Val Leu Leu Thr Asp Lys Ser Arg Val<br>085                  1090               1095               1100 | 3493 |
| TCG TGC CCA TTC CCA GCC CCC TGT TTA TTC ACG GAC ATC AGA GTT CTC<br>Ser Cys Pro Phe Pro Ala Pro Cys Leu Phe Thr Asp Ile Arg Val Leu<br>             1105               1110               1115 | 3541 |
| CAG GAC AGT TGC TCA CAC TTT GTA GAA AAT AAT ATC AAC TTA GGA ACT<br>Gln Asp Ser Cys Ser His Phe Val Glu Asn Asn Ile Asn Leu Gly Thr<br>             1120               1125               1130 | 3589 |
| TCT AGT AAG AAG ACT TTT GCA TCT TAC ATG CCT CAA TTC CAA ACT TGT<br>Ser Ser Lys Lys Thr Phe Ala Ser Tyr Met Pro Gln Phe Gln Thr Cys<br>             1135               1140               1145 | 3637 |
| TCT ACT CAG ACT CAT AAG ATC ATG GAA AAC AAG ATG TGT GAC CTA ACT<br>Ser Thr Gln Thr His Lys Ile Met Glu Asn Lys Met Cys Asp Leu Thr<br>     1150               1155               1160 | 3685 |
| GTG TAATTTCACT GAAGAAACCT TCAGATTTGT GTTATAATGG GTAATATAAA<br>Val<br>1165 | 3738 |
| GTGTAATAGA TTATAGTTGT GGGTGGGAGA GAGAAAAGAA ACCAGAGTCC AAATTTGAAA | 3798 |
| ATAATTGTTC CCAACTGAAA AAAAAAAAAA AAAAAAAAAA AAAAAAAAAA AAAAAAAAAA | 3858 |
| AAAAAAAAAA AAA | 3871 |

(2) INFORMATION FOR SEQ ID NO: 4:

(i) SEQUENCE CHARACTERISTICS:
        (A) LENGTH: 1165 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO: 4:

Met Ile Cys Gln Lys Phe Cys Val Val Leu Leu His Trp Glu Phe Ile
  1              5                   10                  15

Tyr Val Ile Thr Ala Phe Asn Leu Ser Tyr Pro Ile Thr Pro Trp Arg
              20                  25                  30

Phe Lys Leu Ser Cys Met Pro Pro Asn Ser Thr Tyr Asp Tyr Phe Leu

-continued

```
                35                  40                  45
Leu Pro Ala Gly Leu Ser Lys Asn Thr Ser Asn Ser Asn Gly His Tyr
 50                  55                  60
Glu Thr Ala Val Glu Pro Lys Phe Asn Ser Ser Gly Thr His Phe Ser
 65                  70                  75                  80
Asn Leu Ser Lys Thr Thr Phe His Cys Cys Phe Arg Ser Glu Gln Asp
                 85                  90                  95
Arg Asn Cys Ser Leu Cys Ala Asp Asn Ile Glu Gly Lys Thr Phe Val
                100                 105                 110
Ser Thr Val Asn Ser Leu Val Phe Gln Gln Ile Asp Ala Asn Trp Asn
                115                 120                 125
Ile Gln Cys Trp Leu Lys Gly Asp Leu Lys Leu Phe Ile Cys Tyr Val
                130                 135                 140
Glu Ser Leu Phe Lys Asn Leu Phe Arg Asn Tyr Asn Tyr Lys Val His
145                 150                 155                 160
Leu Leu Tyr Val Leu Pro Glu Val Leu Glu Asp Ser Pro Leu Val Pro
                165                 170                 175
Gln Lys Gly Ser Phe Gln Met Val His Cys Asn Cys Ser Val His Glu
                180                 185                 190
Cys Cys Glu Cys Leu Val Pro Val Pro Thr Ala Lys Leu Asn Asp Thr
                195                 200                 205
Leu Leu Met Cys Leu Lys Ile Thr Ser Gly Gly Val Ile Phe Gln Ser
210                 215                 220
Pro Leu Met Ser Val Gln Pro Ile Asn Met Val Lys Pro Asp Pro Pro
225                 230                 235                 240
Leu Gly Leu His Met Glu Ile Thr Asp Asp Gly Asn Leu Lys Ile Ser
                245                 250                 255
Trp Ser Ser Pro Pro Leu Val Pro Phe Pro Leu Gln Tyr Gln Val Lys
                260                 265                 270
Tyr Ser Glu Asn Ser Thr Thr Val Ile Arg Glu Ala Asp Lys Ile Val
                275                 280                 285
Ser Ala Thr Ser Leu Leu Val Asp Ser Ile Leu Pro Gly Ser Ser Tyr
                290                 295                 300
Glu Val Gln Val Arg Gly Lys Arg Leu Asp Gly Pro Gly Ile Trp Ser
305                 310                 315                 320
Asp Trp Ser Thr Pro Arg Val Phe Thr Thr Gln Asp Val Ile Tyr Phe
                325                 330                 335
Pro Pro Lys Ile Leu Thr Ser Val Gly Ser Asn Val Ser Phe His Cys
                340                 345                 350
Ile Tyr Lys Lys Glu Asn Lys Ile Val Pro Ser Lys Glu Ile Val Trp
                355                 360                 365
Trp Met Asn Leu Ala Glu Lys Ile Pro Gln Ser Gln Tyr Asp Val Val
370                 375                 380
Ser Asp His Val Ser Lys Val Thr Phe Phe Asn Leu Asn Glu Thr Lys
385                 390                 395                 400
Pro Arg Gly Lys Phe Thr Tyr Asp Ala Val Tyr Cys Cys Asn Glu His
                405                 410                 415
Glu Cys His His Arg Tyr Ala Glu Leu Tyr Val Ile Asp Val Asn Ile
                420                 425                 430
Asn Ile Ser Cys Glu Thr Asp Gly Tyr Leu Thr Lys Met Thr Cys Arg
                435                 440                 445
Trp Ser Thr Ser Thr Ile Gln Ser Leu Ala Glu Ser Thr Leu Gln Leu
450                 455                 460
```

-continued

```
Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
                500                 505                 510

Ile Arg Ile Asn His Ser Leu Gly Ser Leu Asp Ser Pro Pro Thr Cys
                515                 520                 525

Val Leu Pro Asp Ser Val Val Lys Pro Leu Pro Pro Ser Ser Val Lys
530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
                580                 585                 590

Ser Lys Ser Val Ser Leu Pro Val Pro Asp Leu Cys Ala Val Tyr Ala
                595                 600                 605

Val Gln Val Arg Cys Lys Arg Leu Asp Gly Leu Gly Tyr Trp Ser Asn
610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
                660                 665                 670

Leu Cys Ser Val Gln Arg Tyr Val Ile Asn His His Thr Ser Cys Asn
                675                 680                 685

Gly Thr Trp Ser Glu Asp Val Gly Asn His Thr Lys Phe Thr Phe Leu
690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
                740                 745                 750

Cys Val Ile Val Ser Trp Ile Leu Ser Pro Ser Asp Tyr Lys Leu Met
                755                 760                 765

Tyr Phe Ile Ile Glu Trp Lys Asn Leu Asn Glu Asp Gly Glu Ile Lys
770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
                820                 825                 830

Ile Glu Lys His Gln Ser Asp Ala Gly Leu Tyr Val Ile Val Pro Val
                835                 840                 845

Ile Ile Ser Ser Ser Ile Leu Leu Gly Thr Leu Leu Ile Ser His
850                 855                 860

Gln Arg Met Lys Lys Leu Phe Trp Glu Asp Val Pro Asn Pro Lys Asn
865                 870                 875                 880
```

```
Cys Ser Trp Ala Gln Gly Leu Asn Phe Gln Lys Pro Glu Thr Phe Glu
                885                 890                 895

His Leu Phe Ile Lys His Thr Ala Ser Val Thr Cys Gly Pro Leu Leu
                900                 905                 910

Leu Glu Pro Glu Thr Ile Ser Glu Asp Ile Ser Val Asp Thr Ser Trp
                915                 920                 925

Lys Asn Lys Asp Glu Met Met Pro Thr Thr Val Val Ser Leu Leu Ser
                930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Glu Val Thr Tyr Glu Asp
                965                 970                 975

Glu Ser Gln Arg Gln Pro Phe Val Lys Tyr Ala Thr Leu Ile Ser Asn
                980                 985                 990

Ser Lys Pro Ser Glu Thr Gly Glu Glu Gln Gly Leu Ile Asn Ser Ser
                995                 1000                1005

Val Thr Lys Cys Phe Ser Ser Lys Asn Ser Pro Leu Lys Asp Ser Phe
    1010                1015                1020

Ser Asn Ser Ser Trp Glu Ile Glu Ala Gln Ala Phe Phe Ile Leu Ser
025                 1030                1035                1040

Asp Gln His Pro Asn Ile Ile Ser Pro His Leu Thr Phe Ser Glu Gly
                1045                1050                1055

Leu Asp Glu Leu Leu Lys Leu Glu Gly Asn Phe Pro Glu Glu Asn Asn
                1060                1065                1070

Asp Lys Lys Ser Ile Tyr Tyr Leu Gly Val Thr Ser Ile Lys Lys Arg
                1075                1080                1085

Glu Ser Gly Val Leu Leu Thr Asp Lys Ser Arg Val Ser Cys Pro Phe
    1090                1095                1100

Pro Ala Pro Cys Leu Phe Thr Asp Ile Arg Val Leu Gln Asp Ser Cys
105                 1110                1115                1120

Ser His Phe Val Glu Asn Asn Ile Asn Leu Gly Thr Ser Ser Lys Lys
                1125                1130                1135

Thr Phe Ala Ser Tyr Met Pro Gln Phe Gln Thr Cys Ser Thr Gln Thr
                1140                1145                1150

His Lys Ile Met Glu Asn Lys Met Cys Asp Leu Thr Val
                1155                1160                1165

(2) INFORMATION FOR SEQ ID NO: 5:

(i) SEQUENCE CHARACTERISTICS:
        (A) LENGTH: 488 amino acids
        (B) TYPE: amino acid
        (D) TOPOLOGY: unknown (ii) MOLECULE TYPE: protein (xi) SEQUENCE DESCRIPTION: SEQ ID NO: 5:

Tyr Ile Ser Pro Glu Ser Pro Val Val Gln Leu His Ser Asn Phe Thr
1                   5                   10                  15

Ala Val Cys Val Leu Lys Glu Lys Cys Met Asp Tyr Phe His Val Asn
                20                  25                  30

Ala Asn Tyr Ile Val Trp Lys Thr Asn His Phe Thr Ile Pro Lys Glu
            35                  40                  45

Gln Tyr Thr Ile Ile Asn Arg Thr Ala Ser Ser Val Thr Phe Thr Asp
    50                  55                  60

Ile Ala Ser Leu Asn Ile Gln Leu Thr Cys Asn Ile Leu Thr Phe Gly
```

```
             65                  70                  75                  80
Gln Leu Glu Gln Asn Val Tyr Gly Ile Thr Ile Ile Ser Gly Leu Pro
                    85                  90                  95

Pro Glu Lys Pro Lys Asn Leu Ser Cys Ile Val Asn Glu Gly Lys Lys
               100                 105                 110

Met Arg Cys Glu Trp Asp Gly Gly Arg Glu Thr His Leu Glu Thr Asn
               115                 120                 125

Phe Thr Leu Lys Ser Glu Trp Ala Thr His Lys Phe Ala Asp Cys Lys
               130                 135                 140

Ala Lys Arg Asp Thr Pro Thr Ser Cys Thr Val Asp Tyr Ser Thr Val
145                 150                 155                 160

Tyr Phe Val Asn Ile Glu Val Trp Val Glu Ala Glu Asn Ala Leu Gly
                165                 170                 175

Lys Val Thr Ser Asp His Ile Asn Phe Asp Pro Val Tyr Lys Val Lys
                180                 185                 190

Pro Asn Pro Pro His Asn Leu Ser Val Ile Asn Ser Glu Glu Leu Ser
                195                 200                 205

Ser Ile Leu Lys Leu Thr Trp Thr Asn Pro Ser Ile Lys Ser Val Ile
210                 215                 220

Ile Leu Lys Tyr Asn Ile Gln Tyr Arg Thr Lys Asp Ala Ser Thr Trp
225                 230                 235                 240

Ser Gln Ile Pro Pro Glu Asp Thr Ala Ser Thr Arg Ser Ser Phe Thr
                245                 250                 255

Val Gln Asp Leu Lys Pro Phe Thr Glu Tyr Val Phe Arg Ile Arg Cys
                260                 265                 270

Met Lys Glu Asp Gly Lys Gly Tyr Trp Ser Asp Trp Ser Glu Glu Ala
                275                 280                 285

Ser Gly Ile Thr Tyr Glu Asp Arg Pro Ser Lys Ala Pro Ser Phe Trp
                290                 295                 300

Tyr Lys Ile Asp Pro Ser His Thr Gln Gly Tyr Arg Thr Val Gln Leu
305                 310                 315                 320

Val Trp Lys Thr Leu Pro Pro Phe Glu Ala Asn Gly Lys Ile Leu Asp
                325                 330                 335

Tyr Glu Val Thr Leu Thr Arg Trp Lys Ser His Leu Gln Asn Tyr Thr
                340                 345                 350

Val Asn Ala Thr Lys Leu Thr Val Asn Leu Thr Asn Asp Arg Tyr Leu
                355                 360                 365

Ala Thr Leu Thr Val Arg Asn Leu Val Gly Lys Ser Asp Ala Ala Val
                370                 375                 380

Leu Thr Ile Pro Ala Cys Asp Phe Gln Ala Thr His Pro Val Met Asp
385                 390                 395                 400

Leu Lys Ala Phe Pro Lys Asp Asn Met Leu Trp Val Glu Trp Thr Thr
                405                 410                 415

Pro Arg Glu Ser Val Lys Lys Tyr Ile Leu Glu Trp Cys Val Leu Ser
                420                 425                 430

Asp Lys Ala Pro Cys Ile Thr Asp Trp Gln Gln Glu Asp Gly Thr Val
                435                 440                 445

His Arg Thr Tyr Leu Arg Gly Asn Leu Ala Glu Ser Lys Cys Tyr Leu
                450                 455                 460

Ile Thr Val Thr Pro Val Tyr Ala Asp Gly Pro Gly Ser Pro Glu Ser
465                 470                 475                 480

Ile Lys Ala Tyr Leu Lys Gln Ala
                485
```

```
(2) INFORMATION FOR SEQ ID NO: 6:

(i) SEQUENCE CHARACTERISTICS:
        (A) LENGTH: 5 amino acids
        (B) TYPE: amino acid
        (D) TOPOLOGY: unknown (ii) MOLECULE TYPE: peptide (xi) SEQUENCE DESCRIPTION: SEQ ID NO: 6:

Trp Ser Xaa Trp Ser
 1               5

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

CATCTTACTT CAGAGAA                                                   17

(2) INFORMATION FOR SEQ ID NO: 8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

CATCTTACTT CAGAGAAGTA CAC                                            23

(2) INFORMATION FOR SEQ ID NO: 9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

CATCTTACTT CAGAGAAGTA CACCCATAA                                      29

(2) INFORMATION FOR SEQ ID NO: 10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

CATCTTACTT CAGAGAAGTA CACCCATAAT CCTCT                               35

(2) INFORMATION FOR SEQ ID NO: 11:
```

(i) SEQUENCE CHARACTERISTICS:
    (A) LENGTH: 35 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 11:

AATCATCTTA CTTCAGAGAA GTACACCCAT AATCC                              36

(2) INFORMATION FOR SEQ ID NO: 12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

CTTACTTCAG AGAAGTACAC CCATAATCC                                    29

(2) INFORMATION FOR SEQ ID NO: 13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 13:

TCAGAGAAGT ACACCCATAA TCC                                          23

(2) INFORMATION FOR SEQ ID NO: 14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

AAGTACACCC ATAATCC                                                 17

(2) INFORMATION FOR SEQ ID NO: 15:

(i) SEQUENCE CHARACTERISTICS:
        (A) LENGTH: 56 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO: 15:

ACAGAAUUUU UGACAAAUCA AGCAGANNN NUCUGAGNAG UCCUUACUUC AGAGAA        56

(2) INFORMATION FOR SEQ ID NO: 16:

(i) SEQUENCE CHARACTERISTICS:
        (A) LENGTH: 57 base pairs
        (B) TYPE: nucleic acid
        (C) STRANDEDNESS: single (D) TOPOLOGY: unknown (ii) MOLECULE TYPE: RNA (xi) SEQUENCE DESCRIPTION: SEQ ID NO: 16:

GGCCCGGGCA GCCUGCCCAA AGCCGGNNNN CCGGAGNAGU CGCCAGACCG GCUCGUG        57

(2) INFORMATION FOR SEQ ID NO: 17:

(i) SEQUENCE CHARACTERISTICS:
        (A) LENGTH: 56 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO: 17:

UGGCAUGCAA GACAAAGCAG GNNNNCCUGA GNAGUCCUUA AAUCUCCAAG GAGUAA         56

(2) INFORMATION FOR SEQ ID NO: 18:

(i) SEQUENCE CHARACTERISTICS:
        (A) LENGTH: 50 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO: 18:

UAUAUGACAA AGCUGUNNNN ACAGAGNAGU CCUUGUGUGG UAAAGACACG                50

(2) INFORMATION FOR SEQ ID NO: 19:

(i) SEQUENCE CHARACTERISTICS:
        (A) LENGTH: 61 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO: 19:

AGCACCAAUU GAAUUGAUGG CCAAAGCGGG NNNNCCCGAG NAGUCAACCG UAACAGUAUG     60

U                                                                    61

(2) INFORMATION FOR SEQ ID NO: 20:

(i) SEQUENCE CHARACTERISTICS:
        (A) LENGTH: 69 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO: 20:

UGAAAUUGUU UCAGGCUCCA AAGCCGGNNN NCCGGAGNAG UCAAGAAGAG GACCACAUGU     60

CACUGAUGC                                                            69

(2) INFORMATION FOR SEQ ID NO: 21:

(i) SEQUENCE CHARACTERISTICS:
        (A) LENGTH: 61 base pairs
        (B) TYPE: nucleic acid
        (C) STRANDEDNESS: single (D) TOPOLOGY: unknown (ii) MOLECULE TYPE: RNA (xi) SEQUENCE DESCRIPTION: SEQ ID NO: 21:

GGUUUCUUCA GUGAAAUUAC ACAAAGCAGC NNNNGCUGAG NAGUCAGUUA GGUCACACAU          60

C                                                                         61

(2) INFORMATION FOR SEQ ID NO: 22:

(i) SEQUENCE CHARACTERISTICS:
            (A) LENGTH: 53 base pairs
            (B) TYPE: nucleic acid
            (C) STRANDEDNESS: single
            (D) TOPOLOGY: unknown (ii) MOLECULE TYPE: RNA (xi) SEQUENCE DESCRIPTION: SEQ ID NO: 22:

ACCCAUUAUA ACACAAAGCU GANNNNUCAG AGNAGUCAUC UGAAGGUUUC UUC                 53

(2) INFORMATION FOR SEQ ID NO: 23:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 23:

GCTGCACTTA ACCTGGC                                                        17

(2) INFORMATION FOR SEQ ID NO: 24:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 24:

GGATAACTCA GGAACG                                                         16

(2) INFORMATION FOR SEQ ID NO: 25:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 25:

CACTATTTGC CCTTCAG                                                        17

(2) INFORMATION FOR SEQ ID NO: 26:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 26:

GCCTGAGATA GGGGTGC                                              17

(2) INFORMATION FOR SEQ ID NO: 27:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 27:

CACTATTTGC CCTTCAG                                              17

(2) INFORMATION FOR SEQ ID NO: 28:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 28:

GCCTGAGATA GGGGTGC                                              17

(2) INFORMATION FOR SEQ ID NO: 29:

(i) SEQUENCE CHARACTERISTICS:
            (A) LENGTH: 8 amino acids
            (B) TYPE: amino acid
            (D) TOPOLOGY: unknown (ii) MOLECULE TYPE: peptide (xi) SEQUENCE DESCRIPTION: SEQ ID NO: 29:

Pro Asn Pro Lys Asn Cys Ser Trp
  1               5

(2) INFORMATION FOR SEQ ID NO: 30:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 30:

CCAAACCCCA AGAATTGTTC CTGG                                      24

(2) INFORMATION FOR SEQ ID NO: 31:

(i) SEQUENCE CHARACTERISTICS:
            (A) LENGTH: 9 amino acids
            (B) TYPE: amino acid
            (D) TOPOLOGY: unknown (ii) MOLECULE TYPE: peptide (xi) SEQUENCE DESCRIPTION: SEQ ID NO: 31:

Lys Ile Met Glu Asn Lys Met Cys Asp

-continued

```
            1               5
```

(2) INFORMATION FOR SEQ ID NO: 32:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

TCRCACATYT TRTTNCCCAT TATCTT                                        26

(2) INFORMATION FOR SEQ ID NO: 33:

(i) SEQUENCE CHARACTERISTICS:
        (A) LENGTH: 8 amino acids
        (B) TYPE: amino acid
        (D) TOPOLOGY: unknown (ii) MOLECULE TYPE: peptide (xi) SEQUENCE DESCRIPTION: SEQ ID NO: 33:

Ala Gln Gly Leu Asn Phe Gln Lys
  1             5

(2) INFORMATION FOR SEQ ID NO: 34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 34:

GCACAAGGAC TGAATTTCCA AAAG                                           24

(2) INFORMATION FOR SEQ ID NO: 35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 35:

CTGCCTGAAG TGTTAGAAGA                                               20

(2) INFORMATION FOR SEQ ID NO: 36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 36:

GCTGAACTGA CATTAGAGGT G                                              21

(2) INFORMATION FOR SEQ ID NO: 37:

```
    (i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 37:

ACCTATGAGG ACGAAAGCCA GAGAC                                             25

(2) INFORMATION FOR SEQ ID NO: 38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 38:

TGTGAGCAAC TGTCCTCGAG AACT                                              24

(2) INFORMATION FOR SEQ ID NO: 39:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 39:

GTCACGATGT CGACGTGTAC TTCTCTGAAG TAAGATGATT TG                          42

(2) INFORMATION FOR SEQ ID NO: 40:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 40:

GTCAGGTCAG AAAAGCTTAT CACTCTGTGT TTTTCAATAT CATCTTGAGT GAA              53

(2) INFORMATION FOR SEQ ID NO: 41:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 41:

AAGCTTTTCT GACCTGACNN N                                                 21

(2) INFORMATION FOR SEQ ID NO: 42:

(i) SEQUENCE CHARACTERISTICS:
        (A) LENGTH: 3854 base pairs
        (B) TYPE: nucleic acid
```

```
        (C) STRANDEDNESS: double
        (D) TOPOLOGY: unknown (ii) MOLECULE TYPE: cDNA (ix) FEATURE:
        (A) NAME/KEY: Coding Sequence
        (B) LOCATION: 61...3546

(xi) SEQUENCE DESCRIPTION: SEQ ID NO: 42:

GTCGACCCAC GCGTCCGGAG GAATCGTTCT GCAAATCCAG GTGTACACCT CTGAAGAAAG       60

ATG ATG TGT CAG AAA TTC TAT GTG GTT TTG TTA CAC TGG GAA TTT CTT       108
Met Met Cys Gln Lys Phe Tyr Val Val Leu Leu His Trp Glu Phe Leu
  1               5                  10                  15

TAT GTG ATA GCT GCA CTT AAC CTG GCA TAT CCA ATC TCT CCC TGG AAA       156
Tyr Val Ile Ala Ala Leu Asn Leu Ala Tyr Pro Ile Ser Pro Trp Lys
             20                  25                  30

TTT AAG TTG TTT TGT GGA CCA CCG AAC ACA ACC GAT GAC TCC TTT CTC       204
Phe Lys Leu Phe Cys Gly Pro Pro Asn Thr Thr Asp Asp Ser Phe Leu
         35                  40                  45

TCA CCT GCT GGA GCC CCA AAC AAT GCC TCG GCT TTG AAG GGG GCT TCT       252
Ser Pro Ala Gly Ala Pro Asn Asn Ala Ser Ala Leu Lys Gly Ala Ser
 50                  55                  60

GAA GCA ATT GTT GAA GCT AAA TTT AAT TCA AGT GGT ATC TAC GTT CCT       300
Glu Ala Ile Val Glu Ala Lys Phe Asn Ser Ser Gly Ile Tyr Val Pro
 65                  70                  75                  80

GAG TTA TCC AAA ACA GTC TTC CAC TGT TGC TTT GGG AAT GAG CAA GGT       348
Glu Leu Ser Lys Thr Val Phe His Cys Cys Phe Gly Asn Glu Gln Gly
                 85                  90                  95

CAA AAC TGC TCT GCA CTC ACA GAC AAC ACT GAA GGG AAG ACA CTG GCT       396
Gln Asn Cys Ser Ala Leu Thr Asp Asn Thr Glu Gly Lys Thr Leu Ala
            100                 105                 110

TCA GTA GTG AAG GCT TCA GTT TTT CGC CAG CTA GGT GTA AAC TGG GAC       444
Ser Val Val Lys Ala Ser Val Phe Arg Gln Leu Gly Val Asn Trp Asp
        115                 120                 125

ATA GAG TGC TGG ATG AAA GGG GAC TTG ACA TTA TTC ATC TGT CAT ATG       492
Ile Glu Cys Trp Met Lys Gly Asp Leu Thr Leu Phe Ile Cys His Met
    130                 135                 140

GAG CCA TTA CCT AAG AAC CCC TTC AAG AAT TAT GAC TCT AAG GTC CAT       540
Glu Pro Leu Pro Lys Asn Pro Phe Lys Asn Tyr Asp Ser Lys Val His
145                 150                 155                 160

CTT TTA TAT GAT CTG CCT GAA GTC ATA GAT GAT TCG CCT CTG CCC CCA       588
Leu Leu Tyr Asp Leu Pro Glu Val Ile Asp Asp Ser Pro Leu Pro Pro
                165                 170                 175

CTG AAA GAC AGC TTT CAG ACT GTC CAA TGC AAC TGC AGT CTT CGG GGA       636
Leu Lys Asp Ser Phe Gln Thr Val Gln Cys Asn Cys Ser Leu Arg Gly
            180                 185                 190

TGT GAA TGT CAT GTG CCG GTA CCC AGA GCC AAA CTC AAC TAC GCT CTT       684
Cys Glu Cys His Val Pro Val Pro Arg Ala Lys Leu Asn Tyr Ala Leu
        195                 200                 205

CTG ATG TAT TTG GAA ATC ACA TCT GCC GGT GTG AGT TTT CAG TCA CCT       732
Leu Met Tyr Leu Glu Ile Thr Ser Ala Gly Val Ser Phe Gln Ser Pro
    210                 215                 220

CTG ATG TCA CTG CAG CCC ATG CTT GTT GTG AAA CCC GAT CCA CCC TTA       780
Leu Met Ser Leu Gln Pro Met Leu Val Val Lys Pro Asp Pro Pro Leu
225                 230                 235                 240

GGT TTG CAT ATG GAA GTC ACA GAT GAT GGT AAT TTA AAG ATT TCT TGG       828
Gly Leu His Met Glu Val Thr Asp Asp Gly Asn Leu Lys Ile Ser Trp
                245                 250                 255

GAC AGC CAA ACA ATG GCA CCA TTT CCG CTT CAA TAT CAG GTG AAA TAT       876
Asp Ser Gln Thr Met Ala Pro Phe Pro Leu Gln Tyr Gln Val Lys Tyr
```

```
                260                 265                 270
TTA GAG AAT TCT ACA ATT GTA AGA GAG GCT GCT GAA ATT GTC TCA GCT      924
Leu Glu Asn Ser Thr Ile Val Arg Glu Ala Ala Glu Ile Val Ser Ala
        275                 280                 285

ACA TCT CTG CTG GTA GAC AGT GTG CTT CCT GGA TCT TCA TAT GAG GTC      972
Thr Ser Leu Leu Val Asp Ser Val Leu Pro Gly Ser Ser Tyr Glu Val
        290                 295                 300

CAG GTG AGG AGC AAG AGA CTG GAT GGT TCA GGA GTC TGG AGT GAC TGG     1020
Gln Val Arg Ser Lys Arg Leu Asp Gly Ser Gly Val Trp Ser Asp Trp
305                 310                 315                 320

AGT TCA CCT CAA GTC TTT ACC ACA CAA GAT GTT GTG TAT TTT CCA CCC     1068
Ser Ser Pro Gln Val Phe Thr Thr Gln Asp Val Val Tyr Phe Pro Pro
            325                 330                 335

AAA ATT CTG ACT AGT GTT GGA TCG AAT GCT TCT TTT CAT TGC ATC TAC     1116
Lys Ile Leu Thr Ser Val Gly Ser Asn Ala Ser Phe His Cys Ile Tyr
                340                 345                 350

AAA AAC GAA AAC CAG ATT ATC TCC TCA AAA CAG ATA GTT TGG TGG AGG     1164
Lys Asn Glu Asn Gln Ile Ile Ser Ser Lys Gln Ile Val Trp Trp Arg
            355                 360                 365

AAT CTA GCT GAG AAA ATC CCT GAG ATA CAG TAC AGC ATT GTG AGT GAC     1212
Asn Leu Ala Glu Lys Ile Pro Glu Ile Gln Tyr Ser Ile Val Ser Asp
    370                 375                 380

CGA GTT AGC AAA GTT ACC TTC TCC AAC CTG AAA GCC ACC AGA CCT CGA     1260
Arg Val Ser Lys Val Thr Phe Ser Asn Leu Lys Ala Thr Arg Pro Arg
385                 390                 395                 400

GGG AAG TTT ACC TAT GAC GCA GTG TAC TGC TGC AAT GAG CAG GCG TGC     1308
Gly Lys Phe Thr Tyr Asp Ala Val Tyr Cys Cys Asn Glu Gln Ala Cys
            405                 410                 415

CAT CAC CGC TAT GCT GAA TTA TAC GTG ATC GAT GTC AAT ATC AAT ATA     1356
His His Arg Tyr Ala Glu Leu Tyr Val Ile Asp Val Asn Ile Asn Ile
                420                 425                 430

TCA TGT GAA ACT GAC GGG TAC TTA ACT AAA ATG ACT TGC AGA TGG TCA     1404
Ser Cys Glu Thr Asp Gly Tyr Leu Thr Lys Met Thr Cys Arg Trp Ser
            435                 440                 445

CCC AGC ACA ATC CAA TCA CTA GTG GGA AGC ACT GTG CAG CTG AGG TAT     1452
Pro Ser Thr Ile Gln Ser Leu Val Gly Ser Thr Val Gln Leu Arg Tyr
    450                 455                 460

CAC AGG CGC AGC CTG TAT TGT CCT GAT AGT CCA TCT ATT CAT CCT ACG     1500
His Arg Arg Ser Leu Tyr Cys Pro Asp Ser Pro Ser Ile His Pro Thr
465                 470                 475                 480

TCT GAG CCC AAA AAC TGC GTC TTA CAG AGA GAC GGC TTT TAT GAA TGT     1548
Ser Glu Pro Lys Asn Cys Val Leu Gln Arg Asp Gly Phe Tyr Glu Cys
            485                 490                 495

GTT TTC CAG CCA ATC TTT CTA TTA TCT GGC TAT ACA ATG TGG ATC AGG     1596
Val Phe Gln Pro Ile Phe Leu Leu Ser Gly Tyr Thr Met Trp Ile Arg
            500                 505                 510

ATC AAC CAT TCT TTA GGT TCA CTT GAC TCG CCA CCA ACG TGT GTC CTT     1644
Ile Asn His Ser Leu Gly Ser Leu Asp Ser Pro Pro Thr Cys Val Leu
            515                 520                 525

CCT GAC TCC GTA GTA AAA CCA CTA CCT CCA TCT AAC GTA AAA GCA GAG     1692
Pro Asp Ser Val Val Lys Pro Leu Pro Pro Ser Asn Val Lys Ala Glu
530                 535                 540

ATT ACT GTA AAC ACT GGA TTA TTG AAA GTA TCT TGG GAA AAG CCA GTC     1740
Ile Thr Val Asn Thr Gly Leu Leu Lys Val Ser Trp Glu Lys Pro Val
545                 550                 555                 560

TTT CCG GAG AAT AAC CTT CAA TTC CAG ATT CGA TAT GGC TTA AGT GGA     1788
Phe Pro Glu Asn Asn Leu Gln Phe Gln Ile Arg Tyr Gly Leu Ser Gly
            565                 570                 575

AAA GAA ATA CAA TGG AAG ACA CAT GAG GTA TTC GAT GCA AAG TCA AAG     1836
```

```
                                                                    -continued Lys Glu Ile Gln Trp Lys Thr His Glu Val Phe Asp Ala Lys Ser Lys
            580                 585                 590

TCT GCC AGC CTG CTG GTG TCA GAC CTC TGT GCA GTC TAT GTG GTC CAG        1884
Ser Ala Ser Leu Leu Val Ser Asp Leu Cys Ala Val Tyr Val Val Gln
        595                 600                 605

GTT CGC TGC CGG CGG TTG GAT GGA CTA GGA TAT TGG AGT AAT TGG AGC        1932
Val Arg Cys Arg Arg Leu Asp Gly Leu Gly Tyr Trp Ser Asn Trp Ser
    610                 615                 620

AGT CCA GCC TAT ACG CTT GTC ATG GAT GTA AAA GTT CCT ATG AGA GGG        1980
Ser Pro Ala Tyr Thr Leu Val Met Asp Val Lys Val Pro Met Arg Gly
625                 630                 635                 640

CCT GAA TTT TGG AGA AAA ATG GAT GGG GAC GTT ACT AAA AAG GAG AGA        2028
Pro Glu Phe Trp Arg Lys Met Asp Gly Asp Val Thr Lys Lys Glu Arg
                645                 650                 655

AAT GTC ACC TTG CTT TGG AAG CCC CTG ACG AAA AAT GAC TCA CTG TGT        2076
Asn Val Thr Leu Leu Trp Lys Pro Leu Thr Lys Asn Asp Ser Leu Cys
            660                 665                 670

AGT GTG AGG AGG TAC GTT GTG AAG CAT CGT ACT GCC CAC AAT GGG ACG        2124
Ser Val Arg Arg Tyr Val Val Lys His Arg Thr Ala His Asn Gly Thr
        675                 680                 685

TGG TCA GAA GAT GTG GGA AAT CGG ACC AAT CTC ACT TTC CTG TGG ACA        2172
Trp Ser Glu Asp Val Gly Asn Arg Thr Asn Leu Thr Phe Leu Trp Thr
    690                 695                 700

GAA CCA GCG CAC ACT GTT ACA GTT CTG GCT GTC AAT TCC CTC GGC GCT        2220
Glu Pro Ala His Thr Val Thr Val Leu Ala Val Asn Ser Leu Gly Ala
705                 710                 715                 720

TCC CTT GTG AAT TTT AAC CTT ACC TTC TCA TGG CCC ATG AGT AAA GTG        2268
Ser Leu Val Asn Phe Asn Leu Thr Phe Ser Trp Pro Met Ser Lys Val
                725                 730                 735

AGT GCT GTG GAG TCA CTC AGT GCT TAT CCC CTG AGC AGC AGC TGT GTC        2316
Ser Ala Val Glu Ser Leu Ser Ala Tyr Pro Leu Ser Ser Ser Cys Val
            740                 745                 750

ATC CTT TCC TGG ACA CTG TCA CCT GAT GAT TAT AGT CTG TTA TAT CTG        2364
Ile Leu Ser Trp Thr Leu Ser Pro Asp Asp Tyr Ser Leu Leu Tyr Leu
        755                 760                 765

GTT ATT GAA TGG AAG ATC TTA AAT GAA GAT GAT GGA ATG AAG TGG CTT        2412
Val Ile Glu Trp Lys Ile Leu Asn Glu Asp Asp Gly Met Lys Trp Leu
    770                 775                 780

AGA ATT CCC TCG AAT GTT AAA AAG TTT TAT ATC CAC GAT AAT TTT ATT        2460
Arg Ile Pro Ser Asn Val Lys Lys Phe Tyr Ile His Asp Asn Phe Ile
785                 790                 795                 800

CCC ATC GAG AAA TAT CAG TTT AGT CTT TAC CCA GTA TTT ATG GAA GGA        2508
Pro Ile Glu Lys Tyr Gln Phe Ser Leu Tyr Pro Val Phe Met Glu Gly
                805                 810                 815

GTT GGA AAA CCA AAG ATA ATT AAT GGT TTC ACC AAA GAT GCT ATC GAC        2556
Val Gly Lys Pro Lys Ile Ile Asn Gly Phe Thr Lys Asp Ala Ile Asp
            820                 825                 830

AAG CAG CAG AAT GAC GCA GGG CTG TAT GTC ATT GTA CCC ATA ATT ATT        2604
Lys Gln Gln Asn Asp Ala Gly Leu Tyr Val Ile Val Pro Ile Ile Ile
        835                 840                 845

TCC TCT TGT GTC CTA CTG CTC GGA ACA CTG TTA ATT TCA CAC CAG AGA        2652
Ser Ser Cys Val Leu Leu Leu Gly Thr Leu Leu Ile Ser His Gln Arg
    850                 855                 860

ATG AAA AAG TTG TTT TGG GAC GAT GTT CCA AAC CCC AAG AAT TGT TCC        2700
Met Lys Lys Leu Phe Trp Asp Asp Val Pro Asn Pro Lys Asn Cys Ser
865                 870                 875                 880

TGG GCA CAA GGA CTG AAT TTC CAA AAG CCT GAA ACA TTT GAG CAT CTT        2748
Trp Ala Gln Gly Leu Asn Phe Gln Lys Pro Glu Thr Phe Glu His Leu
                885                 890                 895
```

```
TTT ACC AAG CAT GCA GAA TCA GTG ATA TTT GGT CCT CTT CTT CTG GAG    2796
Phe Thr Lys His Ala Glu Ser Val Ile Phe Gly Pro Leu Leu Leu Glu
            900                 905                 910

CCT GAA CCC ATT TCA GAA GAA ATC AGT GTC GAT ACA GCT TGG AAA AAT    2844
Pro Glu Pro Ile Ser Glu Glu Ile Ser Val Asp Thr Ala Trp Lys Asn
            915                 920                 925

AAA GAT GAG ATG GTC CCA GCA GCT ATG GTC TCC CTT CTT TTG ACC ACA    2892
Lys Asp Glu Met Val Pro Ala Ala Met Val Ser Leu Leu Leu Thr Thr
930                 935                 940

CCA GAC CCT GAA AGC AGT TCT ATT TGT ATT AGT GAC CAG TGT AAC AGT    2940
Pro Asp Pro Glu Ser Ser Ser Ile Cys Ile Ser Asp Gln Cys Asn Ser
945                 950                 955                 960

GCT AAC TTC TCT GGG TCT CAG AGC ACC CAG GTA ACC TGT GAG GAT GAG    2988
Ala Asn Phe Ser Gly Ser Gln Ser Thr Gln Val Thr Cys Glu Asp Glu
            965                 970                 975

TGT CAG AGA CAA CCC TCA GTT AAA TAT GCA ACT CTG GTC AGC AAC GAT    3036
Cys Gln Arg Gln Pro Ser Val Lys Tyr Ala Thr Leu Val Ser Asn Asp
            980                 985                 990

AAA CTA GTG GAA ACT GAT GAA GAG CAA GGG TTT ATC CAT AGT CCT GTC    3084
Lys Leu Val Glu Thr Asp Glu Glu Gln Gly Phe Ile His Ser Pro Val
            995                 1000                1005

AGC AAC TGC ATC TCC AGT AAT CAT TCC CCA CTG AGG CAG TCT TTC TCT    3132
Ser Asn Cys Ile Ser Ser Asn His Ser Pro Leu Arg Gln Ser Phe Ser
     1010                1015                1020

AGC AGC TCC TGG GAG ACA GAG GCC CAG ACA TTT TTC CTT TTA TCA GAC    3180
Ser Ser Ser Trp Glu Thr Glu Ala Gln Thr Phe Phe Leu Leu Ser Asp
1025                1030                1035                1040

CAG CAA CCC ACC ATG ATT TCA CCA CAA CTT TCA TTC TCG GGG TTG GAT    3228
Gln Gln Pro Thr Met Ile Ser Pro Gln Leu Ser Phe Ser Gly Leu Asp
                1045                1050                1055

GAG CTT TTG GAA CTG GAG GGA AGT TTT CCT GAA GAA AAT CAC AGG GAG    3276
Glu Leu Leu Glu Leu Glu Gly Ser Phe Pro Glu Glu Asn His Arg Glu
            1060                1065                1070

AAG TCT GTC TGT TAT CTA GGA GTC ACC TCC GTC AAC AGA AGA GAG AGT    3324
Lys Ser Val Cys Tyr Leu Gly Val Thr Ser Val Asn Arg Arg Glu Ser
        1075                1080                1085

GGT GTG CTT TTG ACT GGT GAG GCA GGA ATC CTG TGC ACA TTC CCA GCC    3372
Gly Val Leu Leu Thr Gly Glu Ala Gly Ile Leu Cys Thr Phe Pro Ala
   1090                 1095                1100

CAG TGT CTG TTC ACT GAC ATC AGG ATC CTC CAG GAG AGA TGC TCA CAC    3420
Gln Cys Leu Phe Thr Asp Ile Arg Ile Leu Gln Glu Arg Cys Ser His
1105                1110                1115                1120

TTT GTA GAA AAT AAT TTG AGT TTA GGG ACC TCT GGT GAG AAC TTT GTA    3468
Phe Val Glu Asn Asn Leu Ser Leu Gly Thr Ser Gly Glu Asn Phe Val
                1125                1130                1135

CCT TAC ATG CCC CAA TTT CAA ACC TGT TCC ACG CAC AGT CAC AAG ATA    3516
Pro Tyr Met Pro Gln Phe Gln Thr Cys Ser Thr His Ser His Lys Ile
            1140                1145                1150

ATG GAG AAT AAG ATG TGT GAC TTA ACT GTG                            3546
Met Glu Asn Lys Met Cys Asp Leu Thr Val
1155                1160

TAATCTCATC CAAGAAGCCT CAAGGTTCCA TTCCAGTAGA GCCTGTCATG TATAATGTGT  3626

TCTTTTATTG TTGTGGATGT GGGAGACAAG TGTCAGAATC TAGTGTGAAA ATGATTGTTT  3666

ATTAATCTAC TAATGTAGAT GGACTCTTAC TGAATATATT CCCAAGATAC TTGGGGAAGT  3786

CTCCCTAATT CTAGCTAAAA GAANTAGAAC TACTAAACAC TGAATCTGGA AAAAAAAAA   3846

AAAAAAAG                                                            3854
```

-continued (2) INFORMATION FOR SEQ ID NO: 43:

(i) SEQUENCE CHARACTERISTICS:
        (A) LENGTH: 1162 amino acids
        (B) TYPE: amino acid
        (D) TOPOLOGY: unknown (ii) MOLECULE TYPE: protein (v) FRAGMENT TYPE: internal (xi) SEQUENCE DESCRIPTION: SEQ ID NO: 43:

```
Met Met Cys Gln Lys Phe Tyr Val Val Leu Leu His Trp Glu Phe Leu
 1               5                  10                  15

Tyr Val Ile Ala Ala Leu Asn Leu Ala Tyr Pro Ile Ser Pro Trp Lys
             20                  25                  30

Phe Lys Leu Phe Cys Gly Pro Pro Asn Thr Thr Asp Asp Ser Phe Leu
         35                  40                  45

Ser Pro Ala Gly Ala Pro Asn Asn Ala Ser Ala Leu Lys Gly Ala Ser
     50                  55                  60

Glu Ala Ile Val Glu Ala Lys Phe Asn Ser Ser Gly Ile Tyr Val Pro
 65                  70                  75                  80

Glu Leu Ser Lys Thr Val Phe His Cys Cys Phe Gly Asn Glu Gln Gly
                 85                  90                  95

Gln Asn Cys Ser Ala Leu Thr Asp Asn Thr Glu Gly Lys Thr Leu Ala
             100                 105                 110

Ser Val Val Lys Ala Ser Val Phe Arg Gln Leu Gly Val Asn Trp Asp
         115                 120                 125

Ile Glu Cys Trp Met Lys Gly Asp Leu Thr Leu Phe Ile Cys His Met
130                 135                 140

Glu Pro Leu Pro Lys Asn Pro Phe Lys Asn Tyr Asp Ser Lys Val His
145                 150                 155                 160

Leu Leu Tyr Asp Leu Pro Glu Val Ile Asp Asp Ser Pro Leu Pro Pro
                 165                 170                 175

Leu Lys Asp Ser Phe Gln Thr Val Gln Cys Asn Cys Ser Leu Arg Gly
             180                 185                 190

Cys Glu Cys His Val Pro Val Pro Arg Ala Lys Leu Asn Tyr Ala Leu
         195                 200                 205

Leu Met Tyr Leu Glu Ile Thr Ser Ala Gly Val Ser Phe Gln Ser Pro
     210                 215                 220

Leu Met Ser Leu Gln Pro Met Leu Val Val Lys Pro Asp Pro Pro Leu
225                 230                 235                 240

Gly Leu His Met Glu Val Thr Asp Asp Gly Asn Leu Lys Ile Ser Trp
                 245                 250                 255

Asp Ser Gln Thr Met Ala Pro Phe Pro Leu Gln Tyr Gln Val Lys Tyr
             260                 265                 270

Leu Glu Asn Ser Thr Ile Val Arg Glu Ala Ala Glu Ile Val Ser Ala
         275                 280                 285

Thr Ser Leu Leu Val Asp Ser Val Leu Pro Gly Ser Ser Tyr Glu Val
     290                 295                 300

Gln Val Arg Ser Lys Arg Leu Asp Gly Ser Gly Val Trp Ser Asp Trp
305                 310                 315                 320

Ser Ser Pro Gln Val Phe Thr Thr Gln Asp Val Val Tyr Phe Pro Pro
                 325                 330                 335

Lys Ile Leu Thr Ser Val Gly Ser Asn Ala Ser Phe His Cys Ile Tyr
             340                 345                 350
```

-continued

Lys Asn Glu Asn Gln Ile Ile Ser Ser Lys Gln Ile Val Trp Arg
    355                 360                 365

Asn Leu Ala Glu Lys Ile Pro Glu Ile Gln Tyr Ser Ile Val Ser Asp
    370                 375                 380

Arg Val Ser Lys Val Thr Phe Ser Asn Leu Lys Ala Thr Arg Pro Arg
385                 390                 395                 400

Gly Lys Phe Thr Tyr Asp Ala Val Tyr Cys Cys Asn Glu Gln Ala Cys
                405                 410                 415

His His Arg Tyr Ala Glu Leu Tyr Val Ile Asp Val Asn Ile Asn Ile
            420                 425                 430

Ser Cys Glu Thr Asp Gly Tyr Leu Thr Lys Met Thr Cys Arg Trp Ser
        435                 440                 445

Pro Ser Thr Ile Gln Ser Leu Val Gly Ser Thr Val Gln Leu Arg Tyr
    450                 455                 460

His Arg Arg Ser Leu Tyr Cys Pro Asp Ser Pro Ser Ile His Pro Thr
465                 470                 475                 480

Ser Glu Pro Lys Asn Cys Val Leu Gln Arg Asp Gly Phe Tyr Glu Cys
                485                 490                 495

Val Phe Gln Pro Ile Phe Leu Leu Ser Gly Tyr Thr Met Trp Ile Arg
            500                 505                 510

Ile Asn His Ser Leu Gly Ser Leu Asp Ser Pro Pro Thr Cys Val Leu
        515                 520                 525

Pro Asp Ser Val Val Lys Pro Leu Pro Pro Ser Asn Val Lys Ala Glu
    530                 535                 540

Ile Thr Val Asn Thr Gly Leu Leu Lys Val Ser Trp Glu Lys Pro Val
545                 550                 555                 560

Phe Pro Glu Asn Asn Leu Gln Phe Gln Ile Arg Tyr Gly Leu Ser Gly
                565                 570                 575

Lys Glu Ile Gln Trp Lys Thr His Glu Val Phe Asp Ala Lys Ser Lys
            580                 585                 590

Ser Ala Ser Leu Leu Val Ser Asp Leu Cys Ala Val Tyr Val Val Gln
        595                 600                 605

Val Arg Cys Arg Arg Leu Asp Gly Leu Gly Tyr Trp Ser Asn Trp Ser
    610                 615                 620

Ser Pro Ala Tyr Thr Leu Val Met Asp Val Lys Val Pro Met Arg Gly
625                 630                 635                 640

Pro Glu Phe Trp Arg Lys Met Asp Gly Asp Val Thr Lys Lys Glu Arg
                645                 650                 655

Asn Val Thr Leu Leu Trp Lys Pro Leu Thr Lys Asn Asp Ser Leu Cys
            660                 665                 670

Ser Val Arg Arg Tyr Val Val Lys His Arg Thr Ala His Asn Gly Thr
        675                 680                 685

Trp Ser Glu Asp Val Gly Asn Arg Thr Asn Leu Thr Phe Leu Trp Thr
    690                 695                 700

Glu Pro Ala His Thr Val Thr Val Leu Ala Val Asn Ser Leu Gly Ala
705                 710                 715                 720

Ser Leu Val Asn Phe Asn Leu Thr Phe Ser Trp Pro Met Ser Lys Val
                725                 730                 735

Ser Ala Val Glu Ser Leu Ser Ala Tyr Pro Leu Ser Ser Ser Cys Val
            740                 745                 750

Ile Leu Ser Trp Thr Leu Ser Pro Asp Asp Tyr Ser Leu Leu Tyr Leu
        755                 760                 765

Val Ile Glu Trp Lys Ile Leu Asn Glu Asp Asp Gly Met Lys Trp Leu

```
                    770              775              780
Arg Ile Pro Ser Asn Val Lys Lys Phe Tyr Ile His Asp Asn Phe Ile
785              790                  795                  800

Pro Ile Glu Lys Tyr Gln Phe Ser Leu Tyr Pro Val Phe Met Glu Gly
                 805                 810                 815

Val Gly Lys Pro Lys Ile Ile Asn Gly Phe Thr Lys Asp Ala Ile Asp
                820                 825                 830

Lys Gln Gln Asn Asp Ala Gly Leu Tyr Val Ile Val Pro Ile Ile Ile
                835                 840                 845

Ser Ser Cys Val Leu Leu Leu Gly Thr Leu Leu Ile Ser His Gln Arg
850                 855                 860

Met Lys Lys Leu Phe Trp Asp Asp Val Pro Asn Pro Lys Asn Cys Ser
865                 870                 875                 880

Trp Ala Gln Gly Leu Asn Phe Gln Lys Pro Glu Thr Phe Glu His Leu
                885                 890                 895

Phe Thr Lys His Ala Glu Ser Val Ile Phe Gly Pro Leu Leu Leu Glu
                900                 905                 910

Pro Glu Pro Ile Ser Glu Glu Ile Ser Val Asp Thr Ala Trp Lys Asn
                915                 920                 925

Lys Asp Glu Met Val Pro Ala Ala Met Val Ser Leu Leu Leu Thr Thr
                930                 935                 940

Pro Asp Pro Glu Ser Ser Ser Ile Cys Ile Ser Asp Gln Cys Asn Ser
945                 950                 955                 960

Ala Asn Phe Ser Gly Ser Gln Ser Thr Gln Val Thr Cys Glu Asp Glu
                965                 970                 975

Cys Gln Arg Gln Pro Ser Val Lys Tyr Ala Thr Leu Val Ser Asn Asp
                980                 985                 990

Lys Leu Val Glu Thr Asp Glu Glu Gln Gly Phe Ile His Ser Pro Val
                995                 1000                1005

Ser Asn Cys Ile Ser Ser Asn His Ser Pro Leu Arg Gln Ser Phe Ser
     1010               1015                1020

Ser Ser Ser Trp Glu Thr Glu Ala Gln Thr Phe Phe Leu Leu Ser Asp
025                 1030                1035                1040

Gln Gln Pro Thr Met Ile Ser Pro Gln Leu Ser Phe Ser Gly Leu Asp
                1045                1050                1055

Glu Leu Leu Glu Leu Glu Gly Ser Phe Pro Glu Glu Asn His Arg Glu
                1060                1065                1070

Lys Ser Val Cys Tyr Leu Gly Val Thr Ser Val Asn Arg Arg Glu Ser
                1075                1080                1085

Gly Val Leu Leu Thr Gly Glu Ala Gly Ile Leu Cys Thr Phe Pro Ala
     1090                1095                1100

Gln Cys Leu Phe Thr Asp Ile Arg Ile Leu Gln Glu Arg Cys Ser His
105                 1110                1115                1120

Phe Val Glu Asn Asn Leu Ser Leu Gly Thr Ser Gly Glu Asn Phe Val
                1125                1130                1135

Pro Tyr Met Pro Gln Phe Gln Thr Cys Ser Thr His Ser His Lys Ile
                1140                1145                1150

Met Glu Asn Lys Met Cys Asp Leu Thr Val
                1155                1160
```

(2) INFORMATION FOR SEQ ID NO: 44:

(i) SEQUENCE CHARACTERISTICS:
        (A) LENGTH: 26 base pairs

```
       (B) TYPE: nucleic acid
       (C) STRANDEDNESS: double
       (D) TOPOLOGY: unknown (ii) MOLECULE TYPE: cDNA (xi) SEQUENCE DESCRIPTION: SEQ ID NO: 44:

TCRCACATYT TRTTNCCCAT TATCTT                                   26

(2) INFORMATION FOR SEQ ID NO: 45:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 45:

CCCAATGTCG ACATGATGTG TCAGAAATTC TAT                           33

(2) INFORMATION FOR SEQ ID NO: 46:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 46:

AAAAAGGATC CGGTCATTCT GCTGCTTGTC GAT                           33

(2) INFORMATION FOR SEQ ID NO: 47:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 47:

CCCAATGTCG ACATGGTGTA CTTCTCTGAA GTA                           33

(2) INFORMATION FOR SEQ ID NO: 48:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 48:

TTTTTGGATC CCACCTGCAT CACTCTGGTG                               30

(2) INFORMATION FOR SEQ ID NO: 49:

(i) SEQUENCE CHARACTERISTICS:
       (A) LENGTH: 48 base pairs
       (B) TYPE: nucleic acid
       (C) STRANDEDNESS: single
       (D) TOPOLOGY: linear
```

-continued

```
    (ii) MOLECULE TYPE: DNA (xi) SEQUENCE DESCRIPTION: SEQ ID NO: 49:

TTTAACTTGT CATATCCAAT TACTCCTTGG AGATTTAAGT TGTCTTGC                    48

(2) INFORMATION FOR SEQ ID NO: 50:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 50:

TTTTTGGATC CCACCTGCAT CACTCTGGTG                                        30
```

What is claimed is:

1. A method for treating a body weight disorder, the method comprising administering to a subject in need of such treatment a therapeutically effective amount of an antibody or fragment thereof that binds ObR.

2. The method of claim 1 wherein the antibody is an activating antibody or fragment thereof.

3. The method of claim 1 wherein the antibody activates ObR signaling.

4. The method of claim 1 wherein the antibody or fragment thereof is any one of a polyclonal, monoclonal, humanized, anti-idiotypic, chimeric or single chain antibody.

5. The method of claim 1 wherein the antibody fragment is any one of an FAb, F(ab')$_2$ or an epitope-binding fragment thereof.

6. The method of claim 1 wherein the body weight disorder is obesity.

* * * * *